US008703199B2

(12) United States Patent
Babcock et al.

(10) Patent No.: US 8,703,199 B2
(45) Date of Patent: *Apr. 22, 2014

(54) PHARMACEUTICAL COMPOSITIONS OF ADSORBATES OF AMORPHOUS DRUG

(75) Inventors: Walter C. Babcock, Bend, OR (US);
Dwayne T. Friesen, Bend, OR (US);
Ravi M. Shanker, Groton, CT (US);
Daniel T. Smithey, Bend, OR (US);
Ralph Tadday, Bend, OR (US)

(73) Assignee: Bend Research, Inc., Bend, OR (US)

( * ) Notice: Subject to any disclaimer, the term of this patent is extended or adjusted under 35 U.S.C. 154(b) by 1604 days.

This patent is subject to a terminal disclaimer.

(21) Appl. No.: 11/566,408

(22) Filed: Dec. 4, 2006

(65) Prior Publication Data

US 2007/0148236 A1    Jun. 28, 2007

Related U.S. Application Data

(62) Division of application No. 10/173,987, filed as application No. PCT/IB02/01792 on May 21, 2002, now abandoned.

(60) Provisional application No. 60/300,260, filed on Jun. 22, 2001.

(51) Int. Cl.
*A61K 9/18* (2006.01)

(52) U.S. Cl.
USPC ........................................................ 424/488

(58) Field of Classification Search
USPC .................................. 424/488, 464; 514/313
See application file for complete search history.

(56) References Cited

U.S. PATENT DOCUMENTS

| | | | |
|---|---|---|---|
| 4,343,789 A | 8/1982 | Kawata et al. .................... 424/78 |
| 4,581,232 A | 4/1986 | Peters et al. .................... 424/155 |
| 4,711,774 A | 12/1987 | Denick, Jr. et al. .............. 424/48 |
| 4,716,033 A | 12/1987 | Denick, Jr. et al. .............. 424/48 |
| 4,717,565 A | 1/1988 | Denick, Jr. et al. ............ 424/155 |
| 4,772,627 A | 9/1988 | Matsui et al. .................... 514/462 |
| 4,835,186 A | 5/1989 | Reuter et al. ..................... 514/570 |
| 4,973,469 A | 11/1990 | Mulligan et al. ............... 424/461 |
| 5,008,114 A | 4/1991 | Lovrecich ....................... 424/484 |
| 5,015,479 A | 5/1991 | Mulligan et al. ............... 424/457 |
| 5,449,521 A | 9/1995 | Lovrecich ....................... 424/489 |
| 5,505,959 A | 4/1996 | Tachon et al. .................. 424/450 |
| 5,610,193 A | 3/1997 | Al-Razzak et al. ............. 514/616 |
| 5,626,878 A * | 5/1997 | Garay et al. .................... 424/489 |
| 5,925,645 A | 7/1999 | Schmidt et al. ................ 514/277 |
| 6,069,148 A | 5/2000 | Schmidt et al. ................ 514/277 |
| 6,107,290 A | 8/2000 | Woo |
| 6,127,383 A | 10/2000 | Schmidt et al. ................ 514/312 |
| 6,140,342 A | 10/2000 | Goldstein et al. .............. 514/313 |
| 6,140,343 A | 10/2000 | DeNinno et al. ............... 514/313 |
| 6,147,089 A | 11/2000 | DeNinno et al. ............... 514/313 |
| 6,147,090 A | 11/2000 | DeNinno et al. ............... 514/313 |
| 6,197,786 B1 | 3/2001 | DeNinno et al. ............... 514/313 |
| 6,207,671 B1 | 3/2001 | Schmidt et al. ................ 514/277 |
| 6,280,770 B1 | 8/2001 | Pather et al. .................... 424/465 |
| 6,291,477 B1 | 9/2001 | Schmidt et al. ................ 514/311 |
| 6,310,075 B1 | 10/2001 | DeNinno et al. ............... 514/313 |
| 6,316,497 B1 | 11/2001 | Liu et al. ........................ 514/475 |
| 6,362,198 B1 | 3/2002 | Goldstein et al. .............. 514/313 |
| 6,602,523 B1 | 8/2003 | Joshi et al. ................... A61K 9/14 |
| 2001/0009677 A1 | 7/2001 | Bruce et al. .................... 424/464 |
| 2002/0103225 A1 | 8/2002 | Curatolo et al. ............... 514/313 |

FOREIGN PATENT DOCUMENTS

| | | | |
|---|---|---|---|
| DE | 19627419 | 1/1998 | .......... C07D 215/20 |
| DE | 19627430 | 1/1998 | .......... C07D 221/16 |
| DE | 19627431 | 1/1998 | .......... C07D 471/04 |
| DE | 19704243 | 8/1998 | .......... C07D 213/74 |
| DE | 19704244 | 8/1998 | ............. C07C 49/83 |
| DE | 19709125 | 9/1998 | .......... C07D 215/20 |
| DE | 19741051 | 3/1999 | .......... C07D 215/26 |
| DE | 19741399 | 3/1999 | .......... C07D 215/20 |
| DE | 19741400 | 3/1999 | ............. C07C 33/46 |
| DE | 19832159 | 3/1999 | ............. C07C 35/52 |
| EP | 0429187 | 1/1994 | ............. A61K 9/18 |
| EP | 0818448 | 1/1998 | .......... C07D 215/20 |
| EP | 0901786 | 3/1999 | ............. A61K 9/14 |
| EP | 0987251 | 3/2000 | .......... C07D 215/50 |
| EP | 0992496 | 4/2000 | .......... C07D 221/06 |
| EP | 0796846 | 7/2000 | .......... C07D 213/30 |
| EP | 1027887 | 8/2000 | ............. A61K 9/26 |
| JP | 11049743 | 2/1999 | .......... C07C 323/40 |
| JP | 11246404 | 9/1999 | ............. A61K 31/40 |
| SI | 9500059 A | 8/1996 | |
| WO | WO 9632126 | 10/1996 | ............. A61K 38/00 |
| WO | WO 9639126 | 12/1996 | ............. A61K 9/18 |
| WO | WO 9804528 | 2/1998 | .......... C07D 213/20 |
| WO | WO 9835937 | 8/1998 | .......... C07C 323/40 |
| WO | WO 9838167 | 9/1998 | .......... C07D 215/54 |
| WO | WO 9839299 | 9/1998 | .......... C07D 215/20 |
| WO | WO 9914174 | 3/1999 | ............. C07C 35/52 |
| WO | WO 9914204 | 3/1999 | .......... C07D 249/12 |
| WO | WO 9914215 | 3/1999 | .......... C07D 409/04 |
| WO | WO 9915504 | 4/1999 | .......... C07D 215/20 |
| WO | WO 9940061 | 8/1999 | .......... C07C 231/00 |
| WO | WO 9941237 | 8/1999 | .......... C07D 213/80 |
| WO | WO 0017164 | 3/2000 | .......... C07D 215/42 |

(Continued)

OTHER PUBLICATIONS

Oguchi et al. ("Improved dissolution of Naproxen from solid dispersion with Porous Additives," in Yakuzaigaku, vol. 57, No. 3, 1997, pp. 168-173).*

(Continued)

*Primary Examiner* — Blessing M Fubara

(74) *Attorney, Agent, or Firm* — Chernoff Vilhauer McClung & Stenzel LLP

(57) ABSTRACT

Pharmaceutical compositions comprise a low-solubility drug adsorbed onto a high surface area substrate to form an adsorbate. The compositions in some embodiments include a concentration-enhancing polymer.

23 Claims, No Drawings

(56) References Cited

FOREIGN PATENT DOCUMENTS

| WO | WO 0017165 | 3/2000 | C07D 215/42 |
|---|---|---|---|
| WO | WO 0017166 | 3/2000 | C07D 215/48 |
| WO | WO 0018721 | 4/2000 | C07C 215/16 |
| WO | WO 0018723 | 4/2000 | C07C 217/52 |
| WO | WO 0018724 | 4/2000 | C07C 217/90 |
| WO | WO 0100180 | 1/2001 | A61K 9/18 |
| WO | WO 0110410 | 2/2001 | A61K 9/10 |
| WO | WO 0168055 | 9/2001 | A61K 9/14 |
| WO | WO 0211710 | 2/2002 | A61K 31/00 |

OTHER PUBLICATIONS

Yamamoto et al. ("Adsorption of Pharmaceutical Organic Compounds onto Porous Materials," in Surfaces of Nanoparticles and Porous Materials, Ch. 29, pp. 763-781, 1999).*

Monkhouse et al. ("Use of Adsorbents in Enhancement of Drug Dissolution I," in Journal of Pharmaceutical Sciences, vol. 61, No. 9, Sep. 1972, pp. 1430-1435).*

Katzhendler, Ifat, et al., "*Crystalline properties of carbamazepine in sustained release hydrophilic matrix tablets based on hydroxproply methylcellulose*", Journal of Controlled Release, 1998, pp. 69-85, vol. 54.

Monkhouse, D.C., et al., "*Use of Adsorbents in Enhancement of Drug Dissolution II*", Journal of Pharmaceutical Sciences, Sep. 1972, pp. 1435-1441, vol. 61, No. 9.

Gore, A.Y., et al., "*Surface Chemistry of Colloidal Silica and a Possible Application to Stabilize Aspirin in Solid Matrixes*", Journal of Pharmaceutical Sciences, Feb. 1979, pp. 197-202, vol. 68, No. 2.

Daniels, R., et al., "*The Stability of Drug Adsorbates on Silica*", Drug Development and Industrial Pharmacy, 1986, pp. 2127-2156, vol. 12(11-13).

Takeuchi, H., et al., "*Spherical Solid Dispersion Containing Amorphous Tolbutamide Embedded in Enteric Coating Polymers or Colloidal Silica Prepared by Spray-Drying Technique*", Chem. Pharm. Bull., 1987, pp. 3800-2806, vol. 35(9).

Nakagami, Hiroaki, "*Solid Dispersions of Indomethacin and Griseofulvin in Non-porous Fumed Silicon Dioxide, Prepared by Melting*", Chemical Pham. Bull., Sep. 1991, pp. 2471-2421, vol. 39(9).

Kinoshita, Masahiro, et al., "*Improvement of Solubility and Oral Bioavailability of a Poorly Water-Soluble Drug, TAS-031, by it Melt-Adsorption of Porous Calcium Silicate*", Journal of Pharmaceutical Sciences, Feb. 2002, pp. 362-370, vol. 91, No. 2.

Yonemochi, Etsuo, et al., "*Thermal Behavior of Methyl p-hydroxybenzoate in Controlled-Pore Glass Solid Dispersion*", Journal of Colloid and Interface Science, 1995, pp. 186-191, vol. 173.

Takenaka, H., "*Preparation of Enteric-Coated Microcapsules for Tableting by Spray-Drying Technique and in Vitro Simulation of Drug Release from the Tablet in GI Tract*", Dec. 1980, pp. 1388-1392, vol. 69, No. 12.

Konno, Tsutomu, "*Physical and Chemical Changes of Medicinals in Mixtures with Adsorbents in the Solid State. III, Determination of Vapor Pressure of Solid Drugs by Steam Distillation*", Chem. Pharm. Bull., 1990, pp. 1032-1034, vol. 38, No. 4.

Yamamoto, K., et al., Adsorption of Pharmaceutical Organic Compounds onto Porous Materials, pp. 763-781.

Monkhouse, D., et al., "Use of Adsorbents in Enhancement of Drug Dissolution I", Journal of Pharmaceutical Sciences, Sep. 1972, pp. 1430-1435, vol. 61, No. 9.

Alsaidan, S., et al., "*Improved Dissolution Rate of Indomethacin by Adsorbents*", Drug Development and Industrial Pharmacy, 1998, pp. 389-394, vol. 24 No. 4.

Oguchi, Toshio, et al., "*Improved Dissolution of Naproxen from Solid Dispersions with Porous Additives*", Yakuzaigaku, 1997, pp. 168-173, vol. 57, No. 3.

Wood, J., et al., "*Improved Holder for Intrinsic Dissolution Rate Studies*", J. Pharm. Science, 1965, pp. 1068, vol. 54.

Kerc et al., Drug Development and Industrial Pharmacy, 24 (4), 359-363 (1998).

Kerc et al, Acta Pharm. Jugosl. 41, 259-265 (1991).

Kerc et al, Acta Pharm. 43, 113-120 (1993).

Chowdary and Hymavathi, Indian Journal of Pharmaceutical Sciences, Apr.-Mar. 2001, 150-154.

Konno et al., Chem. Pharm. Bul. 34 (1) 301-307 (1986).

\* cited by examiner

PHARMACEUTICAL COMPOSITIONS OF ADSORBATES OF AMORPHOUS DRUG

CROSS REFERENCE TO RELATED APPLICATION

This application is a divisional of U.S. patent application Ser. No. 10/173,987 filed Jun. 17, 2002 which claims the benefit of priority of PCT Patent Application Number PCT/IB02/01792 filed May 21, 2002 which claims the benefit of priority of U.S. Provisional Patent Application Ser. No. 60/300,260 filed Jun. 22, 2001.

BACKGROUND OF THE INVENTION

The present invention relates to pharmaceutical compositions of a low-solubility drug and a high surface area substrate, wherein the drug and substrate are combined to form an adsorbate.

Low-solubility drugs often show poor bioavailability or irregular absorption, the degree of irregularity being affected by factors such as dose level, fed state of the patient, and form of the drug. Increasing the bioavailability of low-solubility drugs has been the subject of much research. Increasing bioavailability hinges on improving the concentration of the drug in solution to improve absorption.

It is well known that the amorphous form of a low-solubility drug that is capable of existing in either the crystalline or amorphous form may temporarily provide a greater aqueous concentration of drug relative to the equilibrium concentration obtained by dissolution of drug in a use environment. Such amorphous forms may consist of the amorphous drug alone, a dispersion of the drug in a matrix material, or the drug adsorbed onto a substrate. It is believed that such amorphous forms of the drug may dissolve more rapidly than the crystalline form, often dissolving faster than the drug can precipitate from solution. As a result, the amorphous form may temporarily provide a greater-than equilibrium concentration of drug.

While such amorphous forms may show initially enhanced concentration of the drug in a use environment, nevertheless the improved concentration is often short-lived. Typically, the initially enhanced drug concentration is only temporary and quickly returns to the lower equilibrium concentration.

One problem with using the amorphous form of a drug is that the solid drug may not be stable physically in the amorphous form. Often the crystalline form of the drug has a lower free energy, and thus over time, the amorphous drug will tend to crystallize. The rate of crystallization may be influenced by storage conditions, such as temperature and humidity, as well as the constituents of the composition.

D. Monkhouse, et al., Use of Adsorbents in Enhancement of Drug Dissolution I, J. Pharm. Sciences, Vol. 61, No. 9, p. 1430 (1972), disclose forming adsorbents by mixing a drug and water-insoluble adsorbent such as fumed silicon dioxide or silicic acid, adding a sufficient quantity of an organic solvent to dissolve the drug, and then evaporating the solvent by a stream of filtered air. The authors report improved drug dissolution rates.

Matsui, et al., U.S. Pat. No. 4,772,627, disclose a ground mixture of a poorly soluble crystalline drug and an adsorbent. The mixture of drug and adsorbent is ground to obtain amorphous drug. Enhanced drug dissolution and drug absorption is reported.

Denick, Jr. et al., U.S. Pat. No. 4,711,774, disclose an adsorbate of a drug and a complex magnesium aluminum silicate. The drug is dissolved in a solvent and added to magnesium aluminum silicate, and then dried. The adsorbate is used to mask the taste of bitter drugs.

Lovrecich, U.S. Pat. No. 5,449,521, discloses amorphous drug absorbed onto a support material. The support material may be crosslinked polymers, linear polymers, water soluble complexing agents, and porous inorganic materials. The drug and support material are co-ground in a mill with its grinding chamber saturated with the vapour of one or more solvents able to solubilize the drug. The resulting product is dried and sieved. The resulting compositions are reported to have a reduced heat of fusion, a reduced melting point, an increased dissolution rate and increased solubilization kinetices.

Accordingly, what is still desired is a composition comprising an amorphous drug form that is physically stable under typical storage conditions, and that may enhance the bioavailability of poorly soluble drugs. These needs and others that will become apparent to one of ordinary skill are met by the present invention, which is summarized and described in detail below.

BRIEF SUMMARY OF THE INVENTION

The present invention overcomes the drawbacks of the prior art by providing in a first aspect of the invention, pharmaceutical compositions comprising a solid adsorbate with a low-solubility drug adsorbed onto a substrate, said substrate having a surface area of at least 20 $m^2/g$, wherein at least a major portion of said drug in said adsorbate is amorphous, wherein the adsorbate provides improved concentration of said drug in a use environment relative to a slow-evaporation control composition comprising said drug and said substrate but formed by evaporation of solvent from a suspension of said drug in a solvent with said substrate suspended therein, said evaporation of said solvent for formation of said slow-evaporation control composition being conducted over a period of at least 30 minutes.

In a second aspect, the present invention provides pharmaceutical compositions comprising a solid adsorbate with a low-solubility drug adsorbed onto a substrate, said substrate having a surface area of at least 20 $m^2/g$, wherein at least a major portion of said drug in said adsorbate is amorphous; and a concentration-enhancing polymer.

In one preferred embodiment, the adsorbate provides improved concentration of said drug in a use environment relative to a slow-evaporation control composition comprising said drug and said substrate but formed by evaporation of solvent from a suspension of said drug in a solvent with said substrate suspended therein, said evaporation of said solvent for formation of said slow-evaporation control composition being conducted over a period of at least 30 minutes.

In another preferred embodiment, the adsorbate is more physically stable than said slow-evaporation control composition.

In another preferred embodiment, the drug in said adsorbate has a glass transition temperature substantially different from that of said drug in amorphous form alone that is not adsorbed to said substrate.

In yet another preferred embodiment, the drug is in the form of a layer of drug molecules adsorbed onto said substrate, said layer having a thickness that is no greater than about 3-fold the diameter of said drug.

In another preferred embodiment, the drug is adsorbed onto said substrate substantially in the form of a monolayer.

In still another preferred embodiment, the drug has improved physical stability in said adsorbate relative to a control composition having an equivalent amount of said drug in amorphous form alone that is not adsorbed to said substrate. Preferably, the drug has a rate of crystallization in said adsorbate that is less than 90% of the crystallization rate of said drug in amorphous form.

Another preferred embodiment relates to the drug in said adsorbate having a relative degree of improvement in chemical stability of at least about 1.25 relative to said drug in amorphous form alone and not adsorbed to said substrate.

In another preferred embodiment, the drug in said adsorbate has a relative degree of improvement in chemical stability of at least 1.25 relative to at least one of a first control composition having an equivalent amount of said drug in amorphous form mixed with said concentration-enhancing polymer and a second control composition consisting of a solid amorphous dispersion of an equivalent amount of said drug and said concentration-enhancing polymer.

In still another preferred embodiment, the drug is acid-sensitive and said concentration-enhancing polymer is acidic.

In another preferred embodiment, the surface area of said substrate is at least 50 $m^2/g$, preferably at least 180 $m^2/g$.

In another preferred embodiment, the adsorbate is in the form of agglomerates having a mean average diameter of from about 10 nm to about 100 µm, preferably from about 10 nm to about 1 µm.

In another preferred embodiment, the substrate is an inorganic oxide, preferably $SiO_2$, $TiO_2$, $ZnO_2$, $ZnO$, $Al_2O_3$, or zeolite.

In yet another preferred embodiment, the substrate is a water insoluble polymer, preferably cross-linked polyvinyl pyrrolidinone, cross-linked cellulose acetate phthalate, cross-linked hydroxypropyl methyl cellulose acetate succinate, microcrystalline cellulose, polyethylene/polyvinyl alcohol copolymer, polyethylene/polyvinyl pyrrolidinone copolymer, cross-linked carboxymethyl cellulose, sodium starch glycolate, or cross-linked styrene divinyl benzene.

In another preferred embodiment, the substrate is an activated carbon, preferably a carbonized polymer such as polyimides, polyarylonitrile, phenolic resins, cellulose acetate, regenerated cellulose, and rayon.

Another preferred embodiment includes the drug in said adsorbate as substantially amorphous, preferably the drug is almost completely amorphous.

In another preferred embodiment, the drug and said concentration-enhancing polymer are co-adsorbed onto said substrate, preferably, the drug and said polymer are substantially in the form of an amorphous dispersion, more preferably, the dispersion is substantially homogeneous.

In another preferred embodiment, the composition is a mixture of said adsorbate and said concentration-enhancing polymer, preferably the composition is a mixture of particles of said adsorbate and particles of said concentration-enhancing polymer. More preferably, the adsorbate and said concentration-enhancing polymer are each in respective regions. Preferably, the mixture is formed by wet-granulation and/or dry-granulation.

In another preferred embodiment, the concentration-enhancing polymer has a hydrophobic portion and a hydrophilic portion.

In another preferred embodiment, the concentration-enhancing polymer is a cellulosic ionizable polymer, preferably hydroxypropyl methyl cellulose succinate, cellulose acetate succinate, methyl cellulose acetate succinate, ethyl cellulose acetate succinate, hydroxypropyl cellulose acetate succinate, hydroxypropyl methyl cellulose acetate succinate, hydroxypropyl cellulose acetate phthalate succinate, cellulose propionate succinate, hydroxypropyl cellulose butyrate succinate, hydroxypropyl methyl cellulose phthalate, carboxymethyl cellulose, carboxyethyl cellulose, ethylcarboxymethyl cellulose, cellulose acetate phthalate, methyl cellulose acetate phthalate, ethyl cellulose acetate phthalate, hydroxypropyl cellulose acetate phthalate, hydroxypropyl methyl cellulose acetate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, ethyl picolinic acid cellulose acetate or blends thereof.

In another preferred embodiment, the concentration-enhancing polymer is an ionizable, non-cellulosic polymer, preferably carboxylic acid functionalized polymethacrylates, carboxylic acid functionalized polyacrylates, amine-functionalized polyacrylates, amine-fuctionalized polymethacrylates, proteins, carboxylic acid functionalized starches or blends thereof.

In yet another preferred embodiment, the concentration-enhancing polymer is a non-ionizable cellulosic polymer, preferably hydroxypropyl methyl cellulose acetate, hydroxypropyl methyl cellulose, hydroxypropyl cellulose, methyl cellulose, hydroxyethyl methyl cellulose, hydroxyethyl cellulose acetate, and hydroxyethyl ethyl cellulose or blends thereof.

In another preferred embodiment, the concentration-enhancing polymer is a non-ionizable, non-cellulosic polymer, preferably vinyl polymer or copolymer having at least one substituent selected from the group consisting of hydroxyl, alkylacyloxy, and cyclicamido, vinyl copolymers of at least one hydrophilic, hydroxyl-containing repeat unit and at least one hydrophobic, alkyl- or aryl-containing repeat unit, polyvinyl alcohols that have at least a portion of their repeat units in the unhydrolyzed form, polyvinyl alcohol polyvinyl acetate copolymers, polyethylene glycol polypropylene glycol copolymers, polyvinyl pyrrolidone, polyethylene polyvinyl alcohol copolymers, polyoxyethylene-polyoxypropylene block copolymers and blends thereof.

In another preferred embodiment, the concentration-enhancing polymer is a neutralized acidic polymer.

In still another preferred embodiment, the composition when administered to a use environment provides a dissolution area under the concentration versus time curve for a time period of at least 90 minutes between the time of introduction to said use environment and about 270 minutes following introduction to the use environment that is at least 1.25-fold the corresponding area under the curve provided by a control composition comprising an equivalent amount of crystalline drug alone.

In another preferred embodiment, the composition when administered to a use environment provides a maximum concentration of said drug in said use environment that is at least 1.25-fold a maximum concentration of said drug provided by a control composition comprising an equivalent amount of crystalline drug alone.

In another preferred embodiment, the composition when administered to a use environment provides a relative bioavailability of at least 1.25 relative to a control composition consisting of an equivalent amount of said drug in crystalline form alone.

In another preferred embodiment, the drug is selected from the group consisting of antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, cholesterol-reducing agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, antiviral agents, anti-atherosclerotic agents, glycogen phosphorylase inhibitors, and cholesterol ester transfer protein inhibitors.

In another preferred embodiment, the drug is [R—(R*S*)]-5-chloro-N-[2-hydroxy-3-{methoxymethylamimo}-3-oxo-1-(phenylmethyl)propyl-1H-indole-2-carboxamide, 5-chloro-1H-indole-2-carboxylic acid [(1S)-benzyl-(2R)-hydroxy-3-((3R,4S)-dihydroxy-pyrrolidin-1-yl-)-3-oxypropyl]amide, [2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester, [2R,4S] 4-[acetyl-(3,5-bis-trifluoromethyl-benzyl)-amino]-2-ethyl-6-trifluoromethyl-3,4-dihydro-2H-quinoline-1-carboxylic acid isopropyl ester, [2R, 4S] 4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester, quinoxaline-2-carboxylic acid [4(R)-carbamoyl-1(S)-3-fluorobenzyl)-2(S), 7-dihydroxy-7-methyl-octyl]amide, [2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester, 5-(2-(4-(3-benzisothiazolyl)-piperazinyl)ethyl-6-chlorooxindole, or indomethacin.

A third aspect of the invention relates to methods of administering a drug comprising co-administering to a patient in need of said drug: (a) an adsorbate comprising a low-solubility drug adsorbed onto a substrate, said substrate having a surface area of at least 20 $m^2/g$, wherein at least a major portion of said drug in said adsorbate is amorphous; and (b) a concentration-enhancing polymer.

In a preferred embodiment, the adsorbate is administered separately from said concentration-enhancing polymer or theconcentration-enhancing polymer are administered at approximately the same time.

In another preferred embodiment, the adsorbate and said concentration-enhancing polymer are present in a single dosage form.

A fourth aspect of the present invention relates to methods for forming a pharmaceutical composition that include: (a) providing a substrate having a surface area of at least 20 $m^2/g$; (b) adding said substrate to a solvent to form a suspension and agitating said suspension; (c) dissolving a low-solubility drug in said solvent; and (d) rapidly removing said solvent from said suspension to form an adsorbate comprising said low-solubility drug adsorbed onto said substrate, wherein at least a major portion of said drug in said adsorbate is in amorphous form.

In one preferred embodiment, the step of agitating comprises sonicating said suspension.

In another preferred embodiment, the step of removing said solvent from said suspension is accomplished by spray-drying said suspension.

In another preferred embodiment, the method further comprises the step of adding a concentration-enhancing polymer to said suspension.

In another preferred embodiment, the method further comprises the step of combining said adsorbate with a concentration-enhancing polymer.

In a fifth aspect, the present invention relates to methods for forming a pharmaceutical composition, comprising: (a) providing a substrate having a surface area of at least 20 $m^2/g$; (b) melting a low-solubility drug; (c)
combining said low-solubility drug with said substrate to form a mixture; and (d) cooling said mixture so that said low-solubility drug is adsorbed onto said substrate to form an adsorbate, at least a major portion of said drug in said adsorbate being in amorphous form.

In a preferred embodiment, the method further comprises the step of combining a concentration-enhancing polymer with said low-solubility drug and said substrate.

In another preferred embodiment, the method further comprises the step of combining said adsorbate with a concentration-enhancing polymer.

In a sixth aspect, the present invention also relates to pharmaceutical compositions formed by the above-described methods.

In a seventh aspect, the present invention relates to a solid adsorbate comprising a low solubility drug adsorbed onto a substrate, said substrate having a surface area of at least 20 $m^2/g$, wherein at least a major portion of said drug in said adsorbate is amorphous, wherein said adsorbate provides improved concentration of said drug in a use environment relative to an equivalent amount of a slow-evaporation control composition.

In a preferred embodiment, the solid adsorbate further comprises a concentration-enhancing polymer.

In yet another preferred embodiment, the solid adsorbate is combined with a concentration-enhancing polymer.

The composition in some embodiments provides improved stability of the amorphous drug in the adsorbate. In addition, in some embodiments, the compositions are concentration-enhancing, providing improved concentration of drug in a use environment relative to a control composition comprising an equivalent amount of crystalline drug alone.

One key to the present invention was the recognition by the inventors that the formation of a drug/substrate adsorbate, wherein a major portion of the drug in the adsorbate is amorphous, leads to an initially enhanced concentration of drug in a use environment, and further, that this enhanced concentration can be sustained by interaction of the drug in solution with the adsorbate. Thus, without implying any particular mechanism of action, it is believed that the interaction of the drug in solution with the adsorbate inhibits precipitation or crystallization of the drug, allowing the initially enhanced concentration of drug in solution to be sustained rather than decrease rapidly over time to that obtained when amorphous drug alone is dosed to the use environment.

For those aspects of the invention which include a concentration enhancing polymer, the drug/substrate adsorbate and concentration-enhancing polymer are present together in the use environment. Thus, without implying any particular mechanism of action, it is believed that the concentration-enhancing polymers of this invention may also act as crystallization or precipitation inhibitors. In some cases, the concentration-enhancing polymers may also interact with drug to form various types of polymer-drug assemblies such as aggregates or colloids. In addition, polymer, drug and substrate may all interact in solution to form various drug/polymer/substrate assemblies such as aggregates or colloids.

Regardless of the mechanism, the compositions of the present invention provide improved concentration of drug in the use environment. The adsorbate, when introduced to a use environment, provides an initial concentration of drug that exceeds the equilibrium concentration of drug. The adsorbate and/or the concentration-enhancing polymer retards the rate at which the initially enhanced drug concentration falls to the equilibrium concentration. Thus, the compositions of the present invention provide a dissolution area-under-the-concentration-versus-time-curve ("AUC") that is greater than that provided by crystalline drug alone. In preferred embodiments, the compositions of the present invention provide an AUC that is greater than that provided by the drug in amorphous form alone.

In compositions that include a concentration-enhancing polymer, the compositions preferably provide an AUC or maximum drug concentration that exceeds that of a control composition that consists of amorphous drug alone (that is, free from both the substrate and the concentration-enhancing polymer). Preferably, the compositions provide an AUC or a maximum drug concentration that exceeds that provided by a control consisting of drug/substrate adsorbate but free from the concentration-enhancing polymer. Nevertheless, the advantages of the invention may be obtained by merely retarding the rate at which the enhanced drug concentration falls to the equilibrium concentration, even without increasing the maximum drug concentration relative to a control composition.

As a result of improving the dissolution AUC, the compositions of the present invention may also provide enhanced bioavailability of the drug by increasing the concentration of drug which remains dissolved in the use environment, particularly in the GI tract. Improving the concentration of the drug in solution allows more rapid absorption of drug and, as a result, higher blood levels to be achieved. In some cases this enhanced absorption rate enables an effective level of drug to be reached that might not be reached by administration of conventional forms of the drug. In other cases, administration of the compositions of the invention allows effective blood levels to be reached at lower drug dosage levels, which in turn decreases the amount of drug that must be dosed, and reduces the blood level variability. Such compositions may also allow the size of the dosage form to be decreased, depending on the amount of substrate and/or polymer needed.

Furthermore, because the compositions of the present invention provide for a higher concentration of drug dissolved in the use environment, and because once a high drug concentration is achieved the concentration tends to remain high due to inhibition of precipitation or crystallization of the drug, the compositions may have a number of positive effects. First, in cases where the use environment is the GI tract, the compositions of the present invention may show less variability in drug absorption as a result of variation in the fed/fasted state of the GI tract of the human or animal. Second, due to a prolonged high drug concentration in the GI tract, absorption of drug may continue over a longer time period and an effective concentration of drug in the blood may be maintained over a longer time period.

In some embodiments, stabilizing the drug as an adsorbate of the drug and substrate and then combining the adsorbate with the concentration-enhancing polymer provides another of the advantages of the present invention, which is to allow the use of concentration-enhancing polymers which, for whatever reason, are not suitable for forming a molecular dispersion with the particular drug. The difficulty in forming a stable dispersion may be due to adverse interactions between the drug and polymer in the dispersion, resulting in chemical and/or physical instability of the drug in the dispersion. For example, although an acidic cellulosic polymer may provide superior concentration-enhancement for some drugs, such polymers may chemically degrade acid-sensitive drugs when present in the dispersion.

The present invention solves this problem by forming an adsorbate of the drug and a substrate, and then combines the adsorbate with the concentration-enhancing polymer to form the composition. This provides the benefit of improved drug stability while at the same time providing the additional level of concentration-enhancement conferred by the presence of the concentration-enhancing polymer.

The foregoing and other objectives, features, and advantages of the invention will be more readily understood upon consideration of the following detailed description of the invention.

DETAILED DESCRIPTION OF THE PREFERRED EMBODIMENTS

The present invention is directed toward adsorbates of a low-solubility drug and a high surface area substrate. The compositions may optionally include concentration-enhancing polymers. Suitable drugs, substrates, and concentration-enhancing polymers, as well as methods for preparing the compositions, are discussed in detail below.

The Drug

The term "drug" is conventional, denoting a compound having beneficial prophylactic and/or therapeutic properties when administered to an animal, especially humans. The drug does not need to be a low-solubility drug in order to benefit from this invention, although low-solubility drugs represent a preferred class for use with the invention. Even a drug that nonetheless exhibits appreciable solubility in the desired environment of use can benefit from the increased solubility/bioavailability made possible by this invention if it reduces the size of the dose needed for therapeutic efficacy or increases the rate of drug absorption in cases where a rapid onset of the drug's effectiveness is desired.

Preferably, the drug is a "low-solubility drug," meaning that the drug may be either "substantially water-insoluble," which means that the drug has a minimum aqueous solubility at physiologically relevant pH (e.g., pH 1-8) of less than 0.01 mg/mL, "sparingly water-soluble," that is, has an aqueous solubility up to about 1 to 2 mg/mL, or even low to moderate aqueous-solubility, having an aqueous-solubility from about 1 mg/mL to as high as about 20 to 40 mg/mL. The invention finds greater utility as the solubility of the drug decreases. Thus, compositions of the present invention are preferred for low-solubility drugs having a solubility of less than 10 mg/mL, more preferred for low-solubility drugs having a solubility of less than 1 mg/mL, and even more preferred for low-solubility drugs having a solubility of less than 0.1 mg/mL. In general, it may be said that the drug has a dose-to-aqueous solubility ratio greater than 10 mL, and more typically greater than 100 mL, where the drug solubility (mg/mL) is the minimum value observed in any physiologically relevant aqueous solution (e.g., those with pH values between 1 and 8) including USP simulated gastric and intestinal buffers, and dose is in mg. Thus, a dose-to-aqueous solubility ratio may be calculated by dividing the dose (in mg) by the solubility (in mg/mL).

Preferred classes of drugs include, but are not limited to, antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, cholesterol-reducing agents, anti-atherosclerotic agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, antiviral agents, glycogen phosphorylase inhibitors, and cholesterol ester transfer protein inhibitors.

Each named drug should be understood to include the neutral form of the drug, pharmaceutically acceptable salts, as well as prodrugs. Specific examples of antihypertensives include prazosin, nifedipine, amlodipine besylate, trimazosin and doxazosin; specific examples of a blood glucose-lowering agent are glipizide and chlorpropamide; a specific example of an anti-impotence agent is sildenafil and sildenafil citrate; specific examples of antineoplastics include chlorambucil, lomustine and echinomycin; a specific example of an imidazole-type antineoplastic is tubulazole; a specific example of an anti-hypercholesterolemic is atorvastatin calcium; specific examples of anxiolytics include hydroxyzine hydrochloride and doxepin hydrochloride; specific examples of anti-inflammatory agents include betamethasone, prednisolone, aspirin, piroxicam, valdecoxib, carprofen, celecoxib, flurbiprofen and (+)-N-{4-[3-(4-fluorophenoxy)phenoxy]-2-cyclopenten-1-yl}-N-hyroxyurea; a specific example of a barbiturate is phenobarbital; specific examples of antivirals include acyclovir, nelfinavir, and virazole; specific examples of vitamins/nutritional agents include retinol and vitamin E; specific examples of beta blockers include timolol and nadolol; a specific example of an emetic is apomorphine; specific examples of a diuretic include chlorthalidone and spironolactone; a specific example of an anticoagulant is dicumarol; specific examples of cardiotonics include digoxin and digitoxin; specific examples of androgens include 17-methyltestosterone and testosterone; a specific example of a mineral corticoid is desoxycorticosterone; a specific example of a steroidal hypnotic/anesthetic is alfaxalone; specific examples of anabolic agents include fluoxymesterone and methanstenolone; specific examples of antidepression agents include sulpiride, [3,6-dimethyl-2-(2,4,6-trimethyl-phenoxy)-pyridin-4-yl]-(1-ethylpropyl)-amine, 3,5-dimethyl-4-(3'-pentoxy)-2-(2',4',6'-trimethylphenoxy) pyridine, pyroxidine, fluoxetine, paroxetine, venlafaxine and sertraline; specific examples of antibiotics include carbenicillin indanylsodium, bacampicillin hydrochloride, troleandomycin, doxycyline hyclate, ampicillin and penicillin G; specific examples of anti-infectives include benzalkonium chloride and chlorhexidine; specific examples of coronary vasodilators include nitroglycerin and mioflazine; a specific example of a hypnotic is etomidate; specific examples of carbonic anhydrase inhibitors include acetazolamide and chlorzolamide; specific examples of antifungals include econazole, terconazole, fluconazole, voriconazole, and griseofulvin; a specific example of an antiprotozoal is metronidazole; specific examples of anthelmintic agents include thiabendazole and oxfendazole and morantel; specific examples of antihistamines include astemizole, levocabastine, cetirizine, decarboethoxyloratadine and cinnarizine; specific examples of antipsychotics include ziprasidone, olanzepine, thiothixene hydrochloride, fluspirilene, risperidone and penfluridole; specific examples of gastrointestinal agents include loperamide and cisapride; specific examples of serotonin antagonists include ketanserin and mianserin; a specific example of an anesthetic is lidocaine; a specific example of a hypoglycemic agent is acetohexamide; a specific example of an anti-emetic is dimenhydrinate; a specific example of an antibacterial is cotrimoxazole; a specific example of a dopaminergic agent is L-DOPA; specific examples of anti-Alzheimer's Disease agents are THA and donepezil; a specific example of an anti-ulcer agent/H2 antagonist is famotidine; specific examples of sedative/hypnotic agents include chlordiazepoxide and triazolam; a specific example of a vasodilator is alprostadil; a specific example of a platelet inhibitor is prostacyclin; specific examples of ACE inhibitor/antihypertensive agents include enaprilic acid and lisinopril; specific examples of tetracycline antibiotics include oxytetracycline and minocycline; specific examples of macrolide antibiotics include erythromycin, clarithromycin, and spiramycin; a specific example of an azalide antibiotic is azithromycin; specific examples of glycogen phosphorylase inhibitors include [R—(R*S*)]-5-chloro-N-[2-hydroxy-3-{methoxymethylamino}-3-oxo-1-(phenylmethyl)propyl-1H-indole-2-carboxamide and 5-chloro-1H-indole-2-carboxylic acid [(1S)-benzyl-(2R)-hydroxy-3-((3R,4S)-dihydroxy-pyrrolidin-1-yl-)-3-oxypropyl]amide; and specific examples of cholesterol ester transfer protein (CETP) inhibitors include [2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester, [2R,4S] 4-[acetyl-(3,5-bis-trifluoromethyl-benzyl)-amino]-2-ethyl-6-trifluoromethyl-3,4-dihydro-2H-quinoline-1-carboxylic acid isopropyl ester, [2R, 4S] 4-[(3, 5-Bis-trifluoromethyl-benzyl)-methoxycarbonyl-amino]-2-ethyl-6-trifluoromethyl-3,4-dihydro-2H-quinoline-1-carboxylic acid isopropyl ester.

The invention is not limited by any particular structure or group of CETP inhibitors. Rather, the invention has general applicability to CETP inhibitors as a class, the class tending to be composed of compounds having low solubility. Compounds which may be the subject of the invention may be found in a number of patents and published applications, including DE 19741400 A1; DE 19741399 A1; WO 9914215 A1; WO 9914174; DE 19709125 A1; DE 19704244 A1; DE 19704243 A1; EP 818448 A1; WO 9804528 A2; DE 19627431 A1; DE 19627430 A1; DE 19627419 A1; EP 796846 A1; DE 19832159; DE 818197; DE 19741051; WO 9941237 A1; WO 9914204 A1; WO 9835937 A1; JP 11049743; WO 200018721; WO 200018723; WO 200018724; WO 200017164; WO 200017165; WO 200017166; EP 992496; and EP 987251, all of which are hereby incorporated by reference in their entireties for all purposes.

The invention is useful for CETP inhibitors that have sufficiently low aqueous solubility, low bioavailability or slow rate of absorption such that it is desirable to increase their concentration in an aqueous environment of use. Therefore, anytime one finds it desirable to raise the aqueous concentration of the CETP inhibitor in a use environment, the invention will find utility. The CETP inhibitor is "substantially water-insoluble" which means that the CETP inhibitor has a minimum aqueous solubility of less than about 0.01 mg/mL (or 10 μg/ml) at any physiologically relevant pH (e.g., pH 1-8) and at about 22° C. (Unless otherwise specified, reference to aqueous solubility herein and in the claims is determined at about 22° C.) Compositions of the present invention find greater utility as the solubility of the CETP inhibitors decreases, and thus are preferred for CETP inhibitors with solubilities less than about 2 μg/mL, and even more preferred for CETP inhibitors with solubilities less than about 0.5 μg/mL. Many CETP inhibitors have even lower solubilities (some even less than −0.1 μg/mL), and require dramatic concentration enhancement to be sufficiently bioavailable upon oral dosing for effective plasma concentrations to be reached at practical doses.

In general, it may be said that the CETP inhibitor has a dose-to-aqueous solubility ratio greater than about 100 mL, where the solubility (mg/mL) is the minimum value observed in any physiologically relevant aqueous solution (e.g., those with pH values from 1 to 8) including USP simulated gastric and intestinal buffers, and dose is in mg. Compositions of the present invention, as mentioned above, find greater utility as the solubility of the CETP inhibitor decreases and the dose increases. Thus, the compositions are preferred as the dose-to-solubility ratio increases, and thus are preferred for dose-to-solubility ratios greater than 1000 mL, and more preferred for dose-to-solubility ratios greater than about 5000 ml. The dose-to-solubility ratio may be determined by dividing the dose (in mg) by the aqueous solubility (in mg/ml).

Oral delivery of many CETP inhibitors is particularly difficult because their aqueous solubility is usually extremely low, typically being less than 2 µg/ml, often being less than 0.1 µg/ml. Such low solubilities are a direct consequence of the particular structural characteristics of species that bind to CETP and thus act as CETP inhibitors. This low solubility is primarily due to the hydrophobic nature of CETP inhibitors. Clog P, defined as the base 10 logarithm of the ratio of the drug solubility in octanol to the drug solubility in water, is a widely accepted measure of hydrophobicity. In general, Clog P values for CETP inhibitors are greater than 4 and are often greater than 5 to 7. Thus, the hydrophobic and insoluble nature of CETP inhibitors as a class pose a particular challenge for oral delivery. Achieving therapeutic drug levels in the blood by oral dosing of practical quantities of drug generally requires a large enhancement in drug concentrations in the gastrointestinal fluid and a resulting large enhancement in bioavailability. Such enhancements in drug concentration in gastrointestsinal fluid typically need to be at least about 10-fold and often at least about 50-fold or even at least about 200-fold to achieve desired blood levels. Surprisingly, the dispersions of the present invention have proven to have the required large enhancements in drug concentration and bioavailability.

In contrast to conventional wisdom, the relative degree of enhancement in aqueous concentration and bioavailability generally improves for CETP inhibitors as solubility decreases and hydrophobocity increases. In fact, the inventors have recognized a subclass of these CETP inhibitors that are essentially aqueous insoluble, highly hydrophobic, and are characterized by a set of physical properties. This subclass exhibits dramatic enhancements in aqueous concentration and bioavailability when formulated using the compositions of the present invention.

The first property of this subclass of essentially insoluble, hydrophobic CETP inhibitors is extremely low aqueous solubility. By extremely low aqueous solubility is meant that the minimum aqueous solubility at physiologically relevant pH (pH of 1 to 8) is less than about 10 µg/ml and preferably less than about 1 µg/ml.

A second property is a very high does-to-solubility ratio. Extremely low solubility often leads to poor or slow absorption of the drug from the fluid of the gastrointestinal tract, when the drug is dosed orally in a conventional manner. For extremely low solubility drugs, poor absorption generally becomes progressively more difficult as the dose (mass of drug given orally) increases. Thus, a second property of this subclass of essentially insoluble, hydrophobic CETP inhibitors is a very high dose (in mg) to solubility (in mg/ml) ratio (ml). By "very high dose-to-solubility ratio" is meant that the dose-to-solubility ratio has a value of at least 1000 ml, and preferably at least 5,000 ml, and more preferably at least 10,000 ml.

A third property of this subclass of essentially insoluble, hydrophobic CETP inhibitors is that they are extremely hydrophobic. By extremely hydrophobic is meant that the Clog P value of the drug, has a value of at least 4.0, preferably a value of at least 5.0, and more preferably a value of at least 5.5.

A fourth property of this subclass of essentially insoluble CETP inhibitors is that they have a low melting point. Generally, drugs of this subclass will have a melting point of about 150° C. or less, and preferably about 140° C. or less.

Primarily, as a consequence of some or all of these four properties, CETP inhibitors of this subclass typically have very low absolute bioavailabilities. Specifically, the absolute bioavailibility of drugs in this subclass when dosed orally in their undispersed state is less than about 10% and more often less than about 5%.

Turning now to the chemical structures of specific CETP inhibitors, one class of CETP inhibitors that finds utility with the present invention consists of oxy substituted 4-carboxyamino-2-methyl-1,2,3,4-tetrahydroquinolines having the Formula I

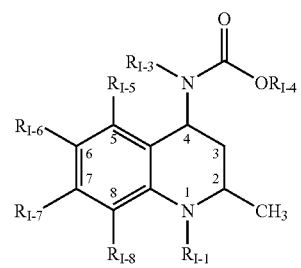

Formula I and pharmaceutically acceptable salts, enantiomers, or stereoisomers of said compounds;

wherein $R_{I-1}$ is hydrogen, $Y_I$, $W_I$—$X_I$, $W_I$—$Y_I$;

wherein $W_I$ is a carbonyl, thiocarbonyl, sulfinyl or sulfonyl;

$X_I$ is —O—$Y_I$, —S—$Y_I$, —N(H)—Y, or —N—$(Y_I)_2$;

wherein $Y_I$ for each occurrence is independently $Z_I$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_I$;

wherein $Z_I$ is a partially saturated, fully saturated or fully unsaturated three to eight membered ring optionally having one to four heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_I$ substituent is optionally mono-, di- or tri-substituted independently with halo, $(C_2$-$C_6)$alkenyl, $(C_1$-$C_6)$ alkyl, hydroxy, $(C_1$-$C_6)$alkoxy, $(C_1$-$C_4)$alkylthio, amino, nitro, cyano, oxo, carboxyl, $(C_1$-$C_6)$alkyloxycarbonyl, mono-N- or di-N,N—$(C_1$-$C_6)$alkylamino wherein said $(C_1$-$C_6)$alkyl substituent is optionally mono-, di- or tri-substituted independently with halo, hydroxy, $(C_1$-$C_6)$alkoxy, $(C_1$-$C_4)$alkylthio, amino, nitro, cyano, oxo, carboxyl, $(C_1$-$C_6)$alkyloxycarbonyl, mono-N- or di-N,N—($C_1$-$C_6$)alkylamino, said ($C_1$-$C_6$) alkyl substituent is also optionally substituted with from one to nine fluorines;

$R_{I-3}$ is hydrogen or $Q_I$;

wherein $Q_I$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $V_I$;

wherein $V_I$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_I$ substituent is optionally mono-, di-, tri-, or tetra-substituted independently with halo, ($C_1$-$C_6$)alkyl, ($C_2$-$C_6$)alkenyl, hydroxy, ($C_1$-$C_6$)alkoxy, ($C_1$-$C_4$)alkylthio, amino, nitro, cyano, oxo, carbamoyl, mono-N- or di-N,N—($C_1$-$C_6$) alkylcarbamoyl, carboxyl, ($C_1$-$C_6$)alkyloxycarbonyl, mono-N- or di-N,N—($C_1$-$C_6$)alkylamino wherein said ($C_1$-$C_6$)alkyl or ($C_2$-$C_6$)alkenyl substituent is optionally mono-, di- or tri-substituted independently with hydroxy, ($C_1$-$C_6$)alkoxy, ($C_1$-$C_4$)alkylthio, amino, nitro, cyano, oxo, carboxyl, ($C_1$-$C_6$)alkyloxycarbonyl, mono-N- or di-N,N—($C_1$-$C_6$)alkylamino, said ($C_1$-$C_6$)alkyl or ($C_2$-$C_6$)alkenyl substituents are also optionally substituted with from one to nine fluorines;

$R_{I-4}$ is $Q_{I-1}$ or $V_{I-1}$ wherein $Q_{I-1}$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $V_{I-1}$;

wherein $V_{I-1}$ is a partially saturated, fully saturated or fully unsaturated three to six membered ring optionally having one to two heteroatoms selected independently from oxygen, sulfur and nitrogen;

wherein said $V_{I-1}$ substituent is optionally mono-, di-, tri-, or tetra-substituted independently with halo, ($C_1$-$C_6$)alkyl, ($C_1$-$C_6$)alkoxy, amino, nitro, cyano, ($C_1$-$C_6$)alkyloxycarbonyl, mono-N- or di-N,N—($C_1$-$C_6$)alkylamino wherein said ($C_1$-$C_6$)alkyl substituent is optionally mono-substituted with oxo, said ($C_1$-$C_6$)alkyl substituent is also optionally substituted with from one to nine fluorines;

wherein either $R_{I-3}$ must contain $V_I$ or $R_{I-4}$ must contain $V_{I-1}$; and $R_{I-5}$, $R_{I-6}$, $R_{I-7}$ and $R_{I-8}$ are each independently hydrogen, hydroxy or oxy wherein said oxy is substituted with $T_I$ or a partially saturated, fully saturated or fully unsaturated one to twelve membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $T_I$;

wherein $T_I$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $T_I$ substituent is optionally mono-, di- or tri-substituted independently with halo, ($C_1$-$C_6$)alkyl, ($C_2$-$C_6$)alkenyl, hydroxy, ($C_1$-$C_6$)alkoxy, ($C_1$-$C_4$)alkylthio, amino, nitro, cyano, oxo, carboxy, ($C_1$-$C_6$)alkyloxycarbonyl, mono-N- or di-N,N—($C_1$-$C_6$)alkylamino wherein said ($C_1$-$C_6$)alkyl substituent is optionally mono-, di- or tri-substituted independently with hydroxy, ($C_1$-$C_6$)alkoxy, ($C_1$-$C_4$)alkylthio, amino, nitro, cyano, oxo, carboxy, ($C_1$-$C_6$)alkyloxycarbonyl, mono-N- or di-N,N—($C_1$-$C_6$)alkylamino, said ($C_1$-$C_6$)alkyl substituent is also optionally substituted with from one to nine fluorines.

Compounds of Formula I and their methods of manufacture are disclosed in commonly assigned U.S. Pat. Nos. 6,140,342, 6,362,198, and European Patent publication 987251, all of which are incorporated herein by reference in their entireties for all purposes.

In a preferred embodiment, the CETP inhibitor is selected from one of the following compounds of Formula I:

[2R,4S] 4-[(3,5-dichloro-benzyl)-methoxycarbonyl-amino]-6,7-dimethoxy-2-methyl-3,4-dihydro-2H-quinoline-1-carboxylic acid ethyl ester;

[2R,4S] 4-[(3,5-dinitro-benzyl)-methoxycarbonyl-amino]-6,7-dimethoxy-2-methyl-3,4-dihydro-2H-quinoline-1-carboxylic acid ethyl ester;

[2R,4S] 4-[(2,6-dichloro-pyridin-4-ylmethyl)-methoxycarbonyl-amino]-6,7-dimethoxy-2-methyl-3,4-dihydro-2H-quinoline-1-carboxylic acid ethyl ester;

[2R,4S] 4-[(3,5-bis-trifluoromethyl-benzyl)-methoxycarbonyl-amino]-6,7-dimethoxy-2-methyl-3,4-dihydro-2H-quinoline-1-carboxylic acid ethyl ester;

[2R,4S] 4-[(3,5-bis-trifluoromethyl-benzyl)-methoxycarbonyl-amino]-6-methoxy-2-methyl-3,4-dihydro-2H-quinoline-1-carboxylic acid ethyl ester;

[2R,4S] 4-[(3,5-bis-trifluoromethyl-benzyl)-methoxycarbonyl-amino]-7-methoxy-2-methyl-3,4-dihydro-2H-quinoline-1-carboxylic acid ethyl ester,

[2R,4S] 4-[(3,5-bis-trifluoromethyl-benzyl)-methoxycarbonyl-amino]-6,7-dimethoxy-2-methyl-3,4-dihydro-2H-quinoline-1-carboxylic acid isopropyl ester;

[2R,4S] 4-[(3,5-bis-trifluoromethyl-benzyl)-ethoxycarbonyl-amino]-6,7-dimethoxy-2-methyl-3,4-dihydro-2H-quinoline-1-carboxylic acid ethyl ester;

[2R,4S] 4-[(3,5-bis-trifluoromethyl-benzyl)-methoxycarbonyl-amino]-6,7-dimethoxy-2-methyl-3,4-dihydro-2H-quinoline-1-carboxylic acid 2,2,2-trifluoro-ethylester;

[2R,4S] 4-[(3,5-bis-trifluoromethyl-benzyl)-methoxycarbonyl-amino]-6,7-dimethoxy-2-methyl-3,4-dihydro-2H-quinoline-1-carboxylic acid propyl ester;

[2R,4S] 4-[(3,5-bis-trifluoromethyl-benzyl)-methoxycarbonyl-amino]-6,7-dimethoxy-2-methyl-3,4-dihydro-2H-quinoline-1-carboxylic acid tert-butyl ester;

[2R,4S] 4-[(3,5-bis-trifluoromethyl-benzyl)-methoxycarbonyl-amino]-2-methyl-6-trifluoromethoxy-3,4-dihydro-2H-quinoline-1-carboxylic acid ethyl ester,

[2R,4S] (3,5-bis-trifluoromethyl-benzyl)-(1-butyryl-6,7-dimethoxy-2-methyl-1,2,3,4-tetrahydro-quinolin-4-yl)-carbamic acid methyl ester;

[2R,4S] (3,5-bis-trifluoromethyl-benzyl)-(1-butyl-6,7-dimethoxy-2-methyl-1,2,3,4-tetrahydro-quinolin-4-yl)-carbamic acid methyl ester; and

[2R,4S] (3,5-bis-trifluoromethyl-benzyl)-[1-(2-ethyl-butyl)-6,7-dimethoxy-2-methyl-1,2,3,4-tetrahydro-quinolin-4-yl]-carbamic acid methyl ester, hydrochloride.

Another class of CETP inhibitors that finds utility with the present invention consists of 4-carboxyamino-2-methyl-1,2,3,4,-tetrahydroquinolines, having the Formula II

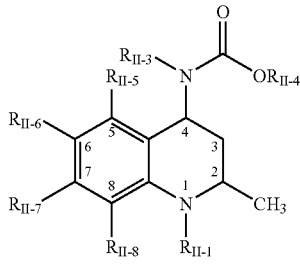

Formula II and pharmaceutically acceptable salts, enantiomers, or stereoisomers of said compounds;

wherein $R_{II-1}$ is hydrogen, $Y_{II}$, $W_{II}-X_{II}$, $W_{II}-Y_{II}$;

wherein $W_{II}$ is a carbonyl, thiocarbonyl, sulfinyl or sulfonyl;

$X_{II}$ is —O—$Y_{II}$, —S—$Y_{II}$, —N(H)—$Y_{II}$, or —N—$(Y_{II})_2$;

wherein $Y_{II}$ for each occurrence is independently $Z_{II}$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_{II}$;

$Z_{II}$ is a partially saturated, fully saturated or fully unsaturated three to twelve membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_{II}$ substituent is optionally mono-, di- or tri-substituted independently with halo, $(C_2-C_6)$alkenyl, $(C_1-C_6)$ alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N—$(C_1-C_6)$alkylamino wherein said $(C_1-C_6)$alkyl substituent is optionally mono-, di- or tri-substituted independently with halo, hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N—$(C_1-C_6)$alkylamino, said $(C_1-C_6)$alkyl is also optionally substituted with from one to nine fluorines;

$R_{II-3}$ is hydrogen or $Q_{II}$;

wherein $Q_{II}$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{II}$;

wherein $V_{II}$ is a partially saturated, fully saturated or fully unsaturated three to twelve membered ring optionally having one to four heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

wherein said $V_{II}$ substituent is optionally mono-, di-, tri-, or tetra-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxamoyl, mono-N- or di-N,N—$(C_1-C_6)$ alkylcarboxamoyl, carboxy, $(C_1-C_6)$alkyloxycarbonyl, mono-N- or di-N,N—$(C_1-C_6)$alkylamino wherein said $(C_1-C_6)$alkyl or $(C_2-C_6)$alkenyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N—$(C_1-C_6)$alkylamino or said $(C_1-C_6)$alkyl or $(C_2-C_6)$alkenyl substituents are optionally substituted with from one to nine fluorines;

$R_{II-4}$ is $Q_{II-1}$ or $V_{II-1}$ wherein $Q_{II-1}$ a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{II-1}$;

wherein $V_{II-1}$ is a partially saturated, fully saturated or fully unsaturated three to six membered ring optionally having one to two heteroatoms selected independently from oxygen, sulfur and nitrogen;

wherein said $V_{II-1}$ substituent is optionally mono-, di-, tri-, or tetra-substituted independently with halo, $(C_1-C_6)$alkyl, $(C_1-C_6)$alkoxy, amino, nitro, cyano, $(C_1-C_6)$alkyloxycarbonyl, mono-N- or di-N,N—$(C_1-C_6)$alkylamino wherein said $(C_1-C_6)$alkyl substituent is optionally mono-substituted with oxo, said $(C_1-C_6)$alkyl substituent is optionally substituted with from one to nine fluorines;

wherein either $R_{II-3}$ must contain $V_{II}$ or $R_{II-4}$ must contain $V_{II-1}$; and $R_{II-5}$, $R_{II-6}$, $R_{II-7}$ and $R_{II-8}$ are each independently hydrogen, a bond, nitro or halo wherein said bond is substituted with $T_{II}$ or a partially saturated, fully saturated or fully unsaturated $(C_1-C_{12})$ straight or branched carbon chain wherein carbon may optionally be replaced with one or two heteroatoms selected independently from oxygen, sulfur and nitrogen wherein said carbon atoms are optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon is optionally mono-substituted with $T_{II}$;

wherein $T_{II}$ is a partially saturated, fully saturated or fully unsaturated three to twelve membered ring optionally having one to four heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

wherein said $T_{II}$ substituent is optionally mono-, di- or tri-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N—$(C_1-C_6)$alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N—$(C_1-C_6)$alkylamino, said $(C_1-C_6)$alkyl substituent is also optionally substituted with from one to nine fluorines;

provided that at least one of substituents $R_{II-5}$, $R_{II-6}$, $R_{II-7}$ and $R_{II-8}$ is not hydrogen and is not linked to the quinoline moiety through oxy.

Compounds of Formula II and their methods of manufacture are disclosed in commonly assigned U.S. Pat. No. 6,147,090, U.S. patent application Ser. No. 09/671,400 filed Sep. 27, 2000, and PCT Publication No. WO00/17166, all of which are incorporated herein by reference in their entireties for all purposes.

In a preferred embodiment, the CETP inhibitor is selected from one of the following compounds of Formula II:

[2R,4S] 4-[(3,5-Bis-trifluoromethyl-benzyl)-methoxycarbonyl-amino]-2-methyl-7-trifluoromethyl-3,4-dihydro-2H-quinoline-1-carboxylic acid ethyl ester;

[2R,4S] 4-[(3,5-Bis-trifluoromethyl-benzyl)-methoxycarbonyl-amino]-7-chloro-2-methyl-3,4-dihydro-2H-quinoline-1-carboxylic acid ethyl ester;

[2R,4S] 4-[(3,5-Bis-trifluoromethyl-benzyl)-methoxycarbonyl-amino]-6-chloro-2-methyl-3,4-dihydro-2H-quinoline-1-carboxylic acid ethyl ester;

[2R,4S] 4-[(3,5-Bis-trifluoromethyl-benzyl)-methoxycarbonyl-amino]-2,6,7-trimethyl-3,4-dihydro-2H-quinoline-1-carboxylic acid ethyl ester;

[2R,4S] 4-[(3,5-Bis-trifluoromethyl-benzyl)-methoxycarbonyl-amino]-6,7-diethyl-2-methyl-3,4-dihydro-2H-quinoline-1-carboxylic acid ethyl ester;

[2R,4S] 4-[(3,5-Bis-trifluoromethyl-benzyl)-methoxycarbonyl-amino]-6-ethyl-2-methyl-3,4-dihydro-2H-quinoline-1-carboxylic acid ethyl ester;

[2R,4S] 4-[(3,5-Bis-trifluoromethyl-benzyl)-methoxycarbonyl-amino]-2-methyl-6-trifluoromethyl-3,4-dihydro-2H-quinoline-1-carboxylic acid ethyl ester; and

[2R,4S] 4-[(3,5-bis-trifluoromethyl-benzyl)-methoxycarbonyl-amino]-2-methyl-6-trifluoromethyl-3,4-dihydro-2H-quinoline-1-carboxylic acid isopropyl ester.

Another class of CETP inhibitors that finds utility with the present invention consists of annulated 4-carboxyamino-2-methyl-1,2,3,4,-tetrahydroquinolines, having the Formula III

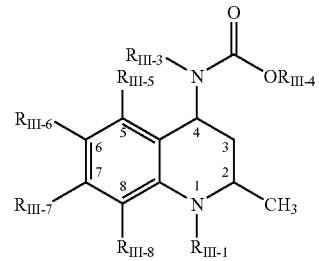

Formula III and pharmaceutically acceptable salts, enantiomers, or stereoisomers of said compounds;

wherein $R_{III-1}$ is hydrogen, $Y_{III}$, $W_{III}$—$X_{III}$, $W_{III}$—$Y_{III}$;

wherein $W_{III}$ is a carbonyl, thiocarbonyl, sulfinyl or sulfonyl;

$X_{III}$ is —O—$Y_{III}$, —S—$Y_{III}$, —N(H)—$Y_{III}$ or —N—$(Y_{III})_2$;

$Y_{III}$ for each occurrence is independently $Z_{III}$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_{III}$;

wherein $Z_{III}$ is a partially saturated, fully saturated or fully unsaturated three to twelve membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_{III}$ substituent is optionally mono-, di- or tri-substituted independently with halo, $(C_2-C_6)$alkenyl, $(C_1-C_6)$ alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N—$(C_1-C_6)$alkylamino wherein said $(C_1-C_6)$alkyl substituent is optionally mono-, di- or tri-substituted independently with halo, hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N—$(C_1-C_6)$alkylamino, said $(C_1-C_6)$alkyl optionally substituted with from one to nine fluorines;

$R_{III-3}$ is hydrogen or $Q_{III}$;

wherein $Q_{III}$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{III}$;

wherein $V_{III}$ is a partially saturated, fully saturated or fully unsaturated three to twelve membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_{III}$ substituent is optionally mono-, di-, tri-, or tetra-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxamoyl, mono-N- or di-N,N—$(C_1-C_6)$ alkylcarboxamoyl, carboxy, $(C_1-C_6)$alkyloxycarbonyl, mono-N- or di-N,N—$(C_1-C_6)$alkylamino wherein said $(C_1-C_6)$alkyl or $(C_2-C_6)$alkenyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N—$(C_1-C_6)$alkylamino or said $(C_1-C_6)$alkyl or $(C_2-C_6)$alkenyl are optionally substituted with from one to nine fluorines;

$R_{III-4}$ is $Q_{III-1}$ or $V_{III-1}$;

wherein $Q_{III-1}$ a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{III-1}$;

wherein $V_{III-1}$ is a partially saturated, fully saturated or fully unsaturated three to six membered ring optionally having one to two heteroatoms selected independently from oxygen, sulfur and nitrogen;

wherein said $V_{III-1}$ substituent is optionally mono-, di-, tri-, or tetra-substituted independently with halo, $(C_1-C_6)$alkyl, $(C_1-C_6)$alkoxy, amino, nitro, cyano, $(C_1-C_6)$alkyloxycarbonyl, mono-N- or di-N,N—$(C_1-C_6)$alkylamino wherein said $(C_1-C_6)$alkyl substituent is optionally mono-substituted with oxo, said $(C_1-C_6)$alkyl substituent optionally having from one to nine fluorines;

wherein either $R_{III-3}$ must contain $V_{III}$ or $R_{III-4}$ must contain $V_{III-1}$; and $R_{III-5}$ and $R_{III-6}$, or $R_{III-6}$ and $R_{III-7}$, and/or $R_{III-7}$ and $R_{III-8}$ are taken together and form at least one four to eight membered ring that is partially saturated or fully unsaturated optionally having one to three heteroatoms independently selected from nitrogen, sulfur and oxygen;

wherein said ring or rings formed by $R_{III-5}$ and $R_{III-6}$, or $R_{III-6}$ and $R_{III-7}$, and/or $R_{III-7}$ and $R_{III-8}$ are optionally mono-, di- or tri-substituted independently with halo, $(C_1-C_6)$alkyl, $(C_1-C_4)$alkylsulfonyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N—$(C_1-C_6)$alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$ alkyloxycarbonyl, mono-N- or di-N,N—$(C_1-C_6)$alkylamino, said $(C_1-C_6)$alkyl substituent optionally having from one to nine fluorines;

provided that the $R_{III-5}$, $R_{III-6}$, $R_{III-7}$ and/or $R_{III-8}$, as the case may be, that do not form at least one ring are each independently hydrogen, halo, $(C_1-C_6)$alkoxy or $(C_1-C_6)$ alkyl, said $(C_1-C_6)$alkyl optionally having from one to nine fluorines.

Compounds of Formula III and their methods of manufacture are disclosed in commonly assigned U.S. Pat. Nos. 6,147,089, 6,310,075, and European Patent Application No. 99307240.4 filed Sep. 14, 1999, all of which are incorporated herein by reference in their entireties for all purposes.

In a preferred embodiment, the CETP inhibitor is selected from one of the following compounds of Formula III:

[2R, 4S] 4-[(3,5-bis-trifluoromethyl-benzyl)-methoxycarbonyl-amino]-2-methyl-2,3,4,6,7,8-hexahydro-cyclopenta[g]quinoline-1-carboxylic acid ethyl ester;

[6R, 8S] 8-[(3,5-bis-trifluoromethyl-benzyl)-methoxycarbonyl-amino]-6-methyl-3,6,7,8-tetrahydro-1H-2-thia-5-aza-cyclopenta[b]naphthalene-5-carboxylic acid ethyl ester;

[6R, 8S] 8-[(3,5-bis-trifluoromethyl-benzyl)-methoxycarbonyl-amino]-6-methyl-3,6,7,8-tetrahydro-2H-furo[2,3-g]quinoline-5-carboxylic acid ethyl ester;

[2R,4S] 4-[(3,5-bis-trifluoromethyl-benzyl)-methoxycarbonyl-amino]-2-methyl-3,4,6,8-tetrahydro-2H-furo[3,4-g]quinoline-1-carboxylic acid ethyl ester;

[2R,4S] 4-[(3,5-bis-trifluoromethyl-benzyl)-methoxycarbonyl-amino]-2-methyl-3,4,6,7,8,9-hexahydro-2H-benzo[g]quinoline-1-carboxylic acid propyl ester;

[7R,9S] 9-[(3,5-bis-trifluoromethyl-benzyl)-methoxycarbonyl-amino]-7-methyl-1,2,3,7,8,9-hexahydro-6-aza-cyclopenta[a]naphthalene-6-carboxylic acid ethyl ester; and

[6S,8R] 6-[(3,5-bis-trifluoromethyl-benzyl)-methoxycarbonyl-amino]-8-methyl-1,2,3,6,7,8-hexahydro-9-aza-cyclopenta[a]naphthalene-9-carboxylic acid ethyl ester.

Another class of CETP inhibitors that finds utility with the present invention consists of 4-carboxyamino-2-substituted-1,2,3,4,-tetrahydroquinolines, having the Formula IV

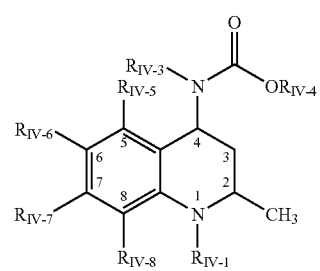

Formula IV and pharmaceutically acceptable salts, enantiomers, or stereoisomers of said compounds;

wherein $R_{IV-1}$ is hydrogen, $Y_{IV}$, $W_{IV}—X_{IV}$ or $W_{IV}—Y_{IV}$;

wherein $W_{IV}$ is a carbonyl, thiocarbonyl, sulfinyl or sulfonyl; $X_{IV}$ is —O—$Y_{IV}$, —S—$Y_{IV}$, —N(H)—$Y_{IV}$ or —N—$(Y_{IV})_2$;

wherein $Y_{IV}$ for each occurrence is independently $Z_{IV}$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_{IV}$;

wherein $Z_{IV}$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_{IV}$ substituent is optionally mono-, di- or tri-substituted independently with halo, $(C_2-C_6)$alkenyl, $(C_1-C_6)$ alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N—$(C_1-C_6)$alkylamino wherein said $(C_1-C_6)$alkyl substituent is optionally mono-, di- or tri-substituted independently with halo, hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N—$(C_1-C_6)$alkylamino, said $(C_1-C_6)$alkyl substituent is also optionally substituted with from one to nine fluorines; $R_{IV-2}$ is a partially saturated, fully saturated or fully unsaturated one to six membered straight or branched carbon chain wherein the carbons, other than the connecting carbon, may optionally be replaced with one or two heteroatoms selected independently from oxygen, sulfur and nitrogen wherein said carbon atoms are optionally mono-, di- or tri-substituted independently with halo, said carbon is optionally mono-substituted with oxo, said carbon is optionally mono-substituted with hydroxy, said sulfur is optionally mono- or di-substituted with oxo, said nitrogen is optionally mono- or di-substituted with oxo; or said $R_{IV-2}$ is a partially saturated, fully saturated or fully unsaturated three to seven membered ring optionally having one to two heteroatoms selected independently from oxygen, sulfur and nitrogen, wherein said $R_{IV-2}$ ring is optionally attached through $(C_1-C_4)$alkyl;

wherein said $R_{IV-2}$ ring is optionally mono-, di- or tri-substituted independently with halo, $(C_2-C_6)$alkenyl, $(C_1-C_6)$ alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N—$(C_1-C_6)$alkylamino wherein said $(C_1-C_6)$alkyl substituent is optionally mono-, di- or tri-substituted independently with halo, hydroxy, $(C_1-C_6)$alkoxy, $(C_1-C_4)$alkylthio, oxo or $(C_1-C_6)$alkyloxycarbonyl;

with the proviso that $R_{IV-2}$ is not methyl;

$R_{IV-3}$ is hydrogen or $Q_{IV}$;

wherein $Q_{IV}$ is a fully saturated, partially unsaturated or fully unsaturated one to six membered straight or branched carbon chain wherein the carbons other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{IV}$;

wherein $V_{IV}$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_{IV}$ substituent is optionally mono-, di-, tri-, or tetra-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxamoyl, mono-N- or di-N,N—$(C_1-C_6)$ alkylcarboxamoyl, carboxy, $(C_1-C_6)$alkyloxycarbonyl, mono-N- or di-N,N—$(C_1-C_6)$alkylamino wherein said $(C_1-C_6)$alkyl or $(C_2-C_6)$alkenyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N—$(C_1-C_6)$alkylamino, said $(C_1-C_6)$alkyl or $(C_2-C_6)$alkenyl substituents are also optionally substituted with from one to nine fluorines;

$R_{IV-4}$ is $Q_{IV-1}$ or $V_{IV-1}$;

wherein $Q_{IV-1}$ a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{IV-1}$;

wherein $V_{IV-1}$ is a partially saturated, fully saturated or fully unsaturated three to six membered ring optionally having one to two heteroatoms selected independently from oxygen, sulfur and nitrogen;

wherein said $V_{IV-1}$ substituent is optionally mono-, di-, tri-, or tetra-substituted independently with halo, $(C_1-C_6)$alkyl, $(C_1-C_6)$alkoxy, amino, nitro, cyano, $(C_1-C_6)$alkyloxycarbonyl, mono-N- or di-N,N—$(C_1-C_6)$alkylamino wherein said $(C_1-C_6)$alkyl substituent is optionally mono-substituted with oxo, said $(C_1-C_6)$alkyl substituent is also optionally substituted with from one to nine fluorines;

wherein either $R_{IV-3}$ must contain $V_{IV}$ or $R_{IV-4}$ must contain $V_{IV-1}$; $R_{IV-5}$, $R_{IV-6}$, $R_{IV-7}$ and $R_{IV-8}$ are each independently hydrogen, a bond, nitro or halo wherein said bond is substituted with $T_{IV}$ or a partially saturated, fully saturated or fully unsaturated $(C_1-C_{12})$ straight or branched carbon chain wherein carbon, may optionally be replaced with one or two heteroatoms selected independently from oxygen, sulfur and nitrogen wherein said carbon atoms are optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon is optionally mono-substituted with $T_{IV}$;

wherein $T_{IV}$ is a partially saturated, fully saturated or fully unsaturated three to eight membered ring optionally having one to four heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

wherein said $T_{IV}$ substituent is optionally mono-, di- or tri-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N—$(C_1-C_6)$alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N—$(C_1-C_6)$alkylamino, said $(C_1-C_6)$alkyl substituent is also optionally substituted with from one to nine fluorines; and wherein $R_{IV-5}$ and $R_{IV-6}$, or $R_{IV-6}$ and $R_{IV-7}$, and/or $R_{IV-7}$ and $R_{IV-8}$ may also be taken together and can form at least one four to eight membered ring that is partially saturated or fully unsaturated optionally having one to three heteroatoms independently selected from nitrogen, sulfur and oxygen;

wherein said ring or rings formed by $R_{IV-5}$ and $R_{IV-6}$, or $R_{IV-6}$ and $R_{IV-7}$, and/or $R_{IV-7}$ and $R_{IV-8}$ are optionally mono-, di- or tri-substituted independently with halo, $(C_1-C_6)$alkyl, $(C_1-C_4)$alkylsulfonyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N—$(C_1-C_6)$alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$ alkyloxycarbonyl, mono-N- or di-N,N—$(C_1-C_6)$alkylamino, said $(C_1-C_6)$alkyl substituent is also optionally substituted with from one to nine fluorines; with the proviso that when $R_{IV-2}$ is carboxyl or $(C_1-C_4)$alkylcarboxyl, then $R_{IV-1}$ is not hydrogen.

Compounds of Formula IV and their methods of manufacture are disclosed in commonly assigned U.S. Pat. No. 6,197,786, U.S. application Ser. No. 09/685,3000 filed Oct. 10, 2000 and PCT Publication No. WO00/17164, all of which are incorporated herein by reference in their entireties for all purposes.

In a preferred embodiment, the CETP inhibitor is selected from one of the following compounds of Formula IV:

[2S,4S] 4-[(3,5-bis-trifluoromethyl-benzyl)-methoxycarbonyl-amino]-2-isopropyl-6-trifluoromethyl-3,4-dihydro-2H-quinoline-1-carboxylic acid isopropyl ester;

[2S,4S] 4-[(3,5-bis-trifluoromethyl-benzyl)-methoxycarbonyl-amino]-6-chloro-2-cyclopropyl-3,4-dihydro-2H-quinoline-1-carboxylic acid isopropyl ester;

[2S,4S] 2-cyclopropyl-4-[(3,5-dichloro-benzyl)-methoxycarbonyl-amino]-6-trifluoromethyl-3,4-dihydro-2H-quinoline-1-carboxylic acid isopropyl ester;

[2S,4S] 4-[(3,5-bis-trifluoromethyl-benzyl)-methoxycarbonyl-amino]-2-cyclopropyl-6-trifluoromethyl-3,4-dihydro-2H-quinoline-1-carboxylic acid tert-butyl ester;

[2R,4R] 4-[(3,5-bis-trifluoromethyl-benzyl)-methoxycarbonyl-amino]-2-cyclopropyl-6-trifluoromethyl-3,4-dihydro-2H-quinaline-1-carboxylic acid isopropyl ester;

[2S,4S] 4-[(3,5-bis-trifluoromethyl-benzyl)-methoxycarbonyl-amino]-2-cyclopropyl-6-trifluoromethyl-3,4-dihydro-2H-quinoline-1-carboxylic acid isopropyl ester;

[2S,4S] 4-[(3,5-bis-trifluoromethyl-benzyl)-methoxycarbonyl-amino]-2-cyclobutyl-6-trifluoromethyl-3,4-dihydro-2H-quinoline-1-carboxylic acid isopropyl ester;

[2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester;

[2S,4S] 4-[(3,5-bis-trifluoromethyl-benzyl)-methoxycarbonyl-amino]-2-methoxymethyl-6-trifluoromethyl-3,4-dihydro-2H-quinoline-1-carboxylic acid isopropyl ester;

[2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid 2-hydroxy-ethyl ester;

[2S,4S] 4-[(3,5-bis-trifluoromethyl-benzyl)-methoxycarbonyl-amino]-2-cyclopropyl-6-trifluoromethyl-3,4-dihydro-2H-quinoline-1-carboxylic acid ethyl ester;

[2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester;

[2S,4S] 4-[(3,5-bis-trifluoromethyl-benzyl)-methoxycarbonyl-amino]-2-cyclopropyl-6-trifluoromethyl-3,4-dihydro-2H-quinoline-1-carboxylic acid propyl ester; and

[2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid propyl ester.

Another class of CETP inhibitors that finds utility with the present invention consists of 4-amino substituted-2-substituted-1,2,3,4,-tetrahydroquinolines, having the Formula V

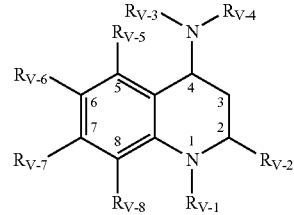

Formula V and pharmaceutically acceptable salts, enantiomers, or stereoisomers of said compounds;

wherein $R_{V-1}$ is $Y_V$, $W_V$—$X_V$ or $W_V$—$Y_V$;

wherein $W_V$ is a carbonyl, thiocarbonyl, sulfinyl or sulfonyl;

$X_V$ is —O—$Y_V$, —S—$Y_V$, —N(H)—$Y_V$ or —N—$(Y_V)_2$;

wherein $Y_V$ for each occurrence is independently $Z_V$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_V$;

wherein $Z_V$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_V$ substituent is optionally mono-, di- or tri-substituted independently with halo, $(C_2-C_6)$alkenyl, $(C_1-C_6)$ alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N—$(C_1-C_6)$alkylamino wherein said $(C_1-C_6)$alkyl substituent is optionally mono-, di- or tri-substituted independently with halo, hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N—$(C_1-C_6)$alkylamino, said $(C_1-C_6)$alkyl substituent is also optionally substituted with from one to nine fluorines;

$R_{V-2}$ is a partially saturated, fully saturated or fully unsaturated one to six membered straight or branched carbon chain wherein the carbons, other than the connecting carbon, may optionally be replaced with one or two heteroatoms selected independently from oxygen, sulfur and nitrogen wherein said carbon atoms are optionally mono-, di- or tri-substituted independently with halo, said carbon is optionally mono-substituted with oxo, said carbon is optionally mono-substituted with hydroxy, said sulfur is optionally mono- or di-substituted with oxo, said nitrogen is optionally mono- or di-substituted with oxo; or said $R_{V-2}$ is a partially saturated, fully saturated or fully unsaturated three to seven membered ring optionally having one to two heteroatoms selected independently from oxygen, sulfur and nitrogen, wherein said $R_{V-2}$ ring is optionally attached through $(C_1-C_4)$alkyl;

wherein said $R_{V-2}$ ring is optionally mono-, di- or tri-substituted independently with halo, $(C_2-C_6)$alkenyl, $(C_1-C_6)$ alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N—$(C_1-C_6)$alkylamino wherein said $(C_1-C_6)$alkyl substituent is optionally mono-, di- or tri-substituted independently with halo, hydroxy, $(C_1-C_6)$alkoxy, $(C_1-C_4)$alkylthio, oxo or $(C_1-C_6)$alkyloxycarbonyl;

$R_{V-3}$ is hydrogen or $Q_V$;

wherein $Q_V$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $V_V$;

wherein $V_V$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_V$ substituent is optionally mono-, di-, tri-, or tetra-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxamoyl, mono-N- or di-N,N—$(C_1-C_6)$ alkylcarboxamoyl, carboxy, $(C_1-C_6)$alkyloxycarbonyl, mono-N- or di-N,N—$(C_1-C_6)$alkylamino wherein said $(C_1-C_6)$alkyl or $(C_2-C_6)$alkenyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N—$(C_1-C_6)$alkylamino, said $(C_1-C_6)$alkyl or $(C_2-C_6)$alkenyl substituents are also optionally substituted with from one to nine fluorines;

$R_{V-4}$ is cyano, formyl, $W_{V-1}Q_{V-1}$, $W_{V-1}V_{V-1}$, $(C_1-C_4)$alkyleneV$_{V-1}$ or $V_{V-2}$;

wherein $W_{V-1}$ is carbonyl, thiocarbonyl, SO or $SO_2$, wherein $Q_{V-1}$ a fully saturated, partially unsaturated or fully unsaturated one to six membered straight or branched carbon chain wherein the carbons may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $V_{V-1}$;

wherein $V_{V-1}$ is a partially saturated, fully saturated or fully unsaturated three to six membered ring optionally having one to two heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_{V-1}$ substituent is optionally mono-, di-, tri-, or tetra-substituted independently with halo, $(C_1-C_6)$alkyl, $(C_1-C_6)$alkoxy, hydroxy, oxo, amino, nitro, cyano, $(C_1-C_6)$alkyloxycarbonyl, mono-N- or di-N,N—$(C_1-C_6)$alkylamino wherein said $(C_1-C_6)$alkyl substituent is optionally mono-substituted with oxo, said $(C_1-C_6)$alkyl substituent is also optionally substituted with from one to nine fluorines;

wherein $V_{V-2}$ is a partially saturated, fully saturated or fully unsaturated five to seven membered ring containing one to four heteroatoms selected independently from oxygen, sulfur and nitrogen;

wherein said $V_{V-2}$ substituent is optionally mono-, di- or tri-substituted independently with halo, $(C_1-C_2)$alkyl, $(C_1-C_2)$alkoxy, hydroxy, or oxo wherein said $(C_1-C_2)$alkyl optionally has from one to five fluorines; and wherein $R_{V-4}$ does not include oxycarbonyl linked directly to the $C^4$ nitrogen;

wherein either $R_{V-3}$ must contain $V_V$ or $R_{V-4}$ must contain $V_{V-1}$;

$R_{V-5}$, $R_{V-6}$, $R_{V-7}$ and $R_{V-8}$ are independently hydrogen, a bond, nitro or halo wherein said bond is substituted with $T_V$ or a partially saturated, fully saturated or fully unsaturated $(C_1-C_2)$ straight or branched carbon chain wherein carbon may optionally be replaced with one or two heteroatoms selected independently from oxygen, sulfur and nitrogen, wherein said carbon atoms are optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $T_V$;

wherein $T_V$ is a partially saturated, fully saturated or fully unsaturated three to twelve membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $T_V$ substituent is optionally mono-, di- or tri-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N—$(C_1-C_6)$alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N—$(C_1-C_6)$alkylamino, said $(C_1-C_6)$alkyl substituent also optionally has from one to nine fluorines;

wherein $R_{V-5}$ and $R_{V-6}$, or $R_{V-6}$ and $R_{V-7}$, and/or $R_{V-7}$ and $R_{V-8}$ may also be taken together and can form at least one ring that is a partially saturated or fully unsaturated four to eight membered ring optionally having one to three heteroatoms independently selected from nitrogen, sulfur and oxygen;

wherein said rings formed by $R_{V-5}$ and $R_{V-6}$, or $R_{V-6}$ and $R_{V-7}$, and/or $R_{V-7}$ and $R_{V-8}$ are optionally mono-, di- or tri-substituted independently with halo, $(C_1-C_6)$alkyl, $(C_1-C_4)$alkylsulfonyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N—$(C_1-C_6)$alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N—$(C_1-C_6)$alkylamino, said $(C_1-C_6)$alkyl substituent also optionally has from one to nine fluorines.

Compounds of Formula V and their methods of manufacture are disclosed in commonly assigned U.S. Pat. No. 6,140,343, U.S. patent application Ser. No 09/671,221 filed Sep. 27, 2000, and PCT Publication No. WO 00/17165, all of which are incorporated herein by reference in their entireties for all purposes.

In a preferred embodiment, the CETP inhibitor is selected from one of the following compounds of Formula V:

[2S,4S] 4-[(3,5-bis-trifluoromethyl-benzyl)-formyl-amino]-2-cyclopropyl-6-trifluoromethyl-3,4-dihydro-2H-quinoline-1-carboxylic acid isopropyl ester;

[2S,4S] 4-[(3,5-bis-trifluoromethyl-benzyl)-formyl-amino]-2-cyclopropyl-6-trifluoromethyl-3,4-dihydro-2H-quinoline-1-carboxylic acid propyl ester;

[2S,4S] 4-[acetyl-(3,5-bis-trifluoromethyl-benzyl)-amino]-2-cyclopropyl-6-trifluoromethyl-3,4-dihydro-2H-quinoline-1-carboxylic acid tert-butyl ester;

[2R,4S] 4-[acetyl-(3,5-bis-trifluoromethyl-benzyl)-amino]-2-ethyl-6-trifluoromethyl-3,4-dihydro-2H-quinoline-1-carboxylic acid isopropyl ester;

[2R,4S] 4-[acetyl-(3,5-bis-trifluoromethyl-benzyl)-amino]-2-methyl-6-trifluoromethyl-3,4-dihydro-2H-quinoline-1-carboxylic acid ethyl ester;

[2S,4S] 4-[1-(3,5-bis-trifluoromethyl-benzyl)-ureido]-2-cyclopropyl-6-trifluoromethyl-3,4-dihydro-2H-quinoline-1-carboxylic acid isopropyl ester;

[2R,4S] 4-[acetyl-(3,5-bis-trifluoromethyl-benzyl)-amino]-2-ethyl-6-trifluoromethyl-3,4-dihydro-2H-quinoline-1-carboxylic acid ethyl ester;

[2S,4S] 4-[acetyl-(3,5-bis-trifluoromethyl-benzyl)-amino]-2-methoxymethyl-6-trifluoromethyl-3,4-dihydro-2H-quinoline-1-carboxylic acid isopropyl ester;

[2S,4S] 4-[acetyl-(3,5-bis-trifluoromethyl-benzyl)-amino]-2-cyclopropyl-6-trifluoromethyl-3,4-dihydro-2H-quinoline-1-carboxylic acid propyl ester;

[2S,4S] 4-[acetyl-(3,5-bis-trifluoromethyl-benzyl)-amino]-2-cyclopropyl-6-trifluoromethyl-3,4-dihydro-2H-quinoline-1-carboxylic acid ethyl ester;

[2R,4S] 4-[(3,5-bis-trifluoromethyl-benzyl)-formyl-amino]-2-ethyl-6-trifluoromethyl-3,4-dihydro-2H-quinoline-1-carboxylic acid isopropyl ester;

[2R,4S] 4-[(3,5-bis-trifluoromethyl-benzyl)-formyl-amino]-2-methyl-6-trifluoromethyl-3,4-dihydro-2H-quinoline-1-carboxylic acid ethyl ester;

[2S,4S] 4-[acetyl-(3,5-bis-trifluoromethyl-benzyl)-amino]-2-cyclopropyl-6-trifluoromethyl-3,4-dihydro-2H-quinoline-1-carboxylic acid isopropyl ester;

[2R,4S] 4-[(3,5-bis-trifluoromethyl-benzyl)-formyl-amino]-2-ethyl-6-trifluoromethyl-3,4-dihydro-2H-quinoline-1-carboxylic acid ethyl ester;

[2S,4S] 4-[(3,5-bis-trifluoromethyl-benzyl)-formyl-amino]-2-cyclopropyl-6-trifluoromethyl-3,4-dihydro-2H-quinoline-1-carboxylic acid ethyl ester;

[2R,4S] 4-[(3,5-bis-trifluoromethyl-benzyl)-formyl-amino]-2-methyl-6-trifluoromethyl-3,4-dihydro-2H-quinoline-1-carboxylic acid isopropyl ester; and

[2R,4S] 4-[acetyl-(3,5-bis-trifluoromethyl-benzyl)-amino]-2-methyl-6-trifluoromethyl-3,4-dihydro-2H-quinoline-1-carboxylic acid isopropyl ester.

Another class of CETP inhibitors that finds utility with the present invention consists of cycloalkano-pyridines having the Formula VI

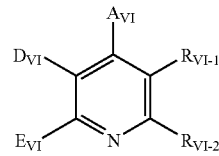

Formula VI and pharmaceutically acceptable salts, enantiomers, or stereoisomers of said compounds;

in which $A_{VI}$ denotes an aryl containing 6 to 10 carbon atoms, which is optionally substituted with up to five identical or different substituents in the form of a halogen, nitro, hydroxyl, trifluoromethyl, trifluoromethoxy or a straight-chain or branched alkyl, acyl, hydroxyalkyl or alkoxy containing up to 7 carbon atoms each, or in the form of a group according to the formula —$BNR_{VI\text{-}3}R_{VI\text{-}4}$, wherein $R_{VI\text{-}3}$ and $R_{VI\text{-}4}$ are identical or different and denote a hydrogen, phenyl or a straight-chain or branched alkyl containing up to 6 carbon atoms, $D_{VI}$ denotes an aryl containing 6 to 10 carbon atoms, which is optionally substituted with a phenyl, nitro, halogen, trifluoromethyl or trifluoromethoxy, or a radical according to the formula $R_{VI\text{-}5}\text{-}L_{VI}$,

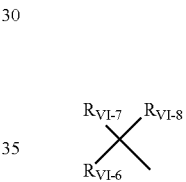

or $R_{VI\text{-}9}\text{-}T_{VI}\text{-}V_{VI}\text{—}X_{VI}$, wherein $R_{VI\text{-}5}$, $R_{VI\text{-}6}$ and $R_{VI\text{-}9}$ denote, independently from one another, a cycloalkyl containing 3 to 6 carbon atoms, or an aryl containing 6 to 10 carbon atom or a 5- to 7-membered, optionally benzo-condensed, saturated or unsaturated, mono-, bi- or tricyclic heterocycle containing up to 4 heteroatoms from the series of S, N and/or O wherein the rings are optionally substituted, in the case of the nitrogen-containing rings also via the N function, with up to five identical or different substituents in the form of a halogen, trifluoromethyl, nitro, hydroxyl, cyano, carboxyl, trifluoromethoxy, a straight-chain or branched acyl, alkyl, alkylthio, alkylalkoxy, alkoxy or alkoxycarbonyl containing up to 6 carbon atoms each, an aryl or trifluoromethyl-substituted aryl containing 6 to 10 carbon atoms each, or an optionally benzo-condensed, aromatic 5- to 7-membered heterocycle containing up to 3 heteoatoms from the series of S, N and/or O, and/or in the form of a group according to the formula $BOR_{VI\text{-}10}$, —$SR_{VI\text{-}11}$, —$SO_2R_{VI\text{-}12}$ or $BNR_{VI\text{-}13}R_{VI\text{-}14}$, wherein $R_{VI\text{-}10}$, $R_{VI\text{-}11}$, and $R_{VI\text{-}12}$ denote, independently from one another, an aryl containing 6 to 10 carbon atoms, which is in turn substituted with up to two identical or different substituents in the form of a phenyl, halogen or a straight-chain or branched alkyl containing up to 6 carbon atoms, $R_{VI\text{-}13}$ and $R_{VI\text{-}14}$ are identical or different and have the meaning of $R_{VI\text{-}3}$ and $R_{VI\text{-}4}$ given above, or $R_{VI-5}$ and/or $R_{VI-6}$ denote a radical according to the formula

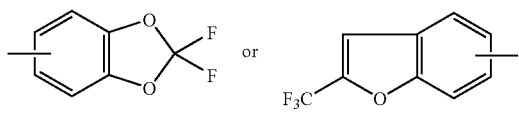

$R_{VI-7}$ denotes a hydrogen or halogen, and
$R_{VI-8}$ denotes a hydrogen, halogen, azido, trifluoromethyl, hydroxyl, trifluoromethoxy, a straight-chain or branched alkoxy or alkyl containing up to 6 carbon atoms each, or a radical according to the formula $$-NR_{VI-15}R_{VI-16},$$

wherein
$R_{VI-15}$ and $R_{VI-16}$ are identical or different and have the meaning of $R_{VI-3}$ and $R_{VI-4}$ given above, or
$R_{VI-7}$ and $R_{VI-8}$ together form a radical according to the formula $=O$ or $=NR_{VI-17}$, wherein
$R_{VI-17}$ denotes a hydrogen or a straight-chain or branched alkyl, alkoxy or acyl containing up to 6 carbon atoms each,
$L_{VI}$ denotes a straight-chain or branched alkylene or alkenylene chain containing up to 8 carbon atoms each, which are optionally substituted with up to two hydroxyl groups,
$T_{VI}$ and $X_{VI}$ are identical or different and denote a straight-chain or branched alkylene chain containing up to 8 carbon atoms, or
$T_{VI}$ or $X_{VI}$ denotes a bond,
$V_{VI}$ denotes an oxygen or sulfur atom or an $BNR_{VI-18}$ group, wherein
$R_{VI-18}$ denotes a hydrogen or a straight-chain or branched alkyl containing up to 6 carbon atoms or a phenyl,
$E_{VI}$ denotes a cycloalkyl containing 3 to 8 carbon atoms, or a straight-chain or branched alkyl containing up to 8 carbon atoms, which is optionally substituted with a cycloalkyl containing 3 to 8 carbon atoms or a hydroxyl, or a phenyl, which is optionally substituted with a halogen or trifluoromethyl,
$R_{VI-1}$ and $R_{VI-2}$ together form a straight-chain or branched alkylene chain containing up to 7 carbon atoms, which must be substituted with a carbonyl group and/or a radical according to the formula

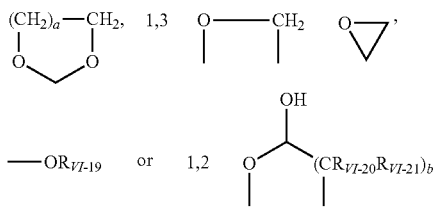

wherein
a and b are identical or different and denote a number equaling 1, 2 or 3,
$R_{VI-19}$ denotes a hydrogen atom, a cycloalkyl containing 3 to 7 carbon atoms, a straight-chain or branched silylalkyl containing up to 8 carbon atoms, or a straight-chain or branched alkyl containing up to 8 carbon atoms, which is optionally substituted with a hydroxyl, a straight-chain or a branched alkoxy containing up to 6 carbon atoms or a phenyl, which may in turn be substituted with a halogen, nitro, trifluoromethyl, trifluoromethoxy or phenyl or tetrazole-substituted phenyl, and an alkyl that is optionally substituted with a group according to the formula $BOR_{VI-22}$, wherein $R_{VI-22}$ denotes a straight-chain or branched acyl containing up to 4 carbon atoms or benzyl, or
$R_{VI-19}$ denotes a straight-chain or branched acyl containing up to 20 carbon atoms or benzoyl, which is optionally substituted with a halogen, trifluoromethyl, nitro or trifluoromethoxy, or a straight-chain or branched fluoroacyl containing up to 8 carbon atoms,
$R_{VI-20}$ and $R_{VI-21}$ are identical or different and denote a hydrogen, phenyl or a straight-chain or branched alkyl containing up to 6 carbon atoms, or
$R_{VI-20}$ and $R_{VI-21}$ together form a 3- to 6-membered carbocyclic ring, and a the carbocyclic rings formed are optionally substituted, optionally also geminally, with up to six identical or different substituents in the form of trifluoromethyl, hydroxyl, nitrile, halogen, carboxyl, nitro, azido, cyano, cycloalkyl or cycloalkyloxy containing 3 to 7 carbon atoms each, a straight-chain or branched alkoxycarbonyl, alkoxy or alkylthio containing up to 6 carbon atoms each, or a straight-chain or branched alkyl containing up to 6 carbon atoms, which is in turn substituted with up to two identical or different substituents in the form of a hydroxyl, benzyloxy, trifluoromethyl, benzoyl, a straight-chain or branched alkoxy, oxyacyl or carboxyl containing up to 4 carbon atoms each and/or a phenyl, which may in turn be substituted with a halogen, trifluoromethyl or trifluoromethoxy, and/or the carbocyclic rings formed are optionally substituted, also geminally, with up to five identical or different substituents in the form of a phenyl, benzoyl, thiophenyl or sulfonylbenzyl, which in turn are optionally substituted with a halogen, trifluoromethyl, trifluoromethoxy or nitro, and/or optionally in the form of a radical according to the formula

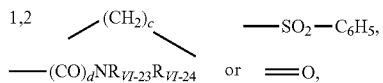

wherein
c is a number equaling 1, 2, 3 or 4,
d is a number equaling 0 or 1,
$R_{VI-23}$ and $R_{VI-24}$ are identical or different and denote a hydrogen, cycloalkyl containing 3 to 6 carbon atoms, a straight-chain or branched alkyl containing up to 6 carbon atoms, benzyl or phenyl, which is optionally substituted with up to two identical or different substituents in the form of halogen, trifluoromethyl, cyano, phenyl or nitro, and/or the carbocyclic rings formed are optionally substituted with a spiro-linked radical according to the formula

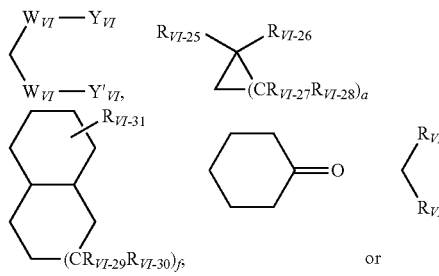

wherein
$W_{VI}$ denotes either an oxygen atom or a sulfur atom,
$Y_{VI}$ and $Y=_{VI}$ together form a 2- to 6-membered straight-chain or branched alkylene chain,
e is a number equaling 1, 2, 3, 4, 5, 6 or 7,
f is a number equaling 1 or 2, $R_{VI-25}$, $R_{VI-26}$, $R_{VI-27}$, $R_{VI-28}$, $R_{VI-29}$, $R_{VI-30}$ and $R_{VI-31}$ are identical or different and denote a hydrogen, trifluoromethyl, phenyl, halogen or a straight-chain or branched alkyl or alkoxy containing up to 6 carbon atoms each, or $R_{VI-25}$ and $R_{VI-26}$ or $R_{VI-27}$ and $R_{VI-28}$ each together denote a straight-chain or branched alkyl chain containing up to 6 carbon atoms or $R_{VI-25}$ and $R_{VI-26}$ or $R_{VI-27}$ and $R_{VI-28}$ each together form a radical according to the formula

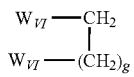

wherein
$W_{VI}$ has the meaning given above,
g is a number equaling 1, 2, 3, 4, 5, 6 or 7,
$R_{VI-32}$ and $R_{VI-33}$ together form a 3- to 7-membered heterocycle, which contains an oxygen or sulfur atom or a group according to the formula SO, $SO_2$ or $BNR_{VI-34}$, wherein $R_{VI-34}$ denotes a hydrogen atom, a phenyl, benzyl, or a straight-chain or branched alkyl containing up to 4 carbon atoms, and salts and N oxides thereof, with the exception of 5(6H)-quinolones, 3-benzoyl-7,8-dihydro-2,7,7-trimethyl-4-phenyl.

Compounds of Formula VI and their methods of manufacture are disclosed in European Patent Application No. EP 818448 A1, U.S. Pat. Nos. 6,207,671 and 6,069,148, all of which are incorporated herein by reference in their entireties for all purposes.

In a preferred embodiment, the CETP inhibitor is selected from one of the following compounds of Formula VI:
2-cyclopentyl-4-(4-fluorophenyl)-7,7-dimethyl-3-(4-trifluoromethylbenzoyl)-4,6,7,8-tetrahydro-1H-quinolin-5-one;
2-cyclopentyl-4-(4-fluorophenyl)-7,7-dimethyl-3-(4-trifluoromethylbenzoyl)-7,8-dihydro-6H-quinolin-5-one;
[2-cyclopentyl-4-(4-fluorophenyl)-5-hydroxy-7,7-dimethyl-5,6,7,8-tetrahydroquinolin-3-yl]-(4-trifluoromethylphenyl)-methanone;
[5-(t-butyldimethylsilanyloxy)-2-cyclopentyl-4-(4-fluorophenyl)-7,7-dimethyl-5,6,7,8-tetrahydroquinolin-3-yl]-(4-trifluoromethylphenyl)-methanone;
[5-(t-butyldimethylsilanyloxy)-2-cyclopentyl-4-(4-fluorophenyl)-7,7-dimethyl-5,6,7,8-tetrahydroquinolin-3-yl]-(4-trifluoromethylphenyl)-methanol;
5-(t-butyldimethylsilanyloxy)-2-cyclopentyl-4-(4-fluorophenyl)-3-[fluoro-(4-trifluoromethylphenyl)-methyl]-7,7-dimethyl-5,6,7,8-tetrahydroquinoline; and
2-cyclopentyl-4-(4-fluorophenyl)-3-[fluoro-(4-trifluoromethylphenyl)-methyl]-7,7-dimethyl-5,6,7,8-tetrahydroquinolin-5-ol.

Another class of CETP inhibitors that finds utility with the present invention consists of substituted-pyridines having the Formula VII

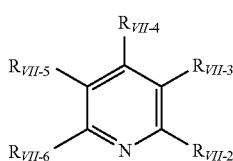

Formula VII or a pharmaceutically acceptable salt or tautomer thereof, wherein $R_{VII-2}$ and $R_{VII-6}$ are independently selected from the group consisting of hydrogen, hydroxy, alkyl, fluorinated alkyl, fluorinated aralkyl, chlorofluorinated alkyl, cycloalkyl, heterocyclyl, aryl, heteroaryl, alkoxy, alkoxyalkyl, and alkoxycarbonyl; provided that at least one of $R_{VII-2}$ and $R_{VII-6}$ is fluorinated alkyl, chlorofluorinated alkyl or alkoxyalkyl;

$R_{VII-3}$ is selected from the group consisting of hydroxy, amido, arylcarbonyl, heteroarylcarbonyl, hydroxymethyl —CHO,
—$CO_2R_{VII-7}$, wherein $R_{VII-7}$ is selected from the group consisting of hydrogen, alkyl and cyanoalkyl; and

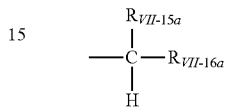

wherein $R_{VII-15a}$ is selected from the group consisting of hydroxy, hydrogen, halogen, alkylthio, alkenylthio, alkynylthio, arylthio, heteroarylthio, heterocyclylthio, alkoxy, alkenoxy, alkynoxy, aryloxy, heteroaryloxy and heterocyclyloxy, and $R_{VII-16a}$ is selected from the group consisting of alkyl, haloalkyl, alkenyl, haloalkenyl, alkynyl, haloalkynyl, aryl, heteroaryl, and heterocyclyl, arylalkoxy, trialkylsilyloxy;

$R_{VII-4}$ is selected from the group consisting of hydrogen, hydroxy, halogen, alkyl, alkenyl, alkynyl, cycloalkyl, cycloalkenyl, haloalkyl, haloalkenyl, haloalkynyl, aryl, heteroaryl, heterocyclyl, cycloalkylalkyl, cycloalkenylalkyl, aralkyl, heteroarylalkyl, heterocyclylalkyl, cycloalkylalkenyl, cycloalkenylalkenyl, aralkenyl, hetereoarylalkenyl, heterocyclylalkenyl, alkoxy, alkenoxy, alkynoxy, aryloxy, heteroaryloxy, heterocyclyloxy, alkanoyloxy, alkenoyloxy, alkynoyloxy, aryloyloxy, heteroaroyloxy, heterocyclyloyloxy, alkoxycarbonyl, alkenoxycarbonyl, alkynoxycarbonyl, aryloxycarbonyl, heteroaryloxycarbonyl, heterocyclyloxycarbonyl, thio, alkylthio, alkenylthio, alkynylthio, arylthio, heteroarylthio, heterocyclylthio, cycloalkylthio, cycloalkenylthio, alkylthioalkyl, alkynylthioalkyl, alkynylthioalkyl, arylthioalkyl, heteroarylthioalkyl, heterocyclylthioalkyl, alkylthioalkenyl, alkenylthioalkenyl, alkynylthioalkenyl, arylthioalkenyl, heteroarylthioalkenyl, heterocyclythioalkenyl, alkylamino, alkenylamino, alkynylamino, arylamino, heteroarylamino, heterocyclylamino, aryldialkylamino, diarylamino, diheteroarylamino, alkylarylamino, alkylheteroarylamino, arylheteroarylamino, trialkylsilyl, trialkenylsilyl, triarylsilyl, —CO(O)N($R_{VII-8a}R_{VII-8b}$), wherein $R_{VII-8a}$ and $R_{VII-8b}$ are independently selected from the group consisting of alkyl, alkenyl, alkynyl, aryl, heteroaryl and heterocyclyl, —$SO_2R_{VII-9}$, wherein $R_{VII-9}$ is selected from the group consisting of hydroxy, alkyl, alkenyl, alkynyl, aryl, heteroaryl and heterocyclyl, —OP(O)(O$R_{VII-10a}$) (O$R_{VII-10b}$), wherein $R_{VII-10a}$ and $R_{VII-10b}$ are independently selected from the group consisting of hydrogen, hydroxy, alkyl, alkenyl, alkynyl, aryl, heteroaryl and heterocyclyl, and —OP(S) (O$R_{VII-11a}$) (O$R_{VII-11b}$), wherein $R_{VII-11a}$ and $R_{VII-11b}$ are independently selected from the group consisting of alkyl, alkenyl, alkynyl, aryl, heteroaryl and heterocyclyl;

$R_{VII-5}$ is selected from the group consisting of hydrogen, hydroxy, halogen, alkyl, alkenyl, alkynyl, cycloalkyl, cycloalkenyl, haloalkyl, haloalkenyl, haloalkynyl, aryl, heteroaryl, heterocyclyl, alkoxy, alkenoxy, alkynoxy, aryloxy, heteroaryloxy, heterocyclyloxy, alkylcarbonyloxyalkyl, alkenylcarbonyloxyalkyl, alkynylcarbonyloxyalkyl, arylcarbonyloxyalkyl, heteroarylcarbonyloxyalkyl, heterocyclylcarbonyloxyalkyl, cycloalkylalkyl, cycloalkenylalkyl, aralkyl, heteroarylalkyl, heterocyclylalkyl, cycloalkylalkenyl, cycloalkenylalkenyl, aralkenyl, heteroarylalkenyl, heterocyclylalkenyl, alkylthioalkyl, cycloalkylthioalkyl, alkenylthioalkyl, alkynylthioalkyl, arylthioalkyl, heteroarylthioalkyl, heterocyclylthioalkyl, alkylthioalkenyl, alkenylthioalkenyl, alkynylthioalkenyl, arylthioalkenyl, heteroarylthioalkenyl, heterocyclylthioalkenyl, alkoxyalkyl, alkenoxyalkyl, alkynoxylalkyl, aryloxyalkyl, heteroaryloxyalkyl, heterocyclyloxyalkyl, alkoxyalkenyl, alkenoxyalkenyl, alkynoxyalkenyl, aryloxyalkenyl, heteroaryloxyalkenyl, heterocyclyloxyalkenyl, cyano, hydroxymethyl, —CO$_2$R$_{VII-14}$, wherein R$_{VII-14}$ is selected from the group consisting of alkyl, alkenyl, alkynyl, aryl, heteroaryl and heterocyclyl;

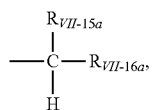

wherein R$_{VII-15b}$ is selected from the group consisting of hydroxy, hydrogen, halogen, alkylthio, alkenylthio, alkynylthio, arylthio, heteroarylthio, heterocyclylthio, alkoxy, alkenoxy, alkynoxy, aryloxy, heteroaryloxy, heterocyclyloxy, aroyloxy, and alkylsulfonyloxy, and R$_{VII-16b}$ is selected form the group consisting of alkyl, alkenyl, alkynyl, aryl, heteroaryl, heterocyclyl, arylalkoxy, and trialkylsilyloxy;

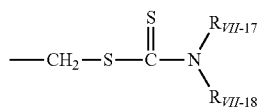

wherein R$_{VII-17}$ and R$_{VII-18}$ are independently selected from the group consisting of alkyl, cycloalkyl, alkenyl, alkynyl, aryl, heteroaryl and heterocyclyl;

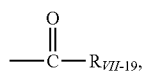

wherein R$_{VII-19}$ is selected from the group consisting of alkyl, cycloalkyl, alkenyl, alkynyl, aryl, heteroaryl, heterocyclyl, —SR$_{VII-20}$, —OR$_{VII-21}$, and BR$_{VII-22}$CO$_2$R$_{VII-23}$, wherein R$_{VII-20}$ is selected from the group consisting of alkyl, alkenyl, alkynyl, aryl, heteroaryl, heterocyclyl, aminoalkyl, aminoalkenyl, aminoalkynyl, aminoaryl, aminoheteroaryl, aminoheterocyclyl, alkylheteroarylamino, arylheteroarylamino, R$_{VII-21}$ is selected from the group consisting of alkyl, alkenyl, alkynyl, aryl, heteroaryl, and heterocyclyl, R$_{VII-22}$ is selected from the group consisting of alkylene or arylene, and R$_{VII-23}$ is selected from the group consisting of alkyl, alkenyl, alkynyl, aryl, heteroaryl, and heterocyclyl;

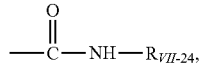

wherein R$_{VII-124}$ is selected from the group consisting of hydrogen, alkyl, cycloalkyl, alkenyl, alkynyl, aryl, heteroaryl, heterocyclyl, aralkyl, aralkenyl, and aralkynyl;

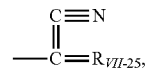

wherein R$_{VII-25}$ is heterocyclylidenyl;

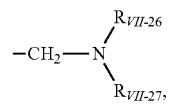

wherein R$_{VII-26}$ and R$_{VII-27}$ are independently selected from the group consisting of hydrogen, alkyl, cycloalkyl, alkenyl, alkynyl, aryl, heteroaryl, and heterocyclyl;

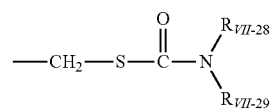

wherein R$_{VII-28}$ and R$_{VII-29}$ are independently selected from the group consisting of hydrogen, alkyl, cycloalkyl, alkenyl, alkynyl, aryl, heteroaryl, and heterocyclyl;

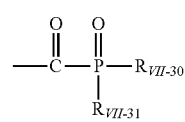

wherein R$_{VII-30}$ and R$_{VII-31}$ are independently alkoxy, alkenoxy, alkynoxy, aryloxy, heteroaryloxy, and heterocyclyloxy; and

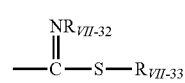

wherein R$_{VII-32}$ and R$_{VII-33}$ are independently selected from the group consisting of hydrogen, alkyl, cycloalkyl, alkenyl, alkynyl, aryl, heteroaryl, and heterocyclyl;

wherein R$_{VII-36}$ is selected from the group consisting of alkyl, alkenyl, aryl, heteroaryl and heterocyclyl;

$$-\text{N} \begin{smallmatrix} R_{VII-37} \\ \\ R_{VII-38} \end{smallmatrix}$$

wherein $R_{VII-37}$ and $R_{VII-38}$ are independently selected from the group consisting of hydrogen, alkyl, cycloalkyl, alkenyl, alkynyl, aryl, heteroaryl, and heterocyclyl;

$$-\text{N}=\text{C} \begin{smallmatrix} R_{VII-39} \\ \\ R_{VII-40} \end{smallmatrix}$$

wherein $R_{VII-39}$ is selected from the group consisting of hydrogen, alkoxy, alkenoxy, alkynoxy, aryloxy, heteroaryloxy, heterocyclyloxy, alkylthio, alkenylthio, alkynylthio, arylthio, heteroarylthio and heterocyclylthio, and $R_{VII-40}$ is selected from the group consisting of haloalkyl, haloalkenyl, haloalkynyl, haloaryl, haloheteroaryl, haloheterocyclyl, cycloalkyl, cycloalkenyl, heterocyclylalkoxy, heterocyclylalkenoxy, heterocyclylalkynoxy, alkylthio, alkenylthio, alkynylthio, arylthio, heteroarylthio and heterocyclylthio;

—N=$R_{VII-41}$, wherein $R_{VII-41}$ is heterocyclylidenyl;

$$-\text{NR}_{VII-42}-\overset{\overset{\text{O}}{\|}}{\text{C}}-R_{VII-43}$$

wherein $R_{VII-42}$ is selected from the group consisting of hydrogen, alkyl, alkenyl, alkynyl, aryl, heteroaryl, and heterocyclyl, and $R_{VII-43}$ is selected from the group consisting of hydrogen, alkyl, alkenyl, alkynyl, aryl, heteroaryl, heterocyclyl, cycloalkyl, cycloalkenyl, haloalkyl, haloalkenyl, haloalkynyl, haloaryl, haloheteroaryl, and haloheterocyclyl;

$$-\text{NH}-\overset{\overset{\text{O}}{\|}}{\text{C}}-\text{NH}-R_{VII-44}$$

wherein $R_{VII-44}$ is selected from the group consisting of hydrogen, alkyl, cycloalkyl, alkenyl, alkynyl, aryl, heteroaryl and heterocyclyl;

—N=S=O;

—N=C=S;

—N=C=O;

—N$_3$;

—S$R_{VII-45}$ wherein $R_{VII-45}$ is selected from the group consisting of hydrogen, alkyl, alkenyl, alkynyl, aryl, heteroaryl, heterocyclyl, haloalkyl, haloalkenyl, haloalkynyl, haloaryl, haloheteroaryl, haloheterocyclyl, heterocyclyl, cycloalkylalkyl, cycloalkenylalkyl, aralkyl, heteroarylalkyl, heterocyclylalkyl, cycloalkylalkenyl, cycloalkenylalkenyl, aralkenyl, heteroarylalkenyl, heterocyclylalkenyl, alkylthioalkyl, alkenylthioalkyl, alkynylthioalkyl, arylthioalkyl, heteroarylthioalkyl, heterocyclylthioalkyl, alkylthioalkenyl, alkenylthioalkenyl, alkynylthioalkenyl, arylthioalkenyl, heteroarylthioalkenyl, heterocyclylthioalkenyl, aminocarbonylalkyl, aminocarbonylalkenyl, aminocarbonylalkynyl, aminocarbonylaryl, aminocarbonylheteroaryl, and aminocarbonylheterocyclyl, —S$R_{VII-46}$, and —CH$_2$$R_{VII-47}$, wherein $R_{VII-46}$ is selected from the group consisting of alkyl, alkenyl, alkynyl, aryl, heteroaryl and heterocyclyl, and $R_{VII-47}$ is selected from the group consisting of hydrogen, alkyl, alkenyl, alkynyl, aryl, heteroaryl and heterocyclyl; and $$-\text{S}-\text{CH} \begin{smallmatrix} R_{VII-48} \\ \\ R_{VII-49} \end{smallmatrix},$$

wherein $R_{VII-48}$ is selected from the group consisting of hydrogen, alkyl, cycloalkyl, alkenyl, alkynyl, aryl, heteroaryl and heterocyclyl, and $R_{VII-49}$ is selected from the group consisting of alkoxy, alkenoxy, alkynoxy, aryloxy, heteroaryloxy, heterocyclyloxy, haloalkyl, haloalkenyl, haloalkynyl, haloaryl, haloheteroaryl and haloheterocyclyl;

$$-\text{S}-\overset{\overset{\text{O}}{\|}}{\text{C}}-R_{VII-50},$$

wherein $R_{VII-50}$ is selected from the group consisting of hydrogen, alkyl, cycloalkyl, alkenyl, alkynyl, aryl, heteroaryl, heterocyclyl, alkoxy, alkenoxy, alkynoxy, aryloxy, heteroaryloxy and heterocyclyloxy;

$$-\overset{\overset{\text{O}}{\|}}{\text{S}}-R_{VII-51},$$

wherein $R_{VII-51}$ is selected from the group consisting of alkyl, alkenyl, alkynyl, aryl, heteroaryl, heterocyclyl, haloalkyl, haloalkenyl, haloalkynyl, haloaryl, haloheteroaryl and haloheterocyclyl; and $$-\overset{\overset{\text{O}}{\|}}{\underset{\underset{\text{O}}{\|}}{\text{S}}}-R_{VII-53},$$

wherein $R_{VII-53}$ is selected from the group consisting of alkyl, alkenyl, alkynyl, aryl, heteroaryl and heterocyclyl;

provided that when $R_{VII-5}$ is selected from the group consisting of heterocyclylalkyl and heterocyclylalkenyl, the heterocyclyl radical of the corresponding heterocyclylalkyl or heterocyclylalkenyl is other than δ-lactone; and provided that when $R_{VII-4}$ is aryl, heteroaryl or heterocyclyl, and one of $R_{VII-2}$ and $R_{VII-6}$ is trifluoromethyl, then the other of $R_{VII-2}$ and $R_{VII-6}$ is difluoromethyl.

Compounds of Formula VII and their methods of manufacture are disclosed in PCT Publication No. WO 9941237-A1, which is incorporated herein by reference in its entirety for all purposes.

In a preferred embodiment, the CETP inhibitor of Formula VII is dimethyl 5,5-dithiobis[2-difluoromethyl-4-(2-methylpropyl)-6-(trifluoromethyl)-3-pyridine-carboxylate].

Another class of CETP inhibitors that finds utility with the present invention consists of substituted biphenyls having the Formula VIII

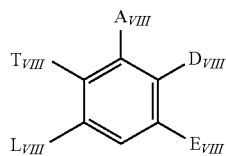

Formula VIII or a pharmaceutically acceptable salt, enantiomers, or stereoisomers thereof, in which $A_{VIII}$ stands for aryl with 6 to 10 carbon atoms, which is optionally substituted up to 3 times in an identical manner or differently by halogen, hydroxy, trifluoromethyl, trifluoromethoxy, or by straight-chain or branched alkyl, acyl, or alkoxy with up to 7 carbon atoms each, or by a group of the formula —$NR_{VIII-1}R_{VIII-2}$, wherein $R_{VIII-1}$ and $R_{VIII-2}$ are identical or different and denote hydrogen, phenyl, or straight-chain or branched alkyl with up to 6 carbon atoms, $D_{VIII}$ stands for straight-chain or branched alkyl with up to 8 carbon atoms, which is substituted by hydroxy, $E_{VIII}$ and $L_{VIII}$ are either identical or different and stand for straight-chain or branched alkyl with up to 8 carbon atoms, which is optionally substituted by cycloalkyl with 3 to 8 carbon atoms, or stands for cycloalkyl with 3 to 8 carbon atoms, or $E_{VIII}$ has the above-mentioned meaning and $L_{VIII}$ in this case stands for aryl with 6 to 10 carbon atoms, which is optionally substituted up to 3 times in an identical manner or differently by halogen, hydroxy, trifluoromethyl, trifluoromethoxy, or by straight-chain or branched alkyl, acyl, or alkoxy with up to 7 carbon atoms each, or by a group of the formula —$NR_{VIII-3}R_{VIII-4}$, wherein $R_{VIII-3}$ and $R_{VIII-4}$ are identical or different and have the meaning given above for $R_{VIII-1}$ and $R_{VIII-2}$, or $E_{VIII}$ stands for straight-chain or branched alkyl with up to 8 carbon atoms, or stands for aryl with 6 to 10 carbon atoms, which is optionally substituted up to 3 times in an identical manner or differently by halogen, hydroxy, trifluoromethyl, trifluoromethoxy, or by straight-chain or branched alkyl, acyl, or alkoxy with up to 7 carbon atoms each, or by a group of the formula —$NR_{VIII-5}R_{VIII-6}$, wherein $R_{VIII-5}$ and $R_{VII-6}$ are identical or different and have the meaning given above for $R_{VIII-1}$ and $R_{VIII-2}$, and $L_{VIII}$ in this case stands for straight-chain or branched alkoxy with up to 8 carbon atoms or for cycloalkyloxy with 3 to 8 carbon atoms, $T_{VIII}$ stands for a radical of the formula

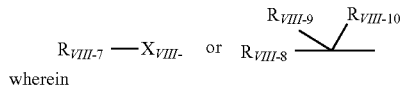

wherein $R_{VIII-7}$ and $R_{VIII-8}$ are identical or different and denote cycloalkyl with 3 to 8 carbon atoms, or aryl with 6 to 10 carbon atoms, or denote a 5- to 7-member aromatic, optionally benzo-condensed, heterocyclic compound with up to 3 heteroatoms from the series S, N and/or O, which are optionally substituted up to 3 times in an identical manner or differently by trifluoromethyl, trifluoromethoxy, halogen, hydroxy, carboxyl, by straight-chain or branched alkyl, acyl, alkoxy, or alkoxycarbonyl with up to 6 carbon atoms each, or by phenyl, phenoxy, or thiophenyl, which can in turn be substituted by halogen, trifluoromethyl, or trifluoromethoxy, and/or the rings are substituted by a group of the formula —$NR_{VIII-11}R_{VIII-2}$, wherein $R_{VIII-11}$ and $R_{VIII-12}$ are identical or different and have the meaning given above for $R_{VIII-1}$ and $R_{VIII-2}$, $X_{VIII}$ denotes a straight or branched alkyl chain or alkenyl chain with 2 to carbon atoms each, which are optionally substituted up to 2 times by hydroxy, $R_{VIII-9}$ denotes hydrogen, and $R_{VIII-10}$ denotes hydrogen, halogen, azido, trifluoromethyl, hydroxy, mercapto, trifluoromethoxy, straight-chain or branched alkoxy with up to 5 carbon atoms, or a radical of the formula —$NR_{VIII-13}R_{VIII-14}$, wherein $R_{VIII-13}$ and $R_{VIII-14}$ are identical or different and have the meaning given above for $R_{VIII-1}$ and $R_{VIII-2}$, or $R_{VIII-9}$ and $R_{VIII-10}$ form a carbonyl group together with the carbon atom.

Compounds of Formula VIII are disclosed in PCT Publication No. WO 9804528, which is incorporated herein by reference in its entirety for all purposes.

Another class of CETP inhibitors that finds utility with the present invention consists of substituted 1,2,4-triazoles having the Formula IX

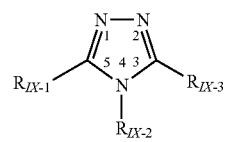

Formula IX or a pharmaceutically acceptable salt or tautomer thereof;

wherein $R_{IX-1}$ is selected from higher alkyl, higher alkenyl, higher alkynyl, aryl, aralkyl, aryloxyalkyl, alkoxyalkyl, alkylthioalkyl, arylthioalkyl, and cycloalkylalkyl;

wherein $R_{IX-2}$ is selected from aryl, heteroaryl, cycloalkyl, and cycloalkenyl, wherein $R_{IX-2}$ is optionally substituted at a substitutable position with one or more radicals independently selected from alkyl, haloalkyl, alkylthio, alkylsulfinyl, alkylsulfonyl, alkoxy, halo, aryloxy, aralkyloxy, aryl, aralkyl, aminosulfonyl, amino, monoalkylamino and dialkylamino; and wherein $R_{IX-3}$ is selected from hydrido, —SH and halo;

provided $R_{IX-2}$ cannot be phenyl or 4-methylphenyl when $R_{IX-1}$ is higher alkyl and when $R_{IX-3}$ is BSH.

Compounds of Formula IX and their methods of manufacture are disclosed in PCT Publication No. WO 9914204, which is incorporated herein by reference in its entirety for all purposes.

In a preferred embodiment, the CETP inhibitor is selected from the following compounds of Formula IX:

2,4-dihydro-4-(3-methoxyphenyl)-5-tridecyl-3H-1,2,4-triazole-3-thione;
2,4-dihydro-4-(2-fluorophenyl)-5-tridecyl-3H-1,2,4-triazole-3-thione;
2,4-dihydro-4-(2-methylphenyl)-5-tridecyl-3H-1,2,4-triazole-3-thione;
2,4-dihydro-4-(3-chlorophenyl)-5-tridecyl-3H-1,2,4-triazole-3-thione;
2,4-dihydro-4-(2-methoxyphenyl)-5-tridecyl-3H-1,2,4-triazole-3-thione;
2,4-dihydro-4-(3-methylphenyl)-5-tridecyl-3H-1,2,4-triazole-3-thione;
4-cyclohexyl-2,4-dihydro-5-tridecyl-3H-1,2,4-triazole-3-thione;
2,4-dihydro-4-(3-pyridyl)-5-tridecyl-3H-1,2,4-triazole-3-thione;
2,4-dihydro-4-(2-ethoxyphenyl)-5-tridecyl-3H-1,2,4-triazole-3-thione;
2,4-dihydro-4-(2,6-dimethylphenyl)-5-tridecyl-3H-1,2,4-triazole-3-thione;
2,4-dihydro-4-(4-phenoxyphenyl)-5-tridecyl-3H-1,2,4-triazole-3-thione;
4-(1,3-benzodioxol-5-yl)-2,4-dihydro-5-tridecyl-3H-1,2,4-triazole-3-thione;
4-(2-chlorophenyl)-2,4-dihydro-5-tridecyl-3H-1,2,4-triazole-3-thione;
2,4-dihydro-4-(4-methoxyphenyl)-5-tridecyl-3H-1,2,4-triazole-3-thione;
2,4-dihydro-5-tridecyl-4-(3-trifluoromethylphenyl)-3H-1,2,4-triazole-3-thione;
2,4-dihydro-5-tridecyl-4-(3-fluorophenyl)-3H-1,2,4-triazole-3-thione;
4-(3-chloro-4-methylphenyl)-2.4-dihydro-5-tridecyl-3H-1,2,4-triazole-3-thione;
2,4-dihydro-4-(2-methylthiophenyl)-5-tridecyl-3H-1,2,4-triazole-3-thione;
4-(4-benzyloxyphenyl)-2,4-dihydro-5-tridecyl-3H-1,2,4-triazole-3-thione;
2,4-dihydro-4-(2-naphthyl)-5-tridecyl-3H-1,2,4-triazole-3-thione;
2,4-dihydro-5-tridecyl-4-(4-trifluoromethylphenyl)-3H-1,2,4-triazole-3-thione;
2,4-dihydro-4-(1-naphthyl)-5-tridecyl-3H-1,2,4-triazole-3-thione;
2,4-dihydro-4-(3-methylthiophenyl)-5-tridecyl-3H-1,2,4-triazole-3-thione;
2,4-dihydro-4-(4-methylthiophenyl)-5-tridecyl-3H-1,2,4-triazole-3-thione;
2,4-dihydro-4-(3,4-dimethoxyphenyl)-5-tridecyl-3H-1,2,4-triazole-3-thione;
2,4-dihydro-4-(2,5-dimethoxyphenyl)-5-tridecyl-3H-1,2,4-triazole-3-thione;
2,4-dihydro-4-(2-methoxy-5-chlorophenyl)-5-tridecyl-3H-1,2,4-triazole-3-thione;
4-(4-aminosulfonylphenyl)-2,4-dihydro-5-tridecyl-3H-1,2,4-triazole-3-thione;
2,4-dihydro-5-dodecyl-4-(3-methoxyphenyl)-3H-1,2,4-triazole-3-thione;
2,4-dihydro-4-(3-methoxyphenyl)-5-tetradecyl-3H-1,2,4-triazole-3-thione;
2,4-dihydro-4-(3-methoxyphenyl)-5-undecyl-3H-1,2,4-triazole-3-thione; and
2,4-dihydro-(4-methoxyphenyl)-5-pentadecyl-3H-1,2,4-triazole-3-thione.

Another class of CETP inhibitors that finds utility with the present invention consists of hetero-tetrahydroquinolines having the Formula X

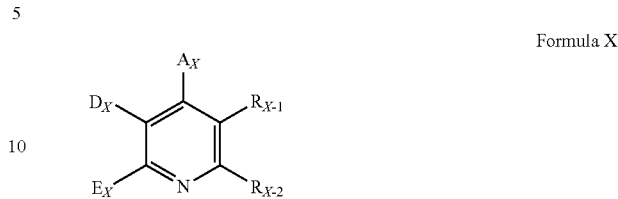

Formula X and pharmaceutically acceptable salts, enantiomers, or stereoisomers or N-oxides of said compounds;
in which
$A_X$ represents cycloalkyl with 3 to 8 carbon atoms or a 5 to 7-membered, saturated, partially saturated or unsaturated, optionally benzo-condensed heterocyclic ring containing up to 3 heteroatoms from the series comprising S, N and/or O, that in case of a saturated heterocyclic ring is bonded to a nitrogen function, optionally bridged over it, and in which the aromatic systems mentioned above are optionally substituted up to 5-times in an identical or different substituents in the form of halogen, nitro, hydroxy, trifluoromethyl, trifluoromethoxy or by a straight-chain or branched alkyl, acyl, hydroxyalkyl or alkoxy each having up to 7 carbon atoms or by a group of the formula $BNR_{X-3}R_{X-4}$,
in which
$R_{X-3}$ and $R_{X-4}$ are identical or different and denote hydrogen, phenyl or straight-chain or branched alkyl having up to 6 carbon atoms,
or
$A_X$ represents a radical of the formula

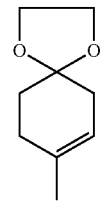

$D_X$ represents an aryl having 6 to 10 carbon atoms, that is optionally substituted by phenyl, nitro, halogen, trifluormethyl or trifluormethoxy, or it represents a radical of the formula

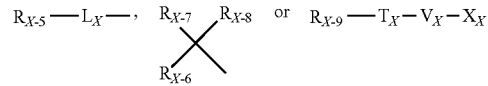

in which
$R_{X-5}$, $R_{X-6}$ and $R_{X-9}$ independently of one another denote cycloalkyl having 3 to 6 carbon atoms, or an aryl having 6 to 10 carbon atoms or a 5- to 7-membered aromatic, optionally benzo-condensed saturated or unsaturated, mono-, bi-, or tricyclic heterocyclic ring wherein the heteroatoms are selected from the series consisting of S, N and/or O, in which the rings are substituted, optionally, in case of the nitrogen containing aromatic rings via the N function, with up to 5 identical or different substituents in the form of halogen, trifluoromethyl, nitro, hydroxy, cyano, carbonyl, trifluoromethoxy, straight straight-chain or branched acyl, alkyl, alkylthio, alkylalkoxy, alkoxy, or alkoxycarbonyl each having up to 6 carbon atoms, by aryl or trifluoromethyl-substituted aryl each having 6 to 10 carbon atoms or by an, optionally benzo-condensed, aromatic 5- to 7-membered heterocyclic ring having up to 3 heteroatoms from the series consisting of S, N, and/or O, and/or substituted by a group of the formula $BOR_{X-10}$, $-SR_{X-11}$, $SO_2R_{X-12}$ or $BNR_{X-13}R_{X-14}$,
in which
$R_{X-10}$, $R_{X-11}$ and $R_{X-12}$ independently from each other denote aryl having 6 to 10 carbon atoms, which is in turn substituted with up to 2 identical or different substituents in the form of phenyl, halogen or a straight-chain or branched alkyl having up to 6 carbon atoms,
$R_{X-13}$ and $R_{X-14}$ are identical or different and have the meaning of $R_{X-3}$ and $R_{X-4}$ indicated above,
or
$R_{X-5}$ and/or $R_{X-6}$ denote a radical of the formula

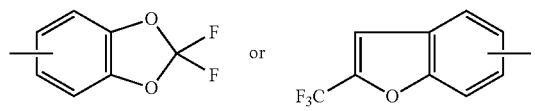

$R_{X-7}$ denotes hydrogen or halogen, and
$R_{X-8}$ denotes hydrogen, halogen, azido, trifluoromethyl, hydroxy, trifluoromethoxy, straight-chain or branched alkoxy or alkyl having up to 6 carbon atoms or a radical of the formula
$BNR_{X-15}R_{X-16}$,
in which
$R_{X-15}$ and $R_{X-16}$ are identical or different and have the meaning of $R_{X-3}$ and $R_{X-4}$ indicated above,
or
$R_{X-7}$ and $R_{X-8}$ together form a radical of the formula =O or $=NR_{X-17}$, in which
$R_{X-17}$ denotes hydrogen or straight chain or branched alkyl, alkoxy or acyl having up to 6 carbon atoms,
$L_X$ denotes a straight chain or branched alkylene or alkenylene chain having up to 8 carbon atoms, that are optionally substituted with up to 2 hydroxy groups,
$T_X$ and $X_X$ are identical or different and denote a straight chain or branched alkylene chain with up to 8 carbon atoms
or
$T_X$ or $X_X$ denotes a bond,
$V_X$ represents an oxygen or sulfur atom or an $BNR_{X-18}$-group, in which
$R_{X-18}$ denotes hydrogen or straight chain or branched alkyl with up to 6 carbon atoms or phenyl,
$E_X$ represents cycloalkyl with 3 to 8 carbon atoms, or straight chain or branched alkyl with up to 8 carbon atoms, that is optionally substituted by cycloalkyl with 3 to 8 carbon atoms or hydroxy, or represents a phenyl, that is optionally substituted by halogen or trifluoromethyl,
$R_{X-1}$ and $R_{X-2}$ together form a straight-chain or branched alkylene chain with up to 7 carbon atoms, that must be substituted by carbonyl group and/or by a radical with the formula

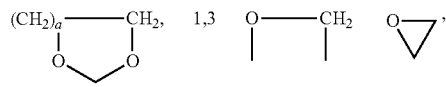

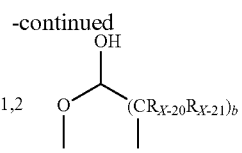

in which a and b are identical or different and denote a number equaling 1, 2, or 3,
$R_{X-19}$ denotes hydrogen, cycloalkyl with 3 up to 7 carbon atoms, straight chain or branched silylalkyl with up to 8 carbon atoms or straight chain or branched alkyl with up to 8 carbon atoms, that are optionally substituted by hydroxyl, straight chain or branched alkoxy with up to 6 carbon atoms or by phenyl, which in turn might be substituted by halogen, nitro, trifluormethyl, trifluoromethoxy or by phenyl or by tetrazole-substituted phenyl, and alkyl, optionally be substituted by a group with the formula $BOR_{X-22}$,
in which
$R_{X-22}$ denotes a straight chain or branched acyl with up to 4 carbon atoms or benzyl,
or
$R_{X-19}$ denotes straight chain or branched acyl with up to 20 carbon atoms or benzoyl, that is optionally substituted by halogen, trifluoromethyl, nitro or trifluoromethoxy, or it denotes straight chain or branched fluoroacyl with up to 8 carbon atoms and 9 fluorine atoms,
$R_{X-20}$ and $R_{X-21}$ are identical or different and denote hydrogen, phenyl or straight chain or branched alkyl with up to 6 carbon atoms,
or
$R_{X-20}$ and $R_{X-21}$ together form a 3- to 6-membered carbocyclic ring, and the carbocyclic rings formed are optionally substituted, optionally also geminally, with up to six identical or different substituents in the form of triflouromethyl, hydroxy, nitrile, halogen, carboxyl, nitro, azido, cyano, cycloalkyl or cycloalkyloxy with 3 to 7 carbon atoms each, by straight chain or branched alkoxycarbonyl, alkoxy or alkylthio with up to 6 carbon atoms each or by straight chain or branched alkyl with up to 6 carbon atoms, which in turn is substituted with up to 2 identically or differently by hydroxyl, benzyloxy, trifluoromethyl, benzoyl, straight chain or branched alkoxy, oxyacyl or carbonyl with up to 4 carbon atoms each and/or phenyl, which may in turn be substituted with a halogen, trifuoromethyl or trifluoromethoxy, and/or the formed carbocyclic rings are optionally substituted, also geminally, with up to 5 identical or different substituents in the form of phenyl, benzoyl, thiophenyl or sulfonylbenzyl, which in turn are optionally substituted by halogen, trifluoromethyl, trifluoromethoxy or nitro, and/or optionally are substituted by a radical with the formula

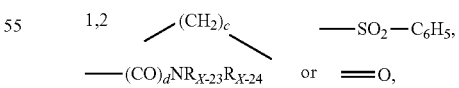

in which
c denotes a number equaling 1, 2, 3, or 4,
d denotes a number equaling 0 or 1,
$R_{X-23}$ and $R_{X-24}$ are identical or different and denote hydrogen, cycloalkyl with 3 to 6 carbon atoms, straight chain or branched alkyl with up to 6 carbon atoms, benzyl or phenyl, that is optionally substituted with up to 2 identically or differently by halogen, trifluoromethyl, cyano, phenyl or nitro, and/or the formed carbocyclic rings are substituted optionally by a spiro-linked radical with the formula

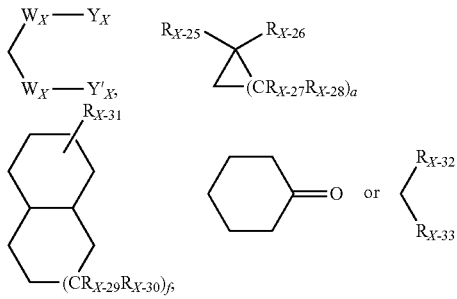

in which $W_X$ denotes either an oxygen or a sulfur atom $Y_X$ and $Y'_X$ together form a 2 to 6 membered straight chain or branched alkylene chain, e denotes a number equaling 1, 2, 3, 4, 5, 6, or 7, f denotes a number equaling 1 or 2, $R_{X-25}$, $R_{X-26}$, $R_{X-27}$, $R_{X-28}$, $R_{X-29}$, $R_{X-30}$ and $R_{X-31}$ are identical or different and denote hydrogen, trifluoromethyl, phenyl, halogen or straight chain or branched alkyl or alkoxy with up to 6 carbon atoms each, or $R_{X-25}$ and $R_{X-26}$ or $R_{X-27}$ and $R_{X-28}$ respectively form together a straight chain or branched alkyl chain with up to 6 carbon atoms, or $R_{X-25}$ and $R_{X-26}$ or $R_{X-27}$ and $R_{X-28}$ each together form a radical with the formula

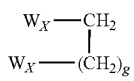

in which $W_X$ has the meaning given above, g denotes a number equaling 1, 2, 3, 4, 5, 6, or 7, $R_{X-32}$ and $R_{X-33}$ form/together a 3- to 7-membered heterocycle, which contains an oxygen or sulfur atom or a group with the formula $SO$, $SO_2$ or $-NR_{X-34}$, in which $R_{X-34}$ denotes hydrogen, phenyl, benzyl or straight or branched alkyl with up to 4 carbon atoms.

Compounds of Formula X and their methods of manufacture are disclosed in PCT Publication No. WO 9914215, which is incorporated herein by reference in its entirety for all purposes.

In a preferred embodiment, the CETP inhibitor is selected from the following compounds of Formula X:

2-cyclopentyl-5-hydroxy-7,7-dimethyl-4-(3-thienyl)-3-(4-trifluoromethylbenxoyl)-5,6,7,8-tetrahydroquinoline;

2-cyclopentyl-3-[fluoro-(4-trifluoromethylphenyl)methyl]-5-hydroxy-7,7-dimethyl-4-(3-thienyl)-5,6,7,8-tetrahydroquinoline; and 2-cyclopentyl-5-hydroxy-7,7-dimethyl-4-(3-thienyl)-3-(trifluoromethylbenxyl)-5,6,7,8-tetrahydroquinoline.

Another class of CETP inhibitors that finds utility with the present invention consists of substituted tetrahydro naphthalines and analogous compound having the Formula XI

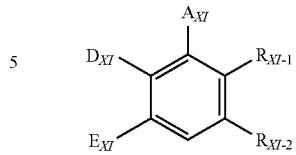

and stereoisomers, stereoisomer mixtures, and salts thereof, in which $A_{XI}$ stands for cycloalkyl with 3 to 8 carbon atoms, or stands for aryl with 6 to 10 carbon atoms, or stands for a 5- to 7-membered, saturated, partially unsaturated or unsaturated, possibly benzocondensated, heterocycle with up to 4 heteroatoms from the series S, N and/or O, where aryl and the heterocyclic ring systems mentioned above are substituted up to 5-fold, identical or different, by cyano, halogen, nitro, carboxyl, hydroxy, trifluoromethyl, trifluoro-methoxy, or by straight-chain or branched alkyl, acyl, hydroxyalkyl, alkylthio, alkoxycarbonyl, oxyalkoxycarbonyl or alkoxy each with up to 7 carbon atoms, or by a group of the formula $-NR_{XI-3}R_{XI-4}$, in which $R_{XI-3}$ and $R_{XI-4}$ are identical or different and denote hydrogen, phenyl, or straight-chain or branched alkyl with up to 6 carbon atoms $D_{XI}$ stands for a radical of the formula

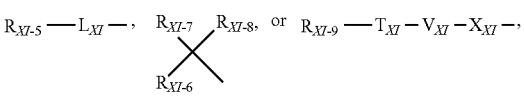

in which $R_{XI-5}$, $R_{XI-6}$ and $R_{XI-9}$, independent of each other, denote cycloalkyl with 3 to 6 carbon atoms, or denote aryl with 6 to 10 carbon atoms, or denote a 5- to 7-membered, possibly benzocondensated, saturated or unsaturated, mono-, bi- or tricyclic heterocycle with up to 4 heteroatoms of the series S, N and/or O, where the cycles are possibly substituted in the case of the nitrogen-containing rings also via the N-function-Cup to 5-fold, identical or different, by halogen, trifluoromethyl, nitro, hydroxy, cyano, carboxyl, trifluoromethoxy, straight-chain or branched acyl, alkyl, alkylthio, alkylalkoxy, alkoxy or alkoxycarbonyl with up to 6 carbon atoms each, by aryl or trifluoromethyl substituted aryl with 6 to 10 carbon atoms each, or by a possibly benzocondensated aromatic 5- to 7-membered heterocycle with up to 3 heteroatoms of the series S, N and/or O, and/or are substituted by a group of the formula

in which $R_{XI-10}$, $R_{XI-11}$ and $R_{XI-12}$, independent of each other, denote aryl with 6 to 10 carbon atoms, which itself is substituted up to 2-fold, identical or different, by phenyl, halogen. or by straight-chain or branched alkyl with up to 6 carbon atoms, $R_{XI-13}$ and $R_{XI-14}$ are identical or different and have the meaning given above for $R_{XI-3}$ and $R_{XI-4}$, or $R_{XI-5}$ and/or $R_{XI-6}$ denote a radical of the formula

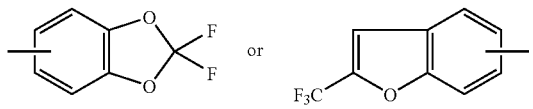

$R_{XI-7}$ denotes hydrogen, halogen or methyl,
and
$R_{XI-8}$ denotes hydrogen, halogen, azido, trifluoromethyl, hydroxy, trifluoromethoxy, straight-chain or branched alkoxy or alkyl with up to 6 carbon atoms each, or a radical of the formula —$NR_{XI-15}R_{XI-16}$,
in which
$R_{XI-15}$ and $R_{XI-16}$ are identical or different and have the meaning given above for $R_{XI-3}$ and $R_{XI-4}$,
or
$R_{XI-17}$ and $R_{XI-8}$ together form a radical of the formula =O or =$NR_{XI-17}$, in which
$R_{XI-17}$ denotes hydrogen or straight-chain or branched alkyl, alkoxy or acyl with up to 6 carbon atoms each,
$L_{XI}$ denotes a straight-chain or branched alkylene- or alkenylene chain with up to 8 carbon atoms each, which is possibly substituted up to 2-fold by hydroxy,
$T_{XI}$ and $X_{XI}$ are identical or different and denote a straight-chain or branched alkylene chain with up to 8 carbon atoms,
or
$T_{XI}$ and $X_{XI}$ denotes a bond,
$V_{XI}$ stands for an oxygen- or sulfur atom or for an —$NR_{XI-18}$ group, in which
$R_{XI-18}$ denotes hydrogen or straight-chain or branched alkyl with up to 6 carbon atoms, or phenyl,
$E_{XI}$ stands for cycloalkyl with 3 to 8 carbon atoms, or stands for straight-chain or branched alkyl with up to 8 carbon atoms, which is possibly substituted by cycloalkyl with 3 to 8 carbon atoms or hydroxy, or stands for phenyl, which is possibly substituted by halogen or trifluoromethyl,
$R_{XI-1}$ and $R_{XI-2}$ together form a straight-chain or branched alkylene chain with up to 7 carbon atoms, which must be substituted by a carbonyl group and/or by a radical of the formula

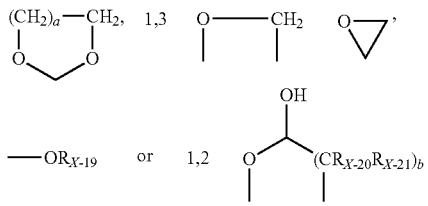

in which
a and b are identical or different and denote a number 1, 2 or 3,
$R_{XI-19}$ denotes hydrogen, cycloalkyl with 3 to 7 carbon atoms, straight-chain or branched silylalkyl with up to 8 carbon atoms, or straight-chain or branched alkyl with up to 8 carbon atoms, which is possibly substituted by hydroxy, straight-chain or branched alkoxy with up to 6 carbon atoms, or by phenyl, which itself can be substituted by halogen, nitro, trifluoromethyl, trifluoromethoxy or by phenyl substituted by phenyl or tetrazol, and alkyl is possibly substituted by a group of the formula —$OR_{XI-22}$, in which
$R_{XI-22}$ denotes straight-chain or branched acyl with up to 4 carbon atoms, or benzyl,
or
$R_{XI-19}$ denotes straight-chain or branched acyl with up to 20 carbon atoms or benzoyl, which is possibly substituted by halogen, trifluoromethyl, nitro or trifluoromethoxy, or denotes straight-chain or branched fluoroacyl with up to 8 carbon atoms and 9 fluorine atoms,
$R_{XI-20}$ and $R_{XI-21}$ are identical or different, denoting hydrogen, phenyl or straight-chain or branched alkyl with up to 6 carbon atoms,
or
$R_{XI-20}$ and $R_{XI-21}$ together form a 3- to 6-membered carbocycle, and, possibly also geminally, the alkylene chain formed by $R_{XI-1}$ and $R_{XI-2}$, is possibly substituted up to 6-fold, identical or different, by trifluoromethyl, hydroxy, nitrile, halogen, carboxyl, nitro, azido, cyano, cycloalkyl or cycloalkyloxy with 3 to 7 carbon atoms each, by straight-chain or branched alkoxycarbonyl, alkoxy or alkoxythio with up to 6 carbon atoms each, or by straight-chain or branched alkyl with up to 6 carbon atoms, which itself is substituted up to 2-fold, identical or different, by hydroxyl, benzyloxy, trifluoromethyl, benzoyl, straight-chain or branched alkoxy, oxyacyl or carboxyl with up to 4 carbon atoms each, and/or phenyl—which itself can be substituted by halogen, trifluoromethyl or trifluoromethoxy, and/or the alkylene chain formed by $R_{XI-1}$ and $R_{XI-2}$ is substituted, also geminally, possibly up to 5-fold, identical or different, by phenyl, benzoyl, thiophenyl or sulfobenzyl—which themselves are possibly substituted by halogen, trifluoromethyl, trifluoromethoxy or nitro, and/or the alkylene chain formed by $R_{XI-1}$ and $R_{XI-2}$ is possibly substituted by a radical of the formula

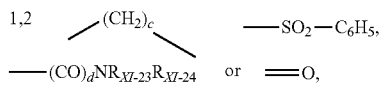

in which
c denotes a number 1, 2, 3 or 4,
d denotes a number 0 or 1,
$R_{XI-23}$ and $R_{XI-24}$ are identical or different and denote hydrogen, cycloalkyl with 3 to 6 carbon atoms, straight-chain or branched alkyl with up to 6 carbon atoms, benzyl or phenyl, which is possibly substituted up to 2-fold. identical or different, by halogen, trifluoromethyl, cyano, phenyl or nitro, and/ or the alkylene chain formed by $R_{XI-1}$ and $R_{XI-2}$ is possibly substituted by a spiro-jointed radical of the formula

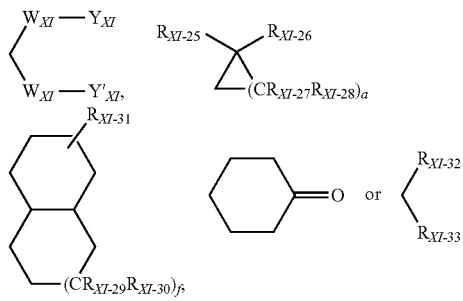

in which

W$_{XI}$ denotes either an oxygen or a sulfur atom,

Y$_{XI}$ and Y'$_{XI}$ together form a 2- to 6-membered straight-chain or branched alkylene chain, e is a number 1, 2, 3, 4, 5, 6 or 7, f denotes a number 1 or 2, R$_{XI-25}$, R$_{XI-26}$, R$_{XI-27}$, R$_{XI-28}$, R$_{XI-29}$, R$_{XI-30}$ and R$_{XI-31}$ are identical or different and denote hydrogen, trifluoromethyl, phenyl, halogen, or straight-chain or branched alkyl or alkoxy with up to 6 carbon atoms each, or R$_{XI-25}$ and R$_{XI-26}$ or R$_{XI-27}$ and R$_{XI-28}$ together form a straight-chain or branched alkyl chain with up to 6 carbon atoms, or R$_{XI-25}$ and R$_{XI-26}$ or R$_{XI-27}$ and R$_{XI-28}$ together form a radical of the formula

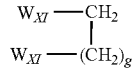

in which

W$_{XI}$ has the meaning given above, g is a number 1, 2, 3, 4, 5, 6 or 7,

R$_{XI-32}$ and R$_{XI-33}$ together form a 3- to 7-membered heterocycle that contains an oxygen- or sulfur atom or a group of the formula SO, SO$_2$ or —NR$_{XI-34}$, in which R$_{XI-34}$ denotes hydrogen, phenyl, benzyl, or straight-chain or branched alkyl with up to 4 carbon atoms.

Compounds of Formula XI and their methods of manufacture are disclosed in PCT Publication No. WO 9914174, which is incorporated herein by reference in its entirety for all purposes.

Another class of CETP inhibitors that finds utility with the present invention consists of 2-aryl-substituted pyridines having the Formula (XII)

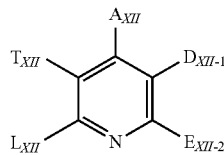

Formula XII or pharmaceutically acceptable salts, enantiomers, or stereoisomers of said compounds, in which A$_{XII}$ and E$_{XII}$ are identical or different and stand for aryl with 6 to 10 carbon atoms which is possibly substituted, up to 5-fold identical or different, by halogen, hydroxy, trifluoromethyl, trifluoromethoxy, nitro or by straight-chain or branched alkyl, acyl, hydroxy alkyl or alkoxy with up to 7 carbon atoms each, or by a group of the formula —NR$_{XII-1}$R$_{XII-2}$, where R$_{XII-1}$ and R$_{XII-2}$ are identical or different and are meant to be hydrogen, phenyl or straight-chain or branched alkyl with up to 6 carbon atoms, D$_{XII}$ stands for straight-chain or branched alkyl with up to 8 carbon atoms, which is substituted by hydroxy, L$_{XII}$ stands for cycloalkyl with 3 to 8 carbon atoms or for straight-chain or branched alkyl with up to 8 carbon atoms, which is possibly substituted by cycloalkyl with 3 to 8 carbon atoms, or by hydroxy, T$_{XII}$ stands for a radical of the formula R$_{XII-3}$—X$_{XII}$- or

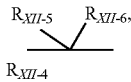

where

R$_{XII-3}$ and R$_{XII-4}$ are identical or different and are meant to be cycloalkyl with 3 to 8 carbon atoms, or aryl with 6 to 10 carbon atoms, or a 5- to 7-membered aromatic, possibly benzocondensated heterocycle with up to 3 heteroatoms from the series S, N and/or O, which are possibly substituted up to 3-fold identical or different, by trifluoromethyl, trifluoromethoxy, halogen, hydroxy, carboxyl, nitro, by straight-chain or branched alkyl acyl, alkoxy or alkoxycarbonyl with up to 6 carbon atoms each or by phenyl, phenoxy or phenylthio which in turn can be substituted by halogen trifluoromethyl or trifluoromethoxy, and/or where the cycles are possibly substituted by a group of the formula —NR$_{XII-7}$R$_{XII-8}$, where R$_{XII-7}$ and R$_{XII-8}$ are identical or different and have the meaning of R$_{XII-1}$ and R$_{XII-2}$ given above, X$_{XII}$ is a straight-chain or branched alkyl or alkenyl with 2 to 10 carbon atoms each, possibly substituted up to 2-fold by hydroxy or halogen, R$_{XII-5}$ stands for hydrogen, and R$_{XII-6}$ means to be hydrogen, halogen, mercapto, azido, trifluoromethyl, hydroxy, trifluoromethoxy, straight-chain or branched alkoxy with up to 5 carbon atoms, or a radical of the formula BNR$_{XII-9}$R$_{XII-10}$, where R$_{XII-9}$ and R$_{XII-10}$ are identical or different and have the meaning of R$_{XII-1}$ and R$_{XII-2}$ given above, or R$_{XII-5}$ and R$_{XII-6}$, together with the carbon atom, form a carbonyl group.

Compounds of Formula XII and their methods of manufacture are disclosed in EP 796846-A1, U.S. Pat. No. 6,127,383 and U.S. Pat. No. 5,925,645, all of which are incorporated herein by reference in their entireties for all purposes.

In a preferred embodiment, the CETP inhibitor is selected from the following compounds of Formula XII:

4,6-bis-(p-fluorophenyl)-2-isopropyl-3-[(p-trifluoromethylphenyl)-(fluoro)methyl]-5-(1-hydroxyethyl)pyridine;

2,4-bis-(4-fluorophenyl)-6-isopropyl-5-[4-(trifluoromethylphenyl)fluoromethyl]-3-hydroxymethyl)pyridine; and 2,4-bis-(4-fluorophenyl)-6-isopropyl-5-[2-(3-trifluoromethylphenyl)vinyl]-3-hydroxymethyl)pyridine.

Another class of CETP inhibitors that finds utility with the present invention consists of compounds having the Formula (XIII)

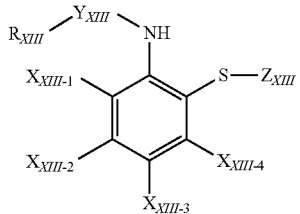

Formula XIII or pharmaceutically acceptable salts, enantiomers, stereoisomers, hydrates, or solvates of said compounds, in which $R_{XIII}$ is a straight chain or branched $C_{1-10}$ alkyl; straight chain or branched $C_{2-10}$ alkenyl; halogenated $C_{1-4}$ lower alkyl; $C_{3-10}$ cycloalkyl that may be substituted; $C_{5-8}$ cycloalkenyl that may be substituted; $C_{3-10}$ cycloalkyl $C_{1-10}$ alkyl that may be substituted; aryl that may be substituted; aralkyl that may be substituted; or a 5- or 6-membered heterocyclic group having 1 to 3 nitrogen atoms, oxygen atoms or sulfur atoms that may be substituted, $X_{XIII-1}$, $X_{XIII-2}$, $X_{XIII-3}$, $X_{XIII-4}$ may be the same or different and are a hydrogen atom; halogen atom; $C_{I-4}$ lower alkyl; halogenated $C_{I-4}$ lower alkyl; $C_{I-4}$ lower alkoxy; cyano group; nitro group; acyl; or aryl, respectively;

$Y_{XIII}$ is —CO—; or $BSO_2$—; and $Z_{XIII}$ is a hydrogen atom; or mercapto protective group.

Compounds of Formula XIII and their methods of manufacture are disclosed in PCT Publication No. WO 98/35937, which is incorporated herein by reference in its entirety for all purposes.

In a preferred embodiment, the CETP inhibitor is selected from the following compounds of Formula XIII;

N,N'-(dithiodi-2,1-phenylene)bis[2,2-dimethyl-propanamide];

N,N'-(dithiodi-2,1-phenylene)bis[1-methyl-cyclohexanecarboxamide];

N,N'-(dithiodi-2,1-phenylene)bis[1-(3-methylbutyl)cyclopentanecarboxamide];

N,N'-(dithiodi-2,1-phenylene)bis[1-(3-methylbutyl)cyclohexanecarboxamide];

N,N'-(dithiodi-2,1-phenylene)bis[1-(2-ethylbutyl)cyclohexanecarboxamide];

N,N'-(dithiodi-2,1-phenylene)bis-tricyclo[3.3.1.1$^{3.7}$]decane-1-carboxamide;

propanethioic acid, 2-methyl-,S-[2[[[1-(2-ethylbutyl)cyclohexyl]carbonyl]amino]phenyl]ester;

propanethioic acid, 2,2-dimethyl-,S-[2-[[[1-(2-ethylbutyl)cyclohexyl]carbonyl]amino]phenyl]ester; and ethanethioic acid, S-[2-[[[1-(2-ethylbutyl)cyclohexyl]carbonyl]amino]phenyl]ester.

Another class of CETP inhibitors that finds utility with the present invention consists of polycyclic aryl and heteroaryl tertiary-heteroalkylamines having the Formula XIV

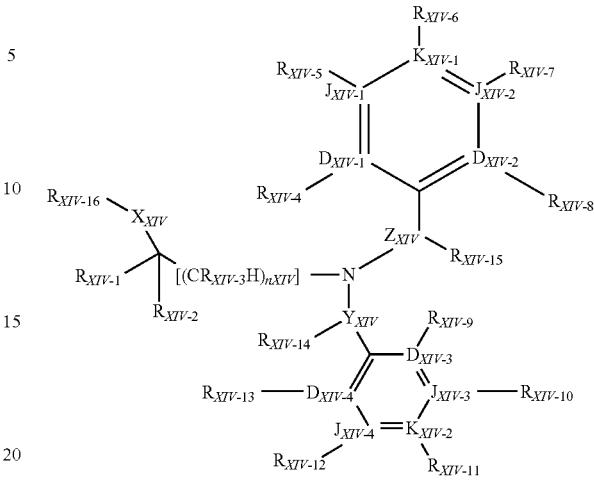

Formula XIV and pharmaceutically acceptable forms thereof, wherein:

$n_{XIV}$ is an integer selected from 0 through 5;

$R_{XIV-1}$ is selected from the group consisting of haloalkyl, haloalkenyl, haloalkoxyalkyl, and haloalkenyloxyalkyl;

$X_{XIV}$ is selected from the group consisting of O, H, F, S, S(O), NH, N(OH), N(alkyl), and N(alkoxy);

$R_{XIV-16}$ is selected from the group consisting of hydrido, alkyl, alkenyl, alkynyl, aryl, aralkyl, aryloxyalkyl, alkoxyalkyl, alkenyloxyalkyl, alkylthioalkyl, arylthioalkyl, aralkoxyalkyl, heteroaralkoxyalkyl, alkylsulfinylalkyl, alkylsulfonylalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxyalkyl, haloalkenyloxyalkyl, halocycloalkoxyalkyl, halocycloalkenyloxyalkyl, perhaloaryl, perhaloaralkyl, perhaloaryloxyalkyl, heteroaryl, heteroarylalkyl, monocarboalkoxyalkyl, monocarboalkoxy, dicarboalkoxyalkyl, monocarboxamido, monocyanoalkyl, dicyanoalkyl, carboalkoxycyanoalkyl, acyl, aroyl, heteroaroyl, heteroaryloxyalkyl, dialkoxyphosphonoalkyl, trialkylsilyl, and a spacer selected from the group consisting of a covalent single bond and a linear spacer moiety having from 1 through 4 contiguous atoms linked to the point of bonding of an aromatic substituent selected from the group consisting of $R_{XIV-4}$, $R_{XIV-8}$, $R_{XIV-9}$, and $R_{XIV-13}$ to form a heterocyclyl ring having from 5 through 10 contiguous members with the provisos that said spacer moiety is other than a covalent single bond when $R_{XIV-2}$ is alkyl and there is no $R_{XIV-16}$ wherein X is H or F;

$D_{XIV-1}$, $D_{XIV-2}$, $J_{XIV-1}$, $J_{XIV-2}$ and $K_{XIV-1}$ are independently selected from the group consisting of C, N, O, S and a covalent bond with the provisos that no more than one of $D_{XIV-1}$, $D_{XIV-2}$, $J_{XIV-1}$, $J_{XIV-2}$ and $K_{XIV-1}$ is a covalent bond, no more than one of $D_{XIV-1}$, $D_{XIV-2}$, $J_{XIV-1}$, $J_{XIV-2}$ and $K_{XIV-1}$ is O, no more than one of $D_{XIV-1}$, $D_{XIV-2}$, $J_{XIV-1}$, $J_{XIV-2}$ and $K_{XIV-1}$ is S, one of $D_{XIV-1}$, $D_{XIV-2}$, $J_{XIV-1}$, $J_{XIV-2}$ and $K_{XIV-1}$ must be a covalent bond when two of $D_{XIV-1}$, $D_{XIV-2}$, $J_{XIV-1}$, $J_{XIV-2}$ and $K_{XIV-1}$ are O and S, and no more than four of $D_{XIV-1}$, $D_{XIV-2}$, $J_{XIV-1}$, $J_{XIV-2}$ and $K_{XIV-1}$ are N;

$D_{XIV-3}$, $D_{XIV-4}$, $J_{XIV-3}$, $J_{XIV-4}$ and $K_{XIV-2}$ are independently selected from the group consisting of C, N, O, S and a covalent bond with the provisos that no more than one of $D_{XIV-3}$, $D_{XIV-4}$, $J_{XIV-3}$, $J_{XIV-4}$ and $K_{XIV-2}$ is a covalent bond, no more than one of $D_{XIV-3}$, $D_{XIV-4}$, $J_{XIV-3}$, $J_{XIV-4}$ and $K_{XIV-2}$ is O, no more than one of $D_{XIV-3}$, $D_{XIV-4}$, $J_{XIV-3}$, $J_{XIV-4}$ and $K_{XIV-2}$ is S, one of $D_{XIV-3}$, $D_{XIV-4}$, $J_{XIV-3}$, $J_{XIV-4}$ and $K_{XIV-2}$ must be a covalent bond when two of $D_{XIV-3}$, $D_{XIV-4}$, $J_{XIV-3}$, $J_{XIV-4}$ and $K_{XIV-2}$ are O and S, and no more than four of $D_{XIV-3}$, $D_{XIV-4}$, $J_{XIV-3}$, $J_{XIV-4}$ and $K_{XIV-2}$ and $K_{XIV-2}$ are N;

$R_{XIV-2}$ is independently selected from the group consisting of hydrido, hydroxy, hydroxyalkyl, amino, aminoalkyl, alkylamino, dialkylamino, alkyl, alkenyl, alkynyl, aryl, aralkyl, aralkoxyalkyl, aryloxyalkyl, alkoxyalkyl, heteroaryloxyalkyl, alkenyloxyalkyl, alkylthioalkyl, aralkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, aloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, alkylsulfinylalkyl, alkylsulfonylalkyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, and diaralkoxyphosphonoalkyl;

$R_{XIV-2}$ and $R_{XIV-3}$ are taken together to form a linear spacer moiety selected from the group consisting of a covalent single bond and a moiety having from 1 through 6 contiguous atoms to form a ring selected from the group consisting of a cycloalkyl having from 3 through 8 contiguous members, a cycloalkenyl having from 5 through 8 contiguous members, and a heterocyclyl having from 4 through 8 contiguous members;

$R_{XIV-3}$ is selected from the group consisting of hydrido, hydroxy, halo, cyano, aryloxy, hydroxyalkyl, amino, alkylamino, dialkylamino, acyl, sulfhydryl, acylamido, alkoxy, alkylthio, arylthio, alkyl, alkenyl, alkynyl, aryl, aralkyl, aryloxyalkyl, alkoxyalkyl, heteroarylthio, aralkylthio, aralkoxyalkyl, alkylsulfinylalkyl, alkylsulfonylalkyl, aroyl, heteroaroyl, aralkylthioalkyl, heteroaralkylthioalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, and diaralkoxyphosphonoalkyl;

$Y_{XIV}$ is selected from a group consisting of a covalent single bond, $(C(R_{XIV-14})_2)_{qXIV}$ wherein $_{qXIV}$ is an integer selected from 1 and 2 and $(CH(R_{XIV-14}))_{gXIV}$—$W_{XIV}$—$(CH(R_{XIV-14}))_{pXIV}$ wherein $_{gXIV}$ and $_{pXIV}$ are integers independently selected from 0 and 1;

$R_{XIV-14}$ is independently selected from the group consisting of hydrido, hydroxy, halo, cyano, aryloxy, amino, alkylamino, dialkylamino, hydroxyalkyl, acyl, aroyl, heteroaroyl, heteroaryloxyalkyl, sulfhydryl, acylamido, alkoxy, alkylthio, arylthio, alkyl, alkenyl, alkynyl, aryl, aralkyl, aryloxyalkyl, aralkoxyalkylalkoxy, alkylsulfinylalkyl, alkylsulfonylalkyl, aralkylthioalkyl, heteroaralkoxythioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl, a spacer selected from a moiety having a chain length of 3 to 6 atoms connected to the point of bonding selected from the group consisting of $R_{XIV-9}$ and $R_{XIV-13}$ to form a ring selected from the group consisting of a cycloalkenyl ring having from 5 through 8 contiguous members and a heterocyclyl ring having from 5 through 8 contiguous members and a spacer selected from a moiety having a chain length of 2 to 5 atoms connected to the point of bonding selected from the group consisting of $R_{XIV-4}$ and $R_{XIV-8}$ to form a heterocyclyl having from 5 through 8 contiguous members with the proviso that, when $Y_{XIV}$ is a covalent bond, an $R_{XIV-14}$ substituent is not attached to $Y_{XIV}$;

$R_{XIV-14}$ and $R_{XIV-14}$, when bonded to the different atoms, are taken together to form a group selected from the group consisting of a covalent bond, alkylene, haloalkylene, and a spacer selected from a group consisting of a moiety having a chain length of 2 to 5 atoms connected to form a ring selected from the group of a saturated cycloalkyl having from 5 through 8 contiguous members, a cycloalkenyl having from 5 through 8 contiguous members, and a heterocyclyl having from 5 through 8 contiguous members;

$R_{XIV-14}$ and $R_{XIV-14}$, when bonded to the same atom are taken together to form a group selected from the group consisting of oxo, thiono, alkylene, haloalkylene, and a spacer selected from the group consisting of a moiety having a chain length of 3 to 7 atoms connected to form a ring selected from the group consisting of a cycloalkyl having from 4 through 8 contiguous members, a cycloalkenyl having from 4 through 8 contiguous members, and a heterocyclyl having from 4 through 8 contiguous members;

$W_{XIV}$ is selected from the group consisting of O, C(O), C(S), C(O)N($R_{XIV-14}$), C(S)N($R_{XIV-14}$), ($R_{XIV-14}$)NC(O), ($R_{XIV-14}$)NC(S), S, S(O), S(O)$_2$, S(O)$_2$N($R_{XIV-14}$), ($R_{XIV-14}$)NS(O)$_2$, and N($R_{XIV-14}$) with the proviso that $R_{XIV-14}$ is selected from other than halo and cyano;

$Z_{XIV}$ is independently selected from a group consisting of a covalent single bond, $(C(R_{XIV-15})_2)_{qXIV-2}$ wherein $_{qXIV-2}$ is an integer selected from 1 and 2, $(CH(R_{XIV-15}))_{jXIV}$—W—$(CH(R_{XIV-15}))_{kXIV}$ wherein $_{jXIV}$ and $_{kXIV}$ are integers independently selected from 0 and 1 with the proviso that, when $Z_{XIV}$ is a covalent single bond, an $R_{XIV-15}$ substituent is not attached to $Z_{XIV}$;

$R_{XIV-15}$ is independently selected, when $Z_{XIV}$ is $(C(R_{XIV-15})_2)_{qXIV}$ wherein $_{qXIV}$ is an integer selected from 1 and 2, from the group consisting of hydrido, hydroxy, halo, cyano, aryloxy, amino, alkylamino, dialkylamino, hydroxyalkyl, acyl, aroyl, heteroaroyl, heteroaryloxyalkyl, sulfhydryl, acylamido, alkoxy, alkylthio, arylthio, alkyl, alkenyl, alkynyl, aryl, aralkyl, aryloxyalkyl, aralkoxyalkyl, alkylsulfinylalkyl, alkylsulfonylalkyl, aralkylthioalkyl, heteroaralkylthioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl, a spacer selected from a moiety having a chain length of 3 to 6 atoms connected to the point of bonding selected from the group consisting of $R_{XIV-4}$ and $R_{XIV-8}$ to form a ring selected from the group consisting of a cycloalkenyl ring having from 5 through 8 contiguous members and a heterocyclyl ring having from 5 through 8 contiguous members, and a spacer selected from a moiety having a chain length of 2 to 5 atoms connected to the point of bonding selected from the group consisting of $R_{XIV-9}$ and $R_{XIV-13}$ to form a heterocyclyl having from 5 through 8 contiguous members;

$R_{XIV-15}$ and $R_{XIV-15}$, when bonded to the different atoms, are taken together to form a group selected from the group consisting of a covalent bond, alkylene, haloalkylene, and a spacer selected from a group consisting of a moiety having a chain length of 2 to 5 atoms connected to form a ring selected from the group of a saturated cycloalkyl having from 5 through 8 contiguous members, a cycloalkenyl having from 5 through 8 contiguous members, and a heterocyclyl having from 5 through 8 contiguous members;

$R_{XIV-15}$ and $R_{XIV-15}$, when bonded to the same atom are taken together to form a group selected from the group consisting of oxo, thiono, alkylene, haloalkylene, and a spacer selected from the group consisting of a moiety having a chain length of 3 to 7 atoms connected to form a ring selected from the group consisting of a cycloalkyl having from 4 through 8 contiguous members, a cycloalkenyl having from 4 through 8 contiguous members, and a heterocyclyl having from 4 through 8 contiguous members;

$R_{XIV-15}$ is independently selected, when $Z_{XIV}$ is (CH $(R_{XIV-15}))_{jXIV}$—W—(CH($R_{XIV-15}))_{kXIV}$ wherein $_{jXIV}$ and $_{kXIV}$ are integers independently selected from 0 and 1, from the group consisting of hydrido, halo, cyano, aryloxy, carboxyl, acyl, aroyl, heteroaroyl, hydroxyalkyl, heteroaryloxyalkyl, acylamido, alkoxy, alkylthio, arylthio, alkyl, alkenyl, alkynyl, aryl, aralkyl, aryloxyalkyl, alkoxyalkyl, heteroaryloxyalkyl, aralkoxyalkyl, heteroaralkoxyalkyl, alkylsulfonylalkyl, alkylsulfinylalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxyalkyl, carboalkoxy, carboxamide, carboxamidoalkyl, carboaralkoxy, dialkoxyphosphonoalkyl, diaralkoxyphosphonoalkyl, a spacer selected from a linear moiety having a chain length of 3 to 6 atoms connected to the point of bonding selected from the group consisting of $R_{XIV-4}$ and $R_{XIV-8}$ to form a ring selected from the group consisting of a cycloalkenyl ring having from 5 through 8 contiguous members and a heterocyclyl ring having from 5 through 8 contiguous members, and a spacer selected from a linear moiety having a chain length of 2 to 5 atoms connected to the point of bonding selected from the group consisting of $R_{XIV-9}$ and $R_{XIV-13}$ to form a heterocyclyl ring having from 5 through 8 contiguous members;

$R_{XIV-4}$, $R_{XIV-5}$, $R_{XIV-6}$, $R_{XIV-7}$, $R_{XIV-8}$, $R_{XIV-9}$, $R_{XIV-10}$, $R_{XIV-11}$, $R_{XIV-12}$, and $R_{XIV-13}$ are independently selected from the group consisting of perhaloaryloxy, alkanoylalkyl, alkanoylalkoxy, alkanoyloxy, N-aryl-N-alkylamino, heterocyclylalkoxy, heterocyclylthio, hydroxyalkoxy, carboxamidoalkoxy, alkoxycarbonylalkoxy, alkoxycarbonylalkenyloxy, aralkanoylalkoxy, aralkenoyl, N-alkylcarboxamido, N-haloalkylcarboxamido, N-cycloalkylcarboxamido, N-arylcarboxamidoalkoxy, cycloalkylcarbonyl, cyanoalkoxy, heterocyclylcarbonyl, hydrido, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, haloalkylthio, alkanoyloxy, alkoxy, alkoxyalkyl, haloalkoxyalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkylamidosulfonyl, dialkylamidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl; haloalkenyl, haloalkoxy, hydroxyhaloalkyl, hydroxyaralkyl, hydroxyalkyl, hydoxyheteroaralkyl, haloalkoxyalkyl, aryl, heteroaralkynyl, aryloxy, aralkoxy, aryloxyalkyl, saturated heterocyclyl, partially saturated heterocyclyl, heteroaryl, heteroaryloxy, heteroaryloxyalkyl, arylalkenyl, heteroarylalkenyl, carboxyalkyl, carboalkoxy, alkoxycarboxamido, alkylamidocarbonylamido, arylamidocarbonylamido, carboalkoxyalkyl, carboalkoxyalkenyl, carboaralkoxy, carboxamido, carboxamidoalkyl, cyano, carbohaloalkoxy, phosphono, phosphonoalkyl, diaralkoxyphosphono, and diaralkoxyphosphonoalkyl with the proviso that there are one to five non-hydrido ring substituents $R_{XIV-4}$, $R_{XIV-5}$, $R_{XIV-6}$, $R_{XIV-7}$, and $R_{XIV-8}$ present, that there are one to five non-hydrido ring substituents $R_{XIV-9}$, $R_{XIV-10}$, $R_{XIV-11}$, $R_{XIV-12}$, and $R_{XIV-13}$ present, and $R_{XIV-4}$, $R_{XIV-5}$, $R_{XIV-6}$, $R_{XIV-7}$, $R_{XIV-8}$, $R_{XIV-9}$, $R_{XIV-10}$, $R_{XIV-11}$, $R_{XIV-12}$, and $R_{XIV-13}$ are each independently selected to maintain the tetravalent nature of carbon, trivalent nature of nitrogen, the divalent nature of sulfur, and the divalent nature of oxygen;

$R_{XIV-4}$ and $R_{XIV-5}$, $R_{XIV-5}$ and $R_{XIV-6}$, $R_{XIV-6}$ and $R_{XIV-7}$, $R_{XIV-7}$ and $R_{XIV-8}$, $R_{XIV-8}$ and $R_{XIV-9}$, $R_{XIV-9}$ and $R_{XIV-10}$, $R_{XIV-10}$ and $R_{XIV-11}$, $R_{XIV-11}$ and $R_{XIV-12}$, and $R_{XIV-12}$ and $R_{XIV-13}$ are independently selected to form spacer pairs wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the provisos that no more than one of the group consisting of spacer pairs $R_{XIV-4}$ and $R_{XIV-5}$, $R_{XIV-5}$ and $R_{XIV-6}$, $R_{XIV-6}$ and $R_{XIV-7}$, and $R_{XIV-7}$ and $R_{XIV-8}$ are used at the same time and that no more than one of the group consisting of spacer pairs $R_{XIV-9}$ and $R_{XIV-10}$, $R_{XIV-10}$ and $R_{XIV-11}$, $R_{XIV-11}$ and $R_{XIV-12}$, and $R_{XIV-12}$ and $R_{XIV-13}$ are used at the same time;

$R_{XIV-4}$ and $R_{XIV-9}$, $R_{XIV-4}$ and $R_{XIV-13}$, $R_{XIV-8}$ and $R_{XIV-9}$ and $R_{XIV-8}$ and $R_{XIV-13}$ are independently selected to form a spacer pair wherein said spacer pair is taken together to form a linear moiety wherein said linear moiety forms a ring selected from the group consisting of a partially saturated heterocyclyl ring having from 5 through 8 contiguous members and a heteroaryl ring having from 5 through 6 contiguous members with the proviso that no more than one of the group consisting of spacer pairs $R_{XIV-4}$ and $R_{XIV-9}$, $R_{XIV-4}$ and $R_{XIV-13}$, $R_{XIV-8}$ and $R_{XIV-9}$, and $R_{XIV-8}$ and $R_{XIV-13}$ is used at the same time.

Compounds of Formula XIV and their methods of manufacture are disclosed in PCT Publication No. WO 00/18721, which is incorporated herein by reference in its entirety for all purposes.

In a preferred embodiment, the CETP inhibitor is selected from the following compounds of Formula XIV:

3-[[3-(3-trifluoromethoxyphenoxy)phenyl][[3-(1,1,2,2-tetrafluoroethoxy)phenyl]methyl]amino]-1,1,1-trifluoro-2-propanol;

3-[[3-(3-isopropylphenoxy)phenyl][[3-(1,1,2,2-tetrafluoroethoxy)phenyl]-methyl]amino]-1,1,1-trifluoro-2-propanol;

3-[[3-(3-cyclopropylphenoxy)phenyl][[3-(1,1,2,2-tetrafluoroethoxy)phenyl]-methyl]amino]-1,1,1-trifluoro-2-propanol;

3-[[3-(3-(2-furyl)phenoxy)phenyl][[3-(1,1,2,2-tetrafluoroethoxy)phenyl]-methyl]amino]1,1,1-trifluoro-2-propanol;

3-[[3-(2,3-dichlorophenoxy)phenyl][[3-(1,1,2,2-tetrafluoroethoxy)phenyl]-methyl]amino]-1,1,1-trifluoro-2-propanol;

3-[[3-(4-fluorophenoxy)phenyl][[3-(1,1,2,2-tetrafluoroethoxy)phenyl]-methyl]amino]-1,1,1-trifluoro-2-propanol;

3-[[3-(4-methlylphenoxy)phenyl][[3-(1,1,2,2-tetrafluoroethoxy)phenyl]-methyl]amino]-1,1,1-trifluoro-2-propanol;

3-[[3-(2-fluoro-5-bromophenoxy)phenyl][[3-(1,1,2,2-tetrafluoroethoxy)phenyl]-methyl]amino]-1,1,1-trifluoro-2-propanol;

3-[[3-(4-chloro-3-ethylphenoxy)phenyl][[3-(1,1,2,2-tetrafluoroethoxy)phenyl]-methyl]amino]-1,1,1-trifluoro-2-propanol;

3-[[3-[3-(1,1,2,2-tetrafluoroethoxy)phenoxy]phenyl][[3-(1,1,2,2-tetrafluoro-ethoxy)phenyl]methyl]amino]-1,1,1-trifluoro-2-propanol;

3-[[3-[3-(pentafluoroethyl)phenoxy]phenyl][[3-(1,1,2,2-tetrafluoroethoxy)-phenyl]methyl]amino]-1,1,1-trifluoro-2-propanol;

3-[[3-(3,5-dimethylphenoxy)phenyl][[3-(1,1,2,2-tetrafluoroethoxy)phenyl]-methyl]amino]-1,1,1-trifluoro-2-propanol;

3-[[3-(3-ethylphenoxy)phenyl][[3-(1,1,2,2-tetrafluoroethoxy)phenyl]-methyl]amino]-1,1,1-trifluoro-2-propanol;

3-[[3-(3-t-butylphenoxy)phenyl][[3-(1,1,2,2-tetrafluoroethoxy)phenyl]-methyl]amino]1,1,1-trifluoro-2-propanol;

3-[[3-(3-methylphenoxy)phenyl][[3-(1,1,2,2-tetrafluoroethoxy)phenyl]-methyl]amino]-1,1,1-trifluoro-2-propanol;

3-[[3-(5,6,7,8-tetrahydro-2-naphthoxy)phenyl][[3-(1,1,2,2-tetrafluoroethoxy)phenyl]methyl]amino]-1,1,1-trifluoro-2-propanol;

3-[[3-(phenoxy)phenyl][[3-(1,1,2,2-tetrafluoroethoxy)phenyl]methyl]amino]-1,1,1-trifluoro-2-propanol;

3-[[3-[3-(N,N-dimethylamino)phenoxy]phenyl][[3-(1,1,2,2-tetrafluoroethoxy)phenyl]methyl]amino]-1,1,1-trifluoro-2-propanol;

3-[[[3-(1,1,2,2-tetrafluoroethoxy)phenyl]methyl][3-[[3-(trifluoromethoxy)phenyl]methoxy]phenyl]amino]-1,1,1-trifluoro-2-propanol;

3-[[[3-(1,1,2,2-tetrafluoroethoxy)phenyl]methyl][3-[[3-(trifluoromethyl)phenyl]methoxy]phenyl]amino]-1,1,1-trifluoro-2-propanol;

3-[[[3-(1,1,2,2-tetrafluoroethoxy)phenyl]methyl][3-[[3,5-dimethylphenyl]-methoxy]phenyl]amino]-1,1,1-trifluoro-2-propanol;

3-[[[3-(1,1,2,2-tetrafluoroethoxy)phenyl]methyl][3-[[3-(trifluoromethylthio)phenyl]methoxy]phenyl]amino]-1,1,-trifluoro-2-propanol;

3-[[[3-(1,1,2,2-tetrafluoroethoxy)phenyl]methyl][3-[[3,5-difluorophenyl]-methoxy]phenyl]amino]-1,1,1-trifluoro-2-propanol;

3-[[[3-(1,1,2,2-tetrafluoroethoxy)phenyl]methyl][3-[cyclohexylmethoxy]-phenyl]amino]-1,1,1-trifluoro-2-propanol;

3-[[3-(2-difluoromethoxy-4-pyridyloxy)phenyl][[3-(1,1,2,2-tetrafluoroethoxy)-phenyl]methyl]amino]-1,1,1-trifluoro-2-propanol;

3-[[3-(2-trifluoromethyl-4-pyridyloxy)phenyl][[3-(1,1,2,2-tetrafluoroethoxy)-phenyl]methyl]amino]-1,1,1-trifluoro-2-propanol;

3-[[3-(3-difluoromethoxyphenoxy)phenyl][[3-(1,1,2,2-tetrafluoroethoxy)phenyl]methyl]amino]-1,1,1-trifluoro-2-propanol;

3-[[[3-(3-trifluoromethylthio)phenoxy)phenyl][[3-(1,1,2,2-tetrafluoroethoxy)-phenyl]methyl]amino]-1,1,1-trifluoro-2-propanol;

3-[[3-(4-chloro-3-trifluoromethylphenoxy)phenyl][[3-(1,1,2,2-tetrafluoroethoxy)-phenyl]methyl]amino]-1,1,1-trifluoro-2-propanol;

3-[[3-(3-trifluoromethoxyphenoxy)phenyl][[3-(pentafluoroethymethyl]amino]-1,1,1-trifluoro-2-propanol;

3-[[3-(3-isopropylphenoxy)phenyl][[3-(pentafluoroethyl)phenyl]methyl-amino]-1,1,1-trifluoro-2-propanol;

3-[[3-(3-cyclopropylphenoxy)phenyl][[3-(pentafluoroethyl)phenyl]methyl-amino]-1,1,1-trifluoro-2-propanol;

3-[[3-(3-(2-furyl)phenoxy)phenyl][[3-(pentafluoroethyl)phenyl]methyl]-amino]-1,1,1-trifluoro-2-propanol;

3-[[3-(2,3-dichlorophenoxy)phenyl][[3-(pentafluoroethyl)phenyl]methyl]-amino]-1,1,1-trifluoro-2-propanol;

3-[[3-(4-fluorophenoxy)phenyl][[3-(pentafluoroethyl)phenyl]methyl]amino]-1,1,1-trifluoro-2-propanol;

3-[[3-(4-methylphenoxy)phenyl][[3-(pentafluoroethyl)phenyl]methyl]amino]-1,1,1-trifluoro-2-propanol;

3-[[3-(2-fluoro-5-bromophenoxy)phenyl][[3-(pentafluoroethyl)phenyl]methyl]-amino]-1,1,1-trifluoro-2-propanol;

3-[[3-(4-chloro-3-ethylphenoxy)phenyl][[3-(pentafluoroethyl)phenyl]methyl]-amino]-1,1,1-trifluoro-2-propanol;

3-[[3-[3-(1,1,2,2-tetrafluoroethoxy)phenoxy]phenyl][[3-(pentafluoroethyl)-phenyl]methyl]amino]-1,1,1-trifluoro-2-propanol;

3-[[3-[3-(pentafluoroethyl)phenoxy]phenyl][[3-(pentafluoroethyl)phenyl]-methyl]amino]-1,1,1-trifluoro-2-propanol;

3-[[3-(3,5-dimethylphenoxy)phenyl][[3-(pentafluoroethyl)phenyl]methyl]-amino]-1,1,1-trifluoro-2-propanol;

3-[[3-(3-ethylphenoxy)phenyl][[3-(pentafluoroethyl)phenyl]methyl]amino]-1,1,1-trifluoro-2-propanol;

3-[[3-(3-t-butylphenoxy)phenyl][[3-(pentafluoroethyl)phenyl]methyl]amino]-1,1,1-trifluoro-2-propanol;

3-[[3-(3-methylphenoxy)phenyl][[3-pentafluoroethyl)phenyl]methyl]amino]-1,1,1-trifluoro-2-propanol;

3-[[3-(5,6,7,8-tetrahydro-2-naphthoxy)phenyl][[3-(pentafluoroethyl)phenyl]-methyl]amino]-1,1,1-trifluoro-2-propanol;

3-[[3-(phenoxy)phenyl][[3-(pentafluoroethyl)phenyl]methyl]amino]-1,1,1-trifluoro-2-propanol;

3-[[3-[3-(N,N-dimethylamino)phenoxy]phenyl][[3-(pentafluoroethyl)phenyl]-methyl]amino]-1,1,1-trifluoro-2-propanol;

3-[[[3-(pentafluoroethyl)phenyl]methyl][3-[[3-(trifluoromethoxy)phenyl]-methoxy]phenyl]amino]-1,1,1-trifluoro-2-propanol;

3-[[[3-(pentafluoroethyl)phenyl]methyl][3-[[3-(trifluoromethyl)phenyl]-methoxy]phenyl]amino]-1,1,1-trifluoro-2-propanol;

3-[[[3-(pentafluoroethyl)phenyl]methyl][3-[[3,5-dimethylphenyl]methoxy]-phenyl]amino]-1,1,1-trifluoro-2-propanol;

3-[[[3-(pentafluoroethyl)phenyl]methyl][3-[[3-(trifluoromethylthio)phenyl]-methoxy]phenyl]amino]-1,1,1-trifluoro-2-propanol;

3-[[[3-(pentafluoroethyl)phenyl]methyl][3-[[3,5-difluorophenyl]methoxy]-phenyl]amino]-1,1,1-trifluoro-2-propanol;

3-[[[3-(pentafluoroethyl)phenyl]methyl][3-[cyclohexylmethoxy]phenyl]-amino]-1,1,1-trifluoro-2-propanol;

3-[[3-(2-difluoromethoxy-4-pyridyloxy)phenyl][[3-(pentafluoroethyl)phenyl]-methyl]amino]-1,1,1-trifluoro-2-propanol;

3-[[3-(2-trifluoromethyl-4-pyridyloxy)phenyl][[3-(pentafluoroethyl)phenyl]-methyl]amino]-1,1,1-trifluoro-2-propanol;

3-[[3-(3-difluoromethoxyphenoxy)phenyl][[3-(pentafluoroethyl)phenyl]-methyl]amino]-1,1,1-trifluoro-2-propanol;

3-[[[3-(3-trifluoromethylthio)phenoxy]phenyl][[3-(pentafluoroethyl)phenyl]-methyl]amino]-1,1,1-trifluoro-2-propanol;

3-[[3-(4-chloro-3-trifluoromethylphenoxy)phenyl][[3-(pentafluoroethyl)phenyl]methyl]amino]-1,1,1-trifluoro-2-propanol;

3-[[3-(3-trifluoromethoxyphenoxy)phenyl][[3-(heptafluoropropyl)phenyl]-methyl]amino]-1,1,1-trifluoro-2-propanol;

3-[[3-(3-isopropylphenoxy)phenyl][[3-(heptafluoropropyl)phenyl]methyl]-amino]-1,1,1-trifluoro-2-propanol;

3-[[3-(3-cyclopropylphenoxy)phenyl][[3-(heptafluoropropyl)phenyl]methyl]-amino]-1,1,1-trifluoro-2-propanol;

3-[[3-(3-(2-furyl)phenoxy)phenyl][[3-(heptafluoropropyl)phenyl]methyl]-amino]-1,1,1-trifluoro-2-propanol;

3-[[3-(2,3-dichlorophenoxy)phenyl][[3-(heptafluoropropyl)phenyl]methyl]-amino]-1,1,1-trifluoro-2-propanol;

3-[[3-(4-fluorophenoxy)phenyl][[3-(heptafluoropropyl)phenyl]methyl]amino]-1,1,1-trifluoro-2-propanol;

3-[[3-(4-methylphenoxy)phenyl][[3-(heptafluoropropyl)phenyl]methyl]amino]-1,1,1-trifluoro-2-propanol;

3-[[3-(2-fluoro-5-bromophenoxy)phenyl][[3-(heptafluoropropyl)phenyl]-methyl]amino]-1,1,1-trifluoro-2-propanol;

3-[[3-(4-chloro-3-ethylphenoxy)phenyl][[3-(heptafluoropropyl)phenyl]methyl]-amino]-1,1,1-trifluoro-2-propanol;

3-[[3-[3-(1,1,2,2-tetrafluoroethoxy)phenoxy]phenyl][[3-(heptafluoropropyl)-phenyl]methyl]amino]-1,1,1-trifluoro-2-propanol;

3-[[3-[3-(pentafluoroethyl)phenoxy]phenyl][[3-(heptafluoropropyl)phenyl]-methyl]amino]-1,1,1-trifluoro-2-propanol;

3-[[3-(3,5-dimethylphenoxy)phenyl][[3-(heptafluoropropyl)phenyl]methyl]-amino]-1,1,1-trifluoro-2-propanol;

3-[[3-(3-ethylphenoxy)phenyl][[3-(heptafluoropropyl)phenyl]methyl]amino]-1,1,1-trifluoro-2-propanol;

3-[[3-(3-t-butylphenoxy)phenyl][[3-(heptafluoropropyl)phenyl]methyl]amino]-1,1,1-trifluoro-2-propanol;

3-[[3-(3-methylphenoxy)phenyl][[3-(heptafluoropropyl)phenyl]methyl]amino]-1,1,1-trifluoro-2-propanol;

3-[[3-(5,6,7,8-tetrahydro-2-naphthoxy)phenyl][[3-(heptafluoropropyl)phenyl]-methyl]amino]-1,1,1-trifluoro-2-propanol;

3-[[3-(phenoxy)phenyl][[3-(heptafluoropropyl)phenyl]methyl]amino]-1,1,1-trifluoro-2-propanol;

3-[[3-[3-(N,N-dimethylamino)phenoxy]phenyl][[3-(heptafluoropropyl)phenyl]-methyl]amino]-1,1,1-trifluoro-2-propanol;

3-[[[3-(heptafluoropropyl)phenyl]methyl][3-[[3-(trifluoromethoxy)phenyl]-methoxy]phenyl]amino]-1,1,1-trifluoro-2-propanol;

3-[[[3-(heptafluoropropyl)phenyl]methyl][3-[[3-(trifluoromethyl)phenyl]-methoxy]phenyl]amino]-1,1,1-trifluoro-2-propanol;

3-[[[3-(heptafluoropropyl)phenyl]methyl][3-[[3,5-dimethylphenyl]methoxy]-phenyl]amino]-1,1,1-trifluoro-2-propanol;

3-[[[3-(heptafluoropropyl)phenyl]methyl][3-[[3-(trifluoromethylthio)phenyl]-methoxy]phenyl]amino]-1,1,1-trifluoro-2-propanol;

3-[[[3-(heptafluoropropyl)phenyl]methyl][3-[[3,5-difluorophenyl]methoxy]-phenyl]amino]-1,1,1-trifluoro-2-propanol;

3-[[[3-(heptafluoropropyl)phenyl]methyl][3-[cyclohexyl-methoxy]phenyl]-amino]-1,1,1-trifluoro-2-propanol;

3-[[3-(2-difluoromethoxy-4-pyridyloxy)phenyl][[3-(heptafluoropropyl)phenyl]-methyl]amino]-1,1,1-trifluoro-2-propanol;

3-[[3-(2-trifluoromethyl-4-pyridyloxy)phenyl][[3-(heptafluoropropyl)phenyl]-methyl]amino]-1,1,1-trifluoro-2-propanol;

3-[[3-(3-difluoromethoxyphenoxy)phenyl][[3-(heptafluoropropyl)phenyl]-methyl]amino]-1,1,1-trifluoro-2-propanol;

3-[[[3-(3-trifluoromethylthio)phenoxy]phenyl][[3-(heptafluoropropyl)phenyl]-methyl]amino]-1,1,1-trifluoro-2-propanol;

3-[[3-(4-chloro-3-trifluoromethylphenoxy)phenyl][[3-(heptafluoropropyl)phenyl]-methyl]amino]-1,1,1-trifluoro-2-propanol;

3-[[3-(3-trifluoromethoxyphenoxy)phenyl][[2-fluoro-5-(trifluoromethyl)phenyl]-methyl]amino]-1,1,1-trifluoro-2-propanol;

3-[[3-(3-isopropylphenoxy)phenyl][[2-fluoro-5-(trifluoromethyl)phenyl]-methyl]amino]-1,1,1-trifluoro-2-propanol;

3-[[3-(3-cyclopropylphenoxy)phenyl][[2-fluoro-5-(trifluoromethyl)phenyl]-methyl]amino]-1,1,1-trifluoro-2-propanol;

3-[[3-(3-(2-furyl)phenoxy)phenyl][[2-fluoro-5-(trifluoromethyl)phenyl]-methyl]amino]-1,1,1-trifluoro-2-propanol;

3-[[3-(2,3-dichlorophenoxy)phenyl][[2-fluoro-5-(trifluoromethyl)phenyl]-methyl]amino]-1,1,1-trifluoro-2-propanol;

3-[[3-(4-fluorophenoxy)phenyl][[2-fluoro-5-(trifluoromethyl)phenyl]-methyl]amino]-1,1,1-trifluoro-2-propanol;

3-[[3-(4-methylphenoxy)phenyl][[2-fluoro-5-(trifluoromethyl)phenyl]-methyl]amino]-1,1,1-trifluoro-2-propanol;

3-[[3-(2-fluoro-5-bromophenoxy)phenyl][[2-fluoro-5-(trifluoromethyl)phenyl]methyl]amino]-1,1,1-trifluoro-2-propanol;

3-[[3-(4-chloro-3-ethyl phenoxy)phenyl][[2-fluoro-5-(trifluoromethyl)phenyl]methyl]amino]-1,1,1-trifluoro-2-propanol;

3-[[3-[3-(1,1,2,2-tetrafluoroethoxy)phenoxy]phenyl][[2-fluoro-5-(trifluoromethyl)phenyl]methyl]amino]-1,1,1-trifluoro-2-propanol;

3-[[3-[3-(pentafluoroethyl)phenoxy]phenyl][[2-fluoro-5-(trifluoromethyl)phenyl]-methyl]amino]-1,1,1-trifluoro-2-propanol;

3-[[3-(3,5-dimethylphenoxy)phenyl][[2-fluoro-5-(trifluoromethyl)phenyl]-methyl]amino]-1,1,1-trifluoro-2-propanol;

3-[[3-(3-ethylphenoxy)phenyl][[2-fluoro-5-(trifluoromethyl)phenyl]methyl]-amino]-1,1,1-trifluoro-2-propanol;

3-[[3-(3-t-butylphenoxy)phenyl][[2-fluoro-5-(trifluoromethyl)phenyl]methyl]-amino]-1,1,1-trifluoro-2-propanol;

3-[[3-(3-methylphenoxy)phenyl][[2-fluoro-5-(trifluoromethyl)phenyl]methyl]-amino]-1,1,1-trifluoro-2-propanol;

3-[[3-(5,6,7,8-tetrahydro-2-naphthoxy)phenyl][[2-fluoro-5-(trifluoromethyl)-phenyl]methyl]amino]-1,1,1-trifluoro-2-propanol;

3-[[3-(phenoxy)phenyl][[2-fluoro-5-(trifluoromethyl)phenyl]methyl]amino]-1,1,1-trifluoro-2-propanol;

3-[[3-[3-(N,N-dimethylamino)phenoxy]phenyl][[2-fluoro-5-(trifluoromethyl)-phenyl]methyl]amino]-1,1,1-trifluoro-2-propanol;

3-[[[2-fluoro-5-(trifluoromethyl)phenyl]methyl][3-[[3-(trifluoromethoxy)phenyl]methoxy]phenyl]amino]-1,1,1-trifluoro-2-propanol;

3-[[[2-fluoro-5-(trifluoromethyl)phenyl]methyl][3-[[3-(trifluoromethyl)phenyl]methoxy]phenyl]amino]-1,1,1-trifluoro-2-propanol;

3-[[[2-fluoro-5-(trifluoromethyl)phenyl]methyl][3-[[3,5-dimethylphenyl]-methoxy]phenyl]amino]-1,1,1-trifluoro-2-propanol;

3-[[[2-fluoro-5-(trifluoromethyl)phenyl]methyl][3-[[3-(trifluoromethylthio)-phenyl]methoxy]phenyl]amino]-1,1,1-trifluoro-2-propanol;

3-[[[2-fluoro-5-(trifluoromethyl)phenyl]methyl][3-[[3,5-difluorophenyl]-methoxy]phenyl]amino]-1,1,1-trifluoro-2-propanol;

3-[[[2-fluoro-5-(trifluoromethyl)phenyl]methyl][3-[cyclohexylmethoxy]-phenyl]amino]-1,1,1-trifluoro-2-propanol;

3-[[3-(2-difluoromethoxy-4-pyridyloxy)phenyl][[2-fluoro-5-(trifluoromethyl)-phenyl]methyl]amino]-1,1,1-trifluoro-2-propanol;

3-[[3-(2-trifluoromethyl-4-pyridyloxy)phenyl][[2-fluoro-5-(trifluoromethyl)-phenyl]methyl]amino]-1,1,1-trifluoro-2-propanol;

3-[[3-(3-difluoromethoxyphenoxy)phenyl][[2-fluoro-5-(trifluoromethyl)phenyl]methyl]amino]-1,1,1-trifluoro-2-propanol;

3-[[[3-(3-trifluoromethylthio)phenoxy]phenyl][[2-fluoro-5-(trifluoromethyl)phenyl]methyl]amino]-1,1,1-trifluoro-2-propanol;

3-[[3-(4-chloro-3-trifluoromethylphenoxy)phenyl][[2-fluoro-5-(trifluoromethyl)phenyl]methyl]amino]-1,1,1-trifluoro-2-propanol;

3-[[3-(3-trifluoromethoxyphenoxy)phenyl][[2-fluoro-4-(trifluoromethyl)phenyl]methyl]amino]-1,1,1-trifluoro-2-propanol;

3-[[3-(3-isopropylphenoxy)phenyl][[2-fluoro-4-(trifluoromethyl)phenyl]-methyl]amino]-1,1,1-trifluoro-2-propanol;

3-[[3-(3-cyclopropylphenoxy)phenyl][[2-fluoro-4-(trifluoromethyl)phenyl]-methyl]amino]-1,1,1-trifluoro-2-propanol;

3-[[3-(3-(2-furyl)phenoxy)phenyl][[2-fluoro-4-(trifluoromethyl)phenyl]-methyl]amino]-1,1,1-trifluoro-2-propanol;

3-[[3-(2,3-dichlorophenoxy)phenyl][[2-fluoro-4-(trifluoromethyl)phenyl]-methyl]amino]-1,1,1-trifluoro-2-propanol;

3-[[3-(4-fluorophenoxy)phenyl][[2-fluoro-4-(trifluoromethyl)phenyl]-methyl]amino]-1,1,1-trifluoro-2-propanol;

3-[[3-(4-methylphenoxy)phenyl][[2-fluoro-4-(trifluoromethyl)phenyl]-methyl]amino]-1,1,1-trifluoro-2-propanol;

3-[[3-(2-fluoro-5-bromophenoxy)phenyl][[2-fluoro-4-(trifluoromethyl)phenyl]methyl]amino]-1,1,1-trifluoro-2-propanol;

3-[[3-(4-chloro-3-ethylphenoxy)phenyl][[2-fluoro-4-(trifluoromethyl)phenyl]methyl]amino]-1,1,1-trifluoro-2-propanol;

3-[[3-[3-(1,1,2,2-tetrafluoroethoxy)phenoxy]phenyl][[2-fluoro-4-(trifluoromethyl)phenyl]methyl]amino]-1,1,1-trifluoro-2-propanol;

3-[[3-[3-(pentafluoroethyl)phenoxy]phenyl][[2-fluoro-4-(trifluoromethyl)phenyl]methyl]amino]-1,1,1-trifluoro-2-propanol;

3-[[3-(3,5-dimethylphenoxy)phenyl][[2-fluoro-4-(trifluoromethyl)phenyl]-methyl]amino]-1,1,1-trifluoro-2-propanol;

3-[[3-(3-ethylphenoxy)phenyl][[2-fluoro-4-(trifluoromethyl)phenyl]methyl]-amino]-1,1,1-trifluoro-2-propanol;

3-[[3-(3-t-butylphenoxy)phenyl][[2-fluoro-4-(trifluoromethyl)phenyl]methyl]-amino]-1,1,1-trifluoro-2-propanol;

3-[[3-(3-methylphenoxy)phenyl][[2-fluoro-4-(trifluoromethyl)phenyl]methyl]-amino]-1,1,1-trifluoro-2-propanol;

3-[[3-(5,6,7,8-tetrahydro-2-naphthoxy)phenyl][[2-fluoro-4-(trifluoromethyl)-phenyl]methyl]amino]-1,1,1-trifluoro-2-propanol;

3-[[3-(phenoxy)phenyl][[2-fluoro-4-(trifluoromethyl)phenyl]methyl]amino]-1,1,1-trifluoro-2-propanol;

3-[[3-[3-(N,N-dimethylamino)phenoxy]phenyl][[2-fluoro-4-(trifluoromethyl)-phenyl]methyl]amino]-1,1,1-trifluoro-2-propanol;

3-[[[2-fluoro-4-(trifluoromethyl)phenyl]methyl][3-[[3-(trifluoromethoxy)phenyl]methoxy]phenyl]amino]-1,1,1-trifluoro-2-propanol;

3-[[[2-fluoro-4-(trifluoromethyl)phenyl]methyl][3-[[3-(trifluoromethyl)phenyl]methoxy]phenyl]amino]-1,1,1-trifluoro-2-propanol;

3-[[[2-fluoro-4-(trifluoromethyl)phenyl]methyl][3-[[3,5-dimethylphenyl]-methoxy]phenyl]amino]-1,1,1-trifluoro-2-propanol;

3-[[[2-fluoro-4-(trifluoromethyl)phenyl]methyl][3-[[3-(trifluoromethylthio)-phenyl]methoxy]phenyl]amino]-1,1,1-trifluoro-2-propanol;

3-[[[2-fluoro-4-(trifluoromethyl)phenyl]methyl][3-[[3,5-difluorophenyl]-methoxy]phenyl]amino]-1,1,1-trifluoro-2-propanol;

3-[[[2-fluoro-4-(trifluoromethyl)phenyl]methyl][3-[cyclohexylmethoxy]-phenyl]amino]-1,1,1-trifluoro-2-propanol;

3-[[3-(2-difluoromethoxy-4-pyridyloxy)phenyl][[2-fluoro-4-(trifluoromethyl)-phenyl]methyl]amino]-1,1,1-trifluoro-2-propanol;

3-[[3-(2-trifluoromethyl-4-pyridyloxy)phenyl][[2-fluoro-4-(trifluoromethyl)-phenyl]methyl]amino]-1,1,1-trifluoro-2-propanol;

3-[[3-(3-difluoromethoxyphenoxy)phenyl][[2-fluoro-4-(trifluoromethyl)phenyl]methyl]amino]-1,1,1-trifluoro-2-propanol;

3-[[[3-(3-trifluoromethylthio)phenoxy]phenyl][[2-fluoro-4-(trifluoromethyl)-phenyl]methyl]amino]-1,1,1-trifluoro-2-propanol; and 3-[[3-(4-chloro-3-trifluoromethylphenoxy)phenyl][[2-fluoro-4-(trifluoromethyl)phenyl]methyl]amino]-1,1,1-trifluoro-2-propanol.

Another class of CETP inhibitors that finds utility with the present invention consists of substituted N-Aliphatic-N-Aromatic tertiary-Heteroalkylamines having the Formula XV

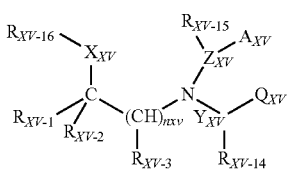

Formula XV and pharmaceutically acceptable forms thereof, wherein:

$n_{XV}$ is an integer selected from 1 through 2;

$A_{XV}$ and $Q_{XV}$ are independently selected from the group consisting of —$CH_2(CR_{XV-37}R_{XV-38})_{vXV}$—$(CR_{XV-33}R_{XV-34})_{uXV}$-$T_{XV}$-$(CR_{XV-35}R_{XV-36})_{wXV}$—H,

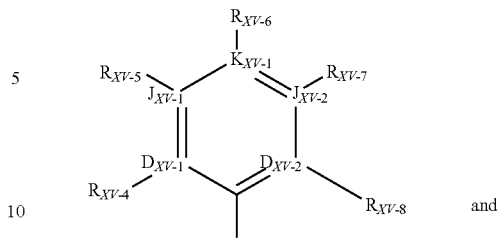

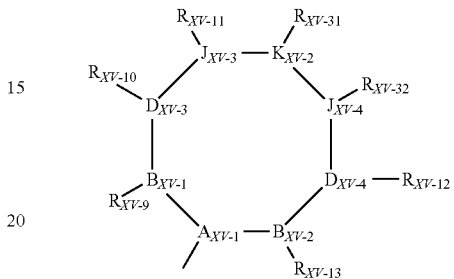

with the provisos that one of $A_{XV}$ and $Q_{XV}$ must be AQ-1 and that one of $A_{XV}$ and $Q_{XV}$ must be selected from the group consisting of AQ-2 and —$CH_2(CR_{XV-37}R_{XV-38})_{vXV}$—$(CR_{XV-33}R_{XV-34})_{uXV}$-$T_{XV}$-$(CR_{XV-35}R_{XV-36})_{wXV}$—H;

$T_{XV}$ is selected from the group consisting of a single covalent bond, O, S, S(O), S(O)$_2$, C($R_{XV-33}$)=C($R_{XV-35}$), and C≡C;

$_{vXV}$ is an integer selected from 0 through 1 with the proviso that $_{vXV}$ is 1 when any one of $R_{XV-33}$, $R_{XV-34}$, $R_{XV-35}$, and $R_{XV-36}$ is aryl or heteroaryl;

$_{uXV}$ and $_{wXV}$ are integers independently selected from 0 through 6;

$A_{XV-1}$ is C($R_{XV-30}$);

$D_{XV-1}$, $D_{XV-2}$, $J_{XV-1}$, $J_{XV-2}$, and $K_{XV-1}$ are independently selected from the group consisting of C, N, O, S and a covalent bond with the provisos that no more than one of $D_{XV-1}$, $D_{XV-2}$, $J_{XV-1}$, $J_{XV-2}$, and $K_{XV-1}$ is a covalent bond, no more than one of $D_{XV-1}$, $D_{XV-2}$, $J_{XV-1}$, $J_{XV-2}$, and $K_{XV-1}$ is O, no more than one of $D_{XV-1}$, $D_{XV-2}$, $J_{XV-1}$, $J_{XV-2}$, and $K_{XV-1}$ is S, one of $D_{XV-1}$, $D_{XV-2}$, $J_{XV-1}$, $J_{XV-2}$, and $K_{XV-1}$ must be a covalent bond when two of $D_{XV-1}$, $D_{XV-2}$, $J_{XV-1}$, $J_{XV-2}$, and $K_{XV-1}$ are O and S, and no more than four of $D_{XV-1}$, $D_{XV-2}$, $J_{XV-1}$, $J_{XV-2}$, and $K_{XV-1}$ are N;

$B_{XV-1}$, $B_{XV-2}$, $D_{XV-3}$, $D_{XV-4}$, $J_{XV-3}$, $J_{XV-4}$, and $K_{XV-2}$ are independently selected from the group consisting of C, C($R_{XV-30}$), N, O, S and a covalent bond with the provisos that no more than 5 of $B_{XV-1}$, $B_{XV-2}$, $D_{XV-3}$, $D_{XV-4}$, $J_{XV-3}$, $J_{XV-4}$, and $K_{XV-2}$ are a covalent bond, no more than two of $B_{XV-1}$, $B_{XV-2}$, $D_{XV-3}$, $D_{XV-4}$, $J_{XV-3}$, $J_{XV-4}$, and $K_{XV-2}$ are O, no more than two of $B_{XV-1}$, $B_{XV-2}$, $D_{XV-3}$, $D_{XV-4}$, $J_{XV-3}$, $J_{XV-4}$, and $K_{XV-2}$ are S, no more than two of $B_{XV-1}$, $B_{XV-2}$, $D_{XV-3}$, $D_{XV-4}$, $J_{XV-3}$, $J_{XV-4}$, and $K_{XV-2}$ are simultaneously O and S, and no more than two of $B_{XV-1}$, $B_{XV-2}$, $D_{XV-3}$, $D_{XV-4}$, $J_{XV-3}$, $J_{XV-4}$, and $K_{XV-2}$ are N;

$B_{XV-1}$ and $D_{XV-3}$, $D_{XV-3}$ and $J_{XV-3}$, $J_{XV-3}$ and $K_{XV-2}$, $K_{XV-2}$ and $J_{XV-4}$, $J_{XV-4}$ and $D_{XV-4}$, and $D_{XV-4}$ and $B_{XV-2}$ are independently selected to form an in-ring spacer pair wherein said spacer pair is selected from the group consisting of C($R_{XV-33}$)=C($R_{XV-35}$) and N=N with the provisos that AQ-2 must be a ring of at least five contiguous members, that no more than two of the group of said spacer pairs are simultaneously C($R_{XV-33}$)=C($R_{XV-35}$) and that no more than one of the group of said spacer pairs can be N=N unless the other spacer pairs are other than C($R_{XV-33}$)=C($R_{XV-35}$), O, N, and S;

$R_{XV-1}$ is selected from the group consisting of haloalkyl and haloalkoxymethyl;

$R_{XV-2}$ is selected from the group consisting of hydrido, aryl, alkyl, alkenyl, haloalkyl, haloalkoxy, haloalkoxyalkyl, perhaloaryl, perhaloaralkyl, perhaloaryloxyalkyl and heteroaryl;

$R_{XV-3}$ is selected from the group consisting of hydrido, aryl, alkyl, alkenyl, haloalkyl, and haloalkoxyalkyl;

$Y_{XV}$ is selected from the group consisting of a covalent single bond, $(CH_2)_q$ wherein q is an integer selected from 1 through 2 and $(CH_2)_j$—O—$(CH_2)_k$ wherein j and k are integers independently selected from 0 through 1;

$Z_{XV}$ is selected from the group consisting of covalent single bond, $(CH_2)_q$ wherein q is an integer selected from 1 through 2, and $(CH_2)_j$—O—$(CH_2)_k$ wherein j and k are integers independently selected from 0 through 1;

$R_{XV-4}$, $R_{XV-8}$, $R_{XV-9}$ and $R_{XV-13}$ are independently selected from the group consisting of hydrido, halo, haloalkyl, and alkyl;

$R_{XV-30}$ is selected from the group consisting of hydrido, alkoxy, alkoxyalkyl, halo, haloalkyl, alkylamino, alkylthio, alkylthioalkyl, alkyl, alkenyl, haloalkoxy, and haloalkoxyalkyl with the proviso that $R_{XV-30}$ is selected to maintain the tetravalent nature of carbon, trivalent nature of nitrogen, the divalent nature of sulfur, and the divalent nature of oxygen;

$R_{XV-30}$, when bonded to $A_{XV-1}$, is taken together to form an intra-ring linear spacer connecting the $A_{XV-1}$-carbon at the point of attachment of $R_{XV-30}$ to the point of bonding of a group selected from the group consisting of $R_{XV-10}$, $R_{XV-11}$, $R_{XV-12}$, $R_{XV-31}$, and $R_{XV-32}$ wherein said intra-ring linear spacer is selected from the group consisting of a covalent single bond and a spacer moiety having from 1 through 6 contiguous atoms to form a ring selected from the group consisting of a cycloalkyl having from 3 through 10 contiguous members, a cycloalkenyl having from 5 through 10 contiguous members, and a heterocyclyl having from through 10 contiguous members;

$R_{XV-30}$, when bonded to $A_{XV-1}$, is taken together to form an intra-ring branched spacer connecting the $A_{XV-1}$-carbon at the point of attachment of $R_{XV-30}$ to the points of bonding of each member of any one of substituent pairs selected from the group consisting of subsititvent pairs $R_{XV-10}$ and $R_{XV-11}$, $R_{XV-10}$ and $R_{XV-31}$, $R_{XV-10}$ and $R_{XV-32}$, $R_{XV-10}$ and $R_{XV-12}$, $R_{XV-11}$ and $R_{XV-31}$, $R_{XV-11}$ and $R_{XV-32}$, $R_{XV-11}$ and $R_{XV-12}$, $R_{XV-31}$ and $R_{XV-32}$, $R_{XV-31}$ and $R_{XV-12}$, and $R_{XV-32}$ and $R_{XV-12}$ and wherein said intra-ring branched spacer is selected to form two rings selected from the group consisting of cycloalkyl having from 3 through 10 contiguous members, cycloalkenyl having from 5 through 10 contiguous members, and heterocyclyl having from 5 through 10 contiguous members;

$R_{XV-4}$, $R_{XV-5}$, $R_{XV-6}$, $R_{XV-7}$, $R_{XV-8}$, $R_{XV-9}$, $R_{XV-10}$, $R_{XV-11}$, $R_{XV-12}$, $R_{XV-13}$, $R_{XV-31}$, $R_{XV-32}$, $R_{XV-33}$, $R_{XV-34}$, $R_{XV-35}$ and $R_{XV-36}$ are independently selected from the group consisting of hydrido, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, haloalkylthio, alkanoyloxy, alkoxy, alkoxyalkyl, haloalkoxyalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkylamidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, hydoxyheteroaralkyl, haloalkoxyalkyl, aryl, heteroaralkynyl, aryloxy, aralkoxy, aryloxyalkyl, saturated heterocyclyl, partially saturated heterocyclyl, heteroaryl, heteroaryloxy, heteroaryloxyalkyl, arylalkenyl, heteroarylalkenyl, carboxyalkyl, carboalkoxy, alkoxycarboxamido, alkylamidocarbonylamido, alkylamidocarbonylamido, carboalkoxyalkyl, carboalkoxyalkenyl, carboaralkoxy, carboxamido, carboxamidoalkyl, cyano, carbohaloalkoxy, phosphono, phosphonoalkyl, diaralkoxyphosphono, and diaralkoxyphosphonoalkyl with the provisos that $R_{XV-4}$, $R_{XV-5}$, $R_{XV-6}$, $R_{XV-7}$, $R_{XV-8}$, $R_{XV-9}$, $R_{XV-10}$, $R_{XV-11}$, $R_{XV-12}$, $R_{XV-13}$, $R_{XV-31}$, $R_{XV-32}$, $R_{XV-33}$, $R_{XV-34}$, $R_{XV-35}$, and $R_{XV-36}$ are each independently selected to maintain the tetravalent nature of carbon, trivalent nature of nitrogen, the divalent nature of sulfur, and the divalent nature of oxygen, that no more than three of the $R_{XV-33}$ and $R_{XV-34}$ substituents are simultaneously selected from other than the group consisting of hydrido and halo, and that no more than three of the $R_{XV-35}$ and $R_{XV-36}$ substituents are simultaneously selected from other than the group consisting of hydrido and halo;

$R_{XV-9}$, $R_{XV-10}$, $R_{XV-11}$, $R_{XV-12}$, $R_{XV-13}$, $R_{XV-31}$, and $R_{XV-32}$ are independently selected to be oxo with the provisos that $B_{XV-1}$, $B_{XV-2}$, $D_{XV-3}$, $D_{XV-4}$, $J_{XV-3}$, $J_{XV-4}$, and $K_{XV-2}$ are independently selected from the group consisting of C and S, no more than two of $R_{XV-9}$, $R_{XV-10}$, $R_{XV-11}$, $R_{XV-12}$, $R_{XV-13}$, $R_{XV-31}$, and $R_{XV-32}$ are simultaneously oxo, and that $R_{XV-9}$, $R_{XV-10}$, $R_{XV-11}$, $R_{XV-12}$, $R_{XV-13}$, $R_{XV-31}$, and $R_{XV-32}$ are each independently selected to maintain the tetravalent nature of carbon, trivalent nature of nitrogen, the divalent nature of sulfur, and the divalent nature of oxygen;

$R_{XV-4}$ and $R_{XV-5}$, $R_{XV-5}$ and $R_{XV-6}$, $R_{XV-6}$ and $R_{XV-7}$, $R_{XV-7}$ and $R_{XV-8}$, $R_{XV-9}$ and $R_{XV-10}$, $R_{XV-10}$ and $R_{XV-11}$, $R_{XV-11}$ and $R_{XV-31}$, $R_{XV-31}$ and $R_{XV-32}$, $R_{XV-32}$ and $R_{XV-12}$, and $R_{XV-12}$ and $R_{XV-13}$ are independently selected to form spacer pairs wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the provisos that no more than one of the group consisting of spacer pairs $R_{XV-4}$ and $R_{XV-5}$, $R_{XV-5}$ and $R_{XV-6}$, $R_{XV-6}$ and $R_{XV-7}$, $R_{XV-7}$ and $R_{XV-8}$ is used at the same time and that no more than one of the group consisting of spacer pairs $R_{XV-9}$ and $R_{XV-10}$, $R_{XV-10}$ and $R_{XV-11}$, $R_{XV-11}$ and $R_{XV-31}$, $R_{XV-31}$ and $R_{XV-32}$, $R_{XV-32}$ and $R_{XV-12}$, and $R_{XV-12}$ and $R_{XV-13}$ are used at the same time;

$R_{XV-9}$ and $R_{XV-11}$, $R_{XV-9}$ and $R_{XV-12}$, $R_{XV-9}$ and $R_{XV-13}$ $R_{XV-9}$ and $R_{XV-31}$, $R_{XV-9}$ and $R_{XV-32}$, $R_{XV-10}$ and $R_{XV-12}$, $R_{XV-10}$ and $R_{XV-13}$, $R_{XV-10}$ and $R_{XV-31}$, $R_{XV-10}$ and $R_{XV-32}$, $R_{XV-11}$ and $R_{XV-12}$, $R_{XV-11}$ and $R_{XV-13}$, $R_{XV-11}$ and $R_{XV-32}$, $R_{XV-12}$ and $R_{XV-31}$, $R_{XV-13}$ and $R_{XV-31}$, and $R_{XV-13}$ and $R_{XV-32}$ are independently selected to form a spacer pair wherein said spacer pair is taken together to form a linear spacer moiety selected from the group consisting of a covalent single bond and a moiety having from 1 through 3 contiguous atoms to form a ring selected from the group consisting of a cycloalkyl having from 3 through 8 contiguous members, a cycloalkenyl having from 5 through 8 contiguous members, a saturated heterocyclyl having from 5 through 8 contiguous members and a partially saturated heterocyclyl having from 5 through 8 contiguous members with the provisos that no more than one of said group of spacer pairs is used at the same time;

$R_{XV-37}$ and $R_{XV-38}$ are independently selected from the group consisting of hydrido, alkoxy, alkoxyalkyl, hydroxy, amino, thio, halo, haloalkyl, alkylamino, alkylthio, alkylthioalkyl, cyano, alkyl, alkenyl, haloalkoxy, and haloalkoxyalkyl.

Compounds of Formula XV and their methods of manufacture are disclosed in PCT Publication No. WO 00/18723, which is incorporated herein by reference in its entirety for all purposes.

In a preferred embodiment, the CETP inhibitor is selected from the following compounds of Formula XV:

3-[[3-(4-chloro-3-ethylphenoxy)phenyl](cyclohexylmethyl) amino]-1,1,1-trifluoro-2-propanol;
3-[[3-(4-chloro-3-ethylphenoxy)phenyl](cyclopentylmethyl)amino]-1,1,1-trifluoro-2-propanol;
3-[[3-(4-chloro-3-ethylphenoxy)phenyl](cyclopropylmethyl)amino]-1,1,1-trifluoro-2-propanol;
3-[[3-(4-chloro-3-ethylphenoxy)phenyl][(3-trifiuoromethyl) cyclohexyl-methyl]amino]-1,1,1-trifluoro-2-propanol;
3-[[3-(4-chloro-3-ethylphenoxy)phenyl][(3-pentafluoroethyl)cyclohexyl-methyl]amino]-1,1,1-trifluoro-2-propanol;
3-[[3-(4-chloro-3-ethylphenoxy)phenyl][(3-trifluoromethoxy)cyclohexyl-methyl]amino]-1,1,1-trifluoro-2-propanol;
3-[[3-(4-chloro-3-ethylphenoxy)phenyl][[3-(1,1,2,2-tetrafluoroethoxy)cyclo-hexylmethyl]amino]-1,1,1-trifluoro-2-propanol;
3-[[3-(3-trifluoromethoxyphenoxy)phenyl](cyclohexylmethyl)amino]-1,1,1-trifluoro-2-propanol;
3-[[3-(3-trifluoromethoxyphenoxy)phenyl](cyclopentylmethyl)amino]-1,1,1-trifluoro-2-propanol;
3-[[3-(3-trifluoromethoxyphenoxy)phenyl](cyclopropylmethyl)amino]-1,1,1-trifluoro-2-propanol;
3-[[3-(3-trifluoromethoxyphenoxy)phenyl][(3-trifluoromethyl)cyclohexyl-methyl]amino]-1,1,1-trifluoro-2-propanol;
3-[[3-(3-trifluoromethoxyphenoxy)phenyl]](3-pentafluoroethyl)cyclohexyl-methyl]amino]-1,1,1-trifluoro-2-propanol;
3-[[3-(3-trifluoromethoxyphenoxy)phenyl][(3-trifluoromethoxy)cyclohexyl-methyl]amino]-1,1,1-trifluoro-2-propanol;
3-[[3-(3-trifluoromethoxyphenoxy)phenyl][[3-(1,1,2,2-tetrafluoroethoxy)cyclohexyl-methyl]amino]-1,1,1-trifluoro-2-propanol;
3-[[3-(3-isopropylphenoxy)phenyl](cyclohexylmethyl] amino]-1,1,1-trifluoro-2-propanol:
3-[[3-(3-isopropylphenoxy)phenyl](cyclopentylmethyl] amino]-1,1,1-trifluoro-2-propanol;
3-[[3-(3-isopropylphenoxy)phenyl](cyclopropylmethyl) amino]-1,1,1-trifluoro-2-propanol;
3-[[3-(3-isopropylphenoxy)phenyl][(3-trifluoromethyl) cyclohexyl-methyl]amino]-1,1,1-trifluoro-2-propanol;
3-[[3-(3-isopropylphenoxy)phenyl][(3-pentafluoroethyl) cyclohexyl-methyl]amino]-1,1,1-trifluoro-2-propanol;
3-[[3-(3-isopropylphenoxy)phenyl][(3-trifluoromethoxy) cyclohexyl-methyl]amino]-1,1,1-trifluoro-2-propanol;
3-[[3-(3-isopropylphenoxy)phenyl][3-(1,1,2,2-tetrafluoroethoxy)cyclohexyl-methyl]amino]-1,1,1-trifluoro-2-propanol;
3-[[3-(2,3-dichlorophenoxy)phenyl](cyclohexylmethyl) amino]-1,1,1-trifluoro-2-propanol;
3-[[3-(2,3-dichlorophenoxy)phenyl](cyclopentylmethyl) amino]-1,1,1-trifluoro-2-propanol;
3-[[3-(2,3-dichlorophenoxy)phenyl](cyclopropylmethyl) amino]-1,1,1-trifluoro-2-propanol;
3-[[3-(2.3-dichlorophenoxy)phenyl][(3-trifluoromethyl)cyclohexyl-methyl]amino]-1,1,1-trifluoro-2-propanol;
3-[[3-(2,3-dichlorophenoxy)phenyl][(3-pentafluoroethyl) cyclohexyl-methyl]amino]-1,1,1-trifluoro-2-propanol;
3-[[3-(2,3-dichlorophenoxy)phenyl][(3-trifluoromethoxy) cyclohexyl-methyl]amino]-1,1,1-trifluoro-2-propanol;
3-[[3-(2,3-dichlorophenoxy)phenyl][3-(1,1,2,2-tetrafluoroethoxy)cyclo-hexyl-methyl]amino]-1,1,1-trifluoro-2-propanol;
3-[[3-(4-fluorophenoxy)phenyl](cyclohexylmethyl)amino]-1,1,1-trifluoro-2-propanol;
3-[[3-(4-fluorophenoxy)phenyl](cyclopentylmethyl) amino]-1,1,1-trifluoro-2-propanol;
3-[[3-(4-fluorophenoxy)phenyl](cyclopropylmethyl)amino-1,1,1-trifluoro-2-propanol;
3-[[3-(4-fluorophenoxy)phenyl][(3-trifluoromethyl)cyclohexyl-methyl]amino]-1,1,1-trifluoro-2-propanol;
3-[[3-(4-fluorophenoxy)phenyl][(3-pentafluoroethyl)cyclohexyl-methyl]amino]-1,1,1-trifluoro-2-propanol;
3-[[3-(4-fluorophenoxy)phenyl][(3-trifluoromethoxy)cyclohexyl-methyl]amino]-1,1,1-trifluoro-2-propanol;
3-[[3-(4-fluorophenoxy)phenyl][[3-(1,1,2,2-tetrafluoroethoxy)cyclohexyl-methyl]amino]-1,1,1-trifluoro-2-propanol;
3-[[3-(3-trifluoromethoxyphenoxy]phenyl](cyclohexylmethyl)amino]-1,1,1-trifluoro-2-propanol;
3-[[3-(3-trifluoromethoxyphenoxy)phenyl](cyclopentylmethyl)amino]-1,1,1-trifluoro-2-propanol;
3-[[3-(3-trifluoromethoxyphenoxy)phenyl](cyclopropylmethyl)amino]-1,1,1-trifluoro-2-propanol;
3-[[3-(3-trifluoromethoxyphenoxy)phenyl][(3-trifluoromethyl)cyclohexyl-methyl]amino]-1,1,1-trifluoro-2-propanol;
3-[[3-(3-trifluoromethoxyphenoxy)phenyl][(3-pentafluoroethyl)cyclohexyl-methyl]amino]-1,1,1-trifluoro-2-propanol;
3-[[3-(3-trifluoromethoxyphenoxy]phenyl][(3-trifluoromethoxy)cyclohexyl-methyl]amino]-1,1,1-trifluoro-2-propanol;
3-[[3-(3-trifluoromethoxyphenoxy)phenyl][3-(1,1,2,2-tetrafluoroethoxy)-cyclohexylmethyl]amino]-1,1,1-trifluoro-2-propanol;
3-[[3-(3-trifluoromethylbenzyloxy)phenyl](cyclohexylmethyl)amino]-1,1,1-trifluoro-2-propanol;
3-[[3-(3-trifluoromethylbenzyloxy)phenyl](cyclopentylmethyl)amino]-1,1,1-trifluoro-2-propanol;
3-[[3-(3-trifluoromethylbenzyloxy)phenyl](cyclopropylmethyl)amino]-1,1,1-trifluoro-2-propanol;

3-[[3-(3-trifluoromethylbenzyloxy)phenyl][(3-trifluorom-ethyl)cyclohexyl-methyl]amino]-1,1,1-trifluoro-2-propanol;

3-[[3-(3-trifluoromethylbenzyloxy)phenyl][(3-pentafluoro-ethyl)cyclohexyl-methyl]amino]-1,1,1-trifluoro-2-propanol;

3-[[3-(3-trifluoromethylbenzyloxy)phenyl][(3-trifluoromethoxy)cyclohexyl-methyl]amino]-1,1,1-trifluoro-2-propanol;

3-[[3-(3-trifluoromethylbenzyloxy)phenyl][3-(1,1,2,2-tetrafluoroethoxy)cyclohexyl-methyl]amino]-1,1,1-trifluoro-2-propanol;

3-[[[(3-trifluoromethyl)phenyl]methyl](cyclohexyl)amino]-1,1,1-trifluoro-2-propanol;

3-[[[(3-pentafluoroethyl)phenyl]methyl](cyclohexyl)amino]-1,1,1-trifluoro-2-propanol;

3-[[[(3-trifluoromethoxy)phenyl]methyl](cyclohexyl)amino]-1,1,1-trifluoro-2-propanol;

3-[[[3-(1,1,2,2-tetrafluoroethoxy)phenyl]methyl](cyclohexyl)amino]-1,1,1-trifluoro-2-propanol;

3-[[[(3-trifluoromethyl)phenyl]methyl](4-methylcyclohexyl)amino]-1,1,1-trifluoro-2-propanol;

3-[[[(3-pentafluoroethyl)phenyl]methyl](4-methylcyclohexyl)amino]-1,1,1-trifluoro-2-propanol;

3-[[[(3-trifluoromethoxy)phenyl]methyl](4-methylcyclohexyl)amino]-1,1,1-trifluoro-2-propanol;

3-[[[3-(1,1,2,2-tetrafluoroethoxy)phenyl]methyl](4-methylcyclohexyl)amino]-1,1,1-trifluoro-2-propanol;

3-[[[(3-trifluoromethyl)phenyl]methyl](3-trifluoromethylcyclohexyl)amino]-1,1,1-trifluoro-2-propanol;

3-[[[(3-pentafluoroethyl)phenyl]methyl](3-trifluoromethylcyclohexyl)amino]-1,1,1-trifluoro-2-propanol;

3-[[[(3-trifluoromethoxy)phenyl]methyl](3-trifluoromethylcyclohexyl)amino]-1,1,1-trifluoro-2-propanol;

3-[[[3-(1,1,2,2-tetrafluoroethoxy)phenyl]methyl](3-trifluoromethylcyclohexyl)amino]-1,1,1-trifluoro-2-propanol;

3-[[[(3-trifluoromethyl)phenyl]methyl][3-(4-chloro-3-ethylphenoxy)cyclo-hexyl]amino]-1,1,1-trifluoro-2-propanol;

3-[[[(3-pentafluoroethyl)phenyl]methyl][3-(4-chloro-3-ethylphenoxy)cyclo-hexyl]amino]-1,1,1-trifluoro-2-propanol;

3-[[[(3-trifluoromethoxy)phenyl]methyl][3-(4-chloro-3-methylphenoxy)cyclo-hexyl]amino]-1,1,1-trifluoro-2-propanol;

3-[[[3-(1,1,2,2-tetrafluoroethoxy)phenyl]methyl][3-(4-chloro-3-ethylphenoxy)-cyclohexyl]amino]-1,1,1-trifluoro-2-propanol;

3-[[[(3-trifluoromethyl)phenyl]methyl](3-phenoxycyclohexyl)amino]-1,1,1-trifluoro-2-propanol;

3-[[[(3-pentafluoroethyl)phenyl]methyl](3-phenoxycyclohexyl)amino]-1,1,1-trifluoro-2-propanol;

3-[[[(3-trifluoromethoxy)phenyl]methyl](3-phenoxycyclohexyl)amino]-1,1,1-trifluoro-2-propanol;

3-[[[3-(1,1,2,2-tetrafluoroethoxy)phenyl]methyl](3-phenoxycyclohexyl)amino]-1,1,1-trifluoro-2-propanol;

3-[[[(3-trifloromethyl)phenyl]methyl](3-isopropoxycyclohexyl)amino]-1,1,1-trifluoro-2-propanol;

3-[[[(3-pentafluoroethyl)phenyl]methyl](3-isopropoxycyclohexyl)amino]-1,1,1-trifluoro-2-propanol;

3-[[[(3-trifluoromethoxy)phenyl]methyl](3-isopropoxycyclohexyl)amino]-1,1,1-trifluoro-2-propanol;

3-[[[3-(1,1,2,2-tetrafluoroethoxy)phenyl]methyl](3-isopropoxycyclohexyl)-amino]-1,1,1-trifluoro-2-propanol;

3-[[[(3-trifluoromethyl)phenyl]methyl](3-cyclopentyloxycyclohexyl]amino]-1,1,1-trifluoro-2-propanol;

3-[[[(3-pentafluoroethyl)phenyl]methyl](3-cyclopentyloxycyclohexyl)amino]-1,1,1-trifluoro-2-propanol;

3-[[[(3-trifluoromethoxy)phenyl]methyl](3-cyclopentyloxycyclohexyl)amino]-1,1,1-trifluoro-2-propanol;

3-[[[3-(1,1,2,2-tetrafluoroethoxy)phenyl]methyl](3-cyclopentyloxycyclohexyl)-amino]-1,1,1-trifluoro-2-propanol;

3-[[[(2-trifluoromethyl)pyrid-6-yl]methyl](3-isopropoxycyclohexyl)amino]-1,1,1-trifluoro-2-propanol;

3-[[[(2-trifluoromethyl)pyrid-6-yl]methyl](3-cyclopentyloxycyclohexyl)-amino]-1,1,1-trifluoro-2-propanol;

3-[[[(2-trifluoromethyl)pyrid-6-yl]methyl](3-phenoxycyclohexyl)amino]-1,1,1-trifluoro-2-propanol;

3-[[[(2-trifluoromethyl)pyrid-6-yl]methyl](3-trifluoromethylcyclohexyl)amino]-1,1,1-trifluoro-2-propanol;

3-[[[(2-trifluoromethyl)pyrid-6-yl]methyl][3-(4-chloro-3-ethylphenoxy)cyclo-hexyl]amino]-1,1,1-trifluoro-2-propanol;

3-[[[(2-trifluoromethyl)pyrid-6-yl]methyl][3-(1,1,2,2-tetrafluoroethoxy)cyclo-hexyl]amino]-1,1,1-trifluoro-2-propanol;

3-[[[(2-trifluoromethyl)pyrid-6-yl]methyl](3-pentafluoroethylcyclohexyl)-amino]-1,1,1-trifluoro-2-propanol;

3-[[[(2-trifluoromethyl)pyrid-6-yl]methyl](3-trifluoromethoxycyclohexyl)-amino]-1,1,1-trifluoro-2-propanol;

3-[[[(3-trifluoromethyl)phenyl]methyl][3-(4-chloro-3-ethylphenoxy)propyl]-amino]-1,1,1-trifluoro-2-propanol;

3-[[[(3-pentafluoroethyl)phenyl]methyl][3-(4-chloro-3-ethylphenoxy)propyl]-amino]-1,1,1-trifluoro-2-propanol;

3-[[[(3-trifluoromethoxy)phenyl]methyl][3-(4-chloro-3-ethylphenoxy)propyl]-amino]-1,1,1-trifluoro-2-propanol;

3-[[[3-(1,1,2,2-tetrafluoroethoxy)phenyl]methyl][3-(4-chloro-3-ethylphenoxy)-propyl]amino]-1,1,1-trifluoro-2-propanol;

3-[[[(3-trifluoromethyl)phenyl]methyl][3-(4-chloro-3-ethylphenoxy)-2,2,-di-fluropropyl]amino]-1,1,1-trifluoro-2-propanol;

3-[[[(3-pentafluoroethyl)phenyl]methyl][3-(4-chloro-3-ethylphenoxy)-2,2-di-fluropropyl]amino]-1,1,1-trifluoro-2-propanol;

3-[[[(3-trifluoromethoxy)phenyl]methyl][3-(4-chloro-3-ethylphenoxy)-2,2,-di-fluropropyl]amino]-1,1,1-trifluoro-2-propanol;

3-[[[3-(1,1,2,2-tetrafluoroethoxy)phenyl]methyl][3-(4-chloro-3-ethylphenoxy)-2,2,-difluropropyl]amino]-1,1,1-trifluoro-2-propanol;

3-[[[(3-trifluoromethyl)phenyl]methyl][3-(isopropoxy)propyl]amino]-1,1,1-trifluoro-2-propanol;

3-[[[(3-pentafluoroethyl)phenyl]methyl][3-(isopropoxy)propyl]amino]-1,1,1-trifluoro-2-propanol;

3-[[[(3-trifluoromethoxy)phenyl]methyl][3-(isopropoxy)propyl]amino]-1,1,1-trifluoro-2-propanol;

3-[[[3-(1,1,2,2-tetrafluoroethoxy)phenyl]methyl]]3-(isopropoxy)propyl]amino]-1,1,1-trifluoro-2-propanol; and 3-[[[3-(1,1,2,2-tetrafluoroethoxy)phenyl]methyl][3-(phenoxy)propyl]amino]-1,1,1-trifluoro-2-propanol.

Another class of CETP inhibitors that finds utility with the present invention consists of (R)-chiral halogenated 1-substituted amino-(n+1)-alkanols having the Formula XVI Formula XVI

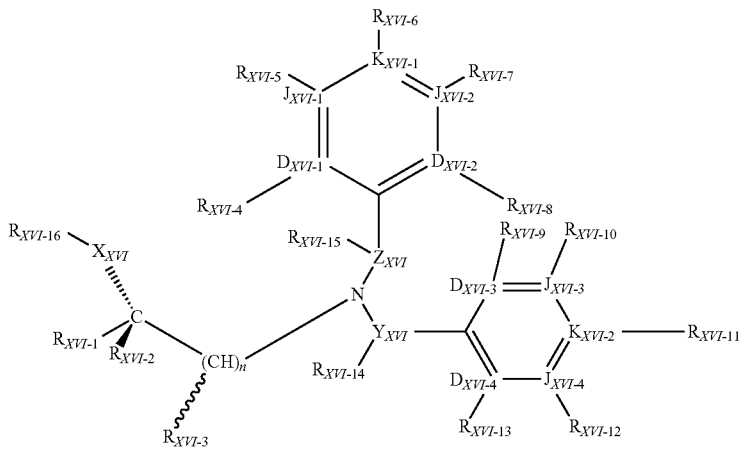

and pharmaceutically acceptable forms thereof, wherein:
$n_{XVI}$ is an integer selected from 1 through 4;
$X_{XVI}$ is oxy;
$R_{XVI-1}$ is selected from the group consisting of haloalkyl, haloalkenyl, haloalkoxymethyl, and haloalkenyloxymethyl with the proviso that $R_{XVI-1}$ has a higher Cahn-Ingold-Prelog stereochemical system ranking than both $R_{XVI-2}$ and $(CHR_{XVI-3})_n$—$N(A_{XVI})Q_{XVI}$ wherein $A_{XVI}$ is Formula XVI-(II) and Q is Formula XVI-(III);

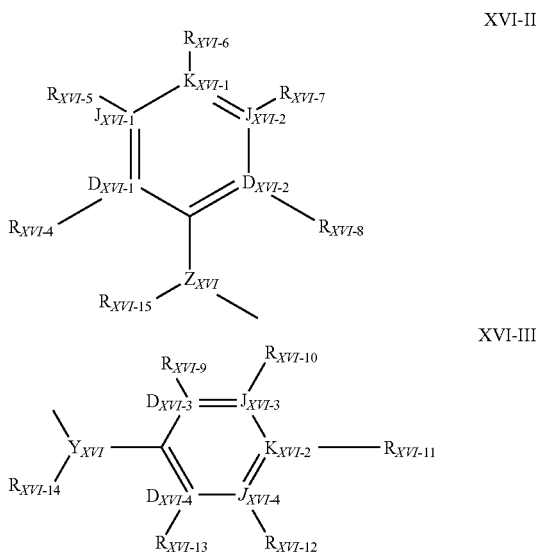

XVI-II

XVI-III $R_{XVI-16}$ is selected from the group consisting of hydrido, alkyl, acyl, aroyl, heteroaroyl, trialkylsilyl, and a spacer selected from the group consisting of a covalent single bond and a linear spacer moiety having a chain length of 1 to 4 atoms linked to the point of bonding of any aromatic substituent selected from the group consisting of $R_{XVI-4}$, $R_{XVI-8}$, $R_{XVI-9}$, and $R_{XVI-13}$ to form a heterocyclyl ring having from 5 through 10 contiguous members;

$D_{XVI-1}$, $D_{XVI-2}$, $J_{XVI-1}$, $J_{XVI-2}$ and $K_{XVI-1}$ are independently selected from the group consisting of C, N, O, S and covalent bond with the provisos that no more than one of $D_{XVI-1}$, $D_{XVI-2}$, $J_{XVI-1}$, $J_{XVI-2}$ and $K_{XVI-1}$ is a covalent bond, no more than one $D_{XVI-1}$, $D_{XVI-2}$, $J_{XVI-1}$, $J_{XVI-2}$ and $K_{XVI-1}$ is be O, no more than one of $D_{XVI-1}$, $D_{XVI-2}$, $J_{XVI-1}$, $J_{XVI-2}$ and $K_{XVI-1}$ is S, one of $D_{XVI-1}$, $D_{XVI-2}$, $J_{XVI-1}$, $J_{XVI-2}$ and $K_{XVI-1}$ must be a covalent bond when two of $D_{XVI-1}$, $D_{XVI-2}$, $J_{XVI-1}$, $J_{XVI-2}$ and $K_{XVI-1}$ are O, and S, and no more than four of $D_{XVI-1}$, $D_{XVI-2}$, $J_{XVI-1}$, $J_{XVI-2}$ and $K_{XVI-1}$ is N;

$D_{XVI-3}$, $D_{XVI-4}$, $J_{XVI-3}$, $J_{XVI-4}$ and $K_{XVI-2}$ are independently selected from the group consisting of C, N, O, S and covalent bond with the provisos that no more than one is a covalent bond, no more than one of $D_{XVI-3}$, $D_{XVI-4}$, $J_{XVI-3}$, $J_{XVI-4}$ and $K_{XVI-2}$ is O, no more than one of $D_{XVI-3}$, $D_{XVI-4}$, $J_{XVI-3}$, $J_{XVI-4}$ and $K_{XVI-2}$ S, no more than two of $D_{XVI-3}$, $D_{XVI-4}$, $J_{XVI-3}$, $J_{XVI-4}$ and $K_{XVI-2}$ is O and S, one of $D_{XVI-3}$, $D_{XVI-4}$, $J_{XVI-3}$, $J_{XVI-4}$ and $K_{XVI-2}$ must be a covalent bond when two of $D_{XVI-3}$, $D_{XVI-4}$, $J_{XVI-3}$, $J_{XVI-4}$ and $K_{XVI-2}$ are O and S, and no more than four of $D_{XVI-3}$, $D_{XVI-4}$, $J_{XVI-3}$, $J_{XVI-4}$ and $K_{XVI-2}$ are N;

$R_{XVI-2}$ is selected from the group consisting of hydrido, aryl, aralkyl, alkyl, alkenyl, alkenyloxyalkyl, haloalkyl, haloalkenyl, halocycloalkyl, haloalkoxy, haloalkoxyalkyl, haloalkenyloxyalkyl, halocycloalkoxy, halocycloalkoxyalkyl, perhaloaryl, perhaloaralkyl, perhaloaryloxyalkyl, heteroaryl, dicyanoalkyl, and carboalkoxycyanoalkyl, with the proviso that $R_{XVI-2}$ has a lower Cahn-Ingold-Prelog system ranking than both $R_{XVI-1}$ and $(CHR_{XVI-3})_n$—$N(A_{XVI})Q_{XVI}$;

$R_{XVI-3}$ is selected from the group consisting of hydrido, hydroxy, cyano, aryl, aralkyl, acyl, alkoxy, alkyl, alkenyl, alkoxyalkyl, heteroaryl, alkenyloxyalkyl, haloalkyl, haloalkenyl, haloalkoxy, haloalkoxyalkyl, haloalkenyloxyalkyl, monocyanoalkyl, dicyanoalkyl, carboxamide, and carboxamidoalkyl, with the provisos that $(CHR_{XVI-3})_n$—$N(A_{XVI})Q_{XVI}$ has a lower Cahn-Ingold-Prelog stereochemical system ranking than $R_{XVI-1}$ and a higher Cahn-Ingold-Prelog stereochemical system ranking than $R_{XVI-2}$;

$Y_{XVI}$ is selected from a group consisting of a covalent single bond, $(C(R_{XVI-14})_2)_q$ wherein q is an integer selected from 1 and 2 and $(CH(R_{XVI-14}))_g$—$W_{XVI}$—$(CH(R_{XVI-14}))_p$ wherein g and p are integers independently selected from 0 and 1;

$R_{XVI-14}$ is selected from the group consisting of hydrido, hydroxy, cyano, hydroxyalkyl, acyl, alkoxy, alkyl, alkenyl, alkynyl, alkoxyalkyl, haloalkyl, haloalkenyl, haloalkoxy, haloalkoxyalkyl, haloalkenyloxyalkyl, monocarboalkoxyalkyl, monocyanoalkyl, dicyanoalkyl, carboalkoxycyanoalkyl, carboalkoxy, carboxamide, and carboxamidoalkyl;

$Z_{XVI}$ is selected from a group consisting of a covalent single bond, $(C(R_{XVI-15})_2)_q$, wherein q is an integer selected from 1 and 2, and $(CH(R_{XVI-15}))_j$—$W_{XVI}$—$(CH(R_{XVI-5}))_k$ wherein j and k are integers independently selected from 0 and 1;

$W_{XVI}$ is selected from the group consisting of O, C(O), C(S),C(O)N($R_{XVI-14}$), C(S)N($R_{XVI-14}$),($R_{XVI-14}$)NC(O), ($R_{XVI-14}$)NC(S), S, S(O), S(O)$_2$, S(O)$_2$N($R_{XVI-14}$), ($R_{XVI-14}$) NS(O)$_2$, and N($R_{XVI-14}$) with the proviso that $R_{XVI-14}$ is other than cyano;

$R_{XVI-15}$ is selected, from the group consisting of hydrido, cyano, hydroxyalkyl, acyl, alkoxy, alkyl, alkenyl, alkynyl, alkoxyalkyl, haloalkyl, haloalkenyl, haloalkoxy, haloalkoxyalkyl, haloalkenyloxyalkyl, monocarboalkoxyalkyl, monocyanoalkyl, dicyanoalkyl, carboalkoxycyanoalkyl, carboalkoxy, carboxamide, and carboxamidoalkyl;

$R_{XVI-4}$, $R_{XVI-5}$, $R_{XVI-6}$, $R_{XVI-7}$, $R_{XVI-8}$, $R_{XVI-9}$, $R_{XVI-10}$, $R_{XVI-11}$, $R_{XVI-12}$, and $R_{XVI-13}$ are independently selected from the group consisting of hydrido, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroaralkyl, heteroarylaminoalkyl, haloalkylthio, alkanoyloxy, alkoxy, alkoxyalkyl, haloalkoxylalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl, amidosulfonyl, monoarylamidosulfonyl, arylsulfonamido, diarylamidosulfonyl, monoalkyl monoarylamidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, hydoxyheteroaralkyl, haloalkoxyalkyl, aryl, heteroaralkynyl, aryloxy, aralkoxy, aryloxyalkyl, saturated heterocyclyl, partially saturated heterocyclyl, heteroaryl, heteroaryloxy, heteroaryloxyalkyl, arylalkenyl, heteroarylalkenyl, carboxyalkyl, carboalkoxy, alkoxycarboxamido, alkylamidocarbonylamino, arylamidocarbonylamido, carboalkoxyalkyl, carboalkoxyalkenyl, carboaralkoxy, carboxamido, carboxamidoalkyl, cyano, carbohaloalkoxy, phosphono, phosphonoalkyl, diaralkoxyphosphono, and diaralkoxyphosphonoalkyl with the proviso that $R_{XVI-4}$, $R_{XVI-5}$, $R_{XVI-6}$, $R_{XVI-7}$, $R_{XVI-8}$, $R_{XVI-9}$, $R_{XVI-10}$, $R_{XVI-11}$, $R_{XVI-12}$, and $R_{XVI-13}$ are each independently selected to maintain the tetravalent nature of carbon, trivalent nature of nitrogen, the divalent nature of sulfur, and the divalent nature of oxygen;

$R_{XVI-4}$ and $R_{XVI-5}$, $R_{XVI-5}$ and $R_{XVI-6}$, $R_{XVI-6}$ and $R_{XVI-7}$, $R_{XVI-7}$ and $R_{XVI-8}$, $R_{XVI-9}$ and $R_{XVI-10}$, $R_{XVI-10}$ and $R_{XVI-11}$, $R_{XVI-11}$ and $R_{XVI-12}$, and $R_{XVI-12}$ and $R_{XVI-13}$ are independently selected to form spacer pairs wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the provisos that no more than one of the group consisting of spacer pairs $R_{XVI-4}$ and $R_{XVI-5}$, $R_{XVI-5}$ and $R_{XVI-6}$, $R_{XVI-6}$ and $R_{XVI-7}$, and $R_{XVI-7}$ and $R_{XVI-8}$ is used at the same time and that no more than one of the group consisting of spacer pairs $R_{XVI-9}$ and $R_{XVI-10}$, $R_{XVI-10}$ and $R_{XVI-11}$, $R_{XVI-11}$ and $R_{XVI-12}$, and $R_{XVI-12}$ and $R_{XVI-13}$ can be used at the same time;

$R_{XVI-4}$ and $R_{XVI-9}$, $R_{XVI-4}$ and $R_{XVI-13}$, $R_{XVI-8}$ and $R_{XVI-9}$, and $R_{XVI-8}$ and $R_{XVI-13}$ is independently selected to form a spacer pair wherein said spacer pair is taken together to form a linear moiety wherein said linear moiety forms a ring selected from the group consisting of a partially saturated heterocyclyl ring having from 5 through 8 contiguous members and a heteroaryl ring having from 5 through 6 contiguous members with the proviso that no more than one of the group consisting of spacer pairs $R_{XVI-4}$ and $R_{XVI-9}$, $R_{XVI-4}$ and $R_{XVI-13}$, $R_{XVI-8}$ and $R_{XVI-9}$, and $R_{XVI-8}$ and $R_{XVI-13}$ is used at the same time.

Compounds of Formula XVI and their methods of manufacture are disclosed in PCT Publication No. WO 00/18724, which is incorporated herein by reference in its entirety for all purposes.

In a preferred embodiment, the CETP inhibitor is selected from the following compounds of Formula XVI:

(2R)-3-[[3-(3-trifluoromethoxyphenoxy)phenyl][[3-(1,1,2,2-tetrafluoroethoxy)phenyl]methyl]amino]-1,1,1-trifluoro-2-propanol;

(2R)-3-[[3-(3-isopropylphenoxy)phenyl][[3-(1,1,2,2-tetrafluoroethoxy)phenyl]-methyl]amino]-1,1,1-trifluoro-2-propanol;

(2R)-3-[[3-(3-cyclopropylphenoxy)phenyl][[3-(1,1,2,2-tetrafluoroethoxy)phenyl]-methyl]amino]-1,1,1-trifluoro-2-propanol;

(2R)-3-[[3-(3-(2-furyl)phenoxy)phenyl][[3-(1,1,2,2-tetrafluoroethoxy)phenyl]-methyl]amino]-1,1,1-trifluoro-2-propanol;

(2R)-3-[[3-(2,3-dichlorophenoxy)phenyl][[3-(1,1,2,2-tetrafluoroethoxy)phenyl]-methyl]amino]-1,1,1-trifluoro-2-propanol;

(2R)-3-[[3-(4-fluorophenoxy)phenyl][[3-(1,1,2,2-tetrafluoroethoxy)phenyl]-methyl]amino]-1,1,1-trifluoro-2-propanol;

(2R)-3-[[3-(4-methyl phenoxy)phenyl][[3-(1,1,2,2-tetrafluoroethoxy)phenyl]-methyl]amino]-1,1,1-trifluoro-2-propanol;

(2R)-3-[[3-(2-fluoro-5-bromophenoxy)phenyl][[3-(1,1,2,2-tetrafluoroethoxy)phenyl]-methyl]amino]-1,1,1-trifluoro-2-propanol;

(2R)-3-[[3-(4-chloro-3-ethylphenoxy)phenyl][[3-(1,1,2,2-tetrafluoroethoxy)phenyl]-methyl]amino]-1,1,1-trifluoro-2-propanol;

(2R)-3-[[3-[3-(1,1,2,2-tetrafluoroethoxy)phenoxy]phenyl][[3-(1,1,2,2-tetrafluoro-ethoxy)phenyl]methyl]amino]-1,1,1-trifluoro-2-propanol;

(2R)-3-[[3-[3-(pentafluoroethyl)phenoxy]phenyl][[3-(1,1,2,2-tetrafluoroethoxy)-phenyl]methyl]amino]-1,1,1-trifluoro-2-propanol;

(2R)-3-[[3-(3,5-dimethylphenoxy)phenyl][[3-(1,1,2,2-tetrafluoroethoxy)phenyl]-methyl]amino]-1,1,1-trifluoro-2-propanol;

(2R)-3-[[3-(3-ethylphenoxy)phenyl][[3-(1,1,2,2-tetrafluoroethoxy)phenyl]-methyl]amino]-1,1,1-trifluoro-2-propanol;

(2R)-3-[[3-(3-t-butylphenoxy)phenyl][[3-(1,1,2,2-tetrafluoroethoxy)phenyl]-methyl]amino]-1,1,1-trifluoro-2-propanol;
(2R)-3-[[3-(3-methylphenoxy)phenyl][[3-(1,1,2,2-tetrafluoroethoxy)phenyl]-methyl]amino]-1,1,1-trifluoro-2-propanol;
(2R)-3-[[3-(5,6,7,8-tetrahydro-2-naphthoxy)phenyl][[3-(1,1,2,2-tetrafluoro-ethoxy)phenyl]methyl]amino]-1,1,1-trifluoro-2-propanol;
(2R)-3-[[3-(phenoxy)phenyl][[3-(1,1,2,2-tetrafluoroethoxy)phenyl]methyl]amino]-1,1,1-trifluoro-2-propanol;
(2R)-3-[[3-[3-(N,N-dimethylamino)phenoxy]phenyl][[3-(1,1,2,2-tetrafluoro-ethoxy)phenyl]methyl]amino]-1,1,1-trifluoro-2-propanol;
(2R)-3-[[[3-(1,1,2,2,-tetrafluoroethoxy)phenyl]methyl][3-[[3-(trifluoromethoxy)-phenyl]methoxy]phenyl]amino]-1,1,1-trifluoro-2-propanol;
(2R)-3-[[[3-(1,1,2,2-tetrafluoroethoxy)phenyl]methyl][3-[[3-(trifluoro-methyl)phenyl]methoxy]phenyl]amino]-1,1,1-trifluoro-2-propanol;
(2R)-3-[[[3-(1,1,2,2-tetrafluoroethoxy)phenyl]methyl][3-[[3,5-dimethylphenyl]-methoxy]phenyl]amino]-1,1,1-trifluoro-2-propanol;
(2R)-3-[[[3-(1,1,2,2-tetrafluoroethoxy)phenyl]methyl][3-[[3-(trifluoromethylthio)-phenyl]methoxy]phenyl]amino]-1,1,1-trifluoro-2-propanol;
(2R)-3-[[[3-(1,1,2,2-tetrafluoroethoxy)phenyl]methyl][3-[[3,5-difluorophenyl]-methoxy]phenyl]amino]-1,1,1-trifluoro-2-propanol;
(2R)-3-[[[3-(1,1,2,2-tetrafluoroethoxy)phenyl]methyl][3-[cyclohexylmethoxy]-phenyl]amino]-1,1,1-trifluoro-2-propanol;
(2R)-3-[[3-(2-difluoromethoxy-4-pyridyloxy)phenyl][[3-(1,1,2,2-tetrafluoroethoxy)-phenyl]methyl]amino]-1,1,1-trifluoro-2-propanol;
(2R)-3-[[3-(2-trifluoromethyl-4-pyridyloxy)phenyl][[3-(1,1,2,2-tetrafluoroethoxy)-phenyl]methyl]amino]-1,1,1-trifluoro-2-propanol;
(2R)-3-[[3-(3-difluoromethoxyphenoxy)phenyl][[3-(1,1,2,2-tetrafluoroethoxy)-phenyl]methyl]amino]-1,1,1-trifluoro-2-propanol;
(2R)-3-[[[3-(3-trifuoromethylthio)phenoxy]phenyl][[3-(1,1,2,2-tetrafluoroethoxy)-phenyl]methyl]amino]-1,1,1-trifluoro-2-propanol;
(2R)-3-[[3-(4-chloro-3-trifluoromethylphenoxy)phenyl][[3-(1,1,2,2-tetrafluoroethoxy)-phenyl]methyl]amino]-1,1,1-trifluoro-2-propanol;
(2R)-3-[[3-(3-trifluoromethoxyphenoxy)phenyl][[3-(pentafluoroethyl)phenyl]-methyl]amino]-1,1,1-trifluoro-2-propanol;
(2R)-3-[[3-(3-isopropylphenoxy)phenyl][[3-(pentafluoroethyl)phenyl]methyl]-amino]-1,1,1-trifluoro-2-propanol;
(2R)-3-[[3-(3-cyclopropylphenoxy)phenyl][[3-(pentafluoroethyl)phenyl]methyl]-amino]-1,1,1-trifluoro-2-propanol;
(2R)-3-[[3-(3-(2-furyl)phenoxy)phenyl][[3-(pentafluoroethyl)phenyl]methyl]-amino]-1,1,1-trifluoro-2-propanol;
(2R)-3-[[3-(2,3-dichlorophenoxy)phenyl][[3-(pentafluoroethyl)phenyl]methyl]-amino]-1,1,1-trifluoro-2-propanol;
(2R)-3-[[3-(4-fluorophenoxy)phenyl][[3-(pentafluoroethyl)phenyl]methyl]amino]-1,1,1-trifluoro-2-propanol;
(2R)-3-[[3-(4-methylphenoxy)phenyl][[3-(pentafluoroethyl)phenyl]methyl]amino]-1,1,1-trifluoro-2-propanol;
(2R)-3-[[3-(2-fluoro-5-bromophenoxy)phenyl][[3-(pentafluoroethyl)phenyl]methyl]-amino]-1,1,1-trifluoro-2-propanol;
(2R)-3-[[3-(4-chloro-3-ethylphenoxy)phenyl][[3-(pentafluoroethyl)phenyl]methyl]-amino]-1,1,1-trifluoro-2-propanol;
(2R)-3-[[3-[3-(1,1,2,2-tetrafluoroethoxy)phenoxy]phenyl][[3-(pentafluoroethyl)-phenyl]methyl]amino]-1,1,1-trifluoro-2-propanol;
(2R)-3-[[3-[3-(pentafluoroethyl)phenoxy]phenyl][[3-(pentafluoroethyl)phenyl]-methyl]amino]-1,1,1-trifluoro-2-propanol;
(2R)-3-[[3-(3,5-dimethylphenoxy)phenyl][[3-(pentafluoroethyl)phenyl]methyl]-amino]-1,1,1-trifluoro-2-propanol;
(2R)-3-[[3-(3-ethylphenoxy)phenyl][[3-(pentafluoroethyl)phenyl]methyl]amino]-1,1,1-trifluoro-2-propanol;
(2R)-3-[[3-(3-t-butylphenoxy)phenyl][[3-(pentafluoroethyl)phenyl]methyl]amino]-1,1,1-trifluoro-2-propanol;
(2R)-3-[[3-(3-methylphenoxy)phenyl][[3-(pentafluoroethyl)phenyl]methyl]amino]-1,1,1-trifluoro-2-propanol;
(2R)-3-[[3-(5,6,7,8-tetrahydro-2-naphthoxy)phenyl][[3-(pentafluoroethyl)phenyl]-methyl]amino]-1,1,1-trifluoro-2-propanol;
(2R)-3-[[3-(phenoxy)phenyl][[3(pentafluoroethyl)phenyl]methyl]amino]-1,1,1-trifluoro-2-propanol;
(2R)-3-[[3-[3-(N,N-dimethylamino)phenoxy]phenyl][[3(pentafluoroethyl)phenyl]-methyl]amino]-1,1,1-trifluoro-2-propanol;
(2R)-3-[[[3-(pentafluoroethyl)phenyl]methyl][3-[[3-(trifluoromethoxy)phenyl]-methoxy]phenyl]amino]-1,1,1-trifluoro-2-propanol;
(2R)-3-[[[3-(pentafluoroethyl)phenyl]methyl][3-[[3-(trifluoromethyl)-phenyl]-methoxy]phenyl]amino]-1,1,1-trifluoro-2-propanol;
(2R)-3-[[[3-(pentafluoroethyl)phenyl]methyl][3-[[3,5-dimethylphenyl]methoxy]-phenyl]amino]-1,1,1-trifluoro-2-propanol;
(2R)-3-[[[3-(pentafluoroethyl)phenyl]methyl][3-[[3-(trifluoromethylthio)phenyl]-methoxy]phenyl]amino]-1,1,1-trifluoro-2-propanol;
(2R)-3-[[[3-(pentafluoroethyl)phenyl]methyl][3-[[3,5-difluorophenyl]methoxy]-phenyl]amino]-1,1,1-trifluoro-2-propanol;
(2R)-3-[[[3-(pentafluoroethyl)phenyl]methyl][3-[cyclohexylmethoxy]phenyl]-amino]-1,1,1-trifluoro-2-propanol;
(2R)-3-[[3-(2-difluoromethoxy-4-pyridyloxy)phenyl][[3-(pentafluoroethyl)phenyl]-methyl]amino]-1,1,1-trifluoro-2-propanol;
(2R)-3-[[3-(2-trifluoromethyl-4-pyridyloxy)phenyl][[3-(pentafluoroethyl)phenyl]-methyl]amino]-1,1,1-trifluoro-2-propanol;
(2R)-3-[[3-(3-difluoromethoxyphenoxy)phenyl][[3-(pentafluoroethyl)phenyl]-methyl]amino]-1,1,1-trifluoro-2-propanol;
(2R)-3-[[[3-(3-trifluoromethylthio)phenoxy]phenyl][[3-(pentafluoroethyl)phenyl]-methyl]amino]-1,1,1-trifluoro-2-propanol;
(2R)-3-[[3-(4-chloro-3-trifluoromethylphenoxy)phenyl][[3-(pentafluoroethyl)-phenyl]methyl]amino]-1,1,1-trifluoro-2-propanol;
(2R)-3-[[3-(3-trifluoromethoxyphenoxy)phenyl][[3-(heptafluoropropyl)phenyl]-methyl]amino]-1,1,1-trifluoro-2-propanol;
(2R)-3-[[3-(3-isopropylphenoxy)phenyl][[3-(heptafluoropropyl)phenyl]methyl]-amino]-1,1,1-trifluoro-2-propanol;
(2R)-3-[[3-(3-cyclopropylphenoxy)phenyl][[3-(heptafluoropropyl)phenyl]methyl]-amino]-1,1,1-trifluoro-2-propanol;

(2R)-3-[[3-(3-(2-furyl)phenoxy)phenyl][[3-(heptafluoropropyl)phenyl]methyl]-amino]-1,1,1-trifluoro-2-propanol;

(2R)-3-[[3-(2,3-dichlorophenoxy)phenyl][[3-(heptafluoropropyl)phenyl]methyl]-amino]-1,1,1-trifluoro-2-propanol;

(2R)-3-[[3-(4-fluorophenoxy)phenyl][[3-(heptafluoropropyl)phenyl]methyl]amino]-1,1,1-trifluoro-2-propanol;

(2R)-3-[[3-(4-methylphenoxy)phenyl][[3-(heptafluoropropyl)phenyl]methyl]amino]-1,1,1-trifluoro-2-propanol;

(2R)-3-[[3-(2-fluoro-5-bromophenoxy)phenyl][[3-(heptafluoropropyl)phenyl]-methyl]amino]-1,1,1-trifluoro-2-propanol;

(2R)-3-[[3-(4-chloro-3-ethylphenoxy)phenyl][[3-(heptafluoropropyl)phenyl]methyl]-amino]-1,1,1-trifluoro-2-propanol;

(2R)-3-[[3-[3-(1,1,2,2-tetrafluoroethoxy)phenoxy]phenyl][[3-(heptafluoropropyl)-phenyl]methyl]amino]-1,1,1-trifluoro-2-propanol;

(2R)-3-[[3-[3-(pentafluoroethyl)phenoxy]phenyl][[3-(heptafluoropropyl)-phenyl]methyl]amino]-1,1,1-trifluoro-2-propanol;

(2R)-3-[[3-(3,5-dimethylphenoxy)phenyl][[3-(heptafluoropropyl)phenyl]methyl]-amino]-1,1,1-trifluoro-2-propanol;

(2R)-3-[[3-(3-ethylphenoxy)phenyl][[3-(heptafluoropropyl)phenyl]methyl]amino]-1,1,1-trifluoro-2-propanol;

(2R)-3-[[3-(3-t-butylphenoxy)phenyl][[3-(heptafluoropropyl)phenyl]methyl]amino]-1,1,1-trifluoro-2-propanol;

(2R)-3-[[3-(3-methylphenoxy)phenyl][[3-(heptafluoropropyl)phenyl]methyl]amino]-1,1,1-trifluoro-2-propanol;

(2R)-3-[[3-(5,6,7,8-tetrahydro-2-naphthoxy)phenyl][[3-(heptafluoropropyl)phenyl]-methyl]amino]-1,1,1-trifluoro-2-propanol;

(2R)-3-[[3-(phenoxy)phenyl][[3-(heptafluoropropyl)phenyl]methyl]amino]-1,1,1-trifluoro-2-propanol;

(2R)-3-[[3-[3-(N,N-dimethylamino)phenoxy]phenyl][[3-(heptafluoropropyl)phenyl]-methyl]amino]-1,1,1-trifluoro-2-propanol;

(2R)-3-[[[3-(heptafluoropropyl)phenyl]methyl][3-[[3-(trifluoromethoxy)phenyl]-methoxy]phenyl]amino]-1,1,1-trifluoro-2-propanol;

(2R)-3-[[[3-(heptafluoropropyl)phenyl]methyl][3-[[3-(trifluoromethyl)phenyl]-methoxy]phenyl]amino]-1,1,1-trifluoro-2-propanol;

(2R)-3-[[[3-(heptafluoropropyl)phenyl]methyl][3-[[3,5-dimethylphenyl]methoxy]-phenyl]amino]-1,1,1-trifluoro-2-propanol;

(2R)-3-[[[3-(heptafluoropropyl)phenyl]methyl][3-[[3-(trifluoromethylthio)phenyl]-methoxy]phenyl]amino]-1,1,1-trifluoro-2-propanol;

(2R)-3-[[[3-(heptafluoropropyl)phenyl]methyl][3-[[3,5-difluorophenyl]methoxy]-phenyl]amino]-1,1,1-trifluoro-2-propanol;

(2R)-3-[[[3-(heptafluoropropyl)phenyl]methyl][3-[cyclohexylmethoxy]phenyl]-amino]-1,1,1-trifluoro-2-propanol;

(2R)-3-[[3-(2-difluoromethoxy-4-pyridyloxy)phenyl][[3-(heptafluoropropyl)phenyl]-methyl]amino]-1,1,1-trifluoro-2-propanol;

(2R)-3-[[3-(2-trifluoromethyl-4-pyridyloxy)phenyl][[3-(heptafluoropropyl)phenyl]-methyl]amino]-1,1,1-trifluoro-2-propanol;

(2R)-3-[[3-(3-difluoromethoxyphenoxy)phenyl][[3-(heptafluoropropyl)phenyl]-methyl]amino]-1,1,1-trifluoro-2-propanol;

(2R)-3-[[[3-(3-trifluoromethylthio)phenoxy]phenyl][[3-(heptafluoropropyl)phenyl]-methyl]amino]-1,1,1-trifluoro-2-propanol;

(2R)-3-[[3-(4-chloro-3-trifluoromethylphenoxy)phenyl][[3-(heptafluoropropyl)-phenyl]methyl]amino]-1,1,1-trifluoro-2-propanol;

(2R)-3-[[3-(3-trifluoromethoxyphenoxy)phenyl][[2-fluoro-5-(trifluoromethyl)-phenyl]methyl]amino]-1,1,1-trifluoro-2-propanol;

(2R)-3-[[3-(3-isopropylphenoxy)phenyl][[2-fluoro-5-(trifluoromethyl)phenyl]-methyl]amino]-1,1,1-trifluoro-2-propanol;

(2R)-3-[[3-(3-cyclopropylphenoxy)phenyl][[2-fluoro-5-(trifluoromethyl)phenyl]-methyl]amino]-1,1,1-trifluoro-2-propanol;

(2R)-3-[[3-(3-(2-furyl)phenoxy)phenyl][[2-fluoro-5-(trifluoromethyl)phenyl]-methyl]amino]-1,1,1-trifluoro-2-propanol;

(2R)-3-[[3-(2,3-dichlorophenoxy)phenyl][[2-fluoro-5-(trifluoromethyl)phenyl]-methyl]amino]-1,1,1-trifluoro-2-propanol;

(2R)-3-[[3-(4-fluorophenoxy)phenyl][[2-fluoro-5-(trifluoromethyl)phenyl]-methyl]amino]-1,1,1-trifluoro-3-propanol;

(2R)-3-[[3-(4-methylphenoxy)phenyl][[2-fluoro-5-(trifluoromethyl)phenyl]-methyl]amino]-1,1,1-trifluoro-2-propanol;

(2R)-3-[[3-(2-fluoro-5-bromophenoxy)phenyl][[2-fluoro-5-(trifluoromethyl)-phenyl]methyl]amino]-1,1,1-trifluoro-2-propanol;

(2R)-3-[[3-(4-chloro-3-ethylphenoxy)phenyl][[2-fluoro-5-(trifluoromethyl)phenyl]methyl]amino]-1,1,1-trifluoro-2-propanol;

(2R)-3-[[3-[3-(1,1,2,2-tetrafluoroethoxy)phenoxy]phenyl][[2-fluoro-5-(trifluoro-methyl)phenyl]methyl]amino]-1,1,1-trifluoro-2-propanol;

(2R)-3-[[3-[3-(pentafluoroethyl)phenoxy]phenyl][[2-fluoro-5-(trifluoromethyl)-phenyl]methyl]amino]-1,1,1-trifluoro-2-propanol;

(2R)-3-[[3-(3,5-dimethylphenoxy)phenyl][[2-fluoro-5-(trifluoromethyl)phenyl]-methyl]amino]-1,1,1-trifluoro-2-propanol;

(2R)-3-[[3-(3-ethylphenoxy)phenyl][[2-fluoro-5-(trifluoromethyl)phenyl]methyl]-amino]-1,1,1-trifluoro-2-propanol;

(2R)-3-[[3-(3-t-butylphenoxy)phenyl][[2-fluoro-5-(trifluoromethyl)phenyl]methyl]-amino]-1,1,1-trifluoro-2-propanol;

(2R)-3-[[3-(3-methylphenoxy)phenyl][[2-fluoro-5-(trifluoromethyl)phenyl]methyl]-amino]-1,1,1-trifluoro-2-propanol;

(2R)-3-[[3-(5,6,7,8-tetrahydro-2-naphthoxy)phenyl][[2-fluoro-5-(trifluoromethyl)-phenyl]methyl]amino]-1,1,1-trifluoro-2-propanol;

(2R)-3-[[3-(phenoxy)phenyl][[2-fluoro-5-(trifluoromethyl)phenyl]methyl]amino]-1,1,1-trifluoro-2-propanol;

(2R)-3-[[3-[3-(N,N-dimethylamino,phenoxy]phenyl][[2-fluoro-5-(trifluoromethyl)-phenyl]methyl]amino]-1,1,1-trifluoro-2-propanol;

(2R)-3-[[[2-fluoro-5-(trifluoromethyl)phenyl]methyl][3-[[3-(trifluoromethoxy)-phenyl]methoxy]phenyl]amino]-1,1,1-trifluoro-3-propanol;

(2R)-3-[[[2-fluoro-5-(trifluoromethyl)phenyl]methyl][3-[[3-(trifluoromethyl)-phenyl]methoxy]phenyl]amino]-1,1,1-trifluoro-2-propanol;

(2R)-3-[[[2-fluoro-5-(trifluoromethyl)phenyl]methyl][3-[[3,5-dimethylphenyl]-methoxy]phenyl]amino]-1,1,1-trifluoro-2-propanol;
(2R)-3-[[[2-fluoro-5-(trifluoromethyl)phenyl]methyl][3-[[3-(trifluoromethylthio)-phenyl]methoxy]phenyl]amino]-1,1,1-trifluoro-2-propanol;
(2R)-3-[[[2-fluoro-5-(trifluoromethyl)phenyl]methyl][3-[[3,5-difluorophenyl]-methoxy]phenyl]amino]-1,1,1-trifluoro-2-propanol;
(2R)-3-[[[2-fluoro-5-(trifluoromethyl)phenyl]methyl][3-[cyclohexylmethoxyl-phenyl]amino]-1,1,1-trifluoro-2-propanol;
(2R)-3-[[3-(2-difluoromethoxy-4-pyridyloxy)phenyl][[2-fluoro-5-(trifluoromethyl)-phenyl]methyl]amino]-1,1,1-trifluoro-2-propanol;
(2R)-3-[[3-(2-trifluoromethyl-4-pyridyloxy)phenyl][[2-fluoro-5-(trifluoromethyl)-phenyl]methyl]amino]-1,1,1-trifluoro-2-propanol;
(2R)-3-[[3-(3-difluoromethoxyphenoxy)phenyl][[2-fluoro-5-(trifluoromethyl)-phenyl]methyl]amino]-1,1,1-trifluoro-2-propanol;
(2R)-3-[[[3-(3-trifluoromethylthio)phenoxy]phenyl][[2-fluoro-5-(trifluoromethyl)-phenyl]methyl]amino]-1,1,1-trifluoro-2-propanol;
(2R)-3-[[3-(4-chloro-3-trifluoromethylphenoxy)phenyl][[2-fluoro-5-(trifluoro-methyl)phenyl]methyl]amino]-1,1,1-trifluoro-2-propanol;
(2R)-3-[[3-(3-trifluoromethoxyphenoxy)phenyl][[2-fluoro-4-(trifluoromethyl)-phenyl]methyl]amino]-1,1,1-trifluoro-2-propanol;
(2R)-3-[[3-(3-isopropylphenoxy)phenyl][[2-fluoro-4-(trifluoromethyl)phenyl]-methyl]amino]-1,1,1-trifluoro-2-propanol;
(2R)-3-[[3-(3-cyclopropylphenoxy)phenyl][[2-flouro-4-(trifluoromethyl)phenyl]-methyl]amino]-1,1,1-trifluoro-2-propanol;
(2R)-3-[[3-(3-(2-furyl)phenoxy)phenyl][[2-fluoro-4-(trifluoromethyl)phenyl]-methyl]amino]-1,1,1-trifluoro-2-propanol;
(2R)-3-[[3-(2,3-dichlorophenoxy)phenyl][[2-fluoro-4-(trifluoromethyl)phenyl]-methyl]amino]-1,1,1-trifluoro-2-propanol;
(2R)-3-[[3-(4-fluorophenoxy)phenyl][[2-fluoro-4-(trifluoromethyl)phenyl]-methyl]amino]-1,1,1-trifluoro-2-propanol;
(2R)-3-[[3-(4-methylphenoxy)phenyl][[2-fluoro-4-(trifluoromethyl)phenyl]-methyl]amino]-1,1,1-trifluoro-2-propanol;
(2R)-3-[[3-(2-fluoro-5-bromophenoxy)phenyl][[2-fluoro-4-(trifluoromethyl)-phenyl]methyl]amino]-1,1,1-trifluoro-2-propanol;
(2R)-3-[[3-(4-chloro-3-ethylphenoxy)phenyl][[2-fluoro-4-(trifluoromethyl)-phenyl]methyl]amino]-1,1,1-trifluoro-2-propanol;
(2R)-3-[[3-[3-(1,1,2,2-tetrafluoroethoxy)phenoxy]phenyl][[2-fluoro-4-(trifluoromethyl)phenyl]methyl]amino]-1,1,1-trifluoro-2-propanol;
(2R)-3-[[3-[3-(pentafluoroethyl)phenoxy]phenyl][[2-fluoro-4-(trifluoromethyl)-phenyl]methyl]amino]-1,1,1-trifluoro-2-propanol;
(2R)-3-[[3-(3,5-dimethylphenoxy)phenyl][[2-fluoro-4-(trifluoromethyl)phenyl]-methyl]aminol-1,1,1-trifluoro-2-propanol;
(2R)-3-[[3-(3-ethylphenoxy)phenyl][[2-fluoro-4-(trifluoromethyl)phenyl]methyl]-amino]-1,1,1-trifluoro-2-propanol;
(2R)-3-[[3-(3-t-butylphenoxy)phenyl][[2-fluoro-4-(trifluoromethyl)phenyl]methyl]-amino]-1,1,1-trifluoro-2-propanol;
(2R)-3-[[3-(3-methylphenoxy)phenyl][[2-fluoro-4-(trifluoromethyl)phenyl]methyl]-amino]-1,1,1-trifluoro-2-propanol;
(2R)-3-[[3-(5,6,7,8-tetrahydro-2-naphthoxy)phenyl][[2-fluoro-4-(trifluoromethyl)-phenyl]methyl]amino]-1,1,1-trifluoro-2-propanol;
(2R)-3-[[3-(phenoxy)phenyl][[2-fluoro-4-(trifluoromethyl)phenyl]methyl]amino]-1,1,1-trifluoro-2-propanol;
(2R)-3-[[3-[3-(N,N-dimethylamino)phenoxy]phenyl][[2-fluoro-4-(trifluoromethyl)-phenyl]methyl]amino]-1,1,1-trifluoro-2-propanol;
(2R)-3-[[[2-fluoro-4-(trifluoromethyl)phenyl]methyl][3-[[3-(trifluoromethoxy)phenyl]methoxy]phenyl]amino]-1,1,1-trifluoro-2-propanol;
(3R)-3-[[[2-fluoro-4-(trifluoromethyl)phenyl]methyl][3-[[3-(trifluoromethyl)phenyl]methoxy]phenyl]amino]-1,1,1-trifluoro-2-propanol;
(2R)-3-[[[2-fluoro-4-(trifluoromethyl)phenyl]methyl][3-[[3,5-dimethylphenyl]-methoxy]phenyl]amino]-1,1,1-trifluoro-2-propanol;
(2R)-3-[[[2-fluoro-4-(trifluoromethyl)phenyl]methyl][3-[[3-(trifluoromethylthio)-phenyl]methoxy]phenyl]amino]-1,1,1-trifluoro-2-propanol;
(2R)-3-[[[2-fluoro-4-(trifluoromethyl)phenyl]methyl][3-[[3,5-difluorophenyl]-methoxy]phenyl]amino]-1,1,1-trifluoro-2-propanol;
(2R)-3-[[[2-fluoro-4-(trifluoromethyl)phenyl]methyl][3-[cyclohexylmethoxy]-phenyl]amino]-1,1,1-trifluoro-2-propanol;
(2R)-3-[[3-(2-difluoromethoxy-4-pyridyloxy)phenyl][[2-fluoro-4-(trifluoromethyl)-phenyl]methyl]amino]-1,1,1-trifluoro-2-propanol;
(2R)-3-[[3-(2-trifluoromethyl-4-pyridyloxy)phenyl][[2-fluoro-4-(trifluoromethyl)-phenyl]methyl]amino]-1,1,1-trifluoro-2-propanol;
(2R)-3-[[3-(3-difluoromethoxyphenoxy)phenyl][[2-fluoro-4-(trifluoromethyl)-phenyl]methyl]amino]-1,1,1-trifluoro-2-propanol;
(2R)-3-[[[3-(3-trifluoromethylthio)phenoxy]phenyl][[2-fluoro-4-(trifluoromethyl)-phenyl]methyl]amino]-1,1,1-trifluoro-2-propanol; and
(2R)-3-[[3-(4-chloro-3-trifluoromethyl phenoxy)phenyl][[2-fluoro-4-(trifluoromethyl)phenyl]methyl]amino]-1,1,1-trifluoro-2-propanol.

Another class of CETP inhibitors that finds utility with the present invention consists of quinolines of Formula XVII

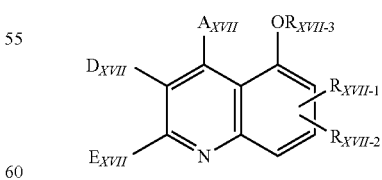

Formula XVII and pharmaceutically acceptable forms thereof, wherein:

$A_{XVII}$ denotes an aryl containing 6 to 10 carbon atoms, which is optionally substituted with up to five identical or different substituents in the form of a halogen, nitro, hydroxyl, trifluoromethyl, trifluoromethoxy or a straight-chain or branched alkyl, acyl, hydroxyalkyl or alkoxy containing up to 7 carbon atoms each, or in the form of a group according to the formula —NR$_{XVII\text{-}4}$R$_{XVII\text{-}5}$ wherein R$_{XVII\text{-}4}$ and R$_{XVII\text{-}5}$ are identical or different and denote a hydrogen, phenyl or a straight-chain or branched alkyl containing up to 6 carbon atoms, D$_{XVII}$ denotes an aryl containing 6 to 10 carbon atoms, which is optionally substituted with a phenyl, nitro, halogen, trifluoromethyl or trifluoromethoxy, or a radical according to the formula

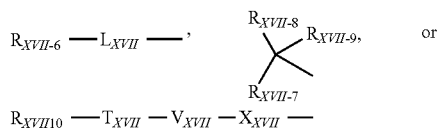

wherein

R$_{XVII\text{-}6}$, R$_{XVII\text{-}7}$, R$_{XVII\text{-}10}$ denote, independently from one another, a cycloalkyl containing 3 to 6 carbon atoms, or an aryl containing 6 to 10 carbon atom or a 5- to 7-membered, optionally benzo-condensed, saturated or unsaturated, mono-, bi- or tricyclic heterocycle containing up to 4 heteroatoms from the series of S, N and/or O, wherein the rings are optionally substituted, in the case of the nitrogen-containing rings also via the N function, with up to five identical or different substituents in the form of a halogen, trifluoromethyl, nitro, hydroxyl, cyano, carboxyl, trifluoromethoxy, a straight-chain or branched acyl, alkyl, alkylthio, alkylalkoxy, alkoxy or alkoxycarbonyl containing up to 6 carbon atoms each, an aryl or trifluoromethyl-substituted aryl containing 6 to 10 carbon atoms each, or an optionally benzo-condensed, aromatic 5- to 7-membered heterocycle containing up to 3 heteoatoms from the series of S, N and/or O, and/or in the form of a group according to the formula —OR$_{XVII\text{-}11}$, —SR$_{XVII\text{-}12}$, —SO$_2$R$_{XVII\text{-}13}$, or —NR$_{XVII\text{-}14}$R$_{XVII\text{-}15}$;

R$_{XVII\text{-}11}$, R$_{XVII\text{-}12}$, and R$_{XVII\text{-}13}$ denote, independently from one another, an aryl containing 6 to 10 carbon atoms, which is in turn substituted with up to two identical or different substituents in the form of a phenyl, halogen or a straight-chain or branched alkyl containing up to 6 carbon atoms, R$_{XVII\text{-}14}$ and R$_{XVII\text{-}15}$ are identical or different and have the meaning of R$_{XVII\text{-}4}$ and R$_{XVII\text{-}5}$ given above, or R$_{XVII\text{-}6}$ and/or R$_{XVII\text{-}7}$ denote a radical according to the formula

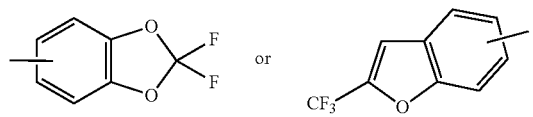

R$_{XVII\text{-}8}$ denotes a hydrogen or halogen, and

R$_{XVII\text{-}9}$ denotes a hydrogen, halogen, azido, trifluoromethyl, hydroxyl, trifluoromethoxy, a straight-chain or branched alkoxy or alkyl containing up to 6 carbon atoms each, or a radical according to the formula NR$_{XVII\text{-}16}$R$_{XVII\text{-}17}$, R$_{XVII\text{-}16}$ and R$_{XVII\text{-}17}$ are identical or different and have the meaning of R$_{XVII\text{-}4}$ and R$_{XVII\text{-}5}$ above; or R$_{XVII\text{-}8}$ and R$_{XVII\text{-}9}$ together form a radical according to the formula =O or =NR$_{XVII\text{-}18}$;

R$_{XVII\text{-}18}$ denotes a hydrogen or a straight-chain or branched alkyl, alkoxy or acyl containing up to 6 carbon atoms each;

L$_{XVII}$ denotes a straight-chain or branched alkylene or alkenylene chain containing up to 8 carbon atoms, which are optionally substituted with up to two hydroxyl groups;

T$_{XVII}$ and X$_{XVII}$ are identical or different and denote a straight-chain or branched alkylene chain containing up to 8 carbon atoms; or T$_{XVII}$ and X$_{XVII}$ denotes a bond;

V$_{XVII}$ denotes an oxygen or sulfur atom or —NR$_{XVII\text{-}19}$;

R$_{XVII\text{-}19}$ denotes a hydrogen or a straight-chain or branched alkyl containing up to 6 carbon atoms or a phenyl;

E$_{XVII}$ denotes a cycloalkyl containing 3 to 8 carbon atoms, or a straight-chain or branched alkyl containing up to 8 carbon atoms, which is optionally substituted with a cycloalkyl containing 3 to 8 carbon atoms or a hydroxyl, or a phenyl, which is optionally substituted with a halogen or trifluoromethyl;

R$_{XVII\text{-}1}$ and R$_{XVII\text{-}2}$ are identical or different and denote a cycloalkyl containing 3 to 8 carbon atoms, hydrogen, nitro, halogen, trifluoromethyl, trifluoromethoxy, carboxy, hydroxy, cyano, a straight-chain or branched acyl, alkoxycarbonyl or alkoxy with up to 6 carbon atoms, or NR$_{XVII\text{-}20}$R$_{XVII\text{-}21}$;

R$_{XVII\text{-}20}$ and R$_{XVII\text{-}21}$ are identical or different and denote hydrogen, phenyl, or a straight-chain or branched alkyl with up to 6 carbon atoms; and or R$_{XVII\text{-}1}$ and/or R$_{XVII\text{-}2}$ are straight-chain or branched alkyl with up to 6 carbon atoms, optionally substituted with halogen, trifluoromethoxy, hydroxy, or a straight-chain or branched alkoxy with up to 4 carbon atoms, aryl containing 6-10 carbon atoms optionally substituted with up to five of the same or different substituents selected from halogen, cyano, hydroxy, trifluoromethyl, trifluoromethoxy, nitro, straight-chain or branched alkyl, acyl, hydroxyalkyl, alkoxy with up to 7 carbon atoms and NR$_{XVII\text{-}22}$R$_{XVII\text{-}23}$;

R$_{XVII\text{-}22}$ and R$_{XVII\text{-}23}$ are identical or different and denote hydrogen, phenyl or a straight-chain or branched akyl up to 6 carbon atoms; and/or R$_{XVII\text{-}1}$ and R$_{XVII\text{-}2}$ taken together form a straight-chain or branched alkene or alkane with up to 6 carbon atoms optionally substituted with halogen, trifluoromethyl, hydroxy or straight-chain or branched alkoxy with up to 5 carbon atoms;

R$_{XVII\text{-}3}$ denotes hydrogen, a straight-chain or branched acyl with up to 20 carbon atoms, a benzoyl optionally substituted with halogen, trifluoromethyl, nitro or trifluoromethoxy, a straight-chained or branched fluoroacyl with up to 8 carbon atoms and 7 fluoro atoms, a cycloalkyl with 3 to 7 carbon atoms, a straight chained or branched alkyl with up to 8 carbon atoms optionally substituted with hydroxyl, a straight-chained or branched alkoxy with up to 6 carbon atoms optionally substituted with phenyl which may in turn be substituted with halogen, nitro, trifluoromethyl, trifluoromethoxy, or phenyl or a tetrazol substitued phenyl, and/or an alkyl that is optionally substituted with a group according to the formula —OR$_{XVII\text{-}24}$;

R$_{XVII\text{-}24}$ is a straight-chained or branched acyl with up to 4 carbon atoms or benzyl.

Compounds of Formula XVII and their methods of manufacture are disclosed in PCT Publication No. WO 98/39299, which is incorporated herein by reference in its entirety for all purposes.

Another class of CETP inhibitors that finds utility with the present invention consists of 4-Phenyltetrahydroquinolines of Formula XVIII

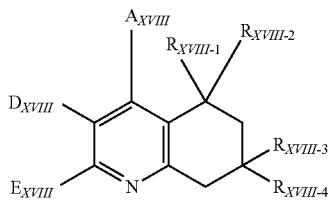

Formula XVIII

N oxides thereof, and pharmaceutically acceptable forms thereof, wherein:

$A_{XVIII}$ denotes a phenyl optionally substituted with up to two identical or different substituents in the form of halogen, trifluoromethyl or a straight-chain or branched alkyl or alkoxy containing up to three carbon atoms;

$D_{XVIII}$ denotes the formula

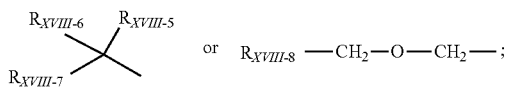

$R_{XVIII-5}$ and $R_{XVIII-6}$ are taken together to form =O; or $R_{XVIII-5}$ denotes hydrogen and $R_{XVIII-6}$ denotes halogen or hydrogen; or $R_{XVIII-5}$ and $R_{XVIII-6}$ denote hydrogen;

$R_{XVIII-7}$ and $R_{XVIII-8}$ are identical or different and denote phenyl, naphthyl, benzothiazolyl, quinolinyl, pyrimidyl or pyridyl with up to four identical or different substituents in the form of halogen, trifluoromethyl, nitro, cyano, trifluoromethoxy, —SO$_2$—CH$_3$ or NR$_{XVIII-9}$R$_{XVIII-10}$;

$R_{XVIII-9}$ and $R_{XVIII-10}$ are identical or different and denote hydrogen or a straight-chained or branched alkyl of up to three carbon atoms;

$E_{XVIII}$ denotes a cycloalkyl of from three to six carbon atoms or a straight-chained or branched alkyl of up to eight carbon atoms;

$R_{XVIII-1}$ denotes hydroxy;

$R_{XVIII-2}$ denotes hydrogen or methyl;

$R_{XVIII-3}$ and $R_{XVIII-4}$ are identical or different and denote straight-chained or branched alkyl of up to three carbon atoms; or $R_{XVIII-3}$ and $R_{XVIII-4}$ taken together form an alkenylene made up of between two and four carbon atoms.

Compounds of Formula XVIII and their methods of manufacture are disclosed in PCT Publication No. WO 99/15504 and U.S. Pat. No. 6,291,477, both of which are incorporated herein by reference in their entireties for all purposes.

The present invention is particularly advantageous for the class of drugs which are both acid-sensitive and low-solubility. Exemplary acid-sensitive, low-solubility drugs include (+)-N-{3-[3-(4-fluorophenoxy)phenyl]-2-cyclopenten-1-yl}-N-hydroxyurea; omeprazole; etoposide; famotidine; erythromycin; quinapril; lansoprazole; and progabide; as well as CCR1 inhibitors such as quinoxaline-2-carboxylic acid [4(R)-carbamoyl-1(S)-3-fluorobenzyl-2(S),7-dihydroxy-7-methyl-octyl]amide and quinoxaline-2-carboxylic acid [1-benzyl-4-(4,4-difluoro-1-hydroxy-cyclohexyl)-2-hydroxy-4-hydroxycarbamoyl-butyl]-amide.

The invention is useful for improving the intrinsic dissolution rate of compounds selected from the following. The intrinsic dissolution rate is defined as the rate of dissolution of a pure pharmaceutical active ingredient when conditions such as surface area, agitation-stirring speed, pH and ionic-strength of the dissolution medium are kept constant. Intrinsic dissolution rate is further defined as being measured in water at 37° C. using a USP II dissolution apparatus equipped with a Wood's apparatus (Wood, J H; Syarto, J E and Letterman, H: J.Pharm. Sci. 54 (1965), 1068) with a stirring speed of 50 rpm. The intrinsic dissolution rate is defined in terms of mg of drug dissolved per minute from a unit surface area, therefore, the intrinsic dissolution rate is referred to in units of mg/min.cm$^2$.

The compositions and methods of the invention are particularly useful for compounds with an intrinsic dissolution rate of preferably less than 0.1 mg/min.cm$^2$ and more preferably with less than 0.05 mg/min.cm$^2$.

Turning now to the chemical structures of specific CCR1 inhibitors, one class of CCR1 inhibitors that finds utility with the present invention consists of dihydroxyhexanoic acid derivatives having the Formula CCR1-I

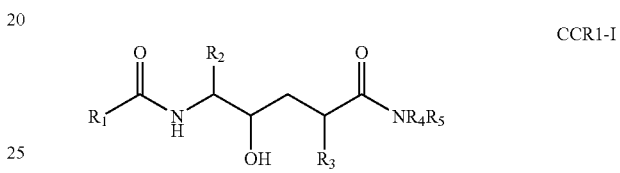

CCR1-I wherein R$_1$ is (C$_2$-C$_9$) heteroaryl optionally substituted with one, two or three substituents independently selected from the group consisting of hydrogen, halo, cyano, (C$_1$-C$_6$) alkyl optionally substituted with one, two or three fluorine atoms, hydroxy, hydroxy-(C$_1$-C$_6$)alkyl, (C$_1$-C$_6$)alkoxy, (C$_1$-C$_6$)alkoxy(C$_1$-C$_6$)alkyl, HO—(C=O)—, (C$_1$-C$_6$)alkyl-O—(C=O)—, HO—(C=O)—(C$_1$-C$_6$)alkyl, (C$_1$-C$_6$)alkyl-O—(C=O)—(C$_1$-C$_6$)alkyl, (C$_1$-C$_6$)alkyl-(C=O)—O—, (C$_1$-C$_6$)alkyl-(C=O)—O—(C$_1$-C$_6$)alkyl, H(O=C)—, H(O=C)—(C$_1$-C$_6$)alkyl, (C$_1$-C$_6$)alkyl(O=C)—, (C$_1$-C$_6$)alkyl(O=C)—(C$_1$-C$_6$)alkyl, NO$_2$, amino, (C$_1$-C$_6$)alkylamino, [(C$_1$-C$_6$)alkyl]$_2$amino, amino(C$_1$-C$_6$)alkyl, (C$_1$-C$_6$)alkylamino(C$_1$-C$_6$)alkyl, [(C$_1$-C$_6$)alkyl]$_2$amino(C$_1$-C$_6$)alkyl, H$_2$N—(C=O)—, (C$_1$-C$_6$)alkyl-NH—(C=O)—, [(C$_1$-C$_6$)alkyl]$_2$N—(C=O)—, H$_2$N(C=O)—(C$_1$-C$_6$)alkyl, (C$_1$-C$_6$)alkyl-HN(C=O)—(C$_1$-C$_6$)alkyl, [(C$_1$-C$_6$)alkyl]$_2$N—(C=O)—(C$_1$-C$_6$)alkyl, H(O=C)—NH—, (C$_1$-C$_6$)alkyl(C=O)—NH, (C$_1$-C$_6$)alkyl(C=O)—[NH](C$_1$-C$_6$)alkyl, (C$_1$-C$_6$)alkyl(C=O)—[N(C$_1$-C$_6$)alkyl](C$_1$-C$_6$)alkyl, (C$_1$-C$_6$)alkyl-S—, (C$_1$-C$_6$)alkyl-(S=O)—, (C$_1$-C$_6$)alkyl-SO$_2$—, (C$_1$-C$_6$)alkyl-SO$_2$—NH—, H$_2$N—SO$_2$—, H$_2$N—SO$_2$—(C$_1$-C$_6$)alkyl, (C$_1$-C$_6$)alkyl-SO$_2$—(C$_1$-C$_6$)alkyl, [(C$_1$-C$_6$)alkyl]$_2$N—SO$_2$—(C$_1$-C$_6$)alkyl, CF$_3$SO$_3$—, (C$_1$-C$_6$)alkyl-SO$_3$—, phenyl, (C$_3$-C$_{10}$)cycloalkyl, (C$_2$-C$_9$) heterocycloalkyl, and (C$_2$-C$_9$)heteroaryl;

wherein R$_2$ is phenyl-(CH$_2$)$_m$—, naphthyl-(CH$_2$)$_m$—, (C$_3$-C$_{10}$)cycloalkyl-(CH$_2$)$_m$—, (C$_1$-C$_6$)alkyl or (C$_2$-C$_9$)heteroaryl-(CH$_2$)$_m$—, wherein each of said phenyl, naphthyl, (C$_3$-C$_{10}$)cycloalkyl or (C$_2$-C$_9$)heteroaryl moieties of said phenyl-(CH$_2$)$_m$—, naphthyl-(CH$_2$)$_m$—, (C$_3$-C$_{10}$)cycloalkyl-(CH$_2$)$_m$— or (C$_2$-C$_9$)heteroaryl-(CH$_2$)$_m$— groups may optionally be substituted with one, two, or three substituents independently selected from the group consisting of hydrogen, halo, cyano, (C$_1$-C$_6$)alkyl, hydroxy, hydroxy-(C$_1$-C$_6$) alkyl, (C$_1$-C$_6$)alkoxy, (C$_1$-C$_6$)alkoxy(C$_1$-C$_6$)alkyl, HO—(C=O)—, (C$_1$-C$_6$)alkyl-O—(C=O)—, HO—(C=O)—(C$_1$-C$_6$)alkyl, (C$_1$-C$_6$)alkyl-O—(C=O)—(C$_1$-C$_6$)alkyl,(C$_1$-C$_6$)alkyl-(C=O)—O—, (C$_1$-C$_6$)alkyl-(C=O)—O—(C$_1$-C$_6$)alkyl, H(O=C)—, H(O=C)—(C$_1$-C$_6$)alkyl, (C$_1$-C$_6$)alkyl(O=C)—, (C$_1$-C$_6$)alkyl(O=C)—(C$_1$-C$_6$)alkyl, NO$_2$, amino, $(C_1-C_6)$alkylamino, $[(C_1-C_6)$alkyl$]_2$amino, amino$(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N-(C=O)-$, $(C_1-C_6)$alkyl-NH—(C=O)—, $[(C_1-C_6)$alkyl$]_2N-(C=O)-$, $H_2N(C=O)-(C_1-C_6)$alkyl, $(C_1-C_6)$alkyl-HN(C=O)—$(C_1-C_6)$alkyl, $[(C_1-C_6)$alkyl$]_2N-(C=O)-(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N($C_1$-$C_6)$alkyl]$(C_1-C_6)$alkyl, $(C_1-C_6)$alkyl-S—, $(C_1-C_6)$alkyl-(S=O)—, $(C_1-C_6)$alkyl-SO$_2$—, $(C_1-C_6)$alkyl-SO$_2$—NH—, $H_2N$—SO$_2$—, $H_2N$—SO$_2$—$(C_1-C_6)$alkyl, $(C_1-C_6)$alkyl-SO$_2$—$(C_1-C_6)$alkyl, $[(C_1-C_6)$alkyl$]_2$N—SO$_2$—$(C_1-C_6)$alkyl, CF$_3$SO$_3$—, $(C_1-C_6)$alkyl-SO$_3$—, phenyl, phenoxy, benzyloxy, $(C_3-C_{10})$cycloalkyl, $(C_2-C_9)$heterocycloalkyl, and $(C_2-C_9)$heteroaryl;

wherein $R^3$ is hydrogen, $(C_1-C_{10})$alkyl, $(C_3-C_{10})$cycloalkyl-$(CH_2)_n$—, $(C_2-C_9)$heterocycloalkyl-$(CH_2)_n$—, $(C_2-C_9)$heteroaryl-$(CH_2)_n$— or aryl-$(CH_2)_n$—; wherein n is an interger from zero to six;

wherein said $R_3$ $(C_1-C_{10})$alkyl group may optionally be substituted with one or more substituents, (preferably from one to three substituents) independently selected from hydrogen, halo, CN, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, NO$_2$, amino, $(C_1-C_6)$alkylamino, $[(C_1-C_6)$alkyl$]_2$amino, amino$(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N-(C=O)-$, $(C_1-C_6)$alkyl-NH—(C=O)—, $[(C_1-C_6)$alkyl$]_2N-(C=O)-$, $H_2N(C=O)-(C_1-C_6)$alkyl, $(C_1-C_6)$alkyl-HN(C=O)—$(C_1-C_6)$alkyl, $[(C_1-C_6)$alkyl$]_2N-(C=O)-(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N($C_1$-$C_6)$alkyl]$(C_1-C_6)$alkyl, $(C_1-C_6)$alkyl-S—, $(C_1-C_6)$alkyl-(S=O)—, $(C_1-C_6)$alkyl-SO$_2$—, $(C_1-C_6)$alkyl-SO$_2$—NH—, $H_2N$—SO$_2$—, $H_2N$—SO$_2$—$(C_1-C_6)$alkyl, $(C_1-C_6)$alkyl-SO$_2$—$(C_1-C_6)$alkyl, $[(C_1-C_6)$alkyl$]_2$N—SO$_2$—$(C_1-C_6)$alkyl, CF$_3$SO$_3$—, $(C_1-C_6)$alkyl-SO$_3$—, phenyl, $(C_3-C_{10})$cycloalkyl, $(C_2-C_9)$heterocycloalkyl, and $(C_2-C_9)$heteroaryl; and wherein any of the carbon-carbon single bonds of said $(C_1-C_{10})$alkyl may optionally be replaced by a carbon-carbon double bond;

wherein the $(C_3-C_{10})$cycloalkyl moiety of said $R_3$ $(C_3-C_{10})$cycloalkyl-$(CH_2)_n$— group may optionally be substituted by one to three substitutents independently selected from the group consisting of hydrogen, halo, CN, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl,$(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, NO$_2$, amino, $(C_1-C_6)$alkylamino, $[(C_1-C_6)$alkyl$]_2$amino, amino$(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N-(C=O)-$, $(C_1-C_6)$alkyl-NH—(C=O)—, $[(C_1-C_6)$alkyl$]_2N-(C=O)-$, $H_2N(C=O)-(C_1-C_6)$alkyl, $(C_1-C_6)$alkyl-HN(C=O)—$(C_1-C_6)$alkyl, $[(C_1-C_6)$alkyl$]_2N-(C=O)-(C_1-C_6)$alkyl, H(O=C)—NH—, $(C_1-C_6)$alkyl(C=O)—[NH]$(C_1-C_6)$alkyl, $(C_1-C_6)$alkyl(C=O)—[N($C_1$-$C_6)$alkyl]$(C_1-C_6)$alkyl, $(C_1-C_6)$alkyl-S—, $(C_1-C_6)$alkyl-(S=O)—, $(C_1-C_6)$alkyl-SO$_2$—, $(C_1-C_6)$alkyl-SO$_2$—NH—, $H_2N$—SO$_2$—, $H_2N$—SO$_2$—$(C_1-C_6)$alkyl, $(C_1-C_6)$alkyl HN—SO$_2$—$(C_1-C_6)$alkyl, $[(C_1-C_6)$alkyl$]_2$N—SO$_2$—$(C_1-C_6)$alkyl, CF$_3$SO$_3$—, $(C_1-C_6)$alkyl-SO$_3$—, phenyl, $(C_3-C_{10})$cycloalkyl, $(C_2-C_9)$heterocycloalkyl, and $(C_2-C_9)$heteroaryl;

wherein the $(C_2-C_9)$heterocycloalkyl moiety of said $R_3$ $(C_2-C_9)$heterocycloalkyl-$(CH_2)_n$— group may contain from one to three heteroatoms independently selected from nitrogen, sulfur, oxygen, >S(=O), >SO$_2$ or >NR$^6$, wherein said $(C_2-C_9)$heterocycloalkyl moiety of said $(C_2-C_9)$heterocycloalkyl-$(CH_2)_n$— group may optionally be substituted on any of the ring carbon atoms capable of forming an additional bond (preferably one to three substituents per ring) with a substituent independently selected from the group consisting of hydrogen, halo, CN, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, NO$_2$, amino, $(C_1-C_6)$alkylamino, $[(C_1-C_6)$alkyl$]_2$amino, amino$(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N-(C=O)-$, $(C_1-C_6)$alkyl-NH—(C=O)—, $[(C_1-C_6)$alkyl$]_2N-(C=O)-$, $H_2N(C=O)-(C_1-C_6)$alkyl, $(C_1-C_6)$alkyl-HN(C=O)—$(C_1-C_6)$alkyl, $[(C_1-C_6)$alkyl$]_2N-(C=O)-(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N($C_1$-$C_6)$alkyl]$(C_1-C_6)$alkyl, $(C_1-C_6)$alkyl-S—, $(C_1-C_6)$alkyl-(S=O)—, $(C_1-C_6)$alkyl-SO$_2$—, $(C_1-C_6)$alkyl-SO$_2$—NH—, $H_2N$—SO$_2$—, $H_2N$—SO$_2$—$(C_1-C_6)$alkyl, $(C_1-C_6)$alkylHN—SO$_2$—$(C_1-C_6)$alkyl, $[(C_1-C_6)$alkyl$]_2$N—SO$_2$—$(C_1-C_6)$alkyl, CF$_3$SO$_3$—, $(C_1-C_6)$alkyl-SO$_3$—, phenyl, $(C_3-C_{10})$cycloalkyl, $(C_2-C_9)$heterocycloalkyl, and $(C_2-C_9)$heteroaryl;

wherein the $(C_2-C_9)$heteroaryl moiety of said $R^3$ $(C_2-C_9)$heteroaryl-$(CH_2)_n$— group may contain from one to three heteroatoms independently selected from nitrogen, sulfur or oxygen, wherein said $(C_2-C_9)$heteroaryl moiety of said $(C_2-C_9)$heteroaryl-$(CH_2)_n$— group may optionally be substituted on any of the ring carbon atoms capable of forming an additional bond (preferably one to three substituents per ring) with a substituent selected from the group consisting of hydrogen, halo, CN, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl,$(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, NO$_2$, amino, $(C_1-C_6)$alkylamino, $[(C_1-C_6)$alkyl$]_2$amino, amino$(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N-(C=O)-$, $(C_1-C_6)$alkyl-NH—(C=O)—, $[(C_1-C_6)$alkyl$]_2N-(C=O)-$, $H_2N(C=O)-(C_1-C_6)$alkyl, $(C_1-C_6)$alkyl-HN(C=O)—$(C_1-C_6)$alkyl, $[(C_1-C_6)$alkyl$]_2N-(C=O)-(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N($C_1$-$C_6)$alkyl]$(C_1-C_6)$alkyl, $(C_1-C_6)$alkyl-S—, $(C_1-C_6)$alkyl-(S=O)—, $(C_1-C_6)$alkyl-SO$_2$—, $(C_1-C_6)$alkyl-SO$_2$—NH—, $H_2N$—SO$_2$—, $H_2N$—SO$_2$—$(C_1-C_6)$alkyl, $(C_1-C_6)$alkylHN—SO$_2$—$(C_1-C_6)$alkyl, $[(C_1-C_6)$alkyl$]_2$N—SO$_2$—$(C_1-C_6)$alkyl, CF$_3$SO$_3$—, $(C_1-C_6)$alkyl-SO$_3$—, phenyl, $(C_3-C_{10})$cycloalkyl, $(C_2-C_9)$heterocycloalkyl, and $(C_2-C_9)$heteroaryl; and wherein said aryl moiety of said $R_3$ aryl-$(CH_2)_n$— group is optionally substituted phenyl or naphthyl, wherein said phenyl and naphthyl may optionally be substituted with from one to three substituents independently selected from the group consisting of hydrogen, halo, CN, $(C_1\text{-}C_6)$alkyl, hydroxy, hydroxy-$(C_1\text{-}C_6)$alkyl, $(C_1\text{-}C_6)$alkoxy, $(C_1\text{-}C_6)$alkoxy$(C_1\text{-}C_6)$alkyl, HO—(C=O)—, $(C_1\text{-}C_6)$alkyl-O—(C=O)—, HO—(C=O)—$(C_1\text{-}C_6)$alkyl, $(C_1\text{-}C_6)$alkyl-O—(C=O)—$(C_1\text{-}C_6)$alkyl,$(C_1\text{-}C_6)$alkyl-(C=O)—O—, $(C_1\text{-}C_6)$alkyl-(C=O)—O—$(C_1\text{-}C_6)$alkyl, H(O=C)—, H(O=C)—$(C_1\text{-}C_6)$alkyl, $(C_1\text{-}C_6)$alkyl(O=C)—, $(C_1\text{-}C_6)$alkyl(O=C)—$(C_1\text{-}C_6)$alkyl, $NO_2$, amino, $(C_1\text{-}C_6)$alkylamino, $[(C_1\text{-}C_6)$alkyl$]_2$amino, amino$(C_1\text{-}C_6)$alkyl, $(C_1\text{-}C_6)$alkylamino$(C_1\text{-}C_6)$alkyl, $[(C_1\text{-}C_6)$alkyl$]_2$amino$(C_1\text{-}C_6)$alkyl, $H_2N$—(C=O)—, $(C_1\text{-}C_6)$alkyl-NH—(C=O)—, $[(C_1\text{-}C_6)$alkyl$]_2N$—(C=O)—, $H_2N$(C=O)—$(C_1\text{-}C_6)$alkyl, $(C_1\text{-}C_6)$alkyl-HN(C=O)—$(C_1\text{-}C_6)$alkyl, $[(C_1\text{-}C_6)$alkyl$]_2N$—(C=O)—$(C_1\text{-}C_6)$alkyl, H(O=C)—NH—, $(C_1\text{-}C_6)$alkyl(C=O)—NH, $(C_1\text{-}C_6)$alkyl(C=O)—[NH]$(C_1\text{-}C_6)$alkyl, $(C_1\text{-}C_6)$alkyl(C=O)—[N$(C_1\text{-}C_6)$alkyl]$(C_1\text{-}C_6)$alkyl, $(C_1\text{-}C_6)$alkyl-S—, $(C_1\text{-}C_6)$alkyl-(S=O)—, $(C_1\text{-}C_6)$alkyl-$SO_2$—, $(C_1\text{-}C_6)$alkyl-$SO_2$—NH—, $H_2N$—$SO_2$—, $H_2N$—$SO_2$—$(C_1\text{-}C_6)$alkyl, $(C_1\text{-}C_6)$alkyl HN—$SO_2$—$(C_1\text{-}C_6)$alkyl, $[(C_1\text{-}C_6)$alkyl$]_2N$—$SO_2$—$(C_1\text{-}C_6)$alkyl, $CF_3SO_3$—, $(C_1\text{-}C_6)$alkyl-$SO_3$—, phenyl, $(C_3\text{-}C_{10})$cycloalkyl, $(C_2\text{-}C_9)$heterocycloalkyl, and $(C_2\text{-}C_9)$heteroaryl;

or $R_3$ and the carbon to which it is attached form a five to seven membered carbocyclic ring, wherein any of the carbon atoms of said five membered carbocyclic ring may optionally be substituted with a substituent selected from the group consisting of hydrogen, halo, CN, $(C_1\text{-}C_6)$alkyl, hydroxy, hydroxy-$(C_1\text{-}C_6)$alkyl, $(C_1\text{-}C_6)$alkoxy, $(C_1\text{-}C_6)$alkoxy$(C_1\text{-}C_6)$alkyl, HO—(C=O)—, $(C_1\text{-}C_6)$alkyl-O—(C=O)—, HO—(C=O)—$(C_1\text{-}C_6)$alkyl, $(C_1\text{-}C_6)$alkyl-O—(C=O)—$(C_1\text{-}C_6)$alkyl,$(C_1\text{-}C_6)$alkyl-(C=O)—O—, $(C_1\text{-}C_6)$alkyl-(C=O)—O—$(C_1\text{-}C_6)$alkyl, H(O=C)—, H(O=C)—$(C_1\text{-}C_6)$alkyl, $(C_1\text{-}C_6)$alkyl(O=C)—, $(C_1\text{-}C_6)$alkyl(O=C)—$(C_1\text{-}C_6)$alkyl, $NO_2$, amino, $(C_1\text{-}C_6)$alkylamino, $[(C_1\text{-}C_6)$alkyl$]_2$amino, amino$(C_1\text{-}C_6)$alkyl, $(C_1\text{-}C_6)$alkylamino$(C_1\text{-}C_6)$alkyl, $[(C_1\text{-}C_6)$alkyl$]_2$amino$(C_1\text{-}C_6)$alkyl, $H_2N$—(C=O)—, $(C_1\text{-}C_6)$alkyl-NH—(C=O)—, $[(C_1\text{-}C_6)$alkyl$]_2N$—(C=O)—, $H_2N$(C=O)—$(C_1\text{-}C_6)$alkyl, $(C_1\text{-}C_6)$alkyl-HN(C=O)—$(C_1\text{-}C_6)$alkyl, $[(C_1\text{-}C_6)$alkyl$]_2N$—(C=O)—$(C_1\text{-}C_6)$alkyl, H(O=C)—NH—, $(C_1\text{-}C_6)$alkyl(C=O)—NH, $(C_1\text{-}C_6)$alkyl(C=O)—[NH]$(C_1\text{-}C_6)$alkyl, $(C_1\text{-}C_6)$alkyl(C=O)—[N$(C_1\text{-}C_6)$alkyl]$(C_1\text{-}C_6)$alkyl, $(C_1\text{-}C_6)$alkyl-S—, $(C_1\text{-}C_6)$alkyl-(S=O)—, $(C_1\text{-}C_6)$alkyl-$SO_2$—, $(C_1\text{-}C_6)$alkyl-$SO_2$—NH—, $H_2N$—$SO_2$—, $H_2N$—$SO_2$—$(C_1\text{-}C_6)$alkyl, $(C_1\text{-}C_6)$alkylHN—$SO_2$—$(C_1\text{-}C_6)$alkyl, $[(C_1\text{-}C_6)$alkyl$]_2N$—$SO_2$—$(C_1\text{-}C_6)$alkyl, $CF_3SO_3$—, $(C_1\text{-}C_6)$alkyl-$SO_3$—, phenyl, $(C_3\text{-}C_{10})$cycloalkyl, $(C_2\text{-}C_9)$heterocycloalkyl, and $(C_2\text{-}C_9)$heteroaryl; wherein one of the carbon-carbon bonds of said five to seven membered carbocyclic ring may optionally be fused to an optionally substituted phenyl ring, wherein said substituents may be independently selected from hydrogen, halo, CN, $(C_1\text{-}C_6)$alkyl, hydroxy, hydroxy-$(C_1\text{-}C_6)$alkyl, $(C_1\text{-}C_6)$alkoxy, $(C_1\text{-}C_6)$alkoxy$(C_1\text{-}C_6)$alkyl, HO—(C=O)—, $(C_1\text{-}C_6)$alkyl-O—(C=O)—, HO—(C=O)—$(C_1\text{-}C_6)$alkyl, $(C_1\text{-}C_6)$alkyl-O—(C=O)—$(C_1\text{-}C_6)$alkyl,$(C_1\text{-}C_6)$alkyl-(C=O)—O—, $(C_1\text{-}C_6)$alkyl-(C=O)—O—$(C_1\text{-}C_6)$alkyl, H(O=C)—, H(O=C)—$(C_1\text{-}C_6)$alkyl, $(C_1\text{-}C_6)$alkyl(O=C)—, $(C_1\text{-}C_6)$alkyl(O=C)—$(C_1\text{-}C_6)$alkyl, $NO_2$, amino, $(C_1\text{-}C_6)$alkylamino, $[(C_1\text{-}C_6)$alkyl$]_2$amino, amino$(C_1\text{-}C_6)$alkyl, $(C_1\text{-}C_6)$alkylamino$(C_1\text{-}C_6)$alkyl, $[(C_1\text{-}C_6)$alkyl$]_2$amino$(C_1\text{-}C_6)$alkyl, $H_2N$—(C=O)—, $(C_1\text{-}C_6)$alkyl-NH—(C=O)—, $[(C_1\text{-}C_6)$alkyl$]_2N$—(C=O)—, $H_2N$(C=O)—$(C_1\text{-}C_6)$alkyl, $(C_1\text{-}C_6)$alkyl-HN(C=O)—$(C_1\text{-}C_6)$alkyl, $[(C_1\text{-}C_6)$alkyl$]_2N$—(C=O)—$(C_1\text{-}C_6)$alkyl, H(O=C)—NH—, $(C_1\text{-}C_6)$alkyl(C=O)—NH, $(C_1\text{-}C_6)$alkyl(C=O)—[NH]$(C_1\text{-}C_6)$alkyl, $(C_1\text{-}C_6)$alkyl(C=O)—[N$(C_1\text{-}C_6)$alkyl]$(C_1\text{-}C_6)$alkyl, $(C_1\text{-}C_6)$alkyl-S—, $(C_1\text{-}C_6)$alkyl-(S=O)—, $(C_1\text{-}C_6)$alkyl-$SO_2$—, $(C_1\text{-}C_6)$alkyl-$SO_2$—NH—, $H_2N$—$SO_2$—, $H_2N$—$SO_2$—$(C_1\text{-}C_6)$alkyl, $(C_1\text{-}C_6)$alkylHN—$SO_2$—$(C_1\text{-}C_6)$alkyl, $[(C_1\text{-}C_6)$alkyl$]_2N$—$SO_2$—$(C_1\text{-}C_6)$alkyl, $CF_3SO_3$—, $(C_1\text{-}C_6)$alkyl-$SO_3$—, phenyl, $(C_3\text{-}C_{10})$cycloalkyl, $(C_2\text{-}C_9)$heterocycloalkyl, and $(C_2\text{-}C_9)$heteroaryl;

wherein $R_4$ is hydrogen, $(C_1\text{-}C_6)$alkyl, hydroxy, $(C_1\text{-}C_6)$alkoxy, hydroxy$(C_1\text{-}C_6)$alkyl, $(C_1\text{-}C_6)$alkoxy(C=O)—, $(C_3\text{-}C_{10})$cycloalkyl-$(CH_2)_q$—, $(C_2\text{-}C_9)$heterocycloalkyl-$(CH_2)_q$—, $(C_2\text{-}C_9)$heteroaryl-$(CH_2)_q$—, phenyl-$(CH_2)_q$—, or naphthyl-$(CH_2)_q$—; wherein said $(C_2\text{-}C_9)$heterocycloalkyl, $(C_2\text{-}C_9)$heteroaryl, phenyl and naphthyl groups may be optionally substituted with one or two substituents from the group consisting of hydrogen, halo, cyano, $(C_1\text{-}C_6)$alkyl, hydroxy, hydroxy-$(C_1\text{-}C_6)$alkyl, $(C_1\text{-}C_6)$alkoxy, $(C_1\text{-}C_6)$alkoxy$(C_1\text{-}C_6)$alkyl, HO—(C=O)—, $(C_1\text{-}C_6)$alkyl-O—(C=O)—, HO—(C=O)—$(C_1\text{-}C_6)$alkyl, $(C_1\text{-}C_6)$alkyl-O—(C=O)—$(C_1\text{-}C_6)$alkyl,$(C_1\text{-}C_6)$alkyl-(C=O)—O—, $(C_1\text{-}C_6)$alkyl-(C=O)—O—$(C_1\text{-}C_6)$alkyl, H(O=C)—, H(O=C)—$(C_1\text{-}C_6)$alkyl, $(C_1\text{-}C_6)$alkyl(O=C)—, $(C_1\text{-}C_6)$alkyl(O=C)—$(C_1\text{-}C_6)$alkyl, $NO_2$, amino, $(C_1\text{-}C_6)$alkylamino, $[(C_1\text{-}C_6)$alkyl$]_2$ amino, amino$(C_1\text{-}C_6)$alkyl, $(C_1\text{-}C_6)$alkylamino $(C_1\text{-}C_6)$alkyl, $[(C_1\text{-}C_6)$alkyl$]_2$amino$(C_1\text{-}C_6)$alkyl, $H_2N$—(C=O)—, $(C_1\text{-}C_6)$alkyl-NH—(C=O)—, $[(C_1\text{-}C_6)$alkyl$]_2N$—(C=O)—, $H_2N$(C=O)—$(C_1\text{-}C_6)$alkyl, $(C_1\text{-}C_6)$alkyl-HN(C=O)—$(C_1\text{-}C_6)$alkyl, $[(C_1\text{-}C_6)$alkyl$]_2N$—(C=O)—$(C_1\text{-}C_6)$alkyl, H(O=C)—NH—, $(C_1\text{-}C_6)$alkyl(C=O)—NH, $(C_1\text{-}C_6)$alkyl(C=O)—[NH]$(C_1\text{-}C_6)$alkyl, $(C_1\text{-}C_6)$alkyl(C=O)—[N$(C_1\text{-}C_6)$alkyl]$(C_1\text{-}C_6)$alkyl, $(C_1\text{-}C_6)$alkyl-S—, $(C_1\text{-}C_6)$alkyl-(S=O)—, $(C_1\text{-}C_6)$alkyl-$SO_2$—, $(C_1\text{-}C_6)$alkyl-$SO_2$—NH—, $H_2N$—$SO_2$—, $H_2N$—$SO_2$—$(C_1\text{-}C_6)$alkyl, $(C_1\text{-}C_6)$alkylHN—$SO_2$—$(C_1\text{-}C_6)$alkyl, $[(C_1\text{-}C_6)$alkyl$]_2N$—$SO_2$—$(C_1\text{-}C_6)$alkyl, $CF_3SO_3$—, $(C_1\text{-}C_6)$alkyl-$SO_3$, phenyl, $(C_3\text{-}C_{10})$cycloalkyl, $(C_2\text{-}C_9)$heterocycloalkyl, and $(C_2\text{-}C_9)$heteroaryl;

wherein $R_5$ is hydrogen, $(C_1\text{-}C_6)$alkyl or amino; or $R_4$ and $R_5$ together with the nitrogen atom to which they are attached form a $(C_2\text{-}C_9)$heterocycloalkyl group optionally substituted with one or two substituents selected from the group consisting of hydrogen, halo, cyano, $(C_1\text{-}C_6)$alkyl, hydroxy, hydroxy-$(C_1\text{-}C_6)$alkyl, $(C_1\text{-}C_6)$alkoxy, $(C_1\text{-}C_6)$alkoxy$(C_1\text{-}C_6)$alkyl, HO—(C=O)—, $(C_1\text{-}C_6)$alkyl-O—(C=O)—, HO—(C=O)—$(C_1\text{-}C_6)$alkyl, $(C_1\text{-}C_6)$alkyl-O—(C=O)—$(C_1\text{-}C_6)$alkyl, $(C_1\text{-}C_6)$alkyl-(C=O)—O—, $(C_1\text{-}C_6)$alkyl-(C=O)—O—$(C_1\text{-}C_6)$alkyl, H(O=C)—, H(O=C)—$(C_1\text{-}C_6)$alkyl, $(C_1\text{-}C_6)$ alkyl(O=C)—, $(C_1\text{-}C_6)$alkyl(O=C)—$(C_1\text{-}C_6)$alkyl, $NO_2$, amino, $(C_1\text{-}C_6)$alkylamino, $[(C_1\text{-}C_6)$alkyl$]_2$ amino, amino$(C_1\text{-}C_6)$alkyl, $(C_1\text{-}C_6)$alkylamino $(C_1\text{-}C_6)$alkyl, $[(C_1\text{-}C_6)$alkyl$]_2$amino$(C_1\text{-}C_6)$alkyl, $H_2N$—(C=O)—, $(C_1\text{-}C_6)$alkyl-NH—(C=O)—, $[(C_1\text{-}C_6)$alkyl$]_2N$—(C=O)—, $H_2N$(C=O)—$(C_1\text{-}C_6)$alkyl, $(C_1\text{-}C_6)$alkyl-HN(C=O)—$(C_1\text{-}C_6)$alkyl, $[(C_1\text{-}C_6)$alkyl$]_2N$—(C=O)—$(C_1\text{-}C_6)$alkyl, H(O=C)—NH—, $(C_1\text{-}C_6)$alkyl(C=O)—NH, $(C_1\text{-}C_6)$alkyl(C=O)—[NH]$(C_1\text{-}C_6)$alkyl, $(C_1\text{-}C_6)$alkyl(C=O)—[N$(C_1\text{-}C_6)$alkyl]$(C_1\text{-}C_6)$alkyl, $(C_1\text{-}C_6)$alkyl-S—, $(C_1\text{-}C_6)$alkyl-(S=O)—, $(C_1\text{-}C_6)$alkyl-$SO_2$—, $(C_1\text{-}C_6)$alkyl-$SO_2$—NH—, $H_2N$—$SO_2$—, $H_2N$—$SO_2$—$(C_1\text{-}C_6)$alkyl, $(C_1\text{-}C_6)$alkylHN—$SO_2$—$(C_1\text{-}C_6)$alkyl, $[(C_1\text{-}C_6)$alkyl$]_2N$—$SO_2$—$(C_1\text{-}C_8)$alkyl, $CF_3SO_3$—, $(C_1\text{-}C_6)$alkyl-$SO_3$—, phenyl, $(C_3\text{-}C_{10})$cycloalkyl, $(C_2\text{-}C_9)$heterocycloalkyl, and $(C_2\text{-}C_9)$heteroaryl;

wherein $R^6$ is hydrogen, $(C_1\text{-}C_6)$alkyl, $(C_1\text{-}C_6)$alkoxy-$(CH_2)_g$—, $(C_1\text{-}C_6)$alkoxy(C=O)—$(CH_2)_g$—, $(C_1\text{-}C_6)$alkyl-$(SO_2)$—$(CH_2)_g$—, $(C_6\text{-}C_{10})$aryloxy-$(CH_2)_g$—, $(C_6\text{-}C_{10})$aryloxy(C=O)—$(CH_2)_g$—, or $(C_6\text{-}C_{10})$aryl-$(SO_2)$—$(CH_2)_g$—;

wherein g is an integer from zero to four;
wherein m is an integer from zero to four;
wherein n is an interger from zero to six;
with the proviso that when one of $R^4$ or $R^5$ is hydrogen, and the other of $R^4$ or $R^5$ is $(C_1-C_6)$alkyl; $R^2$ is $(C_3-C_{10})$cycloalkyl or isopropyl and $R^3$ is $(C_3-C_5)$alkyl, phenyl, methylvinyl, dimethylvinyl, halovinyl, hydroxy$(C_1-C_3)$alkyl or amino$(C_1-C_4)$alkyl then $R^1$ must be other than indol-5-yl, 6-azaindol-2-yl, 2,3-dichloro-pyrrol-5-yl, 4-hydroxyquinolin-3-yl, 2-hydroxyquinoxalin-3-yl, 6-azaindolin-3-yl, or optionally substituted indol-2 or 3-yl;

and the pharmaceutically acceptable salts of such compounds.

Unless otherwise indicated, the alkyl and alkenyl groups referred to herein, as well as the alkyl moieties of other groups referred to herein (e.g., alkoxy), may be linear or branched, and they may also be cyclic (e.g., cyclopropyl, cyclobutyl, cyclopentyl, cyclohexyl or cycloheptyl) or be linear or branched and contain cyclic moieties. Such alkyl and alkoxy groups may be substituted with one, two or three halogen and/or hydroxy atoms, preferably fluorine atoms.

Unless otherwise indicated, "halogen" includes fluorine, chlorine, bromine, and iodine.

"$(C_3-C_{10})$cycloalkyl" when used herein refers to cycloalkyl groups containing zero to two levels of unsaturation such as cyclopropyl, cyclobutyl, cyclopentyl, cyclopentenyl, cyclohexyl, cyclohexenyl, 1,3-cyclohexadiene, cycloheptyl, cycloheptenyl, bicyclo[3.2.1]octane, norbornanyl, and the like.

"$(C_2-C_9)$heterocycloalkyl" when used herein refers to pyrrolidinyl, tetrahydrofuranyl, dihydrofuranyl, tetrahydropyranyl, pyranyl, thiopyranyl, aziridinyl, oxiranyl, methylenedioxyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, chromanyl, and the like. One of ordinary skill in the art will understand that the connection of said $(C_2-C_9)$heterocycloalkyl rings is through a carbon or a $sp^3$ hybridized nitrogen heteroatom.

"$(C_2-C_9)$heteroaryl" when used herein refers to furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5,6,7,8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, benzoxazinyl, and the like. One of ordinary skill in the art will understand that the connection of said $(C_2-C_9)$heterocycloalkyl rings is through a carbon atom or a $sp^3$ hybridized nitrogen heteroatom.

"Aryl" when used herein refers to phenyl or naphthyl.

"Protected amine" and "protected amino" refers to an amine group with one of the hydrogen atoms replaced with a protecting group (P). Any suitable protecting group may be used for amine protection. Suitable protecting groups include carbobenzyloxy, t-butoxy carbonyl (BOC) or 9-fluorenylmethylenoxy carbonyl.

Compounds of Formula CCR1-I and their methods of manufacture are disclosed in commonly assigned U.S. patent application Ser. No. 09/380,269, filed Feb. 5, 1998, U.S. patent application Ser. No. 09/403,218, filed Jan. 18, 1999, PCT Publication No. WO98/38167, and PCT Publication No. WO99/40061, all of which are incorporated herein by reference in their entireties for all purposes.

In a preferred embodiment, the CCR1 inhibitor is selected from one of the following compounds of Formula CCR1-I:

quinoxaline-2-carboxylic acid 4(R)-carbamoyl-1(S)-(3-chloro-benzyl)-2(S),7-dihydroxy-7-methyl-octyl]-amide;

7,8-difluoro-quinoline-3-carboxylic acid (1S)-benzyl-4(R)-carbamoyl-2(S),7-dihydroxy-7-methyl-octyl)-amide;

6,7,8-trifluoro-quinoline-3-carboxylic acid (1(S)-benzyl-4(R)-carbamoyl-2(S),7-dihydroxy-7-methyl-octyl)-amide;

quinoxaline-2-carboxylic acid [4(R)-carbamoyl-1(S)-(3-fluoro-benzyl)-2(S),7-dihydroxy-7-methyl-octyl]-amide;

quinoxaline-2-carboxylic acid (1(S)-benzyl-2(S),7-dihydroxy-4(R)-hydroxycarbamoyl-7-methyl-octyl)-amide;

quinoxaline-2-carboxylic acid [4(R)-carbamoyl-1(S)-(2-chloro-benzyl)-2(S),7-dihydroxy-7-methyl-octyl]-amide;

quinoxaline-2-carboxylic acid [1(S)-(2-fluoro-benzyl)-2(S),7-dihydroxy-4(R)-hydroxycarbamoyl-7-methyl-octyl]-amide;

quinoxaline-2-carboxylic acid [4(R)-carbamoyl-1(S)-(2-fluoro-benzyl)-2(S),7-dihydroxy-7-methyl-octyl]-amide;

quinoxaline-2-carboxylic acid [1(S)-(3,4-difluoro-benzyl)-2(S),7-dihydroxy-4(R)-hydroxycarbamoyl-7-methyl-octyl]-amide;

quinoxaline-2-carboxylic acid [4(R)-carbamoyl-1(S)-(3,4-difluoro-benzyl)-2(S),7-dihydroxy-7-methyl-octyl]-amide;

quinoxaline-2-carboxylic acid (4(R)-carbamoyl-2(S),7-dihydroxy-7-methyl-1(S)-naphthalen-1-ylmethyl-octyl)-amide;

7,8-difluoro-quinoline-3-carboxylic acid 1(S)-benzyl-2(S)-hydroxy-7-methyl-4(R)-methylcarbamoyl-octyl)-amide;

8-fluoro-quinoline-3-carboxylic acid 1(S)-benzyl-2(S)-hydroxy-7-methyl-4(R)-methylcarbamoyl-octyl)-amide;

quinoxaline-2-carboxylic acid [4(R)-carbamoyl-7-fluoro-1-(3(S)-fluoro-benzyl)-2(S)-hydroxy-7-methyl-octyl]-amide;

quinoxaline-2-carboxylic acid [4(R)-carbamoyl-1-(2(S)-fluoro-benzyl)-2(S)-hydroxy-7-methyl-octyl]-amide;

quinoxaline-2-carboxylic acid [1(S)-benzyl-4(S)-carbamoyl-4(S)-(2,6-dimethyl-tetrahydro-pyran-4-yl)-2(S)-hydroxy-butyl]-amide;

quinoxaline-2-carboxylic acid 1(S)-benzyl-4(R)-carbamoyl-7-fluoro-2(S)-hydroxy-7-methyl-octyl)-amide;

quinoxaline-2-carboxylic acid 1(S)-benzyl-5-cyclohexyl-2(S)-hydroxy-4(R)-methylcarbamoyl-pentyl)-amide;

quinoxaline-2-carboxylic acid 1(S)-cyclohexylmethyl-2(S)-hydroxy-7-methyl-4(R)-methylcarbamoyl-octyl)-amide;

quinoxaline-2-carboxylic acid [1(S)-benzyl-2(S)-hydroxy-4(S)-hydroxycarbamoyl-4-(1-hydroxy-4-methyl-cyclohexyl)-butyl]-amide;

quinoxaline-2-carboxylic acid [1(S)-benzyl-4(S)-(4,4-difluoro-1-hydroxy-cyclohexyl)-2(S)-hydroxy-4-hydroxycarbamoyl-butyl]-amide;

quinoxaline-2-carboxylic acid [1(S)-benzyl-4(S)-carbamoyl-4(S)-(4,4-difluoro-cyclohexyl)-2(S)-hydroxy-butyl]-amide;

quinoline-3-carboxylic acid (1(S)-benzyl-4(S)-carbamoyl-4-cyclohexyl-2(S)-hydroxy-butyl)-amide;

quinoxaline-2-carboxylic acid (4(R)-carbamoyl-2(S)-hydroxy-7-methyl-1(S)-thiophen-2-ylmethyl-octyl)-amide;

quinoxaline-2-carboxylic acid 1(S)-benzyl-4(R)-carbamoyl-7-chloro-2(S)-hydroxy-oct-6-enyl)-amide;

quinoxaline-2-carboxylic acid 1(S)-benzyl-4(R)-carbamoyl-2(S)-hydroxy-5-phenyl-pentyl)-amide;

N-1(S)-benzyl-4(R)-carbamoyl-7-fluoro-2(S)-hydroxy-7-methyl-octyl)-5,6-dichloro-nicotinamide;

quinoxaline-2-carboxylic acid (4(R)-carbamoyl-2(S)-hydroxy-7-methyl-1(S)-thiazol-4(R)-ylmethyl-octyl)-amide;

benzothiazole-2-carboxylic acid 1(S)-benzyl-4(R)-carbamoyl-7-fluoro-2(S)-hydroxy-7-methyl-octyl)-amide; and benzofuran-2-carboxylic acid 1(S)-benzyl-4(R)-carbamoyl-7-fluoro-2(S)-hydroxy-7-methyl-octyl)-amide.

In another preferred embodiment, the CCR1 compound has a formula Ia-1:

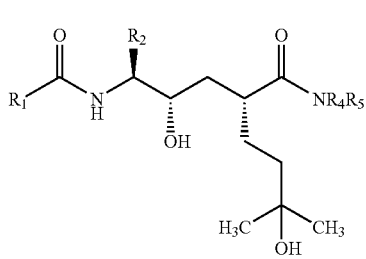
(Ia-1)

wherein the substituents are as defined above.

In a preferred method of making the compound Ia-1, the reaction is started with Scheme 1. In the herein described processes, the substituents are as defined for CCR1-I, and the following:

$R_7$ is hydroxy, $(C_1-C_6)$alkyl, or phenyl wherein the phenyl group unsubstituted or substituted with one, two, or three $(C_1-C_6)$alkyl, hydroxy, or halogen groups;

$R_8$ is hydroxy or halogen;

$R_9$ is phenyl, naphthyl, $(C_3-C_{10})$cycloalkyl, $(C_1-C_6)$alkyl or $(C_2-C_9)$heteroaryl, wherein each of said phenyl, naphthyl, $(C_3-C_{10})$cycloalkyl or $(C_2-C_9)$heteroaryl groups may be unsubstituted or substituted with one, two, or three substituents independently selected from the group consisting of halogen, cyano, and $(C_1-C_6)$alkyl;

P is a protecting group;

X is hydroxy or halogen; and q is 0, 1, 2, 3, or 4.

Scheme 1

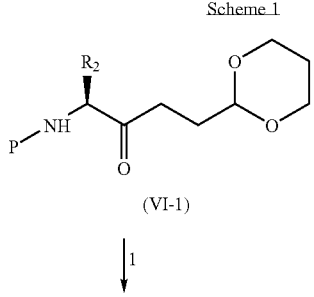
(VI-1)

↓1

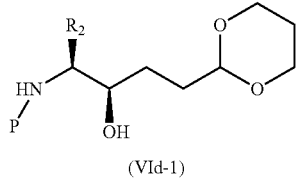
(VId-1)

↓2

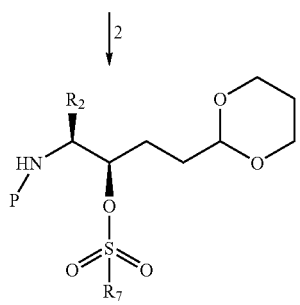
(VIe-1)

↓3

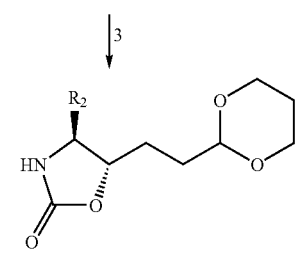
(VIf-1)

↓4

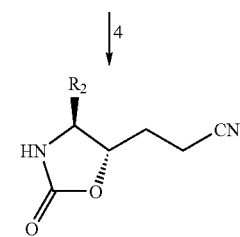
(VIg-1)

↓5

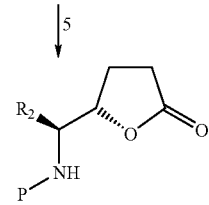
(V-1)

In scheme 1 step 1, a compound of the formula (VI-1) is reduced with a reducing agent under heat to form a compound of the formula (VId-1). In one embodiment, the reducing agent is aluminum triisopropoxide and isopropanol. Preferably, the temperature is maintained above room temperature, more preferably between about 60° C. and about 82° C. The product alcohol can be isolated by either cooling the reaction mixture to room temperature, diluting with more isopropanol and collecting the crystalline material or by cooling the reaction to room temperature and adding 1N HCL and water and collecting the crystalline material.

Step 2 of scheme 1 includes reacting a compound of the formula $R_7$—$SO_2$—X and a compound of the formula (VId- 1) in the presence of a base to form the compound of the formula (VIe-1). Any amine base is suitable, including pyridine, triethylamine, N-methylmayholine, and diisoyropylethylamine. In one embodiment, R₇—SO2-R₈ is p-toluenesulfonic acid, methanesulfonic acid, sulfuric acid, or methanesulfonyl chloride. In another embodiment, the conversion of hydroxy dioxane (VId-1) to dioxane oxazolidinone (VIe-1) can be achieved by treatment of the hydroxy dioxane (VId-1) with methanesulfonyl chloride and triethylamine in tetrahydrofuran solution and heating the mixture to cause the cyclization of the mesylate formed in situ to the oxazolidinone.

In step 3 of scheme 1, a compound of the formula (VIf-1) may be formed by heating the compound of the formula (VIe-1). The reaction may proceed by dissolving compound VIe-1 in a solvent such as pyridine or N-methyl imidazole and heating the mixture for several hours at temperature from about 50° C. to about 100° C.; preferably at about 80° C. The mesylate (VIf-1) may be recovered by extraction into an organic solvent such as ethyl acetate and removal of the amine solvents by extraction of the solution with aqueous acid.

Step 4 of scheme 1 depicts reacting hydroxylamine hydrochloride, a compound of the formula R₇—SO₂—X, and a compound of the formula (VIf-1) to form a compound of the formula (VIg-1). In one embodiment, R₇—SO2-X is p-toluenesulfonic acid, methanesulfonic acid, sulfuric acid, or methanesulfonyl chloride. The reaction may occur in a solvent, such as methanol. In one embodiment, the reaction occurs in methanol with tosic acid at reflux for 8 to 24 hours. The resulting nitrile oxazolidinone contains a small amount of the corresponding ethyl ester which is not removed since it also is converted to the desired lactone in subsequent steps.

Step 5 of scheme 1 includes a) hydrolyzing a compound of the formula (VIg-1) with an aqueous solution in the presence of a base, b) protecting the amine group of the compound so formed, and c) cyclizing the compound so formed with heat and an acid catalyst. In one embodiment, the compound VIg-1 is hydrolyzed with sodium hydroxide. The pH is adjusted to approximately 10 and tetrahydrofuran and BOC dicarbonate are added. This provides the protected hydroxy acid, which may be heated in 10% acetic acid and toluene to provide the protected amine lactone (V-1).

The compound of formula (V-1) may also be produced according to scheme 2.

Scheme 2

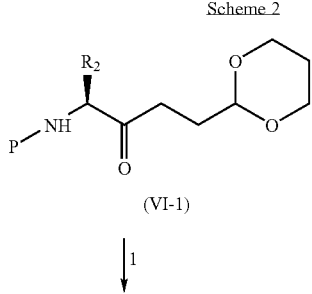

(VI-1)

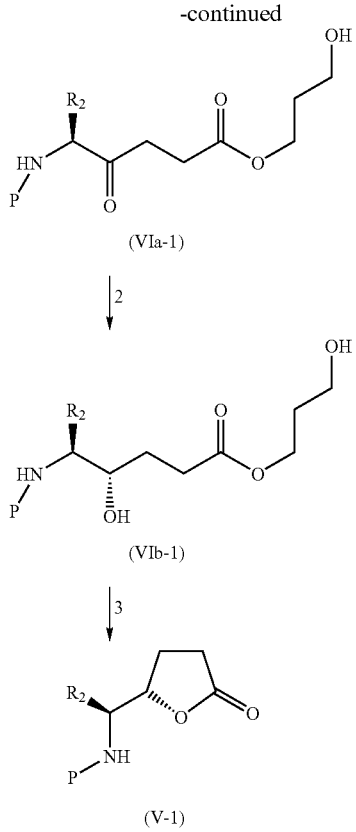

In step 1 of scheme 2, a compound of the formula (VI-1) may be reacted with ozone to for a compound of the formula (VIa-1). The compound VI-1 may be present in a solvent, such as ethyl acetate, and the ozone introduced through sparging at a temperature below room temperature, preferably at about −15° C., until the starting dioxane ketone is substantially reacted. Any excess ozone may be removed by bubbling nitrogen through the solution. The resulting crude ketone ester mixture may be isolated after treatment with aqueous sodium bisulfite to remove any hydroperoxides.

Alternatively, in step 1 of scheme 2, the compound of the formula (VIa-1) may be formed by reacting hypochlorous acid and a compound of the formula (VI-1). Such an oxidation reaction typically produces chlorinated forms of the compound VIa-1 as side products in addition o the compound VIa-1. This oxidation reaction proceeds by mixing the compound VI-1 in solvent, such as acetic acid and/or acetone, and adding sodium hypochlorite, while keeping the mixture at a low temperature, preferably at or below about 0° C.

As a means to convert the side product chlorinated forms of the compound VIa-1 to compounds of the formula V-1, the compounds formed from the hypochlorous acid oxidation reaction may optionally be hydrogenated by reaction with hydrogen in the presence of a catalyst. The hydrogenation may include introducing the products from the hypochlorous acid oxidation reaction into a solvent system of tetrahydrofuran and water, followed by addition of a Pd/C catalyst. The resulting mixture is subjected to hydrogen above atmospheric pressure and temperature. In one embodiment, the pressure is about 80 pounds per square inch and the temperature is maintained from about 60° C. to about 70° C. until the reaction is substantially complete.

In step 2 of scheme 2, the compound of the formula (VIb-1) may be formed by reacting a silyating agent and a compound of the formula (VIa-1) and reacting the compound so formed with a reducing agent. In one embodiment, the reducing agent is N-selectride. In another embodiment, the silyating agent is 1,1,1,3,3,3-hexamethyl-disilazane. The reduction reaction may occur at temperatures below about 0° C., preferably below about −20° C., more preferably below about −50° C. In addition, the reducing agent may be present in slight excess.

In step 3 of scheme 2, the compound of the formula (V-1) is formed by heating a compound of the formula (VIb-1) in the presence of an acid catalyst, such as acetic acid. In one embodiment, the cyclization reaction occurs by introducing the compound VIb-1 into a solvent mixture, such as toluene and 10% acetic acid, at the solvent reflux temperature for 8 to 16 hours. This provides the desired lactone as a crystalline solid after work up.

One method of making the compound of the formula (VI-1) is by reacting a compound of the formula (VII-1)

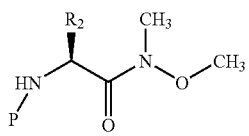

(VII-1)

with a Grinard reagent formed in situ by addition of 2-(2-bromo-ethyl)-[1,3]dioxane to a mixture comprising magnesium and the compound of the formula (VII-1). In one embodiment, the mixture further comprises methyl magnesium chloride and/or methyl magnesium bromide in a solvent. Any exotherm formed from the reaction may be controlled by the rate of addition of the bromide.

The compound of the formula (VII-1) may be formed by coupling N,O-dimethylhydroxylamine hydrochloride and a compound of the formula (VIII-1)

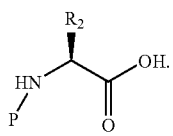

(VIII-1)

This coupling reaction may be performed by mixed anhydride procedure. In one mixed anhydride procedure, compound VIII-1 is combined with methylene chloride and N-methylmorpholine is added followed by isobutyl chloroformate. In a separate mixture, a slurry of N,O-dimethylhydroxylamine hydrochloride is treated with N-methylmorpholine. The two reaction mixtures are combined and then quenched with a solution of citric acid in water. This procedure preferably operates at a temperature below about 20° C., more preferably below about 0° C.

Compounds of formula (V-1) may be used to produce compounds of the formula (IVa1-1) according to scheme 3:

Scheme 3

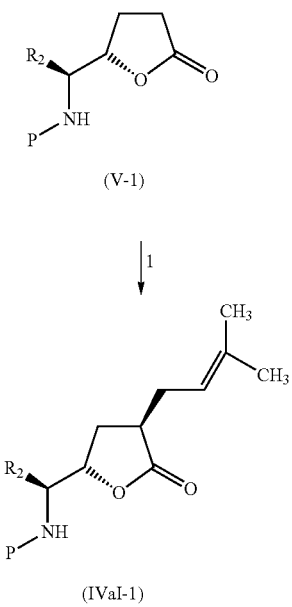

In step 1 of scheme 3, the compound of the formula (IVa1-1) may be formed by reacting 4-halo-2-methyl-2-butene and a compound of the formula (V-1) in the presence of a base. Exemplary bases include lithium dialkyl amides such as lithium N-isopropyl-N-cyclohexylamide, lithium bis(trimethylsilyl)amide, lithium di-isopropylamide, and potassium hydride. Suitable solvents include aprotic polar solvents such as ethers (such as tetrahydrofuran, glyme or dioxane), benzene, or toluene, preferably tetrahydrofuran. The aforesaid reaction is conducted at a temperature from about −78° C. to about 0° C., preferably at about −78° C. In one embodiment, alkylation of the lactone (V-1) is accomplished by reacting the lactone (V-1) with lithium bis(trimethylsilyl)amide and dimethylallyl bromide in tetrahydrofuran at a temperature from about −78° C. to about −50° C. Reaction times range from several hours or if an additive such as dimethyl imidazolidinone is present, the reaction may be complete in minutes.

Compounds of formula (IVa1-1) may be used to produce compounds of the formula (Ia-1) according to scheme 4:

Scheme 4

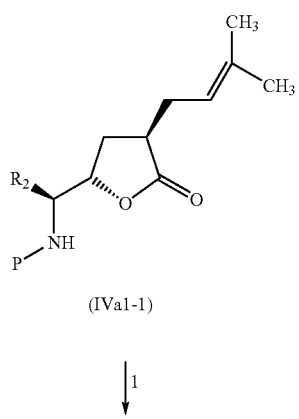

(IVa1-1)

-continued

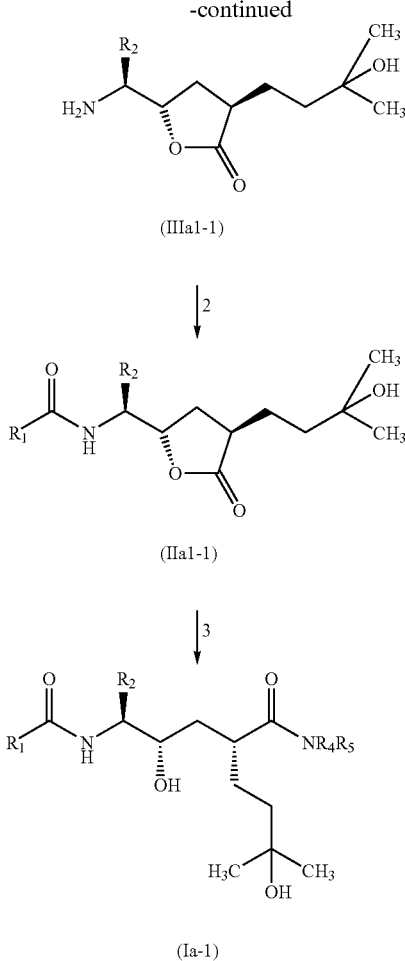

In step 1 of scheme 4, a compound of the formula (IIIa1-1) is formed by reacting a compound of the formula (IVa1-1) with phosphoric acid. Preferably, this reaction occurs in any suitable solvent, such as non-alcoholic solvents. Two preferred solvents include tetrahydrofuran and dichloroethane. The reaction may take place at any suitable temperature, preferably from about −25° C. to about 120° C., more preferably from about 15° C. to about 40° C. Reaction time is dependent on temperature and batch size, amount other factors, but typically reaction time is from about 2 hours to about 14 hours.

Step 2 of scheme 4 depicts coupling a compound IIIa1-1 with a compound having the formula $R_1$—CO—X to form a compound having the formula (IIa1-1). This coupling reaction is generally conducted at a temperature from about −30° C. to about 80° C., preferably from about 0° C. to about 25° C. The coupling reaction may occur with a coupling reagent that activates the acid functionality. Exemplary coupling reagents include dicyclohexylcarbodiimide/hydroxybenzotriazole (DCC/HBT), N-3-dimethylaminopropyl-N'-ethylcarbodiimide (EDC/HBT), 2-ethyoxy-1-ethoxycarbonyl-1,2-dihydroquinoline (EEDQ), carbonyl diimidazole (CDI), and diethylphosphorylcyanide. The coupling is conducted in an inert solvent, preferably an aprotic solvent, such as tetrahydrofuran, acetonitirile, dichloromethane, chloroform, or N,N-dimethylformamide. One preferred solvent is tetrahydrofuran. In one embodiment, quinoxaline acid is combined with CDI in anhydrous tetrahydrofuran and heated to provide the acyl imidazole. Compound IIIa1-1 is added to the acyl imidazole at room temperature to form the compound IIa1-1.

Step 3 of scheme 4 includes reacting the compound of formula IIa1-1 with an amine having a formula $NHR_4R_5$ to form a compound of the formula (Ia-1). In one embodiment, the amine is ammonia either anhydrous in an organic solvent or as an aqueous solution of ammonium hydroxide added to a polar solvent at a temperature from about −10° C. to about 35° C., preferably at about 30° C. Suitable solvents include, alcohols, such as methanol, ethanol, or butanols; ethers such as tetrahydrofuran, glyme or dioxane; or a mixture thereof, including aqueous mixtures. Preferably the solvent is methanol. In one embodiment, the compound IIa1-1 is dissolved in methanol which has been saturated with ammonia gas. In another embodiment, the compound IIa1-1 in methanol is treated with ammonium hydroxide in tetrahydrofuran at room temperature.

Scheme 5 represents an alternative method to form compounds of formula Ia-1 from compounds of formula IVa1-1.

Scheme 5

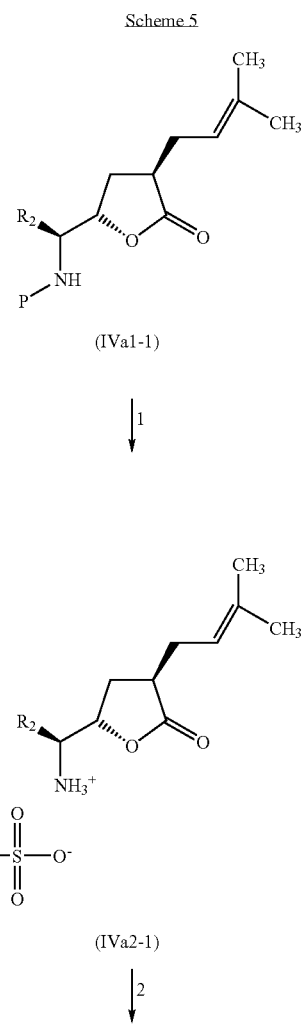

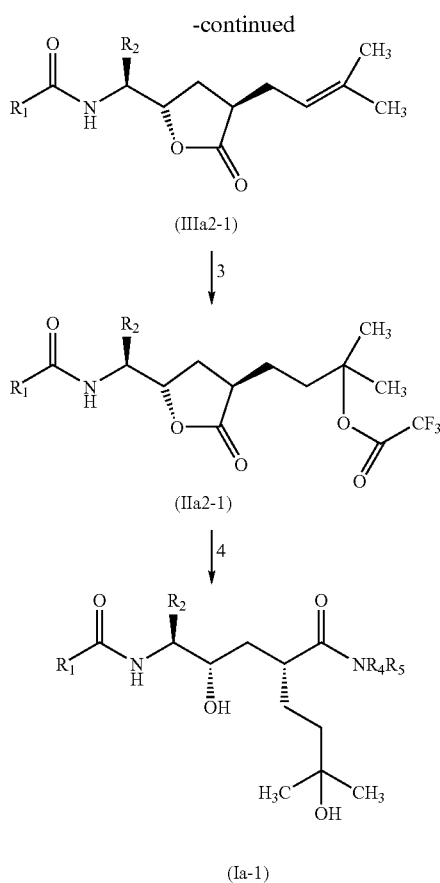

In step 1 of scheme 5, a compound of the formula (IVa1-1) is reacted with a compound of the formula $R_9$—$SO_2$—X to form a compound of the formula (IVa2-1). Any suitable acidic deprotection reaction may be performed. In one example, an excess of p-toluenesulfonic acid hydrate in ethyl acetate is introduced to the compound IVa1-1 at room temperature. Suitable solvents include ethyl acetate, alcohols, tetrahydrofuran, and mixtures thereof. The reaction may proceed at ambient or elevated temperatures. Typically, the reaction is substantially complete within two and twelve hours. The resulting compound IVa2-1 may be crystallized and separated from the reaction mixture, and may be further purified to remove impurities by recrystallization from hot ethyl acetate.

In step 2 of scheme 5, the compound IVa2-1 may be coupled with a compound having the formula $R_1$—CO—X to form a compound of the formula (IIIa2-1). This coupling reaction is generally conducted at a temperature from about −30° C. to about 80° C., preferably from about 0° C. to about 25° C. The coupling reaction may occur with a coupling reagent that activates the acid functionality.

Exemplary coupling reagents include dicyclohexylcarbodi-imide/hydroxybenzotriazole (DCC/HBT), N-3-dimethy-laminopropyl-N'-ethylcarbodiimide (EDC/HBT), 2-ethy-oxy-1-ethoxycarbonyl-1,2-dihydroquinoline (EEDQ), carbonyl diimidazole (CDI)/dimethylaminopyridine (DMAP), and diethylphosphorylcyanide. The coupling is conducted in an inert solvent, preferably an aprotic solvent, such as acetonitirile, dichloromethane, chloroform, or N,N-dimethylformamide. One preferred solvent is methylene chloride. In one embodiment, quinoxaline acid is combined with methylene chloride, oxalyl chloride and a catalytic amount of N,N-dimethylformamide to form an acid chloride complex. The compound IVa2-1 is added to the acid chloride complex followed by triethylamine at a temperature from about 0° C. to about 25° C. to form the compound IIIa2-1.

Step 3 of scheme 5 includes reacting a compound IIIa2-1 with trifluoroacetic acid to produce a compound of the formula (IIIa2-1). In one embodiment, the hydration with trifluoroacetic acid occurs in methylene chloride solution at room temperature. The hydration may take several hours to complete at room temperature. A catalytic amount of sulfuric acid can be added to the reaction solution to increase the rate of reaction.

Step 4 of scheme 5 includes reacting the compound of formula IIa2-1 with an amine having a formula $NHR_4R_5$ to form a compound of the formula (Ia-1). In one embodiment, the amine is ammonia either anhydrous in an organic solvent or as an aqueous solution of ammonium hydroxide added to a polar solvent at a temperature from about −10° C. to about 35° C., preferably at about 30° C. Suitable solvents include, alcohols, such as methanol, ethanol, or butanols; ethers such as tetrahydrofuran, glyme or dioxane; or a mixture thereof, including aqueous mixtures. Preferably the solvent is methanol. In one embodiment, the compound IIa2-1 is dissolved in methanol which has been saturated with ammonia gas. In another embodiment, the compound IIa2-1 in methanol is treated with ammonium hydroxide in tetrahydrofuran at room temperature.

Adsorbates

The drug is present in the composition in the form of an adsorbate comprising a drug and a substrate. At least a major portion of the drug in the adsorbate is amorphous. The term "amorphous" indicates simply that the drug is not crystalline as indicated by any conventional method, such as by powder X-ray diffraction (PXRD) analysis in which the sharp scattering lines associated with the crystal forms of the drug are absent or reduced in magnitude or the absence of an endothermic transition at the melting point of the crystalline drug when subjected to thermal analysis. The term "a major portion" of the drug means that at least 60% of the drug is in amorphous form, rather than a crystalline form. Preferably, the drug in the adsorbate is substantially amorphous. As used herein, "substantially amorphous" means that the amount of the drug in amorphous form is at least 80%. More preferably, the drug in the adsorbate is "almost completely amorphous" meaning that the amount of drug in the amorphous form is at least 90% as measured by powder X-ray diffraction or differential scanning calorimetry ("DSC"), or any other standard quantitative measurement. Most preferrably, the drug in the adsorbate is in a completely amorphous form within the detection limits of the techniques used for characterization.

The adsorbate also includes a high surface area substrate. The substrate may be any material that is inert, meaning that the substrate does not adversely interact with the drug to an unacceptably high degree and which is pharmaceutically acceptable. The substrate also has a high surface area, meaning that the substrate has a surface area of at least 20 $m^2/g$, preferably at least 50 $m^2/g$, more preferably at least 100 $m^2/g$, and most preferably at least 180 $m^2/g$. The surface area of the substrate may be measured using standard procedures. One exemplary method is by low-temperature nitrogen adsorption, based on the Brunauer, Emmett, and Teller (BET) method, well known in the art. As discussed below, the higher the surface area of the substrate, the higher the drug-to-substrate ratio that can be achieved and still maintain high concentration-enhancements and improved physical stability. Thus, effective substrates can have surface areas of up to 200 m²/g, up to 400 m²/g and up to 600 m²/g or more. The substrate should also be in the form of small particles ranging in size of from 10 nm to 1 μm, preferably ranging in size from 20 nm to 100 nm. These particles may in turn form agglomerates ranging in size from 10 nm to 100 μm. The substrate is also insoluble in the process environment used to form the adsorbate. That is, where the adsorbate is formed by solvent processing, the substrate does not dissolve in the solvent. Where the adsorbate is formed by a melt or thermal process, the adsorbate has a sufficiently high melting point that it does not melt.

Exemplary materials which are suitable for the substrate include inorganic oxides, such as $SiO_2$, $TiO_2$, $ZnO_2$, $ZnO$, $Al_2O_3$, MgAlSilicate, CaSilicate, $AlOH_2$, zeolites, and other inorganic molecular seives; water insoluble polymers, such as cross-linked cellulose acetate phthalate, cross-linked hydroxypropyl methyl cellulose acetate succinate, cross-linked polyvinyl pyrrolidinone, (also known as cross povidone) microcrystalline cellulose, polyethylene/polyvinyl alcohol copolymer, polyethylene polyvinyl pyrrolidone copolymer, cross-linked carboxymethyl cellulose, sodium starch glycolate, cross-linked polystyrene divinyl benzene; and activated carbons, including those made by carbonization of polymers such as polyimides, polyacylonitrile, phenolic resins, cellulose acetate, regenerated cellulose, and rayon.

The surface of the substrate may be modified with various substituents to achieve particular interactions of the drug with the substrate. For example, the substrate may have a hydrophobic or hydrophilic surface. By varying the terminating groups of substituents attached to the substrate, the interaction between the drug and substrate may be influenced. For example, where the drug is hydrophobic, it may be desired to select a substrate having hydrophobic substituents to improve the binding of the drug to the substrate.

Generally, the interaction of drug with the substrate should be sufficiently high such that mobility of the drug in the drug/substrate adsorbate is sufficiently decreased such that the composition has improved stability, as described below. However, the drug/substrate interaction should be sufficiently low such that the drug can readily desorb from the adsorbate when it is introduced to a use environment, resulting in a high concentration of drug in solution.

The adsorbates are formed so as to form a thin layer of amorphous drug on the surface of the substrate. By "thin layer" is meant a layer that ranges in average thickness from less than one drug molecule to as many as 10 molecules. When the drug/substrate interaction is large and the average drug layer thickness, based on ratio of the mass of drug-to-substrate surface area, is about the dimensions of one molecule, the drug layer is generally termed a "monolayer."

The adsorption of drug to the substrate may be characterized by a shift in the infra red (IR) spectra of the drug, indicating interaction of the drug with the substrate. Such interactions are generally due to London dispersion forces, dipole-dipole interactions, hydrogen bonding, electron donor-electron acceptor interactions or ionic interactions. Thus, as the number of layers of molecules on the substrate increases, the average shift of the IR absorption decreases. That is, the IR spectrum will show a composite of those molecules that are in contact with the substrate surface as well as those that are further away from the surface. Additionally, if the adsorbate contains more than 2 or 3 layers of drug molecules, the physical stability of the adsorbate may be compromised, since the mobility of the drug molecules furthest from the substrate is relatively high. Thus, crystallization of the drug molecules on a thick adsorbed layer may occur more rapidly than that observed for a thin adsorbed layer.

One exemplary method for forming adsorbates of the present invention is "solvent processing." Solvent processing consists of dissolution of the drug in a solvent containing the substrate followed by rapid removal of the solvent. The term "solvent" is used broadly and includes mixtures of solvents. In general, the substrate will not significantly dissolve in the solvent and remains solid throughout the process.

First, the substrate is added to a solvent which is capable of dissolving the drug. Since it is generally desirable to form adsorbate particles that are small, preferably less than about 1 to 10 μm, the solution is agitated to form a suspension of small particles of substrate suspended in the solvent. Agitation of the solution may be performed by any method that is capable of imparting sufficient energy to the solution to break up agglomerations of substrate particles. A preferred method is sonication. Other methods which may be used to break up the particles to form a suspension of substrate in the solvent include high speed mixing, and high shear mechanical mixing. The solution is agitated for a sufficient length of time so that the substrate remains suspended in the solution for at least a few minutes. Often, to ease processing, it is desirable that the substrate remain suspended for at least 60 minutes without agglomeration. However, this is not required for practice of the invention. The solvent/substrate suspension may be continuously agitated during processing to ensure the substrate remains suspended in the solvent.

The drug is then added to the solvent and dissolved. The amount of drug and substrate present in the solution is chosen to yield an adsorbate having the desired ratio of drug to substrate. In general, good results may be obtained where the solution comprises from 0.1 to 2 wt % drug and from 0.1 to 5 wt % substrate. In general, it is desired to maintain the amount of solids in the solution at less than about 10 wt %, as the substrate when present at higher concentrations may clog or stick to the surfaces of the apparatus used to form the adsorbate. The weight ratio of drug to substrate is chosen such that the desired drug-layer thickness is obtained. Generally, better dissolution performance is obtained at lower drug-to-substrate ratios. However, higher drug-to-substrate weight ratios provide good performance when the substrate surface area is high. Typically, drug-to-substrate weight ratios are less than 1.0 and often less than 0.25 to obtain preferred dissolution performance.

After the substrate has been agitated and the drug has been dissolved, the solvent is rapidly removed by evaporation or by mixing with a non-solvent. Exemplary processes are spray-drying, spray-coating (pan-coating, fluidized bed coating, etc.), and precipitation by rapid mixing of the solution with $CO_2$, hexane, heptane, water of appropriate pH, or some other non-solvent. Preferably, removal of the solvent results in a solid adsorbate. To achieve this end, it is generally desirable to rapidly remove the solvent from the solution such as in a process where the solution is atomized and the drug rapidly solidifies on the substrate.

The adsorbates formed by such processes that rapidly "quench" the material, that is, bring the material from the dissolved state to the solid state very rapidly are generally preferred as they result in a material with superior physical structure and performance.

In one embodiment, the solvent is removed through the process of spray-drying. The term spray-drying is used conventionally and broadly refers to processes involving breaking up liquid mixtures into small droplets (atomization) and rapidly removing solvent from the mixture in a container (spray-drying apparatus) where there is a strong driving force for evaporation of solvent from the droplets. The strong driving force for solvent evaporation is generally provided by maintaining the partial pressure of solvent in the spray-drying apparatus well below the vapor pressure of the solvent at the temperature of the drying droplets. This is accomplished by either (1) maintaining the pressure in the spray-drying apparatus at a partial vacuum (e.g., 0.01 to 0.50 atm); (2) mixing the liquid droplets with a warm drying gas; or (3) both. In addition, at least a portion of the heat required for evaporation of solvent may be provided by heating the spray solution.

Solvents suitable for spray-drying can be water or any organic compound in which the drug is soluble and the substrate insoluble. Preferably, the solvent is also volatile with a boiling point of about 150°C. or less. In addition, the solvent should have relatively low toxicity and be removed from the adsorbate to a level that is acceptable according to The International Committee on Harmonization (ICH) guidelines. Removal of solvent to this level may require a processing step such as tray-drying subsequent to the spray-drying or spray-coating process. Preferred solvents include alcohols such as methanol, ethanol, n-propanol, isopropanol, and butanol; ketones such as acetone, methyl ethyl ketone and methyl iso-butyl ketone; esters such as ethyl acetate and propylacetate; and various other solvents such as acetonitrile, methylene chloride, toluene, and 1,1,1-trichloroethane. Mixtures, particularly mixtures of an organic solvent such as methanol, ethanol or acetone and water are often desirable. Lower volatility solvents such as dimethyl acetamide or dimethylsulfoxide can also be used. Mixtures of solvents, such as 50% methanol and 50% acetone, can also be used, as can mixtures with water as long as the drug is sufficiently soluble to make the spray-drying process practicable.

Generally, the temperature and flow rate of the drying gas is chosen so that the droplets containing the adsorbate are dry enough by the time they reach the wall of the apparatus that they are essentially solid, and so that they form a fine powder and do not stick to the apparatus wall. The actual length of time to achieve this level of dryness depends on the size of the droplets. Droplet sizes generally range from 1 μm to 500 μm in diameter, with 5 to 150 μm being more typical. The large surface-to-volume ratio of the droplets and the large driving force for evaporation of solvent leads to actual drying times of a few seconds or less, and more typically less than 0.1 second. Solidification times should be less than 100 seconds, preferably less than a few seconds, and more preferably less than 1 second. In general, to achieve this rapid solidification of the solution, it is preferred that the size of droplets formed during the spray-drying process are less than about 150 μm in diameter. The resultant solid particles thus formed are generally less than about 150 μm in diameter.

Following solidification, the solid powder typically stays in the spray-drying chamber for about 5 to 60 seconds, further evaporating solvent from the solid powder. The final solvent content of the solid adsorbate as it exits the dryer should be low, since this reduces the mobility of drug molecules in the adsorbate, thereby improving its stability. Generally, the solvent content of the adsorbate as it leaves the spray-drying chamber should be less than 10 wt % and preferably less than 2 wt %. Following spray-drying, the adsorbate may be dried in a solvent drier, such as a tray-dryer or a fluidized-bed dryer to remove residual solvents.

Spray-drying processes and spray-drying equipment are described generally in Perry's *Chemical Engineers' Handbook*, Sixth Edition (R. H. Perry, D. W. Green, J. O. Maloney, eds.) McGraw-Hill Book Co. 1984, pages 20-54 to 20-57. More details on spray-drying processes and equipment are reviewed by Marshall "Atomization and Spray-Drying," 50 *Chem Eng. Prog. Monogr Series* 2 (1954).

As mentioned above, preferred adsorbates of the present invention are made by processes such as spray-drying that rapidly bring the drug from the dissolved state to the solid adsorbed state. Such adsorbates have a unique physical structure and have greater physical stability and dissolution performance relative to those made by processes that slowly remove solvent.

Another method to produce adsorbates of the present invention comprising amorphous drug adsorbed to a substrate is a thermal process. Here, the drug is melted and then coated onto the surface of substrates using, for example, a twin-screw extruder. In one exemplary technique the drug is first uniformly blended with the substrate. The blend may be prepared using methods well known in the art for obtaining powdered mixtures with high content uniformity. For example, the drug and substrate may first be independently milled to obtain a small particle size (e.g., less than about 100 μm) and then added to a V blender and blended for 20 minutes. This blend may then be milled to break up any agglomerates, and then blended in a V blender for an additional period of time to obtain a uniform preblend of drug and substrate.

This preblend of drug and substrate is fed into a twin screw extruder. The screw configuration and mixing paddles are set so as to maximize the degree of fill of the screw sections for maximum heat transfer from the barrel and avoidance of excessive flow restriction. The screw configuration is also selected such that there is sufficient mechanical energy (i.e., shear) to break apart any aggregated substrate still remaining after the preblend step and to uniformly mix the drug and substrates. The barrel temperature should be ramped from approximately room temperature at the feed area to slightly above the melting temperature of the drug in the last barrel zone (discharge end). This technique is applicable for any drug with a melting temperature low enough to melt in the extruder (<400° C.), and for drugs with acceptable chemical stability at the elevated temperatures. Thermal processes such as melt-extrusion processes and equipment are described generally in *Encyclopedia of Chemical Technology*, 4th Edition (John Wiley & Sons, 1991).

A processing aid may optionally be blended with such drug/substrate mixtures to form a three-component (or more) preblend that is fed to the extruder. One object of such additives is to lower the temperature required for liquification of the drug. Thus, the additive typically has a melt point below that of the drug and the drug is typically soluble in the molten additive. The additive may be a volatile material such as water that evaporates from the composition or it may have a high boiling point, such as a mono- or di-glyceride such that it remains part of the composition following processing.

Analogous to the solvent processing method described above, it is preferred to rapidly "quench" the molten material as it exits (is discharged from) the extruder. Any method that results in rapid solidification of the drug as a solid adsorbed layer on the substrate is suitable. Exemplary methods are contact with a cooling fluid such as a cold gas or liquid. Alternatively, the material may enter a cooled mill where heat is transferred from the material at the same time as it is milled into a fine powder with granule sizes from about 100 nm to 100 μm.

Alternatively, a solvent, such as water, can be added to the preblend fed to a twin screw extruder. The screw configuration is designed so that there is sufficient pressure in the extruder to prevent vaporization of the solvent at the temperatures required to melt the drug. When the extrudate exits the extruder, the sudden decrease in pressure causes rapid vaporization of the solvent, leading to rapid cooling and congealing of the adsorbate material. Any residual solvent in the composition can be removed using conventional drying technology such as a tray drier or a fluidized-bed drier.

Thus, preferred adsorbates of the present invention may be made by any solvent or thermal process that rapidly solidifies (that is, quenches) the material by solvent removal, precipitation with a nonsolvent or cooling. Such materials, termed "rapidly quenched adsorbates," have superior properties to adsorbates made by other methods.

In particular, when such "rapidly quenched adsorbates" are delivered to an aqueous use environment, they provide enhanced drug concentrations. Specifically, such rapidly quenched adsorbates provide a higher maximum free drug concentration or a higher maximum total dissolved drug concentration than that provided by a control, termed a "slow-evaporation control composition," formed by evaporating the solvent from a suspension of the same substrate in a solution of drug over a period of 30 minutes or more.

In addition, such rapidly quenched adsorbates may also show improved physical stability, slower crystallization rates and superior thermal properties relative to the slow-evaporation control composition.

The drug/substrate adsorbates resulting from the various preparation techniques are solid materials comprising about 5 wt % to 90 wt % drug. The materials are typically agglomerates of particles, the agglomerates having a mean diameter ranging from 10 nm to 100 µm. The agglomerates typically retain the fine particulate nature of the starting substrate. In the case of high surface area silicon dioxide, these consist of branched chains composed of many particles with mean diameters of about 10 to 30 nm, or agglomerates of very small spheres (<10 µm).

For adsorbates in which the substrate has a surface area of approximately 200 $m^2/g$, it is believed that for low drug loadings (under about 12 wt %), the drug is present primarily as drug molecules directly adsorbed onto the substrate surface. For such high surface area substrates, there is sufficient surface area for all drug to be directly adsorbed to the substrate up to a drug-to-substrate weight ratio of about 8. Drug adsorbed onto such substrates can be considered a mono layer. Drug adsorbed in this way is noncrystalline and thus may be considered amorphous. However, the interaction of the drug and substrate surface give the drug substantially different physical properties than bulk amorphous drug alone. At greater drug loadings in the adsorbate, it is believed that the drug forms additional layers of amorphous drug on top of the initial monolayer. While not wishing to be bound by any particular theory, it is believed that the interaction of the thin layer(s) of the drug with the substrate improves the physical stability of the drug by decreasing the mobility of the drug on the substrate relative to the mobility of drug in a bulk amorphous material. This may result in improved physical stability by hindering diffusion of drug, and thus inhibiting crystal formation.

As the surface area of the substrate increases, the amount of drug that can be incorporated into the adsorbate while maintaining a monolayer (or less) of drug also increases. For example, if the substrate has a surface area of 400 $m^2/g$, the drug loading that leads to a monolayer is approximately 21 wt %, while if the substrate has a surface area of 600 $m^2/g$, the drug loading can be about 32% while maintaining a monolayer of drug on the substrate. Thus, it is desirable to use a substrate with as high a surface area as possible to obtain high drug loadings. Such values for the relationship of "drug load-ing" to substrate surface area are only approximate and depend on the specific size, shape, and orientation of each specific drug.

The amorphous drug adsorbed to the substrate is in a relatively high energy state when dosed to an aqueous use environment. While not wishing to be bound by any particular theory or mechanism of action, it is believed this high energy state is due to generally reduced drug-drug interactions of the drug adsorbed to the substrate compared with amorphous or crystalline drug alone. The substrate stabilizes this high-energy amorphous form of the drug. Thus, when introduced to an aqueous use environment, the drug/substrate adsorbate may provide enhanced aqueous concentration of drug.

The physical nature of this stabilized high-energy state of the amorphous drug may be characterized using IR spectroscopy. Generally, interactions of the drug with the substrate are characterized by a shift in the IR spectrum to a lower wave number, indicating hydrogen bonding of the drug to the substrate. In addition, the physical nature of the adsorbed drug may be evaluated by techniques such as vapor absorption, thermal calorimetry such as differential scanning colorimetry (DSC), or powder x-ray diffraction.

The adsorbate may also include optional additional components, in addition to the processing aids described above, such as surfactants, pH modifiers, disintegrants, binders, lubricants, etc. These materials may help improve processing, performance, or help in preparing dosage forms containing the adsorbates, as discussed below.

Preparation of Compositions Containing Adsorbates and Concentration-Enhancing Polymers In another aspect of the invention, the composition comprises a drug/substrate adsorbate and a concentration-enhancing polymer. While the drug/substrate adsorbate provides enhanced concentration of drug in a use environment relative to amorphous drug alone, the inclusion of a concentration-enhancing polymer in the composition may improve the observed enhancement and/or allow for sustaining the enhanced concentration for a longer period of time.

The compositions of the present invention containing concentration-enhancing polymers may be prepared through a variety of methods The concentration-enhancing polymer may be co-adsorbed onto the substrate with the drug, so as to form an amorphous dispersion of drug and polymer adsorbed onto the substrate. Alternatively, the concentration-enhancing polymer may be combined with the drug/substrate adsorbate in a mixture or a single dosage form. Alternatively, the concentration-enhancing polymer may be co-administered with the adsorbate.

In one preferred method for combining the adsorbate and concentration-enhancing polymer, the concentration-enhancing polymer is co-adsorbed with the drug onto the substrate. This results in an amorphous dispersion of drug and polymer adsorbed onto the surface of the substrate. The concentration-enhancing polymer may be co-adsorbed with the drug on the substrate using any method that results in a thin layer of amorphous drug and polymer adsorbed onto the surface of the substrate. The layer may range in thickness from a complete or discontinuous layer of drug and polymer molecules adsorbed directly to the substrate surface, up to a layer of drug and polymer up to a thickness of about the size of 5 to 10 polymer or drug molecules. At least a major portion of the drug present in the adsorbate is amorphous. Preferably, the drug in the adsorbate is substantially amorphous, and more preferably, the drug is almost completely amorphous. While the dispersion of drug and polymer adsorbed onto the substrate may have drug-rich domains and polymer-rich domains, in one embodiment the dispersion is substantially homogeneous, meaning that the amount of the drug present in drug-rich amorphous domains within the dispersion is less than 20%. Often, for such materials the dispersion is "completely homogeneous," meaning that the amount of drug in drug-rich domains is less than 10%.

One method for adsorbing the concentration-enhancing polymer onto the substrate with the drug is to form the adsorbate using a solvent process as described above. In that case, the concentration-enhancing polymer and drug are dissolved in a common solvent to which the substrate had been added. By "common solvent" is meant a solvent capable of dissolving both the drug and the concentration-enhancing polymer.

In one exemplary method, the substrate is first added to the common solvent and sonicated. The concentration-enhancing polymer is then added to the solution and dissolved. The drug is then added to the solvent and dissolved. The solvent is then rapidly removed from the resulting solution of dissolved drug, dissolved polymer and suspended substrate. The resulting particles of adsorbate are then collected and dried.

An alternative method to co-adsorb drug and polymer onto a substrate is using a thermal process as described above. In one exemplary method, drug, concentration-enhancing polymer, and substrate are preblended and fed to a twin-screw extruder. The extruder is designed to melt the drug and polymer, resulting in adsorption onto the substrate. The composition is then rapidly cooled to form a rapidly quenched adsorbate, as described above. Additives, such as water, solvents, low-melting-point solids, or plasticizers may be added to the preblend to reduce the melting point of the polymer and allow for lower processing temperatures.

The resulting drug/polymer/substrate adsorbates may comprise from 2 wt % to 90 wt % drug, from 2 to 90 wt % substrate, and from 5 wt % to 95 wt % concentration-enhancing polymer. The mean diameter of the drug/polymer/substrate adsorbates ranges from 10 nm to 100 μm, and the adsorbates are typically agglomerates of particles having mean diameters of 10 nm to 50 nm.

Alternatively, a drug/substrate adsorbate and a concentration-enhancing polymer may be mixed together. Mixing processes include physical processing as well as wet- or dry-granulation and coating processes. Any conventional mixing method may be used. The resulting mixture may be a solid composition comprising the drug/substrate adsorbate and concentration-enhancing polymer suspended in a matrix, a mixture of separate adsorbate particles and concentration-enhancing polymer particles interspersed with one another, a series of respective layers of adsorbate and concentration-enhancing polymer, or any other mixture of adsorbate and concentration-enhancing polymer.

For example, mixing methods include convective mixing, shear mixing, or diffusive mixing. Convective mixing involves moving a relatively large mass of material from one part of a powder bed to another, by means of blades or paddles, revolving screw, or an inversion of the powder bed. Shear mixing occurs when slip planes are formed in the material to be mixed. Diffusive mixing involves an exchange of position by single particles. These mixing processes can be performed using equipment in batch or continuous mode. Tumbling mixers (e.g., twin-shell) are commonly used equipment for batch processing. Continuous mixing can be used to improve composition uniformity. Continuous mixers include "in-line" mixers and extruders. Extruders may be single screw or twin-screw. Twin-screw extruders may turn in the same or opposite direction.

Milling may also be employed to prepare the compositions of the present invention. Milling is the mechanical process of reducing the particle size of solids (comminution). The most common types of milling equipment are the rotary cutter, the hammer, the roller and fluid energy mills. Equipment choice depends on the characteristics of the ingredients in the drug form (e.g., soft, abrasive, or friable). Wet- or dry-milling techniques can be chosen for several of these processes, also depending on the characteristics of the ingredients (e.g., drug stability in solvent). The milling process may serve simultaneously as a mixing process if the feed materials are heterogeneous. Conventional mixing and milling processes suitable for use in the present invention are discussed more fully in Lachman, et al., *The Theory and Practice of Industrial Pharmacy* (3d Ed. 1986).

The components of the compositions of this invention may also be combined by dry- or wet-granulating processes. The concentration-enhancing polymer may also be coated onto the drug/substrate adsorbate using coating techniques known in the art. For example, the polymer may be first dissolved into a solvent and the solution spray-coated onto the adsorbate in a pan-coater or a fluid-bed coater.

Alternatively, the mixture may be formed by first combining the adsorbate and concentration-enhancing polymer with a matrix, resulting in a mixture of the adsorbate and concentration-enhancing polymer suspended in a matrix.

In addition to the physical mixtures described above, the compositions of the present invention may constitute any device or collection of devices that accomplishes the objective of delivering to the use environment both the adsorbate and the concentration-enhancing polymer. The adsorbate and concentration-enhancing polymer may be in different regions of the composition. For example, in the case of oral administration to an animal, the dosage form may constitute a layered tablet wherein one or more layers comprise the adsorbate and one or more other layers comprise the concentration-enhancing polymer. Alternatively, the dosage form may be a coated tablet wherein the tablet core comprises the adsorbate and the coating comprises the concentration-enhancing polymer. The dosage form may also be a capsule where the wall of the capsule comprises the concentration-enhancing polymer and the adsorbate is within the capsule. In addition, the adsorbate and the concentration-enhancing polymer may even be present in different dosage forms such as tablets or beads and may be administered simultaneously or separately as long as both the adsorbate and concentration-enhancing polymer are administered in such a way that the drug and concentration-enhancing polymer can come into contact in the use environment. When the adsorbate and the concentration-enhancing polymer are administered separately it is generally preferable to deliver the concentration-enhancing polymer prior to the drug.

The amount of concentration-enhancing polymer relative to the amount of drug present in the mixtures of the present invention depends on the drug and concentration-enhancing polymer and may vary widely from a drug-to-polymer weight ratio of 0.01 to about 20. However, in most cases, except when the drug dose is quite low, e.g., 25 mg or less, it is preferred that the drug-to-polymer ratio is greater than 0.05 and less than about 5 and often excellent enhancement in drug concentration or relative bioavailability is observed at drug-to-polymer ratios of 1 or less or for some drugs even 0.2 or less. In cases where the drug dose is about 25 mg or less, the drug-to-polymer weight ratio may be significantly less than 0.05. In general, regardless of the dose, enhancements in drug concentration or relative bioavailability increase with decreasing drug-to-polymer weight ratio. However, due to the practical limits of keeping the total mass of a tablet, capsule or suspension low, it is often desirable to use a relatively high drug-to-polymer ratio as long as satisfactory results are obtained. The maximum drug:polymer ratio that yields satisfactory results varies from drug to drug and is best determined in the in vitro and/or in vivo dissolution tests discussed below.

Concentration-Enhancing Polymers

Concentration-enhancing polymers suitable for use in the various aspects of the present invention should be pharmaceutically acceptable, and should have at least some solubility in aqueous solution at physiologically relevant pHs (e.g. 1-8). Almost any neutral or ionizable polymer that has an aqueous-solublitity of at least 0.1 mg/mL over at least a portion of the pH range of 1-8 may be suitable.

It is preferred that the concentration-enhancing polymers be "amphiphilic" in nature, meaning that the polymer has hydrophobic and hydrophilic portions. Amphiphilic polymers are preferred because it is believed that such polymers tend to have relatively strong interactions with the drug and may promote the formation of various types of polymer/drug assemblies in solution. A particularly preferred class of amphiphilic polymers are those that are ionizable, the ionizable portions of such polymers, when ionized, constituting at least a portion of the hydrophilic portions of the polymer. For example, while not wishing to be bound by a particular theory, such polymer/drug assemblies may comprise hydrophobic drug clusters surrounded by the concentration-enhancing polymer with the polymer's hydrophobic regions turned inward towards the drug and the hydrophilic regions of the polymer turned outward toward the aqueous environment. Alternatively, depending on the specific chemical nature of the drug, the ionized functional groups of the polymer may associate, for example, via ion pairing or hydrogen bonds, with ionic or polar groups of the drug. In the case of ionizable polymers, the hydrophilic regions of the polymer would include the ionized functional groups. In addition, the repulsion of the like charges of the ionized groups of such polymers (where the polymer is ionizable) may serve to limit the size of the polymer/drug assemblies to the nanometer or submicron scale. Such drug/concentration-enhancing polymer assemblies in solution may well resemble charged polymeric micellar-like structures. In any case, regardless of the mechanism of action, the inventors have observed that such amphiphilic polymers, particularly ionizable cellulosic polymers such as those listed below, have been shown to interact with drug so as to maintain a higher concentration of drug in an aqueous use environment.

One class of polymers suitable for use with the present invention comprises neutral non-cellulosic polymers. Exemplary polymers include: vinyl polymers and copolymers having at least one substituent selected from the group comprising hydroxyl, alkylacyloxy, and cyclicamido; vinyl copolymers of at least one hydrophilic, hydroxyl-containing repeat unit and at least one hydrophobic, alkyl- or aryl-containing repeat unit; polyvinyl alcohols that have at least a portion of their repeat units in the unhydrolyzed (vinyl acetate) form; polyvinyl alcohol polyvinyl acetate copolymers; polyvinyl pyrrolidone; polyethylene polyvinyl alcohol copolymers, and polyoxyethylene-polyoxypropylene block copolymers (also referred to as poloxamers).

Another class of polymers suitable for use with the present invention comprises ionizable non-cellulosic polymers. Exemplary polymers include: carboxylic acid-functionalized vinyl polymers, such as the carboxylic acid functionalized polymethacrylates and carboxylic acid functionalized polyacrylates such as the EUDRAGITS® manufactured by Rohm Tech Inc., of Malden, Mass.; amine-functionalized polyacrylates and polymethacrylates; high molecular weight proteins such as gelatin and albumin; and carboxylic acid functionalized starches such as starch glycolate.

Non-cellulosic polymers that are amphiphilic are copolymers of a relatively hydrophilic and a relatively hydrophobic monomer. Examples include acrylate and methacrylate copolymers. Exemplary commercial grades of such copolymers include the EUDRAGITS, which are copolymers of methacrylates and acrylates.

A preferred class of polymers comprises ionizable and neutral (or non-ionizable) cellulosic polymers with at least one ester- and/or ether-linked substituent in which the polymer has a degree of substitution of at least 0.05 for each substituent. It should be noted that in the polymer nomenclature used herein, ether-linked substituents are recited prior to "cellulose" as the moiety attached to the ether group; for example, "ethylbenzoic acid cellulose" has ethoxybenzoic acid substituents. Analogously, ester-linked substituents are recited after "cellulose" as the carboxylate; for example, "cellulose phthalate" has one carboxylic acid of each phthalate moiety ester-linked to the polymer and the other carboxylic acid unreacted.

It should also be noted that a polymer name such as "cellulose acetate phthalate" (CAP) refers to any of the family of cellulosic polymers that have acetate and phthalate substituents attached via ester linkages to a significant fraction of the cellulosic polymer's hydroxyl groups. Generally, the degree of substitution of each substituent can range from 0.05 to 2.9 as long as the other criteria of the polymer are met. "Degree of substitution" refers to the average number of the three hydroxyls per saccharide repeat unit on the cellulose chain that have been substituted. For example, if all of the hydroxyls on the cellulose chain have been phthalate substituted, the phthalate degree of substitution is 3. Also included within each polymer family type are cellulosic polymers that have additional substituents added in relatively small amounts that do not substantially alter the performance of the polymer.

Amphiphilic cellulosics comprise polymers in which the parent cellulose polymer has been substituted at any or all of the 3 hydroxyl groups present on each saccharide repeat unit with at least one relatively hydrophobic substituent. Hydrophobic substituents may be essentially any substituent that, if substituted to a high enough level or degree of substitution, can render the cellulosic polymer essentially aqueous insoluble. Examples of hydrophobic substitutents include ether-linked alkyl groups such as methyl, ethyl, propyl, butyl, etc.; or ester-linked alkyl groups such as acetate, propionate, butyrate, etc.; and ether- and/or ester-linked aryl groups such as phenyl, benzoate, or phenylate. Hydrophilic regions of the polymer can be either those portions that are relatively unsubstituted, since the unsubstituted hydroxyls are themselves relatively hydrophilic, or those regions that are substituted with hydrophilic substituents. Hydrophilic substituents include ether- or ester-linked nonionizable groups such as the hydroxy alkyl substituents hydroxyethyl, hydroxypropyl, and the alkyl ether groups such as ethoxyethoxy or methoxyethoxy. Particularly preferred hydrophilic substituents are those that are ether- or ester-linked ionizable groups such as carboxylic acids, thiocarboxylic acids, substituted phenoxy groups, amines, phosphates or sulfonates.

One class of cellulosic polymers comprises neutral polymers, meaning that the polymers are substantially non-ionizable in aqueous solution. Such polymers contain non-ionizable substituents, which may be either ether-linked or ester-linked. Exemplary ether-linked non-ionizable substituents include: alkyl groups, such as methyl, ethyl, propyl, butyl, etc.; hydroxy alkyl groups such as hydroxymethyl, hydroxyethyl, hydroxypropyl, etc.; and aryl groups such as phenyl. Exemplary ester-linked non-ionizable substituents include: alkyl groups, such as acetate, propionate, butyrate, etc.; and aryl groups such as phenylate. However, when aryl groups are included, the polymer may need to include a sufficient amount of a hydrophilic substituent so that the polymer has at least some water solubility at any physiologically relevant pH of from 1 to 8.

Exemplary non-ionizable cellulosic polymers that may be used as the polymer include: hydroxypropyl methyl cellulose acetate, hydroxypropyl methyl cellulose, hydroxypropyl cellulose, methyl cellulose, hydroxyethyl methyl cellulose, hydroxyethyl cellulose acetate, and hydroxyethyl ethyl cellulose.

A preferred set of non-ionizable (neutral) cellulosic polymers are those that are amphiphilic. Exemplary polymers include hydroxypropyl methyl cellulose and hydroxypropyl cellulose acetate, where cellulosic repeat units that have relatively high numbers of methyl or acetate substituents relative to the unsubstituted hydroxyl or hydroxypropyl substituents constitute hydrophobic regions relative to other repeat units on the polymer.

A preferred class of cellulosic polymers comprises polymers that are at least partially ionizable at physiologically relevant pH and include at least one ionizable substituent, which may be either ether-linked or ester-linked. Exemplary ether-linked ionizable substituents include: carboxylic acids, such as acetic acid, propionic acid, benzoic acid, salicylic acid, alkoxybenzoic acids such as ethoxybenzoic acid or propoxybenzoic acid, the various isomers of alkoxyphthalic acid such as ethoxyphthalic acid and ethoxyisophthalic acid, the various isomers of alkoxynicotinic acid such as ethoxynicotinic acid, and the various isomers of picolinic acid such as ethoxypicolinic acid, etc.; thiocarboxylic acids, such as thioacetic acid; substituted phenoxy groups, such as hydroxyphenoxy, etc.; amines, such as aminoethoxy, diethylaminoethoxy, trimethylaminoethoxy, etc.; phosphates, such as phosphate ethoxy; and sulfonates, such as sulphonate ethoxy. Exemplary ester linked ionizable substituents include: carboxylic acids, such as succinate, citrate, phthalate, terephthalate, isophthalate, trimellitate, and the various isomers of pyridinedicarboxylic acid, etc.; thiocarboxylic acids, such as thiosuccinate; substituted phenoxy groups, such as amino salicylic acid; amines, such as natural or synthetic amino acids, such as alanine or phenylalanine; phosphates, such as acetyl phosphate; and sulfonates, such as acetyl sulfonate. For aromatic-substituted polymers to also have the requisite aqueous solubility, it is also desirable that sufficient hydrophilic groups such as hydroxypropyl or carboxylic acid functional groups be attached to the polymer to render the polymer aqueous soluble at least at pH values where any ionizable groups are ionized. In some cases, the aromatic substituent may itself be ionizable, such as phthalate or trimellitate substituents.

Exemplary cellulosic polymers that are at least partially ionized at physiologically relevant pHs include: hydroxypropyl methyl cellulose acetate succinate (HPMCAS), hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate (HPMCP), hydroxyethyl methyl cellulose acetate succinate, hydroxyethyl methyl cellulose acetate phthalate, carboxyethyl cellulose, ethylcarboxymethyl cellulose (also referred to as carboxymethylethyl cellulose or CMEC), carboxymethyl cellulose, cellulose acetate phthalate (CAP), methyl cellulose acetate phthalate, ethyl cellulose acetate phthalate, hydroxypropyl cellulose acetate phthalate, hydroxypropyl methyl cellulose acetate phthalate, hydroxypropyl cellulose acetate phthalate succinate, hydroxypropyl methyl cellulose acetate succinate phthalate, hydroxypropyl methyl cellulose succinate phthalate, cellulose propionate phthalate, hydroxypropyl cellulose butyrate phthalate, cellulose acetate trimellitate (CAT), methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate. Of these cellulosic polymers that are at least partially ionized at physiologically relevant pHs, those that the inventors have found to be most preferred are HPMCAS, HPMCP, CAP, CAT, carboxyethyl cellulose, carboxymethyl cellulose, and ethyl carboxymethyl cellulose.

Another preferred class of polymers consists of neutralized acidic polymers. By "neutralized acidic polymer" is meant any acidic polymer for which a significant fraction of the "acidic moieties" or "acidic substituents" have been "neutralized"; that is, exist in their deprotonated form By "acidic polymer" is meant any polymer that possesses a significant number of acidic moieties. In general, a significant number of acidic moieties would be greater than or equal to about 0.1 milliequivalents of acidic moieties per gram of polymer. "Acidic moieties" include any functional groups that are sufficiently acidic that, in contact with or dissolved in water, can at least partially donate a hydrogen cation to water and thus increase the hydrogen-ion concentration. This definition includes any functional group or "substituent," as it is termed when the functional group is covalently attached to a polymer, that has a p$K_a$ of less than about 10. Exemplary classes of functional groups that are included in the above description include carboxylic acids, thiocarboxylic acids, phosphates, phenolic groups, and sulfonates. Such functional groups may make up the primary structure of the polymer such as for polyacrylic acid, but more generally are covalently attached to the backbone of the parent polymer and thus are termed "substituents." Neutralized acidic polymers are described in more detail in commonly assigned patent application U.S. Ser. No. 60/300,256 entitled "Pharmaceutical Compositions of Drugs and Neutralized Acidic Polymers" filed Jun. 22, 2001, the relevant disclosure of which is incorporated by reference.

While specific polymers have been discussed as being suitable for use in the mixtures of the present invention, blends of such polymers may also be suitable. Thus the term "concentration-enhancing polymer" is intended to include blends of polymers in addition to a single species of polymer.

Concentration Enhancement

The compositions of the present invention provide concentration-enhancement relative to a control composition. At a minimum, the compositions of the present invention provide concentration-enhancement relative to a control comprising crystalline drug alone. Thus, when the composition is administered to a use environment, the composition provides improved drug concentration (as described more fully below)

relative to a control consisting of an equivalent amount of crystalline drug alone. Preferably, the compositions of the present invention provide concentration-enhancement relative to a control composition containing an equivalent amount of unadsorbed amorphous drug alone.

For those embodiments of the present invention that comprise concentration-enhancing polymer, preferably, such compositions provide concentration-enhancement or bioavailability enhancement relative to a control composition comprising an equivalent quantity of drug in the from of the adsorbate but free from concentration-enhancing polymer.

As used herein, a "use environment" can be either the in vivo environment of the GI tract, subdermal, intranasal, buccal, intrathecal, ocular, intraaural, subcutaneous spaces, vaginal tract, arterial and venous blood vessels, pulmonary tract or intramuscular tissue of an animal, such as a mammal and particularly a human, or the in vitro environment of a test solution, such as phosphate buffered saline (PBS) or a Model Fasted Duodenal (MFD) solution. Concentration enhancement may be determined through either in vitro dissolution tests or through in vivo tests. It has been determined that enhanced drug concentration in in vitro dissolution tests in Model Fasted Duodenal (MFD) solution or Phosphate Buffered Saline (PBS) is a good indicator of in vivo performance and bioavailability. An appropriate PBS solution is an aqueous solution comprising 20 mM sodium phosphate ($Na_2HPO_4$), 47 mM potassium phosphate ($KH_2PO_4$), 87 mM NaCl, and 0.2 mM KCl, adjusted to pH 6.5 with NaOH. An appropriate MFD solution is the same PBS solution wherein additionally is present 7.3 mM sodium taurocholic acid and 1.4 mM of 1-palmitoyl-2-oleyl-sn-glycero-3-phosphocholine. In particular, a composition may be dissolution-tested by adding it to MFD or PBS solution and agitating to promote dissolution.

The compositions of the present invention provide in an aqueous use environment a concentration versus time Area Under The Curve (AUC), for any period of at least 90 minutes between the time of introduction into the use environment and about 270 minutes following introduction to the use environment that is at least 1.25-fold that of at least one of the control compositions. More preferably, the AUC achieved with the compositions of the present invention are at least 2-fold and more preferably at least 3-fold that of at least one of the control compositions.

A composition of the present invention may also provide a Maximum Drug Concentration (MDC) that is at least 1.25-fold the MDC of at least one of the control compositions. In other words, if the MDC provided by the control composition is 100 μg/mL, then a composition of the present invention provides an MDC of at least 125 μg/mL. More preferably, the MDC of drug achieved with the compositions of the present invention are at least 2-fold, and even more preferably at least 3-fold, that of at least one of the control compositions.

Alternatively, the compositions of the present invention, when dosed orally to a human or other animal, provide an AUC in drug concentration in the blood plasma or serum that is at least 1.25-fold that observed when one of the control compositions is dosed. More preferably, the AUC in the blood plasma or serum is at least 2-fold and more preferably at least 3-fold that observed when one of the control compositions is dosed. Thus, the compositions of the present invention can be evaluated in either an in vitro or in vivo test, or both.

A typical test to evaluate enhanced drug concentration can be conducted by (1) adding a sufficient quantity of test composition (e.g., the adsorbate) to a test medium (such as PBS or MFD solution), such that if all of the drug dissolved, the theoretical concentration of drug would exceed the equilibrium concentration of the drug in the test medium by a factor of at least 2; (2) adding an appropriate amount of control composition to an equivalent amount of test medium, and (3) determining whether the measured MDC and/or AUC of the test composition in the test medium is at least 1.25-fold that of the MDC and/or AUC provided by the control composition. In conducting such a dissolution test, the amount of test composition used is an amount such that if all of the drug dissolved, the drug concentration would be at least 2-fold to 100-fold that of the equilibrium concentration of the drug. The concentration of dissolved drug is typically measured as a function of time by sampling the test medium and plotting drug concentration in the test medium vs. time so that the MDC and/or AUC can be ascertained.

To avoid drug particulates which would give an erroneous determination in in vitro tests, the test solution is centrifuged prior to analysis for the drug. "Dissolved drug" is typically taken as the material that remains in the supernatant following centrifugation. Centrifugation is typically carried out in a polypropylene microcentrifuge tube by centrifuging at 13,000 G for 60 seconds. Other similar centrifugation methods can be employed and useful results obtained.

Alternatively, the compositions of the present invention provide improved relative bioavailability. Relative bioavailability of the drug in the compositions of the present invention can be tested in vivo in animals or humans using conventional methods for making such a determination. An in vivo test, such as a crossover study, may be used to determine whether a test composition provides an enhanced relative bioavailability compared with a control composition. In an in vivo crossover study a "test composition" containing the inventive composition is dosed to half a group of test subjects and, after an appropriate washout period (e.g., one week) the same subjects are dosed with a "control composition." The "control composition" may be any of the control compositions described earlier. The other half of the group is dosed with the control composition first, followed by the test composition. The relative bioavailability is measured as the drug concentration in the blood (serum or plasma) versus time area under the curve (AUC) determined for the test group divided by the AUC in the blood provided by the control composition. Preferably, this test/control ratio is determined for each subject, and then the ratios are averaged over all subjects in the study. In vivo determinations of AUC can be made by plotting the serum or plasma concentration of drug along the ordinate (y-axis) against time along the abscissa (x-axis).

A preferred embodiment of the invention is one in which the relative bioavailability of the test composition is at least 1.25 relative to at least one of the control compositions. (That is, the AUC in the blood provided by the test composition is at least 1.25-fold the AUC provided by the control composition.) An even more preferred embodiment of the invention is one in which the relative bioavailability of the test composition is at least 2.0 relative to at least one of the control compositions and more preferably at least 3. The determination of AUCs is a well-known procedure and is described, for example, in Welling, "Pharmacokinetics Processes and Mathematics," ACS Monograph 185 (1986).

Improved Drug Stability

In one embodiment, the low-solubility drug in the compositions of the present invention has improved physical and/or chemical stability relative to the drug in an appropriate control composition. The control composition may be either (1) the unadsorbed drug in amorphous form (that is, not adsorbed onto a substrate), (2) amorphous drug mixed with a concentration-enhancing polymer, or (3) a solid amorphous dispersion of a drug and concentration-enhancing polymer.

In one aspect, the compositions provide improved physical stability of the amorphous drug when adsorbed onto the substrate. As used herein, "physical stability" refers to the rate of change in the drug from the amorphous state to a crystalline state over time in a typical storage environment. Drugs in any amorphous state that can exist in either an amorphous or crystalline form tend to crystallize over time, because the crystalline form of the drug is a lower-energy state than the amorphous form. The physical stability of the drug in the compositions of the present invention is improved, meaning that the rate at which the drug changes from the amorphous to crystalline form is slower in the inventive composition compared with a control composition. It is believed that the compositions of the present invention provide improved physical stability at least in part because the mobility of the drug on the substrate is decreased, and hence its ability to crystallize is greatly inhibited. In addition, the interaction of the drug and the substrate surface may tend to hold the drug in an orientation or conformation that differs from that of a crystalline state, thereby reducing the rate of crystallization due to a decrease in the fraction of molecules in a state from which crystallization easily occurs. The physical stability of the drug in the composition may be determined by evaluating the change in the physical state (crystalline versus amorphous) of the drug in the inventive composition and comparing the rate to the corresponding rate of change provided by a control composition. The rate of change may be measured by any standard physical measurement, such as X-ray diffraction, DSC, or Scanning Electron Microscope ("SEM") analysis. Physically stable compositions of the present invention will crystallize at a slower rate than a control composition. Preferably, the rate of crystallization of the drug in the inventive composition is less than 90%, and more preferably less than 80%, the rate of crystallization of an appropriate control composition.

In another aspect of the invention, the drug in the inventive-compositions has improved chemical stability compared with an appropriate control composition. As used herein, "chemical stability" refers to the rate of chemical degradation of the drug in a typical storage environment. Types of degradation reactions that can occur include, but are not limited to hydrolysis, lactonization, esterification, oxidation, reduction, ring cyclization, and transesterification.

Adsorbing the drug onto an inert substrate can result in improved chemical stability of the drug by many possible mechanisms. For example, improved chemical stability of the drug may occur by isolating the drug from potential reactants, reducing the mobility of the drug, and hence, the rate of reaction of the drug, or both. In such cases the substrate should be selected such that it preferably does not react with, or catalyze reactions with the drug or if it does, such a reaction should be acceptably slow. In addition, the substrate should be selected such that any degradation products of the substrate itself, if any, are not reactive with the drug. The substrate should also not contain unacceptably high levels of impurities that could lead to degradation of the drug.

In general, drug degradation may be measured using any conventional method for measuring the purity or potency of drug in a pharmaceutical composition. For example, the amount of active drug present in an adsorbate may be initially measured using high-performance liquid chromatography (HPLC) or other analytical techniques well known in the art Alternatively, the amount of drug initially present may be calculated from the amount of drug present in the solution or mixture used to form the adsorbate. The potency of the adsorbate is then measured after storage at controlled temperature and humidity conditions for an appropriate period of time. A decrease in potency indicates that a chemical reaction has occurred, leading to a decrease in the amount of active drug present in the adsorbate, and is an indication of poor chemical stability.

An alternative method used to evaluate chemical stability is to analyze the rate of increase in the amount of drug degradant(s) in the adsorbate, which would indicate reaction of the drug. An HPLC or other analytical technique may be used to determine the concentration of drug degradant(s) in an adsorbate. The amount of the degradant(s) is measured before and after storage under controlled storage conditions. The amount of increase in the drug degradant(s) may be used to determine the amount of decrease in percent "purity of the drug." The "percent drug purity" is defined as 100% times the total amount of drug present divided by the total amount of drug initially present. Thus, percent drug purity may be calculated by the formula:

$$\text{wt \% drug purity} = \left(\frac{\text{total amt. of drug present}}{\text{total amt. of drug init. present}}\right) * 100$$

When percent drug purity is calculated from the total amount of impurities, "percent drug purity" may be calculated by assuming that the "total amount of drug initially present," given in wt %, is equal to 100 wt % minus the wt % of total initial impurities, and that "total amount of drug present" is equal to 100 wt % minus the wt % of total impurities after storage, that is, at some later time. This method is equivalent to calculating "percent drug purity" by the formula:

$$\text{wt \% drug purity} = \left[1 - \left(\frac{\text{total amt. of impurities present}}{\text{total amt. of drug init. present}}\right)\right] * 100$$

The rate at which drug degradation occurs is generally dependent on the storage conditions. The drug, when formulated as a composition of the present invention, should be stable at ambient temperature and humidity conditions (e.g., relative humidities of 20% to 60%) for long periods of time, such as months or years. However, to expedite testing, the storage conditions may employ elevated temperature and/or humidity to simulate longer storage times at ambient conditions. The storage time may vary from a few days to weeks or months, depending on the reactivity of the drug and the storage conditions.

A "degree of degradation" of drug following storage may be determined by subtracting the final drug percent purity (either determined by measuring the decrease in drug present or an increase in the amount of drug degradants present) from the initial percent purity. For example, a composition initially containing 100 mg drug and no measurable impurities would have an initial percent purity of 100 wt %. If, after storage, the amount of drug in the composition decreases to 95 mg, the final percent purity would be 95 wt % and the "degree of degradation" is 5 wt % (100 wt %-95 wt %). Alternatively, if 100 mg of drug substance were found to initially have 1 mg of impurities present, it would have an initial "percent purity" of 99 wt %. If, after storage, the total impurities present had increased to 6 wt %, the final percent purity would be 94 wt % and the "degree of degradation" would be 5 wt % (99 wt %-94 wt %).

Alternatively, "degree of degradation" can be determined by subtracting the amount of one or more specific drug degradants initially present from the amount of that specific degradant present after storage. Such a measure is useful where there are several drug degradants, of which only one (or a few) is of concern. The degree of degradation may be calculated on the basis of only those degradants that are of concern, rather than all of the degradants. For example, if a drug initially contained a specific degradant at a concentration of 1 wt % and after storage the concentration of that degradant was 6 wt %, the degree of degradation would be 5 wt % (6 wt %-1 wt %).

A "relative degree of improvement" in chemical stability may be determined by taking the ratio of the degree of degradation of the drug in a control composition and the degree of degradation of the drug in a test composition of the present invention under the same storage conditions for the same storage time period. The test composition is simply the drug/substrate adsorbate and (if present in the composition) the concentration-enhancing polymer. The control composition may be either amorphous drug alone, or when evaluating compositions containing a concentration-enhancing polymer, amorphous drug mixed with concentration-enhancing polymer, or may be a solid amorphous dispersion of the drug and concentration-enhancing polymer. For example, where the degree of degradation of a drug in a test composition comprised of the drug and substrate is 1 wt %, and the degree of degradation of a control composition of drug and concentration-enhancing polymer is 50 wt %, the relative degree of improvement is 50 wt %/1 wt %, or 50. For compositions of drugs and substrates of this aspect of the present invention, the relative degree of improvement is at least 1.25. When the drug is particularly unstable, larger relative degrees of improvement may be necessary in order for the chemical stability of the composition to be pharmaceutically acceptable. In such cases, the invention provides greater chemical stability when the relative degree of improvement is at least about 2, preferably at least about 5, and even more preferably at least about 10. In fact, some compositions may achieve a relative degree of improvement greater than 100.

The particular storage conditions and time of storage may be chosen as convenient depending on the stability of the drug, the particular concentration-enhancing polymer, and the ratio of drug to concentration-enhancing polymer. Where the drug is particularly unstable, or where the composition has a low ratio of drug to polymer, then shorter storage time periods may be used. Where the rate of drug degradation is linear, the relative degree of improvement will be independent of the storage time. However, where the rate of drug degradation is non-linear under controlled storage conditions, the stability test used to compare the test composition with the control composition is preferably chosen such that the degree of degradation is sufficiently large that it may be accurately measured. Typically, the time period is chosen so as to observe a degree of degradation of at least 0.1 wt % to 0.2 wt %. However, the time period is not so long that the ratio of drug to polymer changes substantially. Typically, the time period is such that the observed degree of degradation for the test composition is less than 50 wt % and preferably less than 20 wt %. When the rate of drug degradation in the control composition is relatively slow, the test is preferably conducted over a long enough period of time under controlled storage conditions to allow a meaningful comparison of the stability of the test composition with the control dispersion.

A stability test which may be used to test whether a composition meets the chemical stability criteria described above is storage of the test composition and the control composition for six months at 40° C. and 75% RH. A relative degree of improvement may become apparent within a shorter time, such as three to five days, and shorter storage times may be used for some drugs. When comparing compositions under storage conditions which approximate ambient conditions, e.g., 25° C. and 60% RH, the storage period may need to be from several months up to two years.

In addition, it is preferred that the compositions comprising drug and substrate result in drug stability such that the drug has a degree of degradation of less than about 2 wt %, more preferably less than about 0.5 wt %, and most preferably less than about 0.1 wt % when stored at 40° C. and 75% RH for six months, or less than about 2 wt %, more preferably less than about 0.5 wt %, and more preferably less than about 0.1 wt %, when stored at 25° C. and 60% RH for one year, or less than about 2 wt %, more preferably less than about 0.5 wt %, and more preferably less than about 0.1 wt %, when stored at ambient conditions for two years. Nevertheless, the compositions of the present invention may have a degree of degradation that is much greater than the preferred values, so long as the test composition achieves the degree of improvement relative to a control composition as described above.

The compositions of the present invention are particularly useful where the drug degrades in the presence of the concentration-enhancing polymer. For example, the present invention may be used where the drug is acid-sensitive and it is desired to use an acidic concentration-enhancing polymer. Often acidic concentration-enhancing polymers are preferred because such polymers result in superior aqueous concentration of the drug in the use environment. However, the acidic polymers may adversely interact with the drug, especially if the drug is dispersed in the acidic polymer. Accordingly, the present invention solves this problem by forming an adsorbate to chemically stabilize the drug. The adsorbate may then be mixed with an acidic concentration-enhancing polymer, resulting in an adsorbate that has improved chemical stability relative to a simple physical mixture of the drug and concentration-enhancing polymer, or a solid amorphous dispersion of the drug and concentration-enhancing polymer.

Excipients and Dosage Forms

Although the key ingredients present in the compositions of the present invention are simply the adsorbate of drug and substrate and the optional concentration-enhancing polymer(s), the inclusion of other excipients in the composition may be useful. These excipients may be utilized with the composition in order to formulate the composition into tablets, capsules, suspensions, powders for suspension, creams, transdermal patches, depots, and the like. In addition, as described above, the adsorbate and the optional concentration-enhancing polymer may be mixed with excipients separately to form different beads, or layers, or coatings, or cores or even separate dosage forms.

One very useful class of excipients is surfactants. Suitable surfactants include fatty acid and alkyl sulfonates; commercial surfactants such as benzethanium chloride (HYAMINE® 1622, available from Lonza, Inc., Fairlawn, N.J.); DOCUSATE SODIUM (available from Mallinckrodt Spec. Chem., St. Louis, Mo.); polyoxyethylene sorbitan fatty acid esters (TWEEN®, available from ICI Americas Inc., Wilmington, Del.); LIPOSORB® P-20 (available from Lipochem Inc., Patterson N.J.); CAPMUL® POE-0 (available from Abitec Corp., Janesville, Wis.), and natural surfactants such as sodium taurocholic acid, 1-palmitoyl-2-oleoyl-sn-glycero-3-phosphocholine, lecithin, and other phospholipids and mono- and diglycerides. Such materials can advantageously be employed to increase the rate of dissolution by facilitating wetting, thereby increasing the maximum dissolved concentration, and also to inhibit crystallization or precipitation of drug by interacting with the dissolved drug by mechanisms such as complexation, formation of inclusion complexes, formation of micelles or adsorbing to the surface of solid drug. These surfactants may comprise up to 5 wt % of the composition.

The addition of pH modifiers such as acids, bases, or buffers may also be beneficial, retarding or enhancing the rate of dissolution of the composition, or, alternatively, helping to improve the chemical stability of the composition.

Other conventional formulation excipients may be employed in the compositions of this invention, including those excipients well-known in the art (e.g., as described in *Remington's Pharmaceutical Sciences* (16$^{th}$ ed. 1980). Generally, excipients such as fillers, disintegrating agents, pigments, binders, lubricants, glidants, flavorants, and so forth may be used for customary purposes and in typical amounts without adversely affecting the properties of the compositions. These excipients may be utilized after the drug/polymer composition has been formed, in order to formulate the composition into tablets, capsules, suspensions, powders for suspension, creams, transdermal patches, and the like.

Examples of matrix materials, fillers, or diluents include lactose; mannitol, xylitol, dextrose, sucrose, sorbitol, compressible sugar, microcrystalline cellulose, powdered cellulose, starch, pregelatinized starch, dextrates, dextran, dextrin, dextrose, maltodextrin, calcium carbonate, dibasic calcium phosphate, tribasic calcium phosphate, calcium sulfate, magnesium carbonate, magnesium oxide, poloxamers such as polyethylene oxide, and hydroxypropyl methyl cellulose.

Examples of surface active agents include sodium lauryl sulfate and polysorbate 80.

Examples of drug complexing agents or solubilizers include the polyethylene glycols, caffeine, xanthene, gentisic acid and cylodextrins.

Examples of disintegrants include sodium starch glycolate, sodium carboxymethyl cellulose, calcium carboxymethyl cellulose, croscarmellose sodium, crospovidone (polyvinylpolypyrrolidone), methyl cellulose, microcrystalline cellulose, powdered cellulose, starch, pregelatinized starch, and sodium alginate.

Examples of tablet binders include acacia, alginic acid, carbomer, carboxymethyl cellulose sodium, dextrin, ethylcellulose, gelatin, guar gum, hydrogenatetd vegetable oil, hydroxyethyl cellulose, hydroxypropyl cellulose, hydroxypropyl methyl cellulose, methyl cellulose, liquid glucose, maltodextrin, polymethacrylates, povidone, pregelatinized starch, sodium alginate, starch, sucrose, tragacanth, and zein.

Examples of lubricants include calcium stearate, glyceryl monostearate, glyceryl palmitostearate, hydrogenated vegetable oil, light mineral oil, magnesium stearate, mineral oil, polyethylene glycol, sodium benzoate, sodium lauryl sulfate, sodium stearyl fumarate, stearic acid, talc, and zinc stearate.

Examples of glidants include silicon dioxide, talc and cornstarch.

Compositions of this invention may be used in a wide variety of dosage forms for administration of drugs. Exemplary dosage forms are powders or granules that may be taken orally either dry or reconstituted by addition of water to form a paste, slurry, suspension or solution; tablets; capsules; multiparticulates; and pills. Various additives may be mixed, ground, or granulated with the compositions of this invention to form a material suitable for the above dosage forms.

In some cases, the overall dosage form or particles, granules or beads that make up the dosage form may have superior performance if coated with an enteric polymer to prevent or retard dissolution until the dosage form leaves the stomach. Exemplary enteric coating materials include HPMCAS, HPMCP, CAP, CAT, carboxymethylethyl cellulose, carboxylic acid-functionalized polymethacrylates, and carboxylic acid-functionalized polyacrylates.

Compositions of this invention may be administered in a controlled release dosage form. In one such dosage form, the composition of the adsorbate and optional concentration-enhancing polymer is incorporated into an erodible polymeric matrix device. By an erodible matrix is meant aqueous-erodible or water-swellable or aqueous-soluble in the sense of being either erodible or swellable or dissolvable in pure water or requiring the presence of an acid or base to ionize the polymeric matrix sufficiently to cause erosion or dissolution. When contacted with the aqueous environment of use, the erodible polymeric matrix imbibes water and forms an aqueous-swollen gel or "matrix" that entraps the mixture of adsorbate and optional concentration-enhancing polymer. The aqueous-swollen matrix gradually erodes, swells, disintegrates or dissolves in the environment of use, thereby controlling the release of the drug mixture to the environment of use.

Alternatively, the compositions of the present invention may be administered by or incorporated into a non-erodible matrix device.

Alternatively, the drug mixture of the invention may be delivered using a coated osmotic controlled release dosage form. This dosage form has two components: (a) the core which contains an osmotic agent and the adsorbate; and (b) a coating surrounding the core, the coating controlling the influx of water to the core from an aqueous environment of use so as to cause drug release by extrusion of some or all of the core to the environment of use. The osmotic agent contained in the core of this device may be an aqueous-swellable hydrophilic polymer, hydrogel, osmogen, or osmagent. The coating is preferably polymeric, aqueous-permeable, and has at least one delivery port. The optional concentration-enhancing polymer may be either mixed with the adsorbate (as described above) or be in a separate region of the core or it may be applied as all or part of the coating that controls the influx of water, or as a separate coating.

Alternatively, the drug mixture of the invention may be delivered via a coated hydrogel controlled release dosage form having three components: (a) a drug-containing composition containing the adsorbate, (b) a water-swellable composition wherein the water-swellable composition is in a separate region within a core formed by the drug-containing composition and the water-swellable composition, and (c) a coating around the core that is water-permeable, and has at least one delivery port therethrough. In use, the core imbibes water through the coating, swelling the water-swellable composition and increasing the pressure within the core, and fluidizing the drug-containing composition. Because the coating remains intact, the drug-containing composition is extruded out of the delivery port into an environment of use. The optional concentration-enhancing polymer may be delivered in a separate dosage form, may be mixed with the adsorbate (as described above) and be present in the drug-containing composition, may be included in the water-swellable composition, may be included in a separate layer within the core, or may constitute all or part of a coating applied to the dosage form, or as a separate coating.

In one embodiment, the compositions of the present invention may be co-administered, meaning that the adsorbate can be administered separately from, but within the same general time frame as, the concentration-enhancing polymer. Thus, an adsorbate can, for example, be administered in its own dosage form which is taken at approximately the same time as the concentration-enhancing polymer which is in a separate dosage form. If administered separately, it is generally preferred to administer both the adsorbate and the concentration-enhancing polymer within 60 minutes of each other, so that the two are present together in the environment of use. When not administered simultaneously, the concentration-enhancing polymer is preferably administered prior to the adsorbate.

In addition to the above additives or excipients, use of any conventional materials and procedures for preparation of suitable dosage forms using the compositions of this invention known by those skilled in the art are potentially useful.

Other features and embodiments of the invention will become apparent from the following examples which are given for illustration of the invention rather than for limiting its intended scope.

EXAMPLES

Example 1

A drug/substrate adsorbate comprising quinoxaline-2-carboxylic acid [4(R)-carbamoyl-1(S)-3-fluorobenzyl)-2(S),7-dihydroxy-7-methyl-octyl]amide ("Drug 1") and zinc oxide (the substrate) was prepared as follows. Drug 1 (0.15 wt %) was dissolved in a suspension of zinc oxide (NanoTek®, 30 to 60 nm, surface area of 15 to 45 m²/gm, 1.33 wt %) in methanol (a solvent for Drug 1) to form a milky suspension. This suspension was pumped into a "mini" spray-drying apparatus via a syringe pump at a rate of 1.3 mL/min. A high frequency vibrational device (Whisper 700—Sound Natural) was attached to the syringe to maintain a homogeneous suspension while the adsorbate was being formed. The spray solution was metered using a Cole Parmer 74900 series rate-controlling syringe pump. The solution was pumped into a Spraying Systems Co. two-fluid nozzle, model number SU1A, with nitrogen as the atomizing gas. The nitrogen was pressurized and heated to a temperature of 100° C. at a flow rate of about 1 scfm. The solution was sprayed from the top of an 11-cm diameter stainless steel chamber. The resulting drug/substrate adsorbate was collected on Whatman® 1 filter paper at a yield of about 53%, dried under vacuum, and stored in a dessicator. After drying, the Example 1 adsorbate contained 10 wt % Drug 1 and 90 wt % ZnO.

Control 1A: Control 1A was crystalline Drug 1 alone.

Example 2

The drug/substrate adsorbate of Example 1 and the crystalline drug of Control 1A were evaluated in an in vitro dissolution test using a microcentrifuge method. In this test, 18 mg of the adsorbate of Example 1, or 1.8 mg of Control 1A, was added to a microcentrifuge tube. The tubes were placed in a 37° C. temperature-controlled chamber, and 1.8 mL phosphate buffered saline (PBS) at pH 6.5 and 290 mOsm/kg was added. The solutions were quickly mixed using a vortex mixer for about 60 seconds, and then centrifuged at 13,000 G at 37° C. for minute. The resulting supernatant solution was then sampled and diluted 1:5 (by volume) with methanol. Diluted samples were analyzed by high-performance liquid chromatography (HPLC) at a UV absorbance of 245 nm using a Phenomenex Kromasil $C_4$ column and a mobile phase of 45% (0.2% $H_3PO_4$)/55% acetonitrile. After sampling, the contents of the tubes were mixed on the vortex mixer and allowed to stand undisturbed at 37° C. until the next sample was taken. Samples were collected at 4, 10, 20, 40, 90, and 1200 minutes. The concentrations of drug obtained in these samples are shown in Table 2A. Results for Example 1 are averages of two tests, while results for Control 1A are averages of 6 tests.

TABLE 2A

| Example | Time (min) | Drug 1 Concentration (µg/mL) | AUC (min * µg/mL) |
|---|---|---|---|
| 1 | 0 | 0 | 0 |
|   | 4 | 986 | 2,000 |
|   | 10 | 1098 | 8,200 |
|   | 20 | 1028 | 18,900 |
|   | 40 | 860 | 37,700 |
|   | 90 | 426 | 69,900 |
|   | 1200 | 404 | 530,500 |
| Control 1A | 0 | 0 | 0 |
|   | 4 | 254 | 510 |
|   | 10 | 298 | 2,200 |
|   | 20 | 306 | 5,200 |
|   | 40 | 302 | 11,300 |
|   | 90 | 329 | 27,000 |
|   | 180 | 325 | 56,500 |
|   | 1200 | 319 | 385,000 |

The results of these tests are summarized in Table 2B, which shows the maximum concentration of Drug 1 in solution during the first 90 minutes of the test ($C_{max,90}$), the area under the aqueous concentration versus time curve after 90 minutes ($AUC_{90}$).

TABLE 2B

| Example | Substrate | Drug 1 Conc. in the Adsorbate (wt %) | $C_{max,90}$ (µg/mL) | $AUC_{90}$ (min * µg/mL) |
|---|---|---|---|---|
| 1 | zinc oxide | 10 | 1100 | 69,900 |
| Control 1A | None | — | 329 | 27,000 |
| 4 | CAB-O-SIL M-5P | 25 | 901 | 77,700 |

These results show that the $C_{max,90}$ provided by the adsorbate of Example 1 was 3.3-fold that of the crystalline Control 1A, while the $AUC_{90}$ was 2.6-fold that of the Control 1A.

Control 1 B; Control 1 B was amorphous Drug 1 alone, prepared by spray drying a solution consisting of 2.02 wt % Drug 1 and 97.98 wt % methanol using the procedures outlined in Example 1 except that the concentration of Drug 1 in the methanol solution was 2.02 wt %, and no vibrational device was required. The resulting amorphous Drug 1 was collected at a yield of about 43%, dried under vacuum, and stored in a dessicator.

Example 3

The stability of Example 1 adsorbate was evaluated in an accelerated storage test. The adsorbate was stored under elevated temperature and humidity conditions to increase the rate of physical changes occurring in the material in order to simulate a longer storage interval in a typical storage environment. Samples of the adsorbate and Control 1B were stored at 40° C./75% relative humidity (RH). Samples were analyzed using a powder X-ray diffraction (PXRD) technique using a Bruker AXS D8 Advance diffractometer as follows. The X-ray tube (KCu, 1.54184 Å) was operated at a voltage of 45 kV and a current of 40 mA with the beam focused through a Göbel mirror and a series of slits into a line focus. Diffractograms were typically collected over the 2☐ range of 4° to 40° with a step size of 0.02°/step. Data were collected for a minimum time of 2.4 sec/step. Scans were obtained by holding the tube at a constant angle (to keep the illuminated area of the sample constant) and scanning a scintillation-counter detector fitted with a thin film collimator through 2☐. All standards and samples were spun in the ☐ plane at a rate of 30 rpm to minimize orientation effects. Sample cups of either
(1) standard Bruker plastic cups that were 1 mm deep (with deeper grooves), or
(2) zero background cups with a depth of 0.5 mm made by fixing Si(511) wafers in the bottoms of standard Bruker cups. Standards (150 to 200 mg) were prepared and leveled into cups by chopping the powder into place with light pressure from a spatula and scraping the excess away.

The results of these tests showed that Drug 1 in the adsorbate of Example 1 did not crystallize after being stored for 4 weeks at 40° C./75% RH. Control 1B showed significant crystallization after being stored for 1 week at the same conditions. Thus, the composition of the present invention had improved physical stability over that of the control.

Example 4

A drug/substrate adsorbate of Drug 1 was prepared using fumed silica from Cabot Corporation sold as CAB-O-SIL M-5P as a substrate. Drug 1 was first mixed with CAB-O-SIL M-5P (surface area of about 200 m²/gm) in methanol to form a suspension. Drug 1 was then dissolved in this suspension such that the suspension comprised 0.25 wt % Drug 1, 0.74 wt % CAB-O-SIL M-5P, and 99.01 wt % methanol. The syringe, containing a 2-cm stir bar, was placed near a stir plate to maintain a homogeneous suspension. This suspension was pumped into a "mini" spray-drying apparatus via a syringe pump at a rate of 1.3 mL/min. The spray solution was metered using a Cole Parmer 74900 series rate-controlling syringe pump. The solution was pumped into a Spraying Systems Co. two-fluid nozzle, model number SU1A, with nitrogen as the atomizing gas. The nitrogen was pressurized and heated to a temperature of 100° C. with a flow rate of 1.08 standard cubic feet per minute (scfm). The resulting drug/substrate adsorbate was collected on Whatman® 1 filter paper at a yield of about 53%, dried under vacuum, and stored at −20° C. After drying, the adsorbate of Example 4 contained 25 wt % Drug 1 and 75 wt % CAB-O-SIL M-5P.

Example 5

The adsorbate of Example 4 was evaluated in an in vitro dissolution test using the procedures outlined in Example 2, except that 7.2 mg of the adsorbate of Example 4 was used. The concentrations of drug obtained in these samples are shown in Table 5A.

TABLE 5A

| Example | Time (min) | Drug 1 Concentration (μg/mL) | AUC (min * μg/mL) |
|---|---|---|---|
| 4 | 0 | 0 | 0 |
|  | 4 | 828 | 1,660 |
|  | 10 | 868 | 6,750 |
|  | 20 | 877 | 15,500 |

TABLE 5A-continued

| Example | Time (min) | Drug 1 Concentration (μg/mL) | AUC (min * μg/mL) |
|---|---|---|---|
|  | 40 | 883 | 33,100 |
|  | 90 | 901 | 77,700 |
|  | 1200 | 398 | 799,000 |

The results of this test are summarized in Table 2B, and show that the $C_{max,90}$ provided by the adsorbate of Example 4 was 2.7-fold that of the crystalline control (Control 1A), while the $AUC_{90}$ for the adsorbate was 2.9-fold that of Control 1A.

Example 6

A drug/substrate adsorbate comprising [2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester ("Drug 2") and CAB-O-SIL M-5P was prepared by first adding CAB-O-SIL M-5P to acetone and then sonicating the mixture using a Fisher Scientific SF15 sonicator for 10 minutes to ensure full suspension and homogeneity. Drug 2 was then dissolved in this suspension resulting in a mixture that contained 0.18 wt % Drug 2, 1.6 wt % CAB-O-SIL M-5P, and 98.2 wt % acetone. This suspension was then pumped into a "mini" spray-drying apparatus via a Cole Parmer 74900 series rate-controlling syringe pump at a rate of 1.0 mL/min. The spray-drying apparatus used a Spraying Systems Co. two-fluid nozzle, model number SU1A, with nitrogen as the atomizing gas. The nitrogen was pressurized and heated to a temperature of 110° C. and had a flow rate of about 1 scfm. The suspension was sprayed from the top of an 11-cm diameter stainless steel chamber. The resulting solid amorphous adsorbate was collected on Whatman® 1 filter paper at a yield of about 46%, dried under vacuum, and stored in a dessicator. After drying, the Example 6 adsorbate contained 10 wt % Drug 2 and 90 wt % CAB-O-SIL M-5P.

Control 2A: Control 2A was crystalline Drug 2 without the substrate.

Control 2B: Control 2B was amorphous Drug 2 without the substrate.

Example 7

The adsorbate of Example 6 and the crystalline drug of Control 2A were evaluated in an in vitro dissolution test using a microcentrifuge method as in Example 2. In this test, 9 mg of the adsorbate of Example 6, or 1.8 mg of Control 2A, was added to a microcentrifuge tube. The tubes were placed in a 37° C. temperature-controlled chamber, and 1.8 mL of 0.5 wt % MFD solution at pH 6.5 and 290 mOsm/kg was added. The samples were quickly mixed using a vortex mixer for about 60 seconds. The samples were centrifuged at 13,000 G at 37° C. for 1 minute. The resulting supernatant solution was then sampled and diluted 1:5 (by volume) with methanol. Diluted samples were analyzed by HPLC at a UV absorbance of 256 nm using a Waters Symmetry $C_8$ column and a mobile phase consisting of 15% (0.2% $H_3PO_4$)/85% methanol. The contents of the tubes were mixed on the vortex mixer and allowed to stand undisturbed at 37° C. until the next sample was taken. Samples were collected at 4, 10, 20, 40, 90, and 1200 minutes. The concentrations of drug obtained in these samples are shown in Table 7A.

TABLE 7A

| Example | Time (min) | Drug 2 Concentration (μg/mL) | AUC (min * μg/mL) |
|---|---|---|---|
| 6 | 0 | 0 | 0 |
|  | 4 | 89 | 180 |
|  | 10 | 63 | 640 |
|  | 20 | 29 | 1,100 |
|  | 40 | <1 | 1,400 |
|  | 90 | <1 | 1,400 |
|  | 1200 | <1 | 1,400 |
| Control 2A | 0 | 0 | 0 |
|  | 4 | 3 | 6 |
|  | 10 | 2 | 21 |
|  | 20 | 8 | 71 |
|  | 40 | 4 | 190 |
|  | 90 | 11 | 570 |
|  | 1200 | 15 | 14,700 |

The results of this test are summarized in Table 7B and show that the adsorbate of Example 6 provided a $C_{max,90}$ value that was at least 11-fold that of the Control 2A and an $AUC_{90}$ that was 2.5-fold that of the Control 2A.

TABLE 7B

| Example | Substrate | Drug 2 Conc. In the Adsorbate (wt %) | $C_{max,90}$ (μg/mL) | $AUC_{90}$ (min * μg/mL) |
|---|---|---|---|---|
| 6 | CAB-O-SIL M-5P | 10 | 89 | 1400 |
| Control 2A | none | — | 11 | 570 |
| 8 | CAB-O-SIL M-5P | 15 | 62 | 790 |
| 9 | CAB-O-SIL M-5P | 25 | 186 | 8700 |

Example 8

A drug/substrate adsorbate was prepared following the procedure of Example 6 except that the suspension consisted of 0.27 wt % Drug 2, 1.52 wt % CAB-O-SIL M-5P, and 98.2 wt % acetone. After drying, the Example 9 adsorbate contained 15 wt % Drug 2 and 85 wt % CAB-O-SIL M-5P.

Example 9

A drug/substrate adsorbate of Drug 2 and CAB-O-SIL M-5P, was prepared using the procedure outlined in Example 6 except that the suspension consisted of 0.56 wt % Drug 2, 1.68 wt % CAB-O-SIL M-5P, and 97.8 wt % acetone, and was pumped via a syringe pump at a rate of 1.2 ml/min. The nitrogen gas was heated to a temperature of 100° C. at a flow rate of about 1 scfm. After drying, the Example 9 adsorbate contained 25 wt % Drug 2 and 75 wt % CAB-O-SIL M-5P.

Example 10

The adsorbates of Example 8 and Example 9 were evaluated in an in vitro dissolution test as in Example 7. In this test, 12 mg of the adsorbate of Example 8 or 7.2 mg of adsorbate of Example 9, was added to a microcentrifuge tube, along with 1.8 mL of a 0.5 wt % MFD solution at pH 6.5 and sampled as described in Example 7. The concentrations of drug obtained in this samples are shown in Table 10A.

TABLE 10A

| Example | Time (min) | Drug 2 Concentration (μg/mL) | AUC (min * μg/mL) |
|---|---|---|---|
| 8 | 0 | 0 | 0 |
|  | 4 | 62 | 130 |
|  | 10 | 33 | 410 |
|  | 20 | 14 | 650 |
|  | 40 | <1 | 790 |
|  | 90 | <1 | 790 |
|  | 1200 | <1 | 790 |
| 9 | 0 | 0 | 0 |
|  | 4 | 158 | 300 |
|  | 10 | 162 | 1,300 |
|  | 20 | 105 | 2,900 |
|  | 40 | 49 | 5,130 |
|  | 90 | 25 | 8,720 |
|  | 1200 | 12 | 45,600 |

The results of this test are summarized in Table 7B and show that the $C_{max,90}$ for the adsorbate of Example 8 was 5.6-fold that of the crystalline drug alone (Control 2A), while the $AUC_{90}$ was 1.4-fold that of the control. The adsorbate of Example 9 provided a $C_{max,90}$ value that was 16.9-fold that of the control and an $AUC_{90}$ that was 15.3-fold of Control 2A.

Example 11

The adsorbate of Example 9 and the crystalline drug of Control 2A were evaluated using a nuclear magnetic resonance (NMR) test. In this test, 0.690 mg of the adsorbate of Example 9, or 0.174 mg of Control 2, was added to a microcentrifuge tube. The tubes were placed in a 37° C. temperature-controlled chamber, and 1.7 mL for Example 9, or 1.8 mL for Control 2A, of 2 wt % deuterated MFD solution (d-MFD) at pH 6.5, 37° C., and 290 mOsm/kg was added. The samples were quickly mixed using a vortex mixer for 60 seconds. The samples were allowed to sit for 30 minutes in the 37° C. warm box before centrifuging at 13,000 G for 1 minute. The supernatant was then carefully transferred to an 8 mm glass NMR tube for Example 9. For Control 2A, the pellet was resuspended using Pasteur pipets and the sample was then carefully transferred to an NMR tube. An internal standard solution of trifluoroacetic acid (TFA) was added to the tubes to give a concentration of 0.2762 mM $^{19}$F for Example 9 or 0.3565 mM $^{19}$F Control 2A.

Fluorine spectra of the sample were recorded at 282.327 MHz on a Varian Gemini 2000, 300 MHz NMR equipped with a Nalorac 8 mm indirect detection probe. The sample temperature was maintained at 37° C. in the probe and the spectra acquired using a 90° pulse width and 20 second pulse delay (delay $>5*t_{1\ drug\ or\ standard}$). Drug resonances were integrated relative to the internal standard peak and the drug concentration determined. The given experiment time was calculated from the time the solvent was added to the solid sample until half of the time the spectrum had been acquired by the NMR. For example, when the spectra has been recorded for 2 hours after the sample was equilibrated for 30 minutes the time listed for the NMR result is 90 minutes.

Fluorine NMR data was collected for the appropriate number of scans to give good signal to noise, which gave an approximate timepoint of 90 minutes for Example 9 or 60 minutes for Control 2A. Acquisition parameters included an acquisition time of 0.788 seconds and a delay time of 19.2 seconds for a total relaxation time of 20 seconds to avoid use of fractional intensity calculations. Peaks were integrated and corrected for number of molecular fluorines in internal standard to determine the concentration of Drug 2.

The results of this test are summarized in Table 11, which shows the concentration of Drug 2 in solution for Example 9 and Control 2A. Note that no dissolved drug was detected at 60 minutes or 240 minutes for Control 2A. After equilibration for 3 days, the dissolved Drug 2 concentration for Control 2A was 13 µgA/mL ("µgA" refers to µg of active drug). Thus, the adsorbate of Example 9 provided an enhanced dissolved drug concentration over that of the control.

TABLE 11

| Example | Substrate | Drug 2 Conc. in the Adsorbate (wt %) | Dissolved Drug 2 Concentration (µgA/mL) (for NMR) |
|---|---|---|---|
| 9 | CAB-O-SIL M-5P | 25 | 59 (90 minutes) |
| Control 2A | none/ crystalline | — | 0 (60 minutes and 240 minutes) |
| 13 | CAB-O-SIL EH-5P | 25 | 41 (90 minutes) |
| 14 | CAB-O-SIL C-90 | 25 | 42 (90 minutes) |

Example 12

Samples of the adsorbate of Example 9 were assessed for physical stability by storing them for 12 weeks at 50° C./75% RH. The samples showed no crystallinity, indicating the adsorbate was physically stable.

Example 13

For Example 13, a drug/substrate adsorbate comprising Drug 2 and CAB-O-SIL EH-5 (Cabot Corp.) (having a surface area of about 380 m$^2$/g) was prepared as described in Example 6 but with a suspension consisting of 0.5 wt % Drug 2, 1.5 wt % CAB-O-SIL EH-5, and 98 wt % acetone. The solution was pumped via a syringe pump at a rate of 1.17 ml/min. The nitrogen gas was heated to a temperature of 100° C. at a flow rate of about 1 scfm. After drying, Example 13 adsorbate contained 25 wt % Drug 2 and 75 wt % CAB-O-SIL EH-5.

Example 14

For Example 14, a drug/substrate adsorbate was made from Drug 2 and CAB-O-SIL L-90 (surface area of 90 m$^2$/g), spray-dried as described in Example 13. After drying, Example 14 adsorbate contained 25 wt % Drug 2 and 75 wt % CAB-O-SIL L-90.

Example 15

The adsorbates of Example 13 and Example 14 were evaluated using the nuclear magnetic resonance (NMR) test described in Example 11. The results of these tests are summarized in Table 11, which shows the concentration of Drug 2 in solution for Example 13 and Example 14, as well as Control 2A.

These results show that the adsorbate of Examples 13 and 14 provided enhanced Drug 2 concentrations relative to the crystalline Control 2A.

Example 16

The adsorbates of Examples 6, 9, 13, and 14 were analyzed by Fourier transform infrared (FTIR) spectroscopy to characterize the interaction of Drug 2 and the silicon dioxide substrate. The analysis was performed using a Nicolet Nexus 670 spectrometer using the Smart MIRacle accessory for single reflection attenuated total reflection (ATR). Approximately 5-10 mg of sample was added to the sample compartment for the measurement of a spectrum. The detector was a nitrogen cooled mercury-cadmium-telluride (MCT) detector. Spectra were averages of 64 scans with 1 cm$^{-1}$ resolution. Comparison was made to an FTIR spectrum of amorphous drug alone (Control 2B).

The spectrum of Control 2B showed a Drug 2 carbonyl (C=O stretch) vibration peak at 1700 cm$^{-1}$. This is the characteristic vibration energy for interactions of the carbonyl group of Drug 2 in amorphous Drug 2 alone.

Example 6 was a Drug 2/CAB-O-SIL M-5P adsorbate, wherein the Drug 2 concentration was 10 wt % and the substrate surface area was about 200 m$^2$/g. The FTIR spectrum of the adsorbate of Example 6 showed a shift in the carbonyl peak to 1680 cm$^{-1}$, indicating the carbonyl groups of Drug 2 were hydrogen bonding with the hydroxyl groups terminating the SiO$_2$ surface of the substrate. The data show that all of the drug in the adsorbate was hydrogen bonding with the substrate, suggesting the drug was adsorbed as a monolayer on the substrate.

Example 9 was a 25 wt % Drug 2 adsorbate on CAB-O-SIL M-5P (with a surface of about 200 m$^2$/g). The FTIR spectrum of the adsorbate of Example 9 showed the drug to exist in two different amorphous states. The spectrum showed evidence of C=O stretch vibrations at both 1700 cm$^{-1}$ and 1680 cm$^{-1}$, indicating that a portion of the drug in the adsorbate was hydrogen bonding to the substrate, while the remainder of the drug was in an amorphous drug environment.

Similar results were observed for the adsorbate of Example 13, which was a 25 wt % Drug 2 adsorbate on CAB-O-SIL EH-5 (with a surface area of about 380 m$^2$/g). The FTIR spectrum of the adsorbate of Example 13 showed a larger fraction of the drug was hydrogen bonding with the substrate than for the adsorbate of Example 9. This is because the surface area of the CAB-O-SIL EH-5 used for Example 13 was larger than that for Example 9, allowing a higher fraction of the drug to be bound to the substrate in a monolayer.

The FTIR spectrum for the adsorbate of Example 14 (a 25 wt % Drug 2 adsorbate on CAB-O-SIL L-90 with a surface area of about 90 m$^2$/g) also showed the drug exists as two amorphous forms. For the adsorbate of Example 14, a smaller fraction of the drug was hydrogen bonding with the substrate than for the adsorbates of Example 9 and Example 13 due to the lower surface area of the substrate in Example 14.

Example 17

A drug/substrate adsorbate of 5-(2-(4-(3-benzisothiazolyl)-piperazinyl)ethyl-6-chlorooxindole ("Drug 3") and CAB-O-SIL M-5P was prepared by first mixing CAB-O-SIL M-5P in a solvent, sonicating, and then adding Drug 3. The solution consisted of 0.194 wt % Drug 3, 0.584 wt % CAB-O-SIL, and 99.22 wt % 7/3 (by weight) methanol/tetrahydrofuran. The CAB-O-SIL was added to the solvent and then sonicated using a Fisher Scientific SF15 sonicator for 10 minutes to ensure full suspension and homogeneity. Then Drug 3 was dissolved in the suspension with additional sonication. The suspension was spray dried by pumping it via a syringe pump at a rate of 0.75 ml/min into a spray-drying apparatus using a Spraying Systems Co. two-fluid nozzle, model number Su1A, with nitrogen as the atomizing gas. The nitrogen was pressurized and headed to a temperature of 120° C. at a flow rate of about 1 scfm. The solution was sprayed from the top of an 11 centimeter diameter stainless steel chamber. The resulting drug/substrate adsorbate was collected on Whatman® filter paper at a yield of about 61%, dried under vacuum, and stored in a dessicator. After drying, Example 17 adsorbate contained 25 wt % Drug 3 and 75 wt % CAB-O-SIL M-5P.

Control 3A: Contol consisted of the crystalline form of Drug 3 without a substrate.

Example 18

The adsorbate of Example 17 was evaluated in an in vitro dissolution test as in Example 2 using 1.44 mg of the adsorbate of Example 20, or 0.36 mg of crystalline Drug 3 (Control 3) in a microcentrifuge tube with 1.8 ml of 0.5 wt % MFD solution. Samples were analyzed by HPLC at a UV absorbance of 254 nm using a Phenomex ODS 20 column and a mobile phase consisting of 60% 0.02 M $KH_2PO_4$(pH 3.0)/40% acetonitrile. The concentrations of drug obtained in these samples are shown in Table 18A.

TABLE 18A

| Example | Time (min) | Drug 3 Concentration (μgA/mL) | AUC (min * μg/mL) |
|---|---|---|---|
| 17 | 0 | 0 | 0 |
|  | 4 | 7 | 10 |
|  | 10 | 5 | 50 |
|  | 20 | 4 | 100 |
|  | 40 | 4 | 180 |
|  | 90 | 3 | 370 |
|  | 1200 | 3 | 3700 |
| Control 3A | 0 | 0 | 0 |
|  | 4 | 3 | 10 |
|  | 10 | 2 | 20 |
|  | 20 | 1 | 30 |
|  | 40 | 2 | 60 |
|  | 90 | 2 | 150 |
|  | 1200 | 5 | 3900 |

The results of this test are summarized in Table 18B and show that the adsorbate of Example 17 provided a $C_{max,90}$ value that was 2.7-fold that of the crystalline Control 3A, and an $AUC_{90}$ that was 2.1-fold that of the Control 3A.

TABLE 18B

| Example | Substrate | Drug 3 Conc. in the Adsorbate (wt %) | $C_{max,90}$ (μg/mL) | $AUC_{90}$ (min * μg/mL) |
|---|---|---|---|---|
| 17 | CAB-O-SIL M-5P | 25 | 8 | 320 |
| Control 3A | none | — | 3 | 150 |

Example 19

The adsorbate of Example 17 was stored at 40°C. and 75% relative humidity for 6 weeks. The aged sample was analyzed by PXRD and a small amount of crystalline drug was detected, indicating the adsorbate had excellent physical stability. Attempts were made to form amorphous Drug 3 using a spray-drying process, but amorphous Drug 3 could not be formed due to rapid crystallization.

Example 20

The adsorbate of Example 17 was analyzed by FTIR as described in Example 16. The Example 17 adsorbate showed hydrogen bonding of Drug 3 onto the $SiO_2$ surface. The carbonyl bond at 1730 $cm^{-1}$ shifted to lower energies at 1710 $cm^{-1}$ when the drug was hydrogen bonded to the $SiO_2$ surface. This suggests a monolayer of Drug 3 had adsorbed to the substrate.

Example 21

A drug/substrate adsorbate of Indomethacin ("Drug 4") was produced using the same equipment and techniques as described in Example 6. To form the adsorbate of Example 21, 150 mg of Drug 4 was added to a suspension of 450.2 mg Silicon Dioxide (Cab-O-Sil M-5P) in 60 g acetone. The homogeneous suspension was pumped into the mini spray drier at a rate of 1.3 mLs/min. The nitrogen gas used to atomize the solution was at a temperature of 105° C. and a flow rate of 1 scfm. The yield of the process was about 63%. The adsorbate was dried under vacuum, and stored in a dessicator. After drying, the adsorbate of Example 21 contained 25 wt % Drug 4 and 75 wt % CAB-O-SIL M-SP.

Control 4: Control 4 was crystalline Drug 4 alone.

Example 22

The adsorbate of Example 21 was evaluated in an in vitro dissolution test as described in Example 2 for Drug 1. In this test, 36 mg of the adsorbate of Example 21, or 9 mg of Control 4, was added to the microcentrifuge tubes used in the test. Samples were analyzed by HPLC at a UV absorbance of 254 nm using an Alltech platinum EPS 1A8 column and a mobile phase consisting of 40% 0.02 M $KH_2PO_4$(pH 4.5)/10% acetonitrile/50% methanol. Samples for this test were collected at 4, 10, 20, 40, and 90 minutes. The concentrations of Drug 4 obtained in these samples are shown in Table 22A.

TABLE 22A

| Example | Time (min) | Drug 4 Concentration (μgA/mL) | AUC (min * μg/mL) |
|---|---|---|---|
| 21 | 0 | 0 | 0 |
|  | 4 | 3520 | 7,100 |
|  | 10 | 2370 | 24,700 |
|  | 20 | 1840 | 45,700 |
|  | 40 | 1670 | 80,800 |
|  | 90 | 1570 | 161,500 |
|  | 1200 | 1030 | 1,605,000 |
| Control 4 | 0 | 0 | 0 |
|  | 4 | 320 | 630 |
|  | 10 | 340 | 2,600 |
|  | 20 | 610 | 7,300 |
|  | 40 | 460 | 8,100 |
|  | 90 | 480 | 41,700 |
|  | 1200 | 400 | 527,700 |

The results of this test are summarized in Table 22B.

TABLE 22B

| Example | Adsorbate Formation Process | Substrate | Drug 4 Conc. in the Adsorbate (wt %) | $C_{max,90}$ (μgA/mL) | $AUC_{90}$ (min * μg/mL) |
|---|---|---|---|---|---|
| 21 | spray-dried | CAB-O-SIL M-5P | 25 | 3520 | 161,500 |
| Control 4 | — | None | — | 610 | 41,700 |
| 23 | melt extrusion | CAB-O-SIL | 20 | 2870 | 174,100 |

These results show that the adsorbate of Example 21 provided a $C_{max,90}$ that was 5.8-fold that of the Control 4 and a $AUC_{90}$ that was 3.9 fold of Control 4.

Example 23

A 20% Drug 4/CAB-O-SIL M-5P adsorbate was produced using melt extrusion technology. A preblend of 80 wt % CAB-O-SIL M-5P and 20 wt % Drug 4 was fed into a 19 mm co-rotating twin screw extruder (B&P Process Equipment TC-19, 25 L/D) operating at 30 rpm. The feed rate was 10 g/min from an Accurate 304-12 volumetric feeder. The extruder was set up to act as a continuous, mixed heat exchanger. The screw configuration consisted of twin lead feed screw elements and mixing paddles set up as forward mixing elements. This setup allowed for filled screw sections for heat transfer from the barrel and avoidance of excessive flow restriction. The die area of the extruder was left open, also to avoid flow restriction. The barrel temperature was ramped from 25° C. at the feed area to 170° C. in the last barrel zone (discharge end). The extrudate was discharged into ambient air, resulting in rapid solidification of the drug on the substrate.

Example 24

The adsorbate of Example 23 was evaluated in the in vitro dissolution test described in Example 22. In this test, 45 mg of the adsorbate of Example 23 was added to the microcentrifuge tubes used in the test. Samples for this test were collected at 4, 10, 20, 40, 90, and 1200 minutes. The concentrations of drug obtained in these samples are shown in Table 24A.

TABLE 24A

| Example | Time (min) | Drug 4 Concentration (μgA/mL) | AUC (min * μg/mL) |
|---|---|---|---|
| 23 | 0 | 0 | 0 |
|  | 4 | 2800 | 5,600 |
|  | 10 | 2870 | 22,600 |
|  | 20 | 1980 | 46,900 |
|  | 40 | 1830 | 84,900 |
|  | 90 | 1740 | 174,100 |
|  | 1200 | 1620 | 2,039,000 |

The results of this test are summarized in Table 22B and show that the adsorbate of Example 23 provided a $C_{max,90}$ that was 4.7-fold and an $AUC_{90}$ that was 4.2-fold that obtained for Control 4. Comparison of the results for Example 21 and Example 23 indicates that adsorbates of Drug 4 and CAB-O-SIL M-5P produced by spray drying and extrusion performs similarly.

Example 25

The physical stability of the adsorbate of Example 23 was evaluated by storing samples of the adsorbate at 40° C. and 75% relative humidity and periodically withdrawing samples and analyzing them by PXRD. After 4 days of storage, the drug in the adsorbate of Example 23 was about 5% crystalline, yielding a crystallization rate of 1.25%/day, whereas an amorphous control had a crystallinity of more than 80% under the same conditions, yielding a crystallization rate of 20%/day. Thus, the adsorbate of Example 23 had improved physical stability compared to the control, having a crystallization rate that was only about 6% of the control.

Example 26

The adsorbates of Example 21 and Example 23 were analyzed by FTIR as described in Example 16. The FTIR spectra showed that Drug 4 in the adsorbate is hydrogen bonded to the surface of the silicon dioxide particles. This was indicated by a shift of the carbonyl bond (identified in amorphous Drug 4 at approximately 1740 cm$^{-1}$) to a 20 cm$^{-1}$ lower energy state.

Example 27

A drug/substrate adsorbate was produced using a rotovapping process that slowly removed solvent from the suspension. In this technique, 450 mg CAB-O-SIL M-5P was sonicated for 15 min in 26.25 g of acetone using the sonication equipment described in Example 6. 150 mg of Drug 2 was then added and the suspension was allowed to equilibrate for 20 minutes, followed by an additional 5 minutes of sonication resulting in dissolution of the drug in the suspension. The suspension was rotovapped in a waterbath that was thermally stabilized at 40° C. The sample was dried under vacuum over night. The rotovapping process yielded about 88% adsorbate product. After drying, the Example 27 adsorbate contained 25 wt % Drug 2 and 75 wt % CAB-O-SIL M-5P.

Example 28

The adsorbate of Example 27 was evaluated using an NMR test using the procedures described in Example 11. The results of this test are presented in Table 28, along with the results for the spray dried adsorbate of Example 9 and the crystalline Control 2A. These data show that the rotovapped adsorbate of Example 27 provided an enhanced Drug 2 concentration compared with the crystalline Control 2A. The data also shows that the spray dried adsorbate of Example 9 provided even greater enhancement.

TABLE 28

| Example | Substrate | Method of Preparing Adsorbate | Drug 2 Conc. in the Adsorbate (wt %) | Dissolved Drug 2 Concentration (μgA/mL) |
|---|---|---|---|---|
| 27 | CAB-O-SIL M-5P | slow evaporation (rotovapping) | 25 | 13 (90 minutes) |
| 9 | CAB-O-SIL M-5P | rapid solvent removal (spray-drying) | 25 | 59 (90 minutes) |

TABLE 28-continued

| Example | Substrate | Method of Preparing Adsorbate | Drug 2 Conc. in the Adsorbate (wt %) | Dissolved Drug 2 Concentration (µgA/mL) |
|---|---|---|---|---|
| Control 2A | none (crystalline control) | — | — | 0 (60 minutes and 240 minutes) |

Example 29

This example illustrates that combining concentration-enhancing polymer with an adsorbate results in improved concentration enhancement. The adsorbate of Example 1 was evaluated in an in vitro dissolution test using the procedure described in Example 2, except that 18 mg of the adsorbate was added to a microcentrifuge tube containing 1.8 mL PBS with 5.4 mg hydroxypropyl methyl cellulose (HPMC) (the concentration-enhancing polymer). The results are presented in Table 29A.

TABLE 29A

| Example | Time (min) | Drug 1 Concentration (µg/mL) | AUC (min * µg/mL) |
|---|---|---|---|
| 29 | 0 | 0 | 0 |
|  | 4 | 1157 | 2,300 |
|  | 10 | 1228 | 9,500 |
|  | 20 | 1348 | 22,300 |
|  | 40 | 1355 | 49,400 |
|  | 90 | 1404 | 118,400 |
|  | 1200 | 1164 | 1,543,600 |

The results of this test are summarized in Table 29B which also includes data for dissolution tests with the adsorbate of Example 1 without concentration-enhancing polymer.

TABLE 29B

| Example | Substrate | Drug 1 Conc. in the Adsorbate (wt %) | Receptor Solution | $C_{max,90}$ (µgA/mL) | $AUC_{90}$ (min * µg/mL) |
|---|---|---|---|---|---|
| 29 | zinc oxide | 10 | PBS/HPMC | 1404 | 118,400 |
| 1 | zinc oxide | 10 | PBS | 1098 | 69,900 |

These results show that the adsorbate mixed with concentration-enhancing polymer in Example 29, provided a $C_{max,90}$ value that was 1.3-fold that provided by the adsorbate alone. The adsorbate mixed with concentration-enhancing polymer also provided an $AUC_{90}$ that was 1.7-fold that provided by the adsorbate alone.

Example 30

The adsorbate of Example 17 was evaluated in an in vitro dissolution test using the procedure described in Example 18, except that 1.44 mg of the adsorbate was added to a microcentrifuge tube containing 1.8 mL 0.5 wt % MDF solution with 1.08 mg of the concentration-enhancing polymer HPMCAS-HF. The results are presented in Table 30A.

TABLE 30A

| Example | Time (min) | Drug 3 Concentration (µg/mL) | AUC (min * µg/mL) |
|---|---|---|---|
| 30 | 0 | 0 | 0 |
|  | 4 | 44 | 88 |
|  | 10 | 23 | 290 |
|  | 20 | 18 | 490 |
|  | 40 | 16 | 820 |
|  | 90 | 14 | 1,600 |
|  | 1200 | 10 | 14,600 |

The results of this test are summarized in Table 30B, along with results of dissolution tests with the adsorbate without concentration-enhancing polymer (see Example 18).

TABLE 30B

| Example | Substrate | Drug 3 Conc. in the Adsorbate (wt %) | Receptor Solution | $C_{max,90}$ (µgA/mL) | $AUC_{90}$ (min * µg/mL) |
|---|---|---|---|---|---|
| 30 | CAB-O-SIL M-5P | 25 | 0.5% MFD/ HPMCAS-HF | 44 | 1600 |
| 17 | CAB-O-SIL M-5P | 25 | 0.5% MFD | 8 | 320 |

These results show that the adsorbate mixed with a concentration-enhancing polymer (Example 30) provided a $C_{max,90}$ value that was 5.5-fold that of the adsorbate alone (Example 17). The adsorbate mixed with a concentration-enhancing polymer also provided an $AUC_{90}$ value that was 5.0-fold that of the adsorbate alone.

Example 31

A drug/concentration-enhancing polymer/substrate adsorbate of Drug 2, HPMCAS-MF and CAB-O-SIL M-5P was prepared by first mixing a "medium fine" (AQUOT-MF) grade of the ionizable cellulosic polymer HPMCAS (manufactured by Shin Etsu, Tokyo, Japan) in solvent and sonicating until fully in solution. CAB-O-SIL M-5P was then added and the solution was sonicated for at least 10 minutes. Then Drug 2 was added and the solution was sonicated a third time until the drug fully dissolved. The resulting suspension consisted of 0.31 wt % Drug 2, 1.84 wt % CAB-O-SIL M-5P, 0.92 wt % HPMCAS, and 96.93 wt % acetone. The spray solution was then pumped into a "mini" spray-drying apparatus via a Cole Parmer 74900 series rate-controlling syringe pump at a rate of 0.83 mL/min. The spray-drying apparatus was a Spraying Systems Co. two-fluid nozzle, model number SU1A, with nitrogen as the atomizing gas. The nitrogen was pressurized and heated to a temperature of 120° C. at a flow rate of about 1 scfm. The solution was sprayed from the top of an 11 centimeter diameter stainless steel chamber. The resulting solid amorphous adsorbate was collected on Whatman® 1 filter paper, dried under vacuum, and stored in a dessicator. After drying, the Example 31 adsorbate contained 10 wt % Drug 2, 60 wt % CAB-O-SIL M-5P, and 30 wt % HPMCAS-MF polymer.

Example 32

The adsorbate of Example 31 was evaluated in an in vitro dissolution test using the procedure described in Example 7, except that 18 mg of the adsorbate was added to a microcentrifuge tube containing 1.8 mL 0.5 wt % MDF solution at pH 6.5 The results are presented in Table 32A.

TABLE 32A

| Example | Time (min) | Drug 2 Concentration (μg/mL) | AUC (min * μg/mL) |
|---|---|---|---|
| 31 | 0 | 0 | 0 |
|  | 4 | 70 | 140 |
|  | 10 | 100 | 650 |
|  | 20 | 190 | 2,100 |
|  | 40 | 230 | 6,290 |
|  | 90 | 286 | 19,200 |
|  | 1200 | 92 | 228,800 |

The results of this test are summarized in Table 32B, along with the results for the adsorbate of Example 6 tested without a concentration-enhancing polymer (see Example 7).

TABLE 32B

| Example | Substrate | Drug/ Substrate/ Polymer in the Adsorbate (wt %) | $C_{max,90}$ (μg/mL) | $AUC_{90}$ (min * μg/mL) |
|---|---|---|---|---|
| 31 | CAB-O-SIL M-5P | 10/60/30 | 286 | 19,200 |
| 6 | CAB-O-SIL M-5P | 10/90/0 | 89 | 1,400 |
| 33 | CAB-O-SIL M-5P | $33^{1/3}/33^{1/3}/33^{1/3}$ | 78 | 4,600 |

Example 33

A drug/concentration-enhancing polymer/substrate adsorbate of Drug 2, HPMCAS-MG, and CAB-O-SIL M-5P was prepared by first mixing Drug 2 in a solvent together with a "medium granular" (AQUOT-MG) grade of the ionizable cellulosic polymer HPMCAS (manufactured by Shin Etsu) to form a solution. CAB-O-SIL M-5P was then suspended in the Drug 2/HPMCAS mixture. The suspension consisted of 2.5 wt % Drug 2, 2.5 wt % CAB-O-SIL M-5P, 2.5 wt % HPMCAS, and 92.5 wt % acetone. The solution was sprayed as described in Example 31. After drying, the Example 33 adsorbate contained 33 wt % Drug 2, 33 wt % CAB-O-SIL M-5P, and 33 wt % HPMCAS-MG polymer.

Example 34

Example 33 was evaluated in an in vitro dissolution test using the procedure describe in Example 7, except that 5.4 mg of the adsorbate was added to a microcentrifuge tube containing 1.8 mL 0.5 wt % MFD solution at pH 6.5. The results are presented in Table 34A and summarized in Table 32B.

TABLE 34A

| Example | Time (min) | Drug 2 Concentration (μg/mL) | AUC (min * μg/mL) |
|---|---|---|---|
| 33 | 0 | 0 | 0 |
|  | 4 | 47 | 94 |
|  | 10 | 39 | 352 |
|  | 20 | 43 | 760 |

TABLE 34A-continued

| Example | Time (min) | Drug 2 Concentration (μg/mL) | AUC (min * μg/mL) |
|---|---|---|---|
|  | 40 | 43 | 1,600 |
|  | 90 | 78 | 4,600 |
|  | 1200 | 37 | 68,600 |

Example 35

A drug/substrate adsorbate of Drug 3 and CAB-O-SIL EH-5 was prepared by using the procedure outlined in Example 17 with the following exceptions. The suspension consisted of 0.67 wt % CAB-O-SIL, 0.22 wt % Drug 3, and 99.11 wt % tetradrofuran. The CAB-O-SIL was added to the solvent and then sonicated for 45 minutes to ensure full suspension and homogeneity. After drying, the Example 35 adsorbate contained 25 wt % Drug 3 and 75 wt % CAB-O-SIL.

Control 3B: Control 3B consisted of the amorphous form of Drug 3 without a substrate.

Example 36

The drug/substrate adsorbate of Example 35 was evaluated in an in vitro dissolution test using the procedure described in Example 18, except that 1.44 mg of the adsorbate, or 0.36 mg of Control 3B, was added to a microcentrifuge tube containing 1.8 mL 0.5 wt % MFD solution at pH 6.5. The results are presented in table 36A and summarized in Table 36B.

TABLE 36A

| Example | Time (min) | Drug 3 Concentration (μgA/mL) | AUC (min * μg/mL) |
|---|---|---|---|
| 35 | 0 | 0 | 0 |
|  | 4 | 22 | 0 |
|  | 10 | 16 | 200 |
|  | 20 | 15 | 300 |
|  | 40 | 14 | 600 |
|  | 90 | 13 | 1,300 |
|  | 1200 | 15 | 16,800 |
| Control 3B | 0 | 0 | 0 |
|  | 4 | 2 | 0 |
|  | 10 | 2 | 0 |
|  | 20 | 2 | 0 |
|  | 40 | 2 | 100 |
|  | 90 | 2 | 200 |
|  | 1200 | 2 | 2,400 |

The results show that the $C_{max,90}$ provided by the adsorbate of Example 35 was 11-fold that of Control 3B while the $AUC_{90}$ was 6.5-fold that of Control 3B.

TABLE 36B

| Example | Substrate | Drug/ Substrate in the Adsorbate (wt %) | $C_{max,90}$ (μgA/mL) | $AUC_{90}$ (min * μg/mL) | $C_{1200}$ (μgA/mL) |
|---|---|---|---|---|---|
| 35 | CAB-O-SIL EH-5 | 25/75 | 22 | 1300 | 15 |
| Control 3B | none | — | 2 | 200 | 2 |

Example 37

A drug/concentration-enhancing polymer/substrate adsorbate of Drug 3, cellulose acetate phthalate (CAP)(NF grade, Eastman Chemical Co., Kingsport, Tenn.), and CAB-O-SIL M-5P was prepared by using the procedure outlined in Example 31 with the following exceptions. The suspension consisted of 0.11 wt % Drug 3, 0.20 wt % CAB-O-SIL M-5P, 0.20 wt % CAP, and 99.49 wt % methanol/acetone (2/1). The spray solution was pumped at a rate of 1.0 mL/min, and the nitrogen gas was heated to 100° C. After drying, the Example 37 adsorbate contained 20 wt % Drug 3, 40 wt % CAB-O-SIL M-5P, and 40 wt % CAP polymer.

Example 38

The drug/concentration-enhancing polymer/substrate adsorbate of Example 37 was evaluated in an in vitro dissolution test using the procedure described in Example 18, except that 1.96 mg of the adsorbate, or 0.39 mg of Control 3A, was added to a microcentrifuge tube containing 1.8 mL 0.5 wt % MFD solution at pH 6.5. The results are presented in Table 38A and summarized in Table 38B.

TABLE 38A

| Example | Time (min) | Drug 3 Concentration (µgA/mL) | AUC (min * µg/mL) |
|---|---|---|---|
| 37 | 0 | 0 | 0 |
|  | 4 | 74 | 100 |
|  | 10 | 70 | 600 |
|  | 20 | 5 | 1,000 |
|  | 40 | 4 | 1,000 |
|  | 90 | 3 | 1,200 |
|  | 1200 | 3 | 4,600 |
| Control 3A | 0 | 0 | 0 |
|  | 4 | 13 | 0 |
|  | 10 | 22 | 100 |
|  | 20 | 26 | 400 |
|  | 40 | 13 | 800 |
|  | 90 | 8 | 1,300 |
|  | 1200 | 9 | 10,700 |

The results show that the $C_{max,90}$ provided by the adsorbate of Example 37 was 2.8-fold that of Control 3A.

TABLE 38B

| Example | Substrate | Drug/ Substrate/ Polymer in the Adsorbate (wt %) | $C_{max,90}$ (µgA/mL) | $AUC_{90}$ (min * µg/mL) | $C_{1200}$ (µgA/mL) |
|---|---|---|---|---|---|
| 37 | CAB-O-SIL M-5P | 20/40/40 | 74 | 1200 | 3 |
| Control 3A | none | — | 26 | 1300 | 9 |

Example 39

This example illustrates that combining concentration-enhancing polymer with a drug/substrate adsorbate results in improved concentration enhancement. The adsorbate of Example 9, consisting of 25 wt % Drug 2 and 75 wt % CAB-O-SIL M-5P, was evaluated in an in vitro dissolution test using the procedure describe in Example 2, except that 7.2 mg of the adsorbate, or 1.8 mg of Control 2B, was added to a microcentrifuge tube containing 1.8 mL PBS alone, or 1.8 mL PBS with 3.6 mg of the concentration-enhancing polymer polyoxyethylene-polyoxypropylene block copolymer (Pluronic® F-127, available from BASF Corp.) HPLC analysis of Drug 2 was performed as described in Example 7. The results presented in Table 39A.

TABLE 39A

| Example | Time (min) | Drug 2 Concentration (µgA/mL) | AUC (min * µg/mL) |
|---|---|---|---|
| Example 9 | 0 | 0 | 0 |
|  | 4 | 23 | 0 |
|  | 10 | 5 | 100 |
|  | 20 | 3 | 200 |
|  | 40 | 2 | 200 |
|  | 90 | 1 | 300 |
|  | 1200 | 2 | 2,200 |
| Example 9 + Pluronic F127 | 0 | 0 | 0 |
|  | 4 | 33 | 100 |
|  | 10 | 30 | 300 |
|  | 20 | 39 | 600 |
|  | 40 | 47 | 1,500 |
|  | 90 | 72 | 4,400 |
|  | 1200 | 71 | 83,800 |
| Control 2B | 0 | <1 | 0 |
|  | 4 | <1 | <2 |
|  | 10 | <1 | <8 |
|  | 20 | <1 | <18 |
|  | 40 | <1 | <38 |
|  | 90 | <1 | <88 |
|  | 1200 | <1 | <1,200 |

The results of this test are summarized in table 39B.

TABLE 39B

| Example | Substrate | Drug 2 Conc. in the Adsorbate (wt %) | Receptor Solution | $C_{max,90}$ (µgA/mL) | $AUC_{90}$ (min * µg/mL) |
|---|---|---|---|---|---|
| 9 | CAB-O-SIL M-5P | 25 | PBS | 23 | 300 |
| 9 + Pluronic F127 | CAB-O-SIL M-5P | 25 | PBS | 72 | 4400 |
| Control 2B | none | 100 | PBS | <1 | <88 |

These results show that the adsorbate of Example 9 mixed with the concentration-enhancing polymer Pluronic F127, provided a $C_{max,90}$ value that was 3.1-fold that provided by the adsorbate alone, and a $C_{max,90}$ value that was greater than 72-fold that provided by Control 2B. The adsorbate mixed with concentration-enhancing polymer also provided an $AUC_{90}$ that was 11-fold that provided by the adsorbate alone, and an $AUC_{90}$ that was greater than 50-fold that provided by Control 2B.

Example 40

A drug/substrate adsorbate of sildenafil citrate (Drug 5) was produced using the procedure outlined in Example 6 with the following exceptions. The suspension consisted of 0.58 wt % CAB-O-SIL M-5P, 0.09 wt % Drug 5, and 99.33 wt % methanol. The nitrogen gas was heated to 100° C. After drying, the Example 40 adsorbate contained 10 wt % active Drug 5.

Control 5: Control 5 was crystalline Drug 5 alone.

Example 41

The drug/substrate adsorbate of Example 40 was evaluated in an in vitro dissolution test using the procedure described in Example 2, except that 12.91 mg of the adsorbate, or 1.29 mg of Control 5, was added to a microcentrifuge tube containing 1.8 mL PBS alone, or 1.8 mL PBS with 2.7 mg of the concentration-enhancing polymer CAP. HPLC analysis was performed using a Waters Symmetry $C_8$ column, with a mobile phase of 0.05M TEA, pH 3.0/methanol/acetonitrile (58/25/17). UV absorbance of Drug 5 was measured at 290 nm. The results presented in Table 41A.

TABLE 41A

| Example | Time (min) | Drug 5 Concentration (µgA/mL) | AUC (min * µg/mL) |
|---|---|---|---|
| Example 40 | 0 | 0 | 0 |
| | 4 | 40 | 100 |
| | 10 | 36 | 300 |
| | 20 | 38 | 700 |
| | 40 | 44 | 1,500 |
| | 90 | 37 | 3,500 |
| | 1200 | 37 | 44,600 |
| Example 40 + CAP | 0 | 0 | 0 |
| | 4 | 146 | 300 |
| | 10 | 151 | 1,200 |
| | 20 | 162 | 2,700 |
| | 40 | 162 | 6,000 |
| | 90 | 172 | 14,300 |
| | 1200 | 145 | 190,300 |
| Control 5 | 0 | 0 | 0 |
| | 4 | 42 | 100 |
| | 10 | 40 | 300 |
| | 20 | 47 | 800 |
| | 40 | 47 | 1,700 |
| | 90 | 42 | 3,900 |
| | 1200 | 31 | 44,400 |

The results of this test are summarized in table 41B.

TABLE 41B

| Example | Substrate | Drug 5 Conc. in the Adsorbate (wt %) | Receptor Solution | $C_{max,90}$ (µgA/mL) | $AUC_{90}$ (min * µg/mL) | $C_{1200}$ (µgA/mL) |
|---|---|---|---|---|---|---|
| 40 | CAB-O-SIL M-5P | 10 | PBS | 44 | 3500 | 37 |
| 40 + CAP | CAB-O-SIL M-5P | 10 | PBS | 172 | 14,300 | 145 |
| Control 5 | none | 100 | PBS | 47 | 3900 | 31 |

These results show that the adsorbate of Example 40 mixed with the concentration-enhancing polymer CAP provided a $C_{max,90}$ value that was 3.7-fold that provided by Control 5. The adsorbate mixed with concentration-enhancing polymer also provided an $AUC_{90}$ that was 3.7-fold that provided by Control 5.

Example 42

A drug/concentration-enhancing polymer/substrate adsorbate consisting of Drug 2, polyoxyethylene-polyoxypropylene block copolymer (Pluronic F127), and CAB-O-SIL M-5P was prepared using the procedure outlined in Example 31 with the following exceptions. The suspension consisted of 0.39 wt % Drug 2, 0.78 wt % CAB-O-SIL M-5P, 0.78 wt % Pluronic F127, and 98.05 wt % acetone. The spray solution was pumped at a rate of 1.2 mL/min, and the nitrogen gas was heated to 100° C. After drying, the adsorbate of Example 42 contained 20 wt % Drug 2, 40 wt % CAB-O-SIL M-5P, and 40 wt % Pluronic F127 polymer.

Example 43

The drug/concentration-enhancing polymer/substrate adsorbate of Example 42 was evaluated in an in vitro dissolution test using the procedure described in Example 2, except that 9.0 mg of the adsorbate, or 1.8 mg of Control 2B, was added to a microcentrifuge tube containing 1.8 mL PBS solution at pH 6.5. HPLC analysis of Drug 2 was performed as described in Example 7. The results presented in Table 43A and summarized in Table 43B.

TABLE 43A

| Example | Time (min) | Drug 2 Concentration (µgA/mL) | AUC (min * µg/mL) |
|---|---|---|---|
| 42 | 0 | 0 | 0 |
| | 4 | 173 | 300 |
| | 10 | 168 | 1,400 |
| | 20 | 163 | 3,000 |
| | 40 | 158 | 6,200 |
| | 90 | 145 | 13,800 |
| | 1200 | 64 | 129,800 |
| Control 2B | 0 | <1 | 0 |
| | 4 | <1 | <2 |
| | 10 | <1 | <8 |
| | 20 | <1 | <18 |
| | 40 | <1 | <38 |
| | 90 | <1 | <88 |
| | 1200 | <1 | <1,200 |

The results of this test are summarized in Table 43B. These results show that the $C_{max,90}$ provided by the adsorbate of Example 42 was greater than 173-fold that of Control 2, and the $AUC_{90}$ was greater than 157-fold that of Control 2.

TABLE 43B

| Example | Substrate | Drug/Substrate/Polymer in the Adsorbate (wt %) | $C_{max,90}$ (µgA/mL) | $AUC_{90}$ (min * µg/mL) | $C_{1200}$ (µgA/mL) |
|---|---|---|---|---|---|
| 42 | CAB-O-SIL M-5P | 20/40/40 | 173 | 13,800 | 64 |
| Control 2B | none | — | <1 | <88 | <1 |

Example 44

A drug/substrate adsorbate of Drug 2 and CAB-O-SIL M-5P was prepared using the procedure outlined in Example 6 with the following exceptions. The suspension consisted of 0.86 wt % CAB-O-SIL M-5P, 0.29 wt % Drug 2, and 98.85 wt % acetone. The spray solution was pumped at a rate of 1.2 mL/min, and the nitrogen gas was heated to 100° C. After drying, the Example 44 adsorbate contained 25 wt % Drug 2 and 75 wt % CAB-O-SIL M-5P.

Example 45

The drug/substrate adsorbate of Example 44 was dosed in the form of an oral powder for constitution (OPC) to evaluate the composition in in vivo tests using male beagle dogs. The OPC was dosed as a suspension in a solution containing 0.5 wt % Methocel® (Dow Chemical Co.), and was prepared as follows. First, 7.5 g of Methocel® was weighed out and added slowly to approximately 490 ml of water at 90°-100° C. to form a Methocel® suspension. After all the Methocel® was added, 1000 mL of cool/room temperature water was added to the suspension, which was then placed in an ice-water bath. When all of the Methocel®D had dissolved, 2.55 g of Tween 80 were added and the mixture stirred until the Tween 80 had dissolved, thus forming a stock suspension solution.

To form the OPC, sufficient quantity of the test composition to result in a 90 mgA amount of Drug 2 was accurately weighed and placed into a mortar. A 20-mL quantity of the stock suspension solution was added to the mortar and the test composition was mixed with a pestle. Additional Methocel® suspension was added gradually with mixing until a total of 400 mL of the stock suspension solution had been added to the mortar. The suspension was then transferred to a flask, thus forming the OPC. In addition, an OPC containing 90 mgA of amorphous Drug 2 (Control 2B) was prepared using the same procedure.

Six male beagle dogs were each dosed with the OPC using a gavage tube and a syringe. Whole blood samples were taken from the jugular vein and analyzed for the concentration of Drug 2. To 25 μL of each plasma sample, 30 μL of Drug 2 internal standard solution was added and samples were vortexed. Next, 1.0 mL acetonitrile was added, and samples were vortexed, centrifuged, and added to glass culture tubes. To each tube, 100 μL 1.0M $KH_2PO_4$ buffer, pH 11, and 20 μL PFBBr was added. Samples were vortexed and incubated for 30 minutes at 85° C. To each tube, 2.0 mL water and 0.5 mL methyl tert-butyl ether was added, and samples were vortexed, centrifuged, and 100 μL removed and added to GC vials. Analysis was carried out by GC The results of these tests are presented in Table 45 and show that the compositions of the present invention provided enhanced drug concentration and relative bioavailability relative to the amorphous Drug 2 control (Control 2B). The composition of Example 44 dosed to fasted beagle dogs provided a $C_{max}$ that was more than 423-fold that of the amorphous control, and a relative bioavailability that was greater than 8400 relative to the amorphous control. The composition of Example 44 dosed to fed beagle dogs provided a $C_{max}$ that was 6.8-fold that of the amorphous control, and a relative bioavailability that was 7.3 relative to the amorphous control.

TABLE 45

| Composition | $C_{max}$ (ng/ml) | $AUC_{(0-24)}$ (ng/ml * hr) |
|---|---|---|
| Example 44 (25 wt % Drug 2/CAB-O-SIL M-5P)- fasted | 427.8 | 1687.4 |
| Control 2B (amorphous Drug 2) - fasted | <0.1 | <0.2 |
| Example 44 (25 wt % Drug 2/CAB-O-SIL M-5P)- fed | 1254.9 | 4365.0 |
| Control 2B (amorphous Drug 2) - fed | 184.8 | 598.5 |

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A pharmaceutical composition comprising:
  (a) a solid adsorbate comprising a low-solubility drug adsorbed onto a substrate, said substrate having a surface area of at least 20 m²/g, wherein at least 90 wt % of said drug in said adsorbate is amorphous;
  (b) a concentration-enhancing polymer co-adsorbed onto said substrate with said drug; and
  (c) wherein said drug has a minimum aqueous solubility of less than 10 mg/mL at a pH of 1-8,
wherein said solid adsorbate is formed by spray drying a spray suspension comprising said drug and said concentration-enhancing polymer dissolved in a solvent having said substrate suspended therein, and rapidly removing said solvent from said spray suspension to form a solid powder.

2. The composition of claim 1 wherein said drug in said adsorbate has a glass transition temperature substantially different from that of said drug in amorphous form alone that is not adsorbed to said substrate.

3. The composition of claim 1 wherein said drug has improved physical stability in said adsorbate relative to a control composition consisting of an equivalent amount of said drug in amorphous form alone that is not adsorbed to said substrate.

4. The composition of claim 1 wherein said drug and said polymer comprise an amorphous dispersion, and said dispersion is substantially homogeneous.

5. The composition of claim 1 wherein said polymer is selected from the group consisting of hydroxypropyl methyl cellulose succinate, cellulose acetate succinate, methyl cellulose acetate succinate, ethyl cellulose acetate succinate, hydroxypropyl cellulose acetate succinate, hydroxypropyl methyl cellulose acetate succinate, hydroxypropyl cellulose acetate phthalate succinate, cellulose propionate succinate, hydroxypropyl cellulose butyrate succinate, hydroxypropyl methyl cellulose phthalate, carboxymethyl cellulose, carboxyethyl cellulose, ethylcarboxymethyl cellulose, cellulose acetate phthalate, methyl cellulose acetate phthalate, ethyl cellulose acetate phthalate, hydroxypropyl cellulose acetate phthalate, hydroxypropyl methyl cellulose acetate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethyl benzoic acid cellulose acetate, ethyl phthalic acid cellulose acetate, ethyl nicotinic acid cellulose acetate, and ethyl picolinic acid cellulose acetate, carboxylic acid functionalized polymethacrylates, carboxylic acid functionalized polyacrylates, amine-functionalized polyacrylates, amine-fuctionalized polymethacrylates, proteins, and carboxylic acid functionalized starches, hydroxypropyl methyl cellulose acetate, hydroxypropyl methyl cellulose, hydroxypropyl cellulose, methyl cellulose, hydroxyethyl methyl cellulose, hydroxyethyl cellulose acetate, and hydroxyethyl ethyl cellulose, vinyl polymers and copolymers having at least one substituent selected from the group consisting of hydroxyl, alkylacyloxy, and cyclicamido, vinyl copolymers of at least one hydrophilic, hydroxyl-containing repeat unit and at least one hydrophobic, alkyl- or aryl-containing repeat unit, polyvinyl alcohols that have at least a portion of their repeat units in the unhydrolyzed form, polyvinyl alcohol polyvinyl acetate copolymers, polyethylene glycol polypropylene glycol copolymers, polyvinyl pyrrolidone, polyethylene polyvinyl alcohol copolymers, polyoxyethylene-polyoxypropylene block copolymers, neutralized forms thereof, and blends thereof.

6. The composition of claim 1 wherein said concentration enhancing polymer is selected from the group consisting of hydroxypropyl methyl cellulose acetate succinate, hydroxypropyl methyl cellulose phthalate, cellulose acetate phthalate, cellulose acetate trimellitate, carboxyethyl cellulose, carboxymethyl cellulose, and ethyl carboxymethyl cellulose.

7. The composition of claim 1 wherein said concentration enhancing polymer is a non-ionizable, non-cellulosic polymer selected from the group consisting of vinyl polymers or copolymers having at least one substituent selected from the group consisting of hydroxyl, alkylacyloxy, and cyclicamido, vinyl copolymers of at least one hydrophilic, hydroxyl-containing repeat unit and at least one hydrophobic, alkyl- or aryl-containing repeat unit, polyvinyl alcohols that have at least a portion of their repeat units in the unhydrolyzed form, polyvinyl alcohol polyvinyl acetate copolymers, polyethylene glycol polypropylene glycol copolymers, polyvinyl pyrrolidone, polyethylene polyvinyl alcohol copolymers, polyoxyethylene-polyoxypropylene block copolymers and blends thereof.

8. The composition of claim 1 wherein said polymer is polyvinyl pyrrolidone.

9. The composition of claim 1 wherein said composition when administered to a use environment provides at least one of:
  (a) a dissolution area under the concentration versus time curve for a time period of at least 90 minutes between the time of introduction to said use environment and about 270 minutes following introduction to the use environment that is at least 1.25-fold the corresponding area under the curve provided by a control composition comprising an equivalent amount of crystalline drug alone;
  (b) a maximum concentration of said drug in said use environment that is at least 1.25-fold a maximum concentration of said drug provided by said control composition comprising an equivalent amount of crystalline drug alone; and
  (c) a relative bioavailability of at least 1.25 relative to said control composition consisting of an equivalent amount of said drug in crystalline form alone.

10. The composition of claim 1 wherein said substrate is selected from the group consisting of inorganic oxides, zeolites, molecular sieves, and mixtures thereof.

11. The composition of claim 1 wherein said substrate is selected from the group consisting of $SiO_2$, $TiO_2$, $ZnO_2$, $ZnO$, $Al_2O_3$, and zeolite.

12. The composition of claim 11 wherein said concentration enhancing polymer is selected from the group consisting of hydroxypropyl methylcellulose acetate succinate, hydroxypropyl methylcellulose phthalate, cellulose acetate phthalate, cellulose acetate trimellitate, carboxyethyl cellulose, carboxymethyl cellulose, and ethyl carboxymethyl cellulose.

13. The composition of claim 11 wherein said concentration enhancing polymer is selected from the group consisting of vinyl polymers or copolymers having at least one substituent selected from the group consisting of hydroxyl, alkylacyloxy, and cyclicamido, vinyl copolymers of at least one hydrophilic, hydroxyl containing repeat unit and at least one hydrophobic, alkyl- or aryl-containing repeat unit, polyvinyl alcohols that have at least a portion of their repeat units in the unhydrolyzed form, polyvinyl alcohol polyvinyl acetate copolymers, polyethylene glycol polypropylene glycol copolymers, polyvinyl pyrrolidone, polyethylene polyvinyl alcohol copolymers, polyoxyethylene-polyoxypropylene block copolymers and blends thereof.

14. The composition of claim 1 wherein said substrate is $SiO_2$.

15. The composition of claim 1 wherein said low-solubility drug has a minimum aqueous solubility of less than 0.1 mg/mL at a pH of 1 to 8.

16. The composition of claim 1 wherein said low-solubility drug is selected from the group consisting of antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, cholesterol-reducing agents, anti-atherosclerotic agents, anti-obesity agents, autoimmune disorder agents; anti-impotence agents, antibacterial and antifungal agents, hypnotic agents, anti-Parkinsonism agents, anti-Alzheimer's disease agents, antibiotics, anti-depressants, antiviral agents, glycogen phosphorylase inhibitors, and cholesterol ester transfer protein inhibitors.

17. The composition of claim 1 wherein said drug is (2R)-3-[[3-(4-chloro-3-ethylphenoxy)phenyl][[3-(1,1,2,2-tetrafluoroethoxy)phenyl]methyl]amino]-1, 1,1-trifluoro-2-propanol.

18. The composition of claim 1 wherein said drug is (2R)-3-[[3-(4-chloro-3-ethylphenoxy)phenyl][[3-(1,1,2,2-tetrafluoroethoxy)phenyl]methyl]amino]-1,1,1-trifluoro-2-propanol, said substrate is $SiO_2$, and said polymer is polyvinyl pyrrolidone.

19. The composition of claim 1 wherein said drug is (2R)-3-[[3-(4-chloro-3-ethylphenoxy)phenyl][[3-(1,1,2,2-tetrafluoroethoxy)phenyl]methyl]amino]-1,1,1-trifluoro-2-propanol, said substrate is $SiO_2$, and said polymer is hydroxypropyl methyl cellulose acetate succinate.

20. The composition of claim 1 wherein said drug and said concentration-enhancing polymer are in the form of an amorphous dispersion on said substrate.

21. A method for forming a pharmaceutical composition, comprising:
  (a) providing a substrate having a surface area of at least 20 $m^2/g$;
  (b) adding said substrate to a solvent to form a suspension and agitating said suspension;
  (c) dissolving a drug having a minimum aqueous solubility of less than 10 mg/mL at a pH of 1-8 in said solvent;
  (d) rapidly removing said solvent from said suspension to form a rapidly quenched adsorbate comprising said drug adsorbed onto said substrate, wherein at least 90 wt % of said drug in said adsorbate is in amorphous form; and
  (e) wherein said drug is a cholesteryl ester transfer protein inhibitor.

22. A method for forming a pharmaceutical composition, comprising:
  (a) providing a substrate having a surface area of at least 20 $m^2/g$;
  (b) melting a drug having a minimum aqueous solubility of less than 10 mg/mL at a pH of 1-8;
  (c) combining said drug with said substrate to form a mixture;
  (d) cooling said mixture so that said drug is adsorbed onto said substrate to form an adsorbate, at least 90 wt % of said drug in said adsorbate being in amorphous form; and
  (e) wherein said drug is a cholesteryl ester transfer protein inhibitor.

23. The method of anyone of claim 21 or 22 further comprising the step of combining a concentration-enhancing polymer with said low solubility drug and said substrate.

* * * * *